US007951810B2

(12) United States Patent
Critchley et al.

(10) Patent No.: US 7,951,810 B2
(45) Date of Patent: May 31, 2011

(54) SUBSTITUTED PYRROLO[2,3-D]PYRIMIDINES AS INHIBITORS OF E1 ACTIVATING ENZYMES

(75) Inventors: Stephen Critchley, Braintree, MA (US); Thomas G. Gant, Carlsbad, CA (US); Steven P. Langston, North Andover, MA (US); Edward J. Olhava, Brookline, MA (US); Stephane Peluso, Somerville, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 1230 days.

(21) Appl. No.: 11/346,469

(22) Filed: Feb. 2, 2006

(65) Prior Publication Data
US 2006/0189636 A1 Aug. 24, 2006

Related U.S. Application Data

(60) Provisional application No. 60/650,433, filed on Feb. 4, 2005.

(51) Int. Cl.
*C07D 487/04* (2006.01)
*A61K 31/519* (2006.01)
*A61P 35/00* (2006.01)
*A61P 25/28* (2006.01)
*A61P 29/00* (2006.01)
(52) U.S. Cl. .................... 514/265.1; 544/280
(58) Field of Classification Search ............. 544/280; 514/265.1
See application file for complete search history.

(56) References Cited

U.S. PATENT DOCUMENTS

| 3,622,561 | A | 11/1971 | Robins et al. |
| 5,039,689 | A | 8/1991 | Daluge |
| 5,726,302 | A | 3/1998 | Ugarkar et al. |
| 5,763,596 | A | 6/1998 | Boyer et al. |
| 5,767,097 | A | 6/1998 | Tam |
| 5,824,657 | A | 10/1998 | Hill et al. |
| 5,864,033 | A | 1/1999 | Browne et al. |
| 6,210,917 | B1 | 4/2001 | Carson et al. |
| 6,734,283 | B1 | 5/2004 | Chau |

FOREIGN PATENT DOCUMENTS

| EP | 0832091 B1 | 1/2004 |
| EP | 0832092 B1 | 11/2004 |
| GB | 2284811 A | 6/1995 |
| GB | 2287464 A | 9/1995 |
| JP | 62-108897 | 7/1987 |
| JP | 11-228422 | 8/1999 |
| JP | 11-228446 | 8/1999 |
| WO | WO 03/049739 A1 | 6/2003 |
| WO | WO 2005/007621 A2 | 1/2005 |
| WO | WO 2006/002284 A1 | 1/2006 |

OTHER PUBLICATIONS

Baker, David C., et al., "An evaluation of certain chain-extended analogues of 9-β-D-arabinofuranosyladenine for antiviral and cardiovascular activity," *Journal of Medicinal Chemistry*, vol. 26, No. 10 (1983) pp. 1530-1534.
Bernier, Stephane, et al., "Glutamylsulfamoyladenosine and pyroglutamylsulfamoyladenosine are competitive inhibitors of E. coli glutamyl-tRNA synthetase," *Journal of Enzyme Inhibition and Medicinal Chemistry*, vol. 20, No. 1 (Feb. 2005) pp. 61-67.
Bloch, A., et al., "Inhibition of protein synthesis by 5'-sulfamoyladenosine," *Biochemistry*, vol. 10, No. 24 (1971) pp. 4394-4398.
Bookser, Brett C., et al., "Adenosine kinase inhibitors. 4. 6,8-disubstituted purine nucleoside derivatives. Synthesis, conformation, and enzyme inhibition," *Journal of Medicinal Chemistry*, vol. 48, No. 9 (2005) pp. 3389-3399.
Boyer, Serge H., et al., "Adenosine kinase inhibitors. 5. Synthesis, enzyme inhibition, and analgesic activity of diaryl-*erythro*-furanosyltubercidin analogues," *Journal of Medicinal Chemistry*, vol. 48, No. 20 (2005) pp. 6430-6441.
Brown, Pamela, et al., "Molecular recognition of tyrosinyl adenylate analogues by prokaryotic tyrosyl tRNA synthetases," *Bioorganic & Medicinal Chemistry*, vol. 7 (1999) pp. 2473-2485.
Crimmins, Michael T., et al., "An efficient, general asymmetric synthesis of carbocyclic nucleosides: application of an asymmetric aldol/ring-closing metathesis strategy," *Journal of Organic Chemistry*, vol. 65, No. 25 (2000) pp. 8499-8509.
Gough, Geoffrey R., "New inhibitors of platelet aggregation. 5'-phosphate, 5'-phosphorothioate, and 5'-O-sulfamoyl derivatives of 2-substituted adenosine analogues," *Journal of Medicinal Chemistry*, vol. 21, No. 6 (1978) pp. 520-525.
Kristinsson, Haukur, et al., "A novel synthesis of sulfamoyl nucleosides," *Tetrahedron*, vol. 50, No. 23 (1994) pp. 6825-6838.
Kristinsson, Haukur, et al., "Herbicidally active sulfamoyl nucleosides," *ACS Symposium Series 584, Synthesis and Chemistry of Agrochemicals IV*, Chapter 19, Baker, Don R., et al., editors (1995) pp. 206-219.
Kuang, Rongze, et al., Enantioselective syntheses of carbocyclic ribavirin and its analogs: linear versus convergent approaches, *Tetrahedron Letters*, vol. 41 (2000) pp. 9575-9579. Lee, Jeewoo, et al., "N-alkoxysulfamide, N-hydroxysulfamide, and sulfamate analogues of methionyl and isoleucyl adenylates as inhibitors of methionyl-tRNA and isoleucyl-tRNA synthetases," *Bioorganic & Medicinal Chemistry Letters*, vol. 13 (2003) pp. 1087-1092.
Pan, Zhen-Qiang, et al., "Nedd8 on cullin: building an expressway to protein destruction," *Oncogene*, vol. 23 (2004) pp. 1985-1987.
Peterson, Eileen M., et al., "Synthesis and biological evaluation of 5'-sulfamoylated purinyl carbocyclic nucleosides," *Journal of Medicinal Chemistry*, vol. 35, No. 22 (1992) pp. 3991-4000.

(Continued)

Primary Examiner — Susanna Moore

(57) ABSTRACT

This invention relates to compounds of formula (I-A)

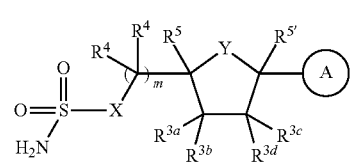

(I-A)

wherein Ring A and the variables X, Y, $R^{3a}$, $R^{3b}$, $R^{3c}$, $R^{3d}$, $R^4$, $R^5$, $R^{5'}$, and m are defined herein. The compounds of formula (I-A) inhibit E1 activating enzymes, pharmaceutical compositions comprising the compounds, and methods of using the compounds. The compounds of the invention are useful for treating disorders, particularly cell proliferation disorders, including cancers, inflammatory and neurodegenerative disorders; and inflammation associated with infection and cachexia.

19 Claims, No Drawings

OTHER PUBLICATIONS

Shuman, Dennis A., et al., "The synthesis of nucleoside sulfamates related to nucleocidin," *Journal of the American Chemical Society*, vol. 92, No. 11 (Jun. 3, 1970) pp. 3434-3440.

Somu, Ravindranadh V., et al., "Rationally designed nucleoside antibiotics that inhibit siderophore biosynthesis of *Mycobacterium tuberculosis*," *Journal of Medicinal Chemistry*, vol. 49, No. 1 (2006) pp. 31-34.

Ubukata, Makoto, et al., "Total synthesis of nucleoside antibiotic, ascamycin," *Tetrahedron Letters*, vol. 27, No. 33 (1986) pp. 3907-3908.

Ubukata, Makoto, et al., "Synthesis and biological activity of aminoacyl analogs of ascamycin," *Agricultural and Biological Chemistry*, vol. 52, No. 5 (1988) pp. 1117-1122.

Ugarkar, Bheemarao G., et al., "Adenosine kinase inhibitors. 3. Synthesis, SAR, and anti-inflammatory activity of a series of L-lyxofuranosyl nucleosides," *Journal of Medicinal Chemistry*, vol. 46, No. 22 (2003) pp. 4750-4760.

Winum, Jean-Yves, et al., "Sulfamates and their therapeutic potential," *Medicinal Research Reviews*, vol. 25, No. 2 (2005) pp. 186-228.

International Search Report dated Jul. 17, 2006 from PCT/US2006/004637 corresponding to U.S. Appl. No. 11/346,649.

Office Action dated Sep. 14, 2009 in pending U.S. Appl. No. 11/700,614.

Advisory Action dated Dec. 14, 2009 in pending U.S. Appl. No. 11/700,614.

Terminal Disclaimer and Supplemental Reply filed Feb. 11, 2010 in pending U.S. Appl. No. 11/700,614.

Amendment and Response under 37 CFR §1.116 filed Nov. 13, 2009 in pending U.S. Appl. No. 11/700,614.

US 7,951,810 B2

SUBSTITUTED PYRROLO[2,3-D]PYRIMIDINES AS INHIBITORS OF E1 ACTIVATING ENZYMES

RELATED APPLICATIONS

This application claims priority from U.S. Provisional Patent Application No. 60/650,433, filed on Feb. 4, 2005, which is hereby incorporated by reference in its entirety.

FIELD OF THE INVENTION

This invention relates to compounds, compositions and methods for the treatment of various disorders, particularly disorders of cell proliferation, including cancers, and inflammatory disorders. In particular, the invention provides compounds which inhibit the activity of E1 type activating enzymes.

BACKGROUND OF THE INVENTION

The post-translational modification of proteins by ubiquitin-like molecules (ubls) is an important regulatory process within cells, playing key roles in controlling many biological processes including cell division, cell signaling and the immune response. Ubls are small proteins that are covalently attached to a lysine on a target protein via an isopeptide linkage with a C-terminal glycine of the ubl. The ubiquitin-like molecule alters the molecular surface of the target protein and can affect such properties as protein-protein interactions, enzymatic activity, stability and cellular localization of the target.

Ubiquitin and other ubls are activated by a specific E1 enzyme which catalyzes the formation of an acyl-adenylate intermediate with the C-terminal glycine of the ubl. The activated ubl molecule is then transferred to the catalytic cysteine residue within the E1 enzyme through formation of a thioester bond intermediate. The E1-ubl intermediate and an E2 associate, resulting in a thioester exchange wherein the ubl is transferred to the active site cysteine of the E2. The ubl is then conjugated to the target protein, either directly or in conjunction with an E3 ligase, through isopeptide bond formation with the amino group of a lysine side chain in the target protein.

The biological consequence of ubl modification depends on the target in question. Ubiquitin is the best characterized of the ubls and a consequence of modification by ubiquitination is the degradation of poly-ubiquitinated proteins by the 26S proteasome. Ubiquitin is conjugated to its target proteins through an enzymatic cascade involving its specific E1 activating enzyme, Uba1 (ubiquitin activating enzyme, UAE), a conjugating enzyme from the family of E2s, and a ubiquitin ligase from either the RING or HECT classes of E3s. See, Huang et al., *Oncogene.* 23:1958-71 (2004). Target specificity is controlled by the particular combination of E2 and E3 protein, with >40 E2s and >100 E3s being known at present. In addition to ubiquitin, there are at least 10 ubiquitin-like proteins, each believed to be activated by a specific E1 activating enzyme and processed through similar but distinct downstream conjugation pathways. Other ubls for which E1 activating enzymes have been identified include Nedd8 (APPBP1-Uba3), ISG15 (UBE1L) and the SUMO family (Aos1-Uba2).

The ubl Nedd8 is activated by the heterodimer Nedd8-activating enzyme (APPBP1-Uba3) (NAE) and is transferred to a single E2 (Ubc12), ultimately resulting in ligation to cullin proteins. The function of neddylation is the activation of cullin-based ubiquitin ligases involved in the ubiquitination and hence turnover of many cell cycle and cell signaling proteins, including p27 and I-κB. See Pan et al., *Oncogene.* 23:1985-97, (2004). The ubl SUMO is activated by the heterodimer sumo activating enzyme (Aos1-Uba2) (SAE) and is transferred to a single E2 (Ubc9), followed by coordination with multiple E3 ligases, ultimately resulting in sumoylation of target proteins. Sumo modification can affect the cellular localization of target proteins and proteins modified by SUMO family members are involved in nuclear transport, signal transduction and the stress response. See Seeler and Dejean, *Nat Rev Mol Cell Biol.* 4:690-9, (2003). The function of sumoylation includes activation of cell signaling pathways (e.g., cytokine, WNT, growth factor, and steroid hormone signaling) involved in transcription regulation; as well as pathways involved in control of genomic integrity (e.g., DNA replication, response to DNA damage, recombination and repair). See Muller et al, *Oncogene.* 23:1998-2006, (2004). There are other ubls (e.g., ISG15, FAT10, Apg12p) for which the biological functions are still under investigation.

A particular pathway of importance which is regulated via E1 activating enzyme activities is the ubiquitin-proteasome pathway (UPP). As discussed above, the enzymes UAE and NAE regulate the UPP at two different steps in the ubiquitination cascade. UAE activates ubiquitin in the first step of the cascade, while NAE, via activation of Nedd8, is responsible for the activation of the cullin based ligases, which in turn are required for the final transfer of ubiquitin to certain target proteins A functional UPP pathway is required for normal cell maintenance. The UPP plays a central role in the turnover of many key regulatory proteins involved in transcription, cell cycle progression and apoptosis, all of which are important in disease states, including tumor cells. See, e.g., King et al., *Science* 274: 1652-1659 (1996); Vorhees et al., *Clin. Cancer Res.,* 9: 6316-6325 (2003); and Adams et al., *Nat. Rev. Cancer,* 4: 349-360 (2004). Proliferating cells are particularly sensitive to inhibition of the UPP. See, Drexler, *Proc. Natl. Acad. Sci., USA* 94: 855-860 (1977). The role of the UPP pathway in oncogenesis has led to the investigation of proteasome inhibition as a potential anticancer therapy. For example, modulation of the UPP pathway by inhibition of the 26S proteasome by VELCADE® (bortezomib) has proven to be an effective treatment in certain cancers and is approved for the treatment of relapsed and refractory multiple myeloma. Examples of proteins whose levels are controlled by cullin-based ubiquitin ligases which are downstream of NAE and UAE activity include the CDK inhibitor $p27^{Kip1}$ and the inhibitor of NFκB, IκB. See, Podust et al., *Proc. Natl. Acad. Sci.,* 97: 4579-4584, (2000), and Read et al., *Mol. Cell Biol.,* 20: 2326-2333, (2000). Inhibition of the degradation of p27 is expected to block the progression of cells through the G1 and S phases of the cell cycle. Interfering with the degradation of IκB should prevent the nuclear localization of NF-κB, transcription of various NF-κB-dependent genes associated with the malignant phenotype, and resistance to standard cytotoxic therapies. Additionally, NF-κB plays a key role in the expression of a number of pro-inflammatory mediators, implicating a role for such inhibitors in inflammatory diseases. Furthermore, inhibition of UPP has been implicated as a useful target for additional therapeutics, such as inflammatory disorders, including, e.g., rheumatoid arthritis, asthma, multiple sclerosis, psoriasis and reperfusion injury; neurodegenerative disorders, including e.g., Parkinson's disease, Alzheimer's disease, triplet repeat disorders; neuropathic pain; ischemic disorders, e.g., stroke, infarction, kidney disorders; and cachexia. See, e.g., Elliott and Ross, *Am J Clin Pathol.* 116:637-46 (2001); Elliott et al., *J Mol Med.* 81:235-

45 (2003); Tarlac and Storey, *J. Neurosci. Res.* 74: 406-416 (2003); Mori et al., *Neuropath. Appl. Neurobiol.*, 31: 53-61 (2005); Manning, *Curr Pain Headache Rep.* 8: 192-8 (2004); Dawson and Dawson, *Science* 302: 819-822 (2003); Kukan, *J Physiol Pharmacol.* 55: 3-15 (2004); Wojcik and DiNapoli, *Stroke.* 35:1506-18 (2004); Lazarus et al., *Am J Physiol.* 27:E332-41 (1999).

Targeting E1 activating enzymes provides a unique opportunity to interfere with a variety of biochemical pathways important for maintaining the integrity of cell division and cell signaling. E1 activating enzymes function at the first step of ubl conjugation pathways; thus, inhibition of an E1 activating enzyme will specifically modulate the downstream biological consequences of the ubl modification. As such, inhibition of these activating enzymes, and the resultant inhibition of downstream effects of ubl-conjugation, represents a method of interfering with the integrity of cell division, cell signaling, and several aspects of cellular physiology which are important for disease mechanisms. Thus, E1 enzymes such as UAE NAE, and SAE, as regulators of diverse cellular functions, are potentially important therapeutic targets for the identification of novel approaches to treatment of diseases and disorders.

DESCRIPTION OF THE INVENTION

This invention provides compounds that are effective inhibitors of E1 activating enzymes, particularly NAE. The compounds are useful for inhibiting E1 activity in vitro and in vivo, and are useful for the treatment of disorders of cell proliferation, particularly cancers, and other disorders associated with E1 activity. Compounds of the invention are of the general formula I-A:

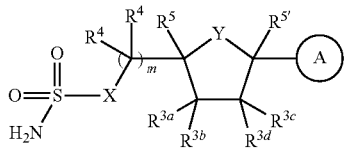

(I-A)

or a pharmaceutically acceptable salt thereof,
wherein:
Ring A is selected from the group consisting of:

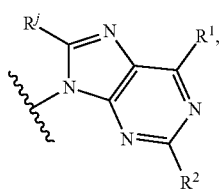

A-i

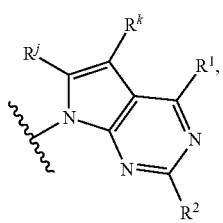

A-ii

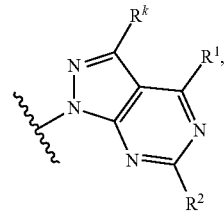

A-iii

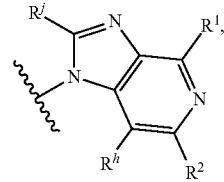

A-iv

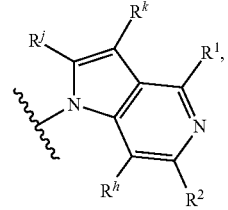

A-v

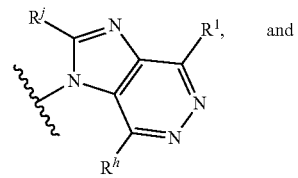

A-vi and

A-vii wherein one ring nitrogen atom in Ring A optionally is oxidized;

X is —CH$_2$—, —CHF—, —CF$_2$—, —NH—, or —O—;
Y is —O—, —S—, or —C(R$^m$)(R$^n$)—;
each R$^h$ independently is hydrogen, halo, —CN, —OH, —O—(C$_{1-4}$ aliphatic), —NH$_2$, —NH—(C$_{1-4}$ aliphatic), —N(C$_{1-4}$ aliphatic)$_2$, —SH, —S—(C$_{1-4}$ aliphatic), or an optionally substituted C$_{1-4}$ aliphatic group;
R$^j$ is hydrogen, —OR$^5$, —SR$^6$, —N(R$^4$)$_2$, or an optionally substituted aliphatic, aryl, or heteroaryl group;
R$^k$ is hydrogen, halo, —OR$^5$, —SR$^6$, —N(R$^4$)$_2$, or an optionally substituted C$_{1-4}$ aliphatic group;
R$^m$ is hydrogen, fluoro, —N(R$^4$)$_2$, or an optionally substituted C$_{1-4}$ aliphatic group, and R$^n$ is hydrogen, fluoro, or an optionally substituted C$_{1-4}$ aliphatic group, or R$^m$ and R$^n$ together form =O or =C(R$^5$)$_2$;
R$^1$ is hydrogen, chloro, bromo, fluoro, iodo, —NR$^7$R$^8$, —R$^9$, —SH, —SCH$_3$, —S—R$^{10}$, —OH, —OCH$_3$, or —O—R$^{11}$;
R$^2$ is hydrogen, chloro, bromo, fluoro, iodo, —N(R$^6$)$_2$, —CN, —O—(C$_{1-4}$ aliphatic), —OH, —SR$^6$, or an optionally substituted C$_{1-4}$ aliphatic group;
R$^{3a}$ is selected from the group consisting of hydrogen, fluoro, —CN, —N$_3$, hydroxy, —OR$^{21}$, —NH$_2$, —NH ($R^{21}$), —N(H)CO$_2$R$^{21}$, —N(H)C(O)R$^{21}$, —CON(H)R$^{21}$, —OC(O)N(H)R$^{21}$, —OC(O)R$^{21}$, —OC(O)OR$^{21}$, —C$_{1-4}$ fluoroaliphatic, or a —C$_{1-4}$ aliphatic optionally substituted with one or two substituents independently selected from the group consisting of —OR$^{5x}$, —N(R$^{4x}$)(R$^{4y}$), —CO$_2$R$^{5x}$, or —C(O)N(R$^{4x}$)(R$^{4y}$); or R$^{3a}$ and R$^{3c}$ together form a bond;

R$^{3b}$ is selected from the group consisting of hydrogen, fluoro, C$_{1-4}$ aliphatic, and C$_{1-4}$ fluoroaliphatic;

R$^{3c}$ is selected from the group consisting of hydrogen, fluoro, —CN, —N$_3$, hydroxy, —OR$^{21}$, —NH$_2$, —NH(R$^{21}$), —N(H)CO$_2$R$^{21}$, —N(H)C(O)R$^{21}$, —CON(H)R$^{21}$, —OC(O)N(H)R$^{21}$, —OC(O)R$^{21}$, —OC(O)OR$^{21}$, —C$_{1-4}$ fluoroaliphatic, or a —C$_{1-4}$ aliphatic optionally substituted with one or two substituents independently selected from the group consisting of OR$^{5x}$, —N(R$^{4x}$)(R$^{4y}$), —CO$_2$R$^{5x}$, or —C(O)N(R$^{4x}$)(R$^{4y}$); or R$^a$ and R$^c$ together form a bond;

R$^{3d}$ is selected from the group consisting of hydrogen, fluoro, C$_{1-4}$ aliphatic, and C$_{1-4}$ fluoroaliphatic;

each R$^4$ is independently hydrogen, fluoro, C$_{1-4}$ aliphatic, or C$_{1-4}$ fluoroaliphatic; or two R$^4$, taken together with the carbon atom to which they are attached, form a 3- to 6-membered carbocyclic ring; or one R$^4$, taken together with R$^5$ and the intervening carbon atoms, forms a 3- to 6-membered spirocyclic ring; or two R$^4$ together form =O;

R$^5$ is hydrogen, or C$_{1-4}$ aliphatic; or R$^5$, taken together with one R$^4$ and the intervening carbon atoms, forms a 3- to 6-membered spirocyclic ring;

R$^{5'}$ is hydrogen, or C$_{1-4}$ aliphatic;

each R$^6$ is independently hydrogen or C$_{1-4}$ aliphatic;

R$^7$ is an optionally substituted C$_{1-10}$ aliphatic, aryl, heteroaryl, or heterocyclyl group;

R$^8$ is hydrogen or C$_{1-4}$ aliphatic;

R$^9$ is —V—Z—R$^{12a}$, —V—Z—R$^{12b}$, —R$^{12c}$, or an optionally substituted aliphatic, aryl, heterocyclyl, or heteroaryl group;

R$^{10}$ is an unsubstituted C$_{2-10}$ aliphatic, a substituted C$_{1-10}$ aliphatic, or an optionally substituted aryl, heteroaryl, or heterocyclyl;

R$^{11}$ is an unsubstituted C$_{2-10}$ aliphatic, a substituted C$_{1-10}$ aliphatic, or an optionally substituted aryl, heteroaryl, or heterocyclyl;

R$^{4x}$ is hydrogen, C$_{1-4}$ alkyl, C$_{1-4}$ fluoroalkyl, or C$_{6-10}$ ar(C$_{1-4}$)alkyl, the aryl portion of which may be optionally substituted;

R$^{4y}$ is hydrogen, C$_{1-4}$ alkyl, $_{1-4}$ fluoroalkyl, C$_{6-10}$ ar(C$_{1-4}$)alkyl, the aryl portion of which may be optionally substituted, or an optionally substituted 5- or 6-membered aryl, heteroaryl, or heterocyclyl ring; or R$^{4x}$ and R$^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S;

each R$^{5x}$ independently is hydrogen, C$_{1-4}$ alkyl, C$_{1-4}$ fluoroalkyl, or an optionally substituted C$_{6-10}$ aryl or C$_{6-10}$ ar(C$_{1-4}$)alkyl;

V is —S(O)$_2$—, —S(O)—, —C(O)O—, —C(O)—, —C(NR$^{13}$)=N—, —C(=N(R$^{13}$))—N(R$^{13}$)—, —C(OR$^{11}$)=N—, —CON(R$^{13}$)—, —N(R$^{13}$)C(O)—, —N(R$^{13}$)C(O)N(R$^{13}$)—, —N(R$^{13}$)S(O)$_2$—, —N(R$^{13}$)SO$_2$—N(R$^{13}$)—, —N(R$^{13}$)CO$_2$—, —SO$_2$N(R$^{13}$)—, —OC(O)—, —OC(O)O—, —OC(O)N(R$^{13}$)—, —N(R$^{13}$)—N(R$^{13}$)—;

Z is an optionally substituted C$_{1-6}$ alkylene chain, wherein the alkylene chain is optionally interrupted by —C(R$^{13}$)=C(R$^{13}$)—, —C≡C—, —O—, —S—, —N(R$^{13}$)—, —N(R$^{13}$)CO—, —N(R$^{13}$)CO$_2$—, —C(O)N(R$^{13}$)—, —C(O)—, —C(O)—C(O)—, —CO$_2$—, —OC(O)—, —OC(O)O—, —N(R$^{13}$)C(O)N(R$^{13}$)—, —N(R$^{13}$)N(R$^{13}$)—, —OC(O)N(R$^{13}$)—, —S(O)—, —S(O)$_2$—, —N(R$^{13}$)S(O)$_2$—, —S(O)$_2$N(R$^{13}$)—;

R$^{12a}$ is an optionally substituted aryl, heteroaryl, heterocyclyl, or cycloaliphatic group;

R$^{12b}$ is halo, —NO$_2$, —CN, —OR$^{14}$, —SR$^{15}$, —N(R$^{16}$)$_2$, —N(R$^{16}$)C(O)R$^{15}$, —N(R$^{16}$)C(O)N(R$^{16}$)$_2$, —N(R$^{16}$)CO$_2$R$^{14}$, —O—CO$_2$—R$^{14}$, —OC(O)N(R$^{16}$)$_2$, —OC(O)R$^{14}$, —N(R$^{16}$)—N(R$^{16}$)$_2$, —N(R$^{16}$)—OR$^{15}$, —N(R$^{16}$)S(O)$_2$R$^{15}$, or —N(R$^{16}$)SO$_2$—N(R$^{16}$)$_2$, —C(R$^{14}$)=C(R$^{14}$)$_2$, C≡C—R$^{14}$, —S(O)R$^{15}$, —SO$_2$R$^{15}$, —SO$_2$—N(R$^{16}$)$_2$, —C(R$^{14}$)=N—OR$^{14}$, —CO$_2$R$^{14}$, —C(O)—C(O)R$^{14}$, —C(O)R$^{14}$, —C(O)N(R$^{16}$)$_2$, —C(=NR$^{16}$)—N(R$^{16}$)$_2$, or —C(=NR$^{16}$)—OR$^{14}$;

R$^{12c}$ is —NO$_2$, —CN, —S(O)R$^{15}$, —SO$_2$R$^{15}$, SO$_2$—N(R$^{16}$)$_2$, —C(R$^{14}$)=N—OR$^{14}$, —N(R$^{16}$)C(O)R$^{15}$, —N(R$^{16}$)C(O)N(R$^{16}$)$_2$, —O—CO$_2$—R$^{14}$, —OC(O)N(R$^{16}$)$_2$, —OC(O)R$^{14}$, —CO$_2$R$^{14}$, —C(O)—C(O)R$^{14}$, —C(O)R$^{14}$, —C(O)N(R$^{16}$)$_2$, —C(=NR$^{16}$)—N(R$^{16}$)$_2$, —C(=NR$^{16}$)—OR$^{14}$, —N(R$^{16}$)—N(R$^{16}$)$_2$, —N(R$^{16}$)—OR$^{15}$, —N(R$^{16}$)S(O)$_2$R$^{15}$, or —N(R$^{16}$)SO$_2$—N(R$^{16}$)$_2$;

each R$^{13}$ is independently hydrogen, or an optionally substituted aliphatic, aryl, heteroaryl, or heterocyclyl group;

each R$^{14}$ independently is hydrogen, or an optionally substituted aliphatic, aryl, heteroaryl, or heterocyclyl group;

each R$^{15}$ independently is an optionally substituted aliphatic, or aryl group;

each R$^{16}$ independently is an optionally substituted aliphatic, aryl, heteroaryl, or heterocyclyl group; or two R$^{16}$ on the same nitrogen atom, taken together with the nitrogen atom, form an optionally substituted five to eight membered heterocyclyl ring having, in addition to the nitrogen atom, zero to two additional ring heteroatoms selected from the group consisting of N, O, and S;

each R$^{21}$ independently is an optionally substituted C$_{1-10}$ aliphatic, aryl, heteroaryl, or heterocyclyl group; and m is 1, 2, or 3.

Compounds of the invention include those described generally above, and are further defined and illustrated by the detailed description and examples herein.

As used herein, the term "E1," "E1 enzyme," or "E1 activating enzyme" refers to any one of a family of related ATW-dependent activating enzymes involved in activating or promoting ubiquitin or ubiquitin-like (collectively "ubl") conjugation to target molecules. E1 activating enzymes function through an adenylation/thioester intermediate formation to transfer the appropriate ubl to the respective E2 conjugating enzyme through a transthiolation reaction. The resulting activated ubl-E2 promotes ultimate conjugation of the ubl to a target protein. A variety of cellular proteins that play a role in cell signaling, cell cycle, and protein turnover are substrates for ubl conjugation which is regulated through E1 activating enzymes (e.g., NAE, UAE, SAE). Unless otherwise indicated by context, the term "E1 enzyme" is meant to refer to any E1 activating enzyme protein, including, without limitation, nedd8 activating enzyme (NAE (APPBP1/Uba3)), ubiquitin activating enzyme (UAE (Uba1)), sumo activating enzyme (SAE (Aos1/Uba2)), or ISG15 activating enzyme (Ube1L), preferably human NAE, SAE or UAE, and more preferably NAE.

The term "E1 enzyme inhibitor" or "inhibitor of E1 enzyme" is used to signify a compound having a structure as defined herein, which is capable of interacting with an E1 enzyme and inhibiting its enzymatic activity. Inhibiting E1 enzymatic activity means reducing the ability of an E1 enzyme to activate ubiquitin like (ubl) conjugation to a substrate peptide or protein (e.g., ubiquitination, neddylation, sumoylation). In various embodiments, such reduction of E1 enzyme activity is at least about 50%, at least about 75%, at least about 90%, at least about 95%, or at least about 99%. In various embodiments, the concentration of E1 enzyme inhibitor required to reduce an E1 enzymatic activity is less than about 1 μM, less than about 500 nM, less than about 100 nM, less than about 50 nM, or less than about 10 nM.

In some embodiments, such inhibition is selective, i.e., the E1 enzyme inhibitor reduces the ability of one or more E1 enzymes (e.g., NAE, UAE, or SAE) to promote ubl conjugation to substrate peptide or protein at a concentration that is lower than the concentration of the inhibitor that is required to produce another, unrelated biological effect. In some such embodiments, the E1 enzyme inhibitor reduces the activity of one E1 enzyme at a concentration that is lower than the concentration of the inhibitor that is required to reduce enzymatic activity of a different E1 enzyme. In other embodiments, the E1 enzyme inhibitor also reduces the enzymatic activity of another E1 enzyme, preferably one that is implicated in regulation of pathways involved in cancer (e.g., NAE and UAE).

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "aliphatic", as used herein, means straight-chain, branched or cyclic $C_1$-$C_{12}$ hydrocarbons which are completely saturated or which contain one or more units of unsaturation, but which are not aromatic. For example, suitable aliphatic groups include substituted or unsubstituted linear, branched or cyclic alkyl, alkenyl, alkynyl groups and hybrids thereof, such as cycloalkyl, (cylcoalkyl)alkyl, (cycloalkenyl) alkyl or (cycloalkyl)alkenyl. In various embodiments, the aliphatic group has one to ten, one to eight, one to six, one to four, or one, two, or three carbons.

The terms "alkyl", "alkenyl", and "alkynyl", used alone or as part of a larger moiety, refer to a straight and branched chain aliphatic group having from one to twelve carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl. The term "alkoxy" refers to an —O-alkyl radical.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on a cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on an aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Thus, when used in reference to a ring atom of a heteroaryl, the term "nitrogen" includes an oxidized nitrogen (as in pyridine N-oxide). Certain nitrogen atoms of 5-membered heteroaryl groups also are substitutable, as further defined below. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl.

In some embodiments, two adjacent substituents on a heteroaryl ring, taken together with the intervening ring atoms, form an optionally substituted fused 5 to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", or "heteroaryl group", any of which terms include rings that are optionally substituted. The term "heteroaralkyl" refers to an alkyl group substituted by a heteroaryl, wherein the alkyl and heteroaryl portions independently are optionally substituted.

As used herein, the terms "aromatic ring" and "aromatic ring system" refer to an optionally substituted mono-, bi-, or tricyclic group having 0-6, preferably 0-4 ring heteroatoms, and having 6, 10, or 14π electrons shared in a cyclic array. Thus, the terms "aromatic ring" and "aromatic ring system" encompass both aryl and heteroaryl groups.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "linker group" or "linker" means an organic moiety that connects two parts of a compound. Linkers typically comprise an atom such as oxygen or sulfur, a unit such as —NH—, —CH$_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a $C_{1-6}$ alkylene chain which is optionally substituted.

The term "alkylene" refers to a bivalent alkyl group. An "alkylene chain" is a polymethylene group, i.e., —(CH$_2$)$_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)═C(R*)—, —C≡C—, —O—, —S—, —S(O)—, —S(O)$_2$—, —S(O)$_2$N(R$^+$)—, —N(R*)—, —N(R$^+$)CO—, —N(R$^+$)C(O)N(R$^+$)—, —N(R$^+$)CO$_2$—, —C(O)N(R$^+$)—, —C(O)—, —C(O)—C (O)—, —CO$_2$—, —OC(O)—, —OC(O)O—, —OC(O)N (R$^+$)—, —C(NR$^+$)═N, —C(OR*)═N—, —N(R$^+$)—N (R$^+$)—, or —N(R$^+$)S(O)$_2$—. Each R$^+$, independently, is hydrogen or an optionally substituted aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms selected from N, O, and S. Each R* independently is hydrogen or an optionally substituted aliphatic, aryl, heteroaryl, or heterocyclyl group.

Examples of $C_{3-6}$ alkylene chains that have been "interrupted" with —O— include —$CH_2OCH_2$—, —$CH_2O$ $(CH_2)_2$—, —$CH_2O(CH_2)_3$—, —$CH_2O(CH_2)_4$—, —$(CH_2)_2$ $OCH_2$—, —$(CH_2)_2O(CH_2)_2$—, —$(CH_2)_2O(CH_2)_3$—, —$(CH_2)_3O(CH_2)$—, —$(CH_2)_3O(CH_2)_2$—, and —$(CH_2)_4O$ $(CH_2)$—. Other examples of alkylene chains that are "interrupted" with functional groups include —$CH_2GCH_2$—, —$CH_2G(CH_2)_2$—, —$CH_2G(CH_2)_3$—, —$CH_2G(CH_2)_4$—, —$(CH_2)_2GCH_2$—, —$(CH_2)_2G(CH_2)_2$—, —$(CH_2)_2G$ $(CH_2)_3$—, —$(CH_2)_3G(CH_2)$—, —$(CH_2)_3G(CH_2)_2$—, and —$(CH_2)_4G(CH_2)$—, wherein G is one of the "interrupting" functional groups listed above.

For purposes of clarity, all bivalent groups described herein, including, e.g., the alkylene chain linkers described above and the variables V and Z, are intended to be read from left to right, with a corresponding left-to-right reading of the formula or structure in which the variable appears.

One of ordinary skill in the art will recognize that when an alkylene chain having an interruption is attached to a functional group, certain combinations are not sufficiently stable for pharmaceutical use. Only stable or chemically feasible compounds are within the scope of the present invention. A stable or chemically feasible compound is one in which the chemical structure is not substantially altered when kept at a temperature from about −80° C. to about +40° C., preferably from about −20° C. to about +40° C., in the absence of moisture or other chemically reactive conditions, for at least a week, or a compound which maintains its integrity long enough to be useful for therapeutic or prophylactic administration to a patient.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

An aryl (including the aryl moiety in aralkyl, aralkoxy, aryloxyalkyl and the like) or heteroaryl (including the heteroaryl moiety in heteroarylalkyl and heteroaralkoxy and the like) group may contain one or more substituents. Examples of suitable substituents on the unsaturated carbon atom of an aryl or heteroaryl group include -halo, —$NO_2$, —CN, —R*, —C(R*)=C(R*)$_2$, —C≡C—R*, —OR*, —SR$^o$, —S(O) R$^o$, —$SO_2$R$^o$, —$SO_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC (O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C (=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, wherein R$^o$ is an optionally substituted aliphatic or aryl group, and R$^+$ and R* are as defined above, or two adjacent substituents, taken together with their intervening atoms, form a 5- to 6-membered unsaturated or partially unsaturated ring having 0-3 ring atoms selected from the group consisting of N, O, and S.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—N(R$^+$)$_2$, =N—OR*, =N—NHC(O)R*, =N—NHCO$_2$R$^o$, =N—NHSO$_2$R$^o$, or =N—R*, where each R* and R$^o$ is as defined above. For the purposes of clarity, the term "substituted aliphatic" refers to an aliphatic group having at least one non-aliphatic substituent.

Suitable substituents on a substitutable nitrogen atom of a heteroaryl or heterocyclic ring include —R*, —N(R*)$_2$, —C(O)R*, —CO$_2$R*, —C(O)—C(O)R*—C(O)CH$_2$C(O) R*, —SO$_2$R*, —SO$_2$N(R*)$_2$, —C(=S)N(R*)$_2$, —C(=NH)—N(R*)$_2$, and —NR*SO$_2$R*; wherein each R* is as defined above.

It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. By way of example, the compounds of formula I wherein $R^{3a}$ is hydroxy can have R or S configuration at the carbon atom bearing $R^{3a}$. Both the R and the S stereochemical isomers, as well as all mixtures thereof, are included within the scope of the invention.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

Compounds of formula (I-A) are useful in decreasing E1 enzyme activity and treating or ameliorating disorders. Certain of these compounds, as provided in further detail below, are new. Accordingly, one aspect of this invention relates to such compounds, as represented by formula (I-A), as described above, provided that: if Ring A is A-i, X is —O—, Y is —O— or —CH$_2$—, $R^2$ is hydrogen or chloro, $R^{3a}$ is hydroxyl or —OCOR$^{21}$, $R^{3b}$ is hydrogen, $R^{3c}$ is hydroxyl or —OCOR$^{21}$, $R^{3d}$ is hydrogen, $R^4$ and $R^5$ are each hydrogen, and m is 1; then $R^1$ is bromo, fluoro, —NR$^7$R$^8$, —R$^9$, —SR$^{10}$, or —OR$^{11}$, $R^7$ is a substituted aliphatic, or an optionally substituted aryl, heteroaryl, aralkyl, heteroaralkyl, cycloaliphatic, heterocyclyl, (cycloaliphatic)alkyl, or (heterocyclyl)alkyl, and $R^9$ is other than unsubstituted imidazole.

In the compounds of formula (I-A), X is —CH$_2$—, —CHF—, —CF$_2$—, —NH—, or —O—. In some embodiments, X is —CH$_2$—, —NH—, or —O—. In certain embodiments, X is —O—.

In the compounds of formula (I-A), Y is —O—, —S—, or —C(R$^m$)(R$^n$)—, where R$^m$ and R$^n$ are as described above. In some embodiments, R$^m$ is hydrogen, fluoro, —NH$_2$, —NH (C$_{1-4}$ aliphatic), —N(C$_{1-4}$ aliphatic)$_2$, or C$_{1-4}$ aliphatic. In some embodiments, Y is —O— or —CH$_2$.

In the compounds of formula (I-A), $R^{3a}$ is selected from the group consisting of hydrogen, fluoro, —CN, —N$_3$—, hydroxy, —OR$^{21}$, —NH$_2$, —NH(R$^{21}$), —N(H)CO$_2$R$^{21}$, —N(H)C(O)R$^{21}$, —C(O)R$^{21}$, —CON(H)R$^{21}$, —OC(O)N (H)R$^{21}$, —OC(O)R$^{21}$, —OC(O)OR$^{21}$, —C$_{1-4}$ fluoroaliphatic, or a —C$_{1-4}$ aliphatic optionally substituted with one or two substituents independently selected from the group consisting of —OR$^{5x}$, —N(R$^{4x}$)(R$^{4y}$), —CO$_2$R$^{5x}$, or —C(O)N(R$^{4x}$)(R$^{4y}$). In some embodiments R$^{3a}$ is selected from the group consisting of hydrogen, hydroxy, —NH$_2$, C$_{1-4}$ aliphatic, fluoro, —CN, C$_{1-4}$ fluoroaliphatic, —OR$^{21}$, —NH(R$^{21}$), —N(H)CO$_2$R$^{21}$, —N(H)C(O)R$^{21}$, —C(O)NHR$^{21}$, —C(O)R$^{21}$, —OC(O)NHR$^{21}$, —OC(O)R$^{21}$, and —OC(O)OR$^{21}$. In some embodiments, R$^{3a}$ is selected from the group consisting of hydrogen, —OH, —OCH$_3$, C$_{1-4}$ aliphatic, C$_{1-4}$ fluoroaliphatic, and fluoro. In certain embodiments, R$^{3a}$ is selected from the group consisting of hydrogen, —OH, —OCH$_3$, —CH$_3$, and fluoro. In certain particular embodiments, R$^{3a}$ is —OH.

In the compounds of formula (I-A), R$^{3c}$ is selected from the group consisting of hydrogen, fluoro, —CN, —N$_3$, hydroxy, —OR$^{21}$, —NH$_2$, —NH(R$^{21}$), —N(H)CO$_2$R$^{21}$, —N(H)C(O)R$^{21}$, —CON(H)R$^{21}$, —OC(O)N(H)R$^{21}$, —OC(O)R$^{21}$, —OC(O)OR$^{21}$, —C$_{1-4}$ fluoroaliphatic, or a —C$_{1-4}$ aliphatic optionally substituted with one or two substituents independently selected from the group consisting of —OR$^{5x}$, —N(R$^{4x}$)(R$^{4y}$), —CO$_2$R$^{5x}$, or —C(O)N(R$^{4x}$)(R$^{4y}$). In some embodiments, R$^{3c}$ is selected from the group consisting of hydrogen, hydroxy, —NH$_2$, C$_{1-4}$ aliphatic, fluoro, —CN, —C$_{1-4}$ fluoroaliphatic, —OR$^{21}$, —NH(R$^{21}$), —N(H)CO$_2$R$^{21}$, —N(H)C(O)R$^{21}$, —CON(H)R$^{21}$, —OC(O)N(H)R$^{21}$, —OC(O)R$^{21}$, and —OC(O)OR$^{21}$. In certain embodiments, R$^{3c}$ is hydrogen, —OH, —OCF$_3$, or fluoro. In certain particular embodiments, R$^{3c}$ is hydrogen or —OH.

In the compounds of formula (I-A), R$^{3b}$ and R$^{3d}$ are each independently selected from the group consisting of hydrogen, fluoro, C$_{1-4}$ aliphatic, and C$_{1-4}$ fluoroaliphatic. In some embodiments, one of R$^{3b}$ and R$^{3d}$ is C$_{1-4}$ aliphatic and the other is hydrogen. In some embodiments, R$^{3b}$ and R$^{3d}$ are each hydrogen.

In one embodiment, R$^{3a}$ and R$^{3c}$ are each —OH, and R$^{3b}$ and R$^{3d}$ are each hydrogen. In another embodiment, R$^{3a}$ is —OH, and each of R$^{3b}$, R$^{3c}$, and R$^{3d}$ is hydrogen. In another embodiment, R$^{3a}$ is —OH, R$^{3c}$ is fluoro or —OCH$_3$, and R$^{3b}$ and R$^{3d}$ are each hydrogen. In another embodiment, R$^{3a}$ is —OH, R$^{3b}$ is —CH$_3$, R$^{3c}$ is hydrogen or —OH, and R$^{3d}$ is hydrogen. In another embodiment, R$^{3a}$ and R$^{3c}$ together form a bond, and R$^{3b}$ and R$^{3d}$ are each hydrogen.

In the compounds of formula (I-A), each R$^4$ is independently hydrogen, fluoro, C$_{1-4}$ aliphatic, or C$_{1-4}$ fluoroaliphatic; or two R$^4$, taken together with the carbon atom to which they are attached, form a 3- to 6-membered carbocyclic ring; or one R$^4$, taken together with R$^5$ and the intervening carbon atoms, forms a 3- to 6-membered spirocyclic ring; or two R$^4$ together form =O. In some embodiments, each R$^4$ independently is hydrogen or C$_{1-4}$ aliphatic. In some such embodiments, each R$^4$ independently is hydrogen or —CH$_3$. In certain embodiments, one R$^4$ is hydrogen or —CH$_3$, and the other R$^4$ is hydrogen. In certain particular embodiments, each R$^4$ is hydrogen.

In the compounds of formula (I-A), R$^5$ is hydrogen or C$_{1-4}$ aliphatic; or R$^5$, taken together with one R$^4$ and the intervening carbon atoms, forms a 3- to 6-membered spirocyclic ring. In some embodiments, R$^5$ is hydrogen or C$_{-14}$ aliphatic. In some such embodiments, R$^5$ is hydrogen or —CH$_3$. In certain embodiments, R$^5$ is hydrogen.

In the compounds of formula (I-A), R$^{5'}$ is hydrogen or C$_{1-4}$ aliphatic. In some embodiments, R$^{5'}$ is hydrogen or C$_{1-4}$ aliphatic. In some such embodiments, R$^{5'}$ is hydrogen or —CH$_3$. In certain embodiments, R$^{5'}$ is hydrogen.

In the compounds of formula (I-A), Ring A is selected from the group consisting of:

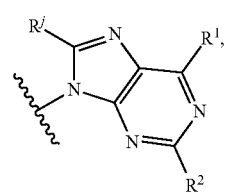
A-i

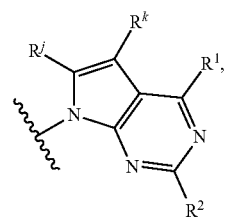
A-ii

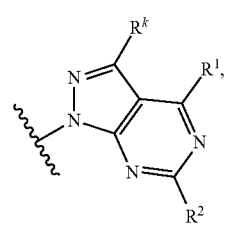
A-iii

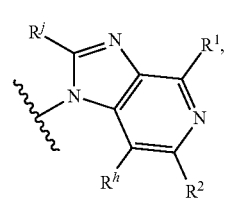
A-iv

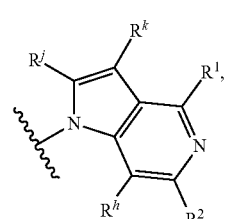
A-v

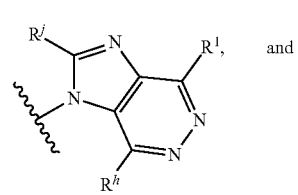
A-vi and

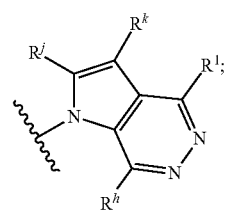
A-vii where R$^1$, R$^2$, R$^h$, R$^j$ and R$^k$ are as defined above and as further defined below.

In the compounds of formula (I-A), R$^2$ is hydrogen, chloro, bromo, fluoro, iodo, —N(R$^6$)$_2$, —CN, —O—(C$_{1-4}$ aliphatic), —OH, —SR⁶, or an optionally substituted C₁₋₄ aliphatic group. In some embodiments, R² is hydrogen, chloro, or —N(R⁶)₂. In certain embodiments, R² is hydrogen or chloro. In certain particular embodiments, R² is hydrogen.

In some embodiments, the compound of formula (I-A) is characterized by at least one of the following features:
(a) X is —O—;
(b) Y is —O— or —CH₂—;
(c) R³ᵃ is —OH;
(d) R³ᵇ and R³ᵈ are each independently hydrogen or C₁₋₄ aliphatic;
(e) R³ᶜ is hydrogen, fluoro, or —OR⁵;
(f) R⁵ and R⁵' are each hydrogen;
(g) each R⁴ is hydrogen;
(h) each R² is hydrogen;
(i) Rʰ is hydrogen;
(j) Rʲ is hydrogen; and
(k) Rᵏ is hydrogen, halo, or C₁₋₄ aliphatic.

One embodiment of the invention relates to a subgenus of the compounds of formula (I-A) represented by formula (I):

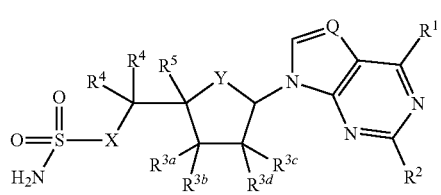

(I)

or a pharmaceutically acceptable salt thereof, wherein Q is =N— or =CH—, and the variables X, Y, R¹, R², R³ᵃ, R³ᵇ, R³ᶜ, R³ᵈ, R⁴, and R⁵ have the values and preferred values described above for formula (I-A).

The invention also relates to a compound of formula (I), or a pharmaceutically acceptable salt thereof, wherein:
X is —CH₂—, —NH—, or —O—;
Y is —O—, or —CH₂—;
Q is =N— or =CH—;
R¹ is chloro, bromo, fluoro, iodo, —NPR⁷R⁸, —R⁹, —S—R¹⁰, or —O—R¹¹;
R² is hydrogen, chloro, bromo, fluoro, iodo, —N(R⁶)₂, —CN, —O—(C₁₋₄ aliphatic), —OH, —SR⁶, or an optionally substituted C₁₋₄ aliphatic group;
R³ᵃ is selected from the group consisting of hydrogen, hydroxy, —NH₂, —C₁₋₄ aliphatic, fluoro, —CN, —C₁₋₄ fluoroaliphatic, —OR²¹, —NH(R²¹), —N(H)CO₂R²¹, —N(H)C(O)R²¹, —CON(O)R²¹, —OC(O)N(H)R²¹, —OC(O)R²¹, and —OC(O)OR²¹;
R³ᵇ is selected from the group consisting of hydrogen, fluoro, C₁₋₄ aliphatic, and C₁₋₄ fluoroaliphatic;
R³ᶜ is selected from the group consisting of hydrogen, hydroxy, —NH₂, —C₁₋₄ aliphatic, fluoro, —CN, —C₁₋₄ fluoroaliphatic, —OR²¹, —NH(R²¹), —N(H)CO₂R²¹, —N(H)C(O)R²¹, —CON(H)R²¹, —OC(O)N(H)R²¹, —OC(O)R²¹, and —OC(O)OR²¹;
R³ᵈ is selected from the group consisting of hydrogen, fluoro, C₁₋₄ aliphatic, and C₁₋₄ fluoroaliphatic;
each R⁴ is independently hydrogen or C₁₋₄ aliphatic; or two R⁴, taken together with the carbon atom to which they are attached, form a 3- to 6-membered carbocyclic ring; or one R⁴, taken together with R⁵ and the intervening carbon atoms, forms a 3- to 6-membered spirocyclic ring;

R⁵ is hydrogen, or C₁₋₄ aliphatic; or R⁵, taken together with one R⁴ and the intervening carbon atoms, forms a 3- to 6-membered spirocyclic ring;
each R⁶ is independently hydrogen or C₁₋₄ aliphatic;
R⁷ is an optionally substituted C₁₋₁₀ aliphatic, aryl, heteroaryl, or heterocyclyl group;
R⁸ is hydrogen or C₁₋₄ aliphatic;
R⁹ is —V—Z—R¹²ᵃ, —V—Z—R¹²ᵇ, —R¹²ᶜ, or an optionally substituted aliphatic, aryl, heterocyclyl, or heteroaryl group, wherein the heteroaryl group is attached at a carbon atom;
R¹⁰ is an optionally substituted C₂₋₁₀ aliphatic, aryl, heteroaryl, or heterocyclyl;
R¹¹ is an optionally substituted C₂₋₁₀ aliphatic, aryl, heteroaryl, or heterocyclyl;
V is —S(O)₂—, —S(O)—, —C(O)O—, —C(O)—, —C(NR¹³)=N—, —C(=N(R¹³))—N(R¹³)—, —C(OR¹¹)=N—, —CON(R¹³)—, —N(R¹³)C(O)—, —N(R¹³)C(O)N(R¹³)—, —N(R¹³)S(O)₂—, —N(R¹³)SO₂—N(R¹³)—, —N(R¹³)CO₂—, —SO₂N(R¹³)—, —OC(O)—, —OC(O)O—, —OC(O)N(R¹³)—, —N(R¹³)—N(R¹³)—;
Z is an optionally substituted C₁₋₆ alkylene chain, wherein the alkylene chain is optionally interrupted by —C(R¹³)=C(R¹³)—, —C≡C—, —O—, —S—, —N(R¹³)—, —N(R¹³)CO—, —N(R¹³)CO₂—, —C(O)N(R¹³)—, —C(O)—, —C(O)—C(O)—, —CO₂—, —OC(O)—, —OC(O)O—, —N(R¹³)C(O)N(R¹³)—, —N(R¹³)N(R¹³)—, —OC(O)N(R¹³)—, —S(O)—, —S(O)₂—, —N(R¹³)S(O)₂—, —S(O)₂N(R¹³)—;
R¹²ᵃ is an optionally substituted aryl, heteroaryl, heterocyclyl, or cycloaliphatic group;
R¹²ᵇ is halo, —NO₂, —CN, —OR¹⁴, —SR¹⁵, —N(R¹⁶)₂, —N(R¹⁶)C(O)R¹⁵, —N(R¹⁶)C(O)N(R¹⁶)₂, —N(R¹⁶)CO₂R¹⁴, —O—CO₂—R¹⁴, —OC(O)N(R¹⁶)₂, —OC(O)R¹⁴, —N(R¹⁶)—N(R¹⁶)₂, —N(R¹⁶)S(O)₂R¹⁵, or —N(R¹⁶)SO₂—N(R¹⁶)₂, —C(R¹⁴)=C(R¹⁴)₂, —C≡C—R¹⁴, —S(O)R¹⁵, —SO₂R¹⁵, —SO₂—N(R¹⁶)₂, —C(R¹⁴)=N—OR¹⁴, —CO₂R¹⁴, —C(O)—C(O)R¹⁴, —C(O)R¹⁴, —C(O)N(R¹⁶)₂, —C(=NR¹⁶)—N(R¹⁶)₂, or —C(=NR¹⁶)N—OR¹⁴;
R¹²ᶜ is —NO₂, —CN, —S(O)R¹⁵, —SO₂R¹⁵, —SO₂—N(R¹⁶)₂, —C(R¹⁴)=N—OR¹⁴, —N(R¹⁶)C(O)R¹⁵, —N(R¹⁶)C(O)N(R¹⁶)₂, —O—CO₂—R¹⁴, —OC(O)N(R¹⁶)₂, —OC(O)R¹⁴, —CO₂R¹⁴, —C(O)—C(O)R¹⁴, —C(O)R¹⁴, —C(O)N(R¹⁶)₂, —C(=NR¹⁶)—N(R¹⁶)₂, —C(=NR¹⁶)—OR¹⁴, —N(R¹⁶)—N(R¹⁶)₂, —N(R¹⁶)S(O)₂R¹⁵, or —N(R¹⁶)SO₂—N(R¹⁶)₂;
each R¹³ is independently hydrogen, or an optionally substituted aliphatic, aryl, heteroaryl, or heterocyclyl group;
each R¹⁴ independently is hydrogen, or an optionally substituted aliphatic, aryl, heteroaryl, or heterocyclyl group;
each R¹⁵ independently is an optionally substituted aliphatic, or aryl group;
each R¹⁶ independently is an optionally substituted aliphatic, aryl, heteroaryl, or heterocyclyl group; or two R¹⁶ on the same nitrogen atom, taken together with the nitrogen atom, form an optionally substituted five to eight membered heterocyclyl ring having, in addition to the nitrogen atom, zero to two additional ring heteroatoms selected from the group consisting of N, O, and S; and
each R²¹ independently is an optionally substituted C₁₋₁₀ aliphatic, aryl, heteroaryl, or heterocyclyl group.

Various particular embodiments of the invention relate to subgenera of the compounds of formula (I-A), represented by formulae (II-A), (II-B), (III-A), (III-B), (IV-A), and (IV-B):

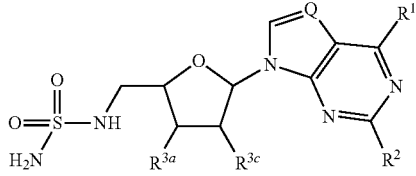
(II-A)

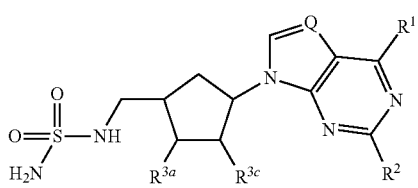
(II-B)

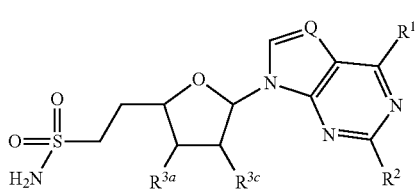
(III-A)

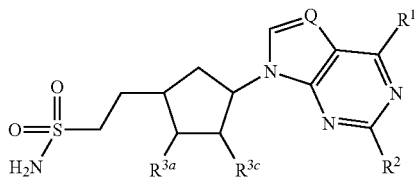
(III-B)

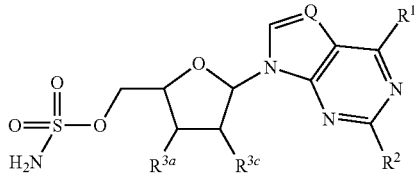
(IV-A)

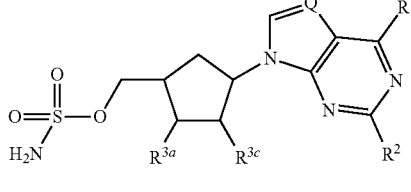
(IV-B)

or a pharmaceutically acceptable salt thereof, wherein the variables Q, $R^1$, $R^2$, $R^{3a}$, and $R^{3c}$ have the values and preferred values described herein for formulae (I) and (I-A).

Another embodiment of the invention relates to a compound of formula (I) or (I-A), wherein $R^1$ is an optionally substituted aryl, heteroaryl, or heterocyclyl group. In some such embodiments, the compound is characterized by formula (V):

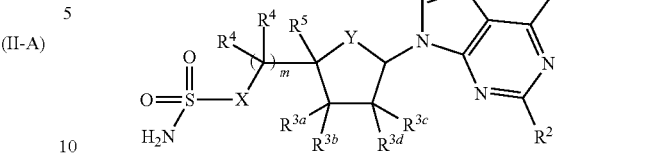
(V)

or a pharmaceutically acceptable salt thereof, wherein:

Ring B is an optionally substituted 5- or 6-membered aryl or heteroaryl ring having zero to three ring nitrogen atoms and optionally one additional ring heteroatom selected from oxygen and sulfur. In some embodiments, two adjacent substituents on Ring B, taken together with the intervening ring atoms, form an optionally substituted fused 5- or 6-membered aromatic or non-aromatic ring having zero to three ring heteroatoms selected from the group consisting of O, N, and S; and the variables Q, X, Y, $R^j$, $R^2$, $R^{3a}$, $R^{3b}$, $R^{3c}$, $R^{3d}$, $R^4$, $R^5$, and m have the values and preferred values described above for formulae (1) and (I-A).

In some embodiments, Ring B is an optionally substituted furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyridazinyl, pyrimidinyl, pyrazinyl, or triazinyl, wherein one ring nitrogen atom in Ring B optionally is oxidized. In certain particular embodiments, Ring B is an optionally substituted phenyl, imidazolyl, or triazolyl.

Substitutable ring carbon atoms in Ring B preferably are substituted with zero to two substituents independently selected from the group consisting of $C_{1-6}$ aliphatic, $C_{1-6}$ fluoroaliphatic, halo, $—R^{a17}$, $—R^{b17}$, $—Z^{17}—R^{a17}$, and $—Z^{17}—R^{b17}$, or two adjacent substituents on Ring B, taken together with the intervening ring atoms, form an optionally substituted fused 5- or 6-membered aromatic or non-aromatic ring having 0-3 ring heteroatoms selected from the group consisting of O, N, and S. The variables $Z^{17}$, $R^{a17}$, and $R^{b17}$ have the values described below.

$Z^{17}$ is an optionally substituted $C_{1-6}$ alkylene chain, wherein the alkylene chain optionally is interrupted by $—C(R^{14})=C(R^{14})—$, $—C≡C—$, $—O—$, $—S—$, $—S(O)—$, $—S(O)_2—$, $—SO_2N(R^{15})—$, $—N(R^{15})—$, $—N(R^{15})C(O)—$, $—NR^{15}C(O)N(R^{15})—$, $—N(R^{15})CO_2—$, $—N(R^{15})SO_2—$, $—C(O)N(R^{15})—$, $—C(O)—$, $—CO_2—$, $—OC(O)—$, $—OC(O)O—$, or $—OC(O)N(R^{15})—$, and wherein $Z^{17}$ or a portion thereof optionally forms part of a 37 membered ring. In some embodiments, $Z^{17}$ is a $C_{1-6}$, $C_{1-4}$, or $C_{2-4}$ alkylene chain optionally substituted with one or two $R^x$ or $R^y$, wherein $R^x$ and $R^y$ have the values and preferred values described above.

Each $R^{a17}$ independently is an optionally substituted aryl, heteroaryl, heterocyclyl, or cycloaliphatic ring.

Each $R^{b17}$ independently is $—NO_2$, $—CN$, $—C(R^{14})=C(R^{14})_2$, $—C≡C—R^{14}$, $—OR^{14}$, $—OR^{14}$, $—SR^{15}$, $—S(O)R^{15}$, $—SO_2R^{15}$, $—SO_2N(R^{16})_2$, $—N(R^{16})_2$, $—NR^{16}C(O)R^{14}$, $—NR^{16}C(O)N(R^{16})_2$, $—NR^{16}CO_2R^{14}$, $—O—CO_2R^{14}$, $—OC(O)N(R^{16})_2$, $—O—C(O)R^{14}$, $—CO_2R^{14}$, $—C(O)R^{14}$, $—C(O)N(R^{16})_2$, $—C(O)N(R^{16})C(=NR^{16})—N(R^{16})_2$, $—C(=NR^{16})—N(R^{16})_2$, $—C(=NR^{16})—OR^{14}$, $—C(R^{14})=N—OR^{14}$, $—N(R^{16})C(=NR^{16})—N(R^{16})_2$, $—N(R^{16})$ $SO_2R^{15}$, $-N(R^{16})SO_2N(R^{16})_2$. In some embodiments, each $R^{b17}$ independently is $-CN$, $-N(R^4)_2$, $-NR^4C(O)R^5$, $-NR^4-C(O)N(R^4)_2$, $-NR^4CO_2R^6$, $-C(O)N(R^4)_2$, $-CO_2R^5$, or $-OR^5$.

In some embodiments, the substitutable ring carbon atoms in Ring B are substituted with zero, one, or two substituents independently selected from the group consisting of halo, $-OH$, $-O(C_{1-3}$ alkyl), $-CN$, $-N(R^4)_2$, $-C(O)(C_{1-3}$ alkyl), $-CO_2H$, $-CO_2(C_{1-3}$ alkyl), $-C(O)NH_2$, $-C(O)NH(C_{1-3}$ alkyl), $-C_{1-3}$ aliphatic, $-C_{1-3}$ fluoroaliphatic, $-O(C_{1-3}$ fluoroaliphatic), optionally substituted aryl, and optionally substituted heteroaryl. Preferred halo groups in Ring B substitutions include F and Cl.

Another embodiment of the invention relates to a compound of formula (I) or (I-A), wherein $R^1$ is $C_{1-10}$ aliphatic, $-Z-R^{12a}$, $-Z-R^{12b}$, $-L-Z-R^{12a}$, $-L-Z-R^{12b}$, $-L-R^{12a}$ or $-L-R^{12d}$; where L is $-C(R^{13})=C(R^{13})-$ or $-C\equiv C-$; $R^{12d}$ is $-NO_2$, $-CN$, $-S(O)R^{15}$, $-SO_2R^{15}$, $-SO_2-N(R^{16})_2$, $-CO_2R^{14}$, $-C(O)R^{14}$, or $-C(O)N(R^{16})_2$; and the variables Z, $R^{12a}$, $R^{12b}$ and $R^{13}$ are as defined above for formula (I-A). In some such embodiments, $R^1$ is $-L-Z-R^{12a}$, $-L-Z-R^{12b}$, $-L-R^{12a}$ or $-L-R^{12d}$, where L is $-C\equiv C-$.

Another embodiment of the invention relates to a compound of formula (I) or (I-A), wherein $R^1$ is $-V-Z-R^{12a}$, $-V-Z-R^{12b}$, or $-R^{12c}$. The invention also relates to a compound of formula (I) or (I-A), wherein $R^1$ is $-Z-V-R^{12a}$ or $-V-R^{12a}$. The variables V, Z, $R^{12a}$, $R^{12b}$, and $R^{12c}$ are as defined above for formulae (I) and (I-A).

Preferably, V is selected from the group consisting of $-S(O)_2-$, $-C(O)O-$, $-C(O)-$, $-CON(R^{13})-$, $-N(R^{13})C(O)-$, $-N(R^{13})C(O)N(R^{13})-$, $-N(R^{13})S(O)_2-$, $-N(R^{13})SO_2-N(R^{13})-$, $-N(R^{13})CO_2-$, and $-SO_2N(R^{13})-$. More preferably, V is selected from the group consisting of $-CON(R^{13})-$, $-N(R^{13})C(O)-$, $-N(R^{13})C(O)N(R^{13})-$, $-N(R^{13})S(O)_2-$, $-N(R^{13})SO_2-N(R^{13})-$, and $-N(R^{13})CO_2$. In certain particular embodiments, V is $-N(R^{13})C(O)-$ or $-N(R^{13})C(O)N(R^{13})-$.

Preferably, Z is a $C_{1-6}$ alkylene chain optionally substituted with one to four substituents. Suitable substituents for Z include those described generally above for substituted aliphatic groups. In preferred embodiments, Z is optionally substituted with one or two $R^x$ or $R^y$, where each $R^x$ independently is selected from the group consisting of -halo, $-OH$, $-O(C_{1-4}$ alkyl), $-O(C_{1-4}$ haloalkyl), $-CN$, $-N(R^4)_2$, $-C(O)(C_{1-4}$alkyl), $-CO_2H$, $-CO_2(C_{1-4}$alkyl), $-C(O)NH_2$, $-C(O)NH(C_{1-4}$alkyl), or optionally substituted aryl; and each $R^y$ independently is a $C_{1-3}$ aliphatic optionally substituted with $R^x$ or an optionally substituted aryl or heteroaryl group; or two $R^y$ on the same carbon atom, taken together with the carbon atom to which they are attached form a 3- to 6-membered cycloaliphatic ring. More preferably, Z is a $C_{1-4}$ alkylene chain, optionally substituted with $C_{1-3}$ aliphatic, $C_{1-3}$ fluoroaliphatic, $-F$, $-OH$, $-O(C_{1-3}$alkyl), $-CO_2H$, $-CO_2(C_{1-3}$alkyl), $-C(O)NH_2$, $-C(O)NH(C_{1-4}$alkyl), $-CN$, $-N(R)_2$, or $-C(O)(C_{1-3}$alkyl).

Preferably, $R^{12c}$ is selected from the group consisting of $-CON(R^{16})_2$, $-N(R^{16})C(O)R^{15}$, $-N(R^{16})C(O)N(R^{16})_2$, $-N(R^{16})S(O)_2R^{15}$, $-N(R^{16})SO_2-N(R^{16})_2$, and $-N(R^{16})CO_2R^{15}$. In certain particular embodiments, $R^{12c}$ is $-N(R^{16})C(O)R^{15}$, $-N(R^{16})C(O)N(R^{16})_2$, Another embodiment of the invention relates to a compound of formula (VI):

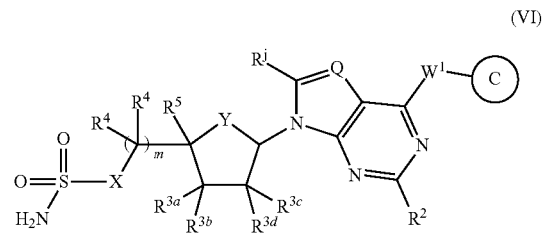

(VI)

or a pharmaceutically acceptable salt thereof, wherein:
$W^1$ is $-Z-$, $-L-$, $-V-$, $-V-Z-$, or $-Z-V-$;
Ring C is an optionally substituted 5- or 6-membered aryl, cycloaliphatic, heteroaryl, or heterocyclyl ring having zero to three ring nitrogen atoms and optionally one additional ring heteroatom selected from oxygen and sulfur; and
the variables Q, X, Y, L, V, Z, $R^j$, $R^2$, $R^{3a}$, $R^{3b}$, $R^{3c}$, $R^{3d}$, $R^4$, $R^5$, and m have the values and preferred values described above for formulae (I), (I-A), and (V).

In some embodiments, $W^1$ is $-Z-$ or $-L-$.

In some embodiments, two adjacent substituents on Ring C, taken together with the intervening ring atoms, form an optionally substituted fused 5- or 6-membered aromatic or non-aromatic ring having zero to three ring heteroatoms selected from the group consisting of O, N, and S.

In some embodiments, Ring C is an optionally substituted mono- or bicyclic aryl, heteroaryl, heterocyclyl or cycloaliphatic group. Exemplary Ring C mono- or bicyclic aryl, heteroaryl, heterocyclyl or cycloaliphatic rings include optionally substituted furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, indolyl, isoindolyl, indazolyl, benzimidazolyl, benzthiazolyl, benzothienyl, benzofuranyl, purinyl, quinolyl, isoquinolyl, cinnolinyl, phthalazinyl, quinazolinyl, quinoxalinyl, naphthyridinyl, pteridinyl, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, quinuclidinyl, tetrahydroquinolinyl, tetrahydroisoquinolinyl, indanyl, phenanthridinyl, tetrahydronaphthyl, indolinyl, benzodioxanyl, benzodioxolyl cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl groups. In certain particular embodiments, Ring C is an optionally substituted phenyl ring or an optionally substituted $C_{3-6}$ cycloaliphatic ring.

Suitable substituents on Ring C include those generally described above for substituted aryl, heteroaryl, heterocyclyl and cycloaliphatic groups. Substitutable ring carbon atoms in Ring C preferably are substituted with zero to four, preferably zero to two substituents independently selected from the group consisting of $C_{1-6}$ aliphatic, $C_{1-6}$ fluoroaliphatic, halo, $-R^{a12}$, $-R^{b12}$, $-Z^{12}-R^{a12}$, and $-Z^{12}-R^{b12}$. The variables $Z^{12}$, $R^{a12}$, and $R^{b12}$ have the values described below.

$Z^{12}$ is an optionally substituted $C_{1-6}$ alkylene chain, wherein the alkylene chain optionally is interrupted by $-C(R^{14})=C(R^{14})-$, $-C\equiv C-$, $-O-$, $-S-$, $-S(O)-$, $-S(O)_2-$, $-SO_2N(R^{15})-$, $-N(R^{15})-$, $-N(R^{15})C(O)-$, $-NR^{15}C(O)N(R^{15})-$, $-N(R^{15})CO_2-$, $-N(R^{15})SO_2-$, $-C(O)N(R^{15})-$, $-C(O)-$, $-CO_2-$, $-OC(O)-$, $-OC(O)O-$, or $-OC(O)N(R^{15})-$, and wherein $Z^{12}$ or a portion thereof optionally forms part of a 3-7 membered ring. In some embodiments, $Z^{12}$ is a $C_{1-6}$ or $C_{1-4}$ alkylene chain optionally substituted with one or two $R^x$ or $R^y$, wherein $R^x$ and $R^y$ have the values and preferred values described above.

Each $R^{a12}$ independently is an optionally substituted aryl, heteroaryl, heterocyclyl, or cycloaliphatic ring.

Each $R^{b12}$ independently is —$NO_2$, —CN, —$C(R^{14})$=C$(R^{14})_2$, —C≡C—$R^{14}$, —$OR^{14}$, —$SR^{15}$, —$S(O)R^{15}$, —$SO_2R^{15}$, —$SO_2N(R^{16})_2$, —$N(R^{16})_2$, —$NR^{16}C(O)R^{14}$, —$NR^{16}C(O)N(R^{16})_2$, —$NR^{16}CO_2R^{14}$, —O—$CO_2R^{14}$, —$OC(O)N(R^{16})_2$, —O—$C(O)R^{14}$, —$CO_2R^{14}$, —$C(O)R^{14}$, —$C(O)N(R^{16})_2$, —$C(O)N(R^{16})C(=NR^{16})$—$N(R^{16})_2$, —$C(=NR^{16})$—$N(R^{16})_2$, —$C(=NR^{16})$—$OR^{14}$, —$C(R^{14})$=N—$OR^{14}$, —$N(R^{16})C(=NR^{16})$—$N(R^{16})_2$, —$N(R^{16})SO_2R^{15}$, —$N(R^{16})SO_2N(R^{16})_2$. In some embodiments, each $R^{b12}$ independently is —CN, —$N(R^4)_2$, —$NR^4C(O)R^5$, —$NR^4$—$C(O)N(R^4)_2$, —$NR^4CO_2R^6$, —$C(O)N(R^4)_2$, —$CO_2R^5$, or —$OR^5$.

In some embodiments, the substitutable ring carbon atoms in Ring C are substituted with zero, one, or two substituents independently selected from the group consisting of halo, —OH, —$O(C_{1-3}$ alkyl), —CN, —$N(R^4)_2$, —$C(O)(C_{1-3}$ alkyl), —$CO_2H$, —$CO_2(C_{1-3}$ alkyl), —$C(O)NH_2$, —$C(O)NH(C_{1-3}$ alkyl), —$C_{1-3}$ aliphatic, —$C_{1-3}$ fluoroaliphatic, —$O(C_{1-3}$ fluoroaliphatic), optionally substituted aryl, and optionally substitued heteroaryl. Preferred halo substituents on Ring C include F and Cl.

In another embodiment, the invention relates to a compound of formula (I) or (I-A), wherein $R^1$ is —$NR^7R^8$, and $R^7$ is an optionally substituted aryl, heteroaryl, heterocyclyl or cycloaliphatic group. In more particular embodiments, $R^7$ is an optionally substituted 5- to 6-membered monocyclic or 8- to 10-membered bicyclic aryl or heteroaryl ring, or a 3- to 8-membered monocyclic or 6- to 10-membered bicyclic heterocyclyl or cycloaliphatic ring. $R^8$ is hydrogen or $C_{1-4}$ aliphatic, and preferably is hydrogen.

One embodiment of the invention relates to a compound of formula (VII):

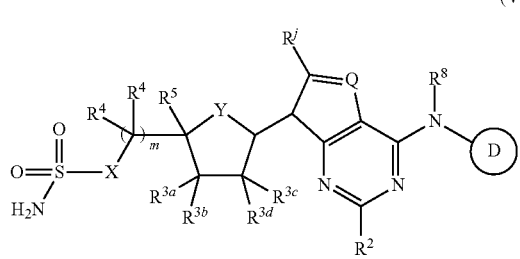

(VII)

or a pharmaceutically acceptable salt thereof, wherein:
$R^8$ is hydrogen or $C_{1-4}$ aliphatic;
Ring D is an optionally substituted aryl, heteroaryl, heterocyclyl, or cycloaliphatic ring; and
the variables X, Y, $R^j$, $R^2$, $R^{3a}$, $R^{3b}$, $R^{3c}$, $R^{3d}$, $R^4$, $R^5$, and m have the values and preferred values described above for formulae (I) and (I-A).

In some embodiments, Ring D is a mono- or bicyclic aryl, heteroaryl, heterocyclyl or cycloaliphatic ring. In some such embodiments, Ring D selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, indolyl, isoindolyl, indazolyl, benzimidazolyl, benzthiazolyl, benzothienyl, benzofuranyl, purinyl, quinolyl, isoquinolyl, cinnolinyl, phthalazinyl, quinazolinyl, quinoxalinyl, naphthyridinyl, pteridinyl, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, quinuclidinyl, tetrahydroquinolinyl, tetrahydroisoquinolinyl, indanyl, phenanthridinyl, tetrahydronaphthyl, indolinyl, benzodioxanyl, benzodioxolyl, chromanyl, cyclopropyl, cyclobutyl, cyclopentyl, cyclopentenyl, cyclohexyl, cyclohexenyl, cycloheptyl, cycloheptenyl, cyclooctyl, cyclooctenyl, cyclooctadienyl, bicycloheptanyl and bicyclooctanyl.

Suitable substituents on Ring D include those generally described above for substituted aryl, heteroaryl, heterocyclyl and cycloaliphatic groups. Each substitutable saturated ring carbon atom preferably is unsubstituted or substituted with =O, =S, =$C(R^{14})_2$, =N—$N(R^{16})_2$, =N—$OR^{14}$, =N—$NHC(O)R^{14}$, =N—$NHCO_2R^{15}$, =N—$NHSO_2R^{15}$, =N—$R^{14}$, or —$R^d$. Each substitutable unsaturated ring carbon atom preferably is unsubstituted or substituted with —$R^d$. Ring D may be unsubstituted or may be substituted on any one or more of its component rings, wherein the substituents may be the same or different.

Each $R^d$ independently is —$NO_2$, —CN, —$C(R^{14})$=C$(R^{14})_2$, —C≡C—$R^{14}$, —$OR^{14}$, —$SR^{15}$, —$S(O)R^{15}$, —$SO_2R^{15}$, —$SO_2N(R^{16})_2$, —$N(R^{16})_2$, —$NR^{16}C(O)R^{14}$, —$NR^{16}C(O)N(R^{16})_2$, —$NR^{16}CO_2R^{14}$, —O—$CO_2R^{14}$, —$OC(O)N(R^{16})_2$, —O—$C(O)R^{14}$, —$CO_2R^{14}$, —$C(O)R^{14}$, —$C(O)N(R^{16})_2$, —$C(O)N(R^{16})C(=NR^{16})$—$N(R^{16})_2$, —$C(=NR^{16})$—$N(R^{16})_2$, —$C(=NR^{16})$—$OR^{14}$, —$C(R^{14})$=N—$OR^{14}$, —$N(R^{16})C(=NR^{16})$—$N(R^{16})_2$, —$N(R^{16})SO_2R^{15}$, —$N(R^{16})SO_2N(R^{16})_2$, or an optionally substituted aliphatic, aryl, heteroaryl, or heterocyclyl group.

In some embodiments, each $R^d$ independently is selected from the group consisting of $C_{1-6}$ aliphatic, $C_{1-6}$ fluoroaliphatic, halo, —$R^{a7}$, —$R^{b7}$, —$Z^7$—$R^{a7}$, and —$Z^7$—$R^{b7}$. The variables $Z^7$, $R^{a7}$, and $R^{b7}$ have the values described below.

$Z^7$ is an optionally substituted $C_{1-6}$ alkylene chain, wherein the alkylene chain optionally is interrupted by —$C(R^{14})$=C$(R^{14})$—, —C≡C—, —O—, —S—, —S(O)—, —S(O)$_2$—, —$SO_2N(R^{15})$—, —$N(R^{15})$—, —$N(R^{15})C(O)$—, —$NR^{15}C(O)N(R^{15})$—, —$N(R^{15})CO_2$—, —$N(R^{15})SO_2$—, —$C(O)N(R^{15})$—, —$C(O)$—, —$CO_2$—, —$OC(O)$—, —$OC(O)O$, or —$OC(O)N(R^{15})$—, and wherein $Z^7$ or a portion thereof optionally forms part of a 37 membered ring. In some embodiments, $Z^7$ is a $C_{1-6}$ or $C_{1-4}$ alkylene chain optionally substituted with one or two $R^x$ or $R^y$, wherein $R^x$ and $R^y$ have the values and preferred values described above.

Each $R^{a7}$ independently is an optionally substituted aryl, heteroaryl, heterocyclyl, or cycloaliphatic ring.

Each $R^{b7}$ independently is —$NO_2$, —CN, —$C(R^{14})$=C$(R^{14})_2$—C≡C—$R^{14}$, —$OR^{14}$, —$SR^{15}$, —$S(O)R^{15}$, —$SO_2R^{15}$, —$SO_2N(R^{16})_2$, —$N(R^{16})_2$, —$NR^{16}C(O)R^{14}$, —$NR^{16}C(O)N(R^{16})_2$, —$NR^{16}CO_2R^{14}$, —O—$CO_2R^{14}$, —$OC(O)N(R^{16})_2$, —O—$C(O)R^{14}$, —$CO_2R^{14}$, —$C(O)R^{14}$, —$C(O)N(R^{16})_2$, —$C(O)N(R^{16})C(=NR^{16})$—$N(R^{16})_2$, —$C(=NR^{16})$—$N(R^{16})_2$, —$C(=NR^{16})$—$OR^{14}$, —$C(R^{14})$=N—$OR^{14}$, —$N(R^{16})C(=NR^{16})$—$N(R^{16})_2$, —$N(R^{16})SO_2R^{15}$, —$N(R^{16})SO_2N(R^{16})_2$. In some embodiments, each $R^{b7}$ independently is —CN, —$N(R^4)_2$, —$NR^4C(O)R^5$, —$NR^4$—$C(O)N(R^4)_2$, —$NR^4CO_2R^6$, —$C(O)N(R^4)_2$, —$CO_2R^5$, or —$OR^5$.

In some embodiments, the substitutable ring carbon atoms in Ring D are substituted with zero, one, or two substituents independently selected from the group consisting of halo, —OH, —$O(C_{1-3}$ alkyl), —CN, —$N(R^4)_2$, —$C(O)(C_{1-3}$ alkyl), —CO$_2$H, —CO$_2$(C$_{1-3}$ alkyl), —C(O)NH$_2$, —C(O)NH(C$_{1-3}$ alkyl), —C$_{1-3}$ aliphatic, —C$_{1-3}$ fluoroaliphatic, —O(C$_{1-3}$ fluoroaliphatic), and optionally substituted aryl. Preferred halo group substituents on Ring D include F and Cl.

In certain embodiments, Ring D is an optionally substituted phenyl, naphthyl, or indanyl ring. In certain other embodiments, Ring D is an optionally substituted 5- or 6-membered heterocyclyl or cycloaliphatic ring. Optionally, two adjacent substituents on the heterocyclyl or cycloaliphatic ring, taken together with the intervening carbon atoms, form an optionally substituted fused phenyl ring.

In certain particular embodiments, Ring D is selected from the group consisting of:

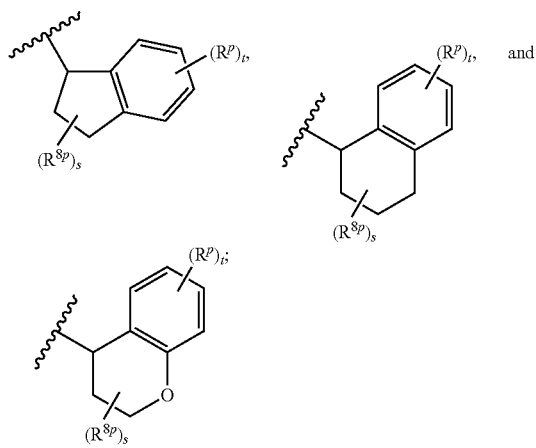

where
each R$^{8p}$ independently is selected from the group consisting of =O, fluoro, —OR$^{5x}$, or a C$_{1-4}$ aliphatic or C$_{1-4}$ fluoroaliphatic optionally substituted with —OR$^{5x}$, —N(R$^{4x}$)(R$^{4y}$), —CO$_2$R$^{5x}$, or —C(O)N(R$^{4x}$)(R$^{4y}$), provided that R$^{8p}$ is other than —OR$^{5x}$ when located at a position adjacent to a ring oxygen atom;
s is 0, 1, or 2;
t is 0, 1, or 2; and
the variables R$^{4x}$, R$^{4y}$, and R$^{5x}$ have the values described above for formulae (I) and (I-A).

Another embodiment of the invention relates to a compound of formula (1) or (I-A), wherein R$^1$ is —O—R$^{11}$, —S—R$^{10}$, or —NR$^7$R$^8$, and R$^7$ is an optionally substituted C$_{1-10}$ aliphatic. Preferably, R$^8$ is hydrogen. In some embodiments, R$^7$ is C$_{1-10}$ aliphatic or a substituted aliphatic group of the formula —Z$^a$R$^{18}$, —Z$^b$R$^{19}$, or —Z$^a$R$^{20}$; R$^{10}$ is C$_{2-10}$ aliphatic or a substituted aliphatic group of the formula —Z$^a$R$^{18}$, —Z$^b$R$^{19}$, or —Z$^a$R$^{20}$; and R$^{11}$ is C$_{2-10}$ aliphatic or a substituted aliphatic group of the formula —Z$^a$R$^{18}$, —Z$^a$R$^{19}$, or —Z$^a$R$^{20}$. The variables Z$^a$, Z$^b$, R$^{18}$, R$^{19}$, and R$^{20}$ have the values described below.

Z$^a$ is an optionally substituted C$_{1-6}$ alkylene chain, wherein the alkylene chain is optionally interrupted by —C(R$^{13}$)=C(R$^{13}$)—, —C≡C—, —O—, —S—, —N(R$^{13}$)—, —N(R$^{13}$)C(O)—, —N(R$^{13}$)CO$_2$—, —C(O)N(R$^{13}$)—, —C(O)—, —C(O)—C(O)—, —CO$_2$—, —OC(O)—, —OC(O)—, —N(R$^{13}$)C(O)N(R$^{13}$)—, —N(R$^{13}$)N(R$^{13}$)—, —OC(O)N(R$^{13}$)—, —S(O)—, —S(O)$_2$—, —N(R$^{13}$)S(O)$_2$—, —S(O)$_2$N(R$^{13}$)—. In some embodiments, Z$^a$ is optionally substituted with one to four R$^x$ or R$^y$, wherein R$^x$ and R$^y$ are as defined above for formula (VI). Preferably, Z$^a$ is substituted with zero, one, or two substituents independently selected from the group consisting of —F, —OH, —O(C$_{1-3}$ alkyl), —CN, —N(R$^4$)$_2$, —C(O)(C$_{1-3}$ alkyl), —CO$_2$H, —CO$_2$(C$_{1-3}$ alkyl), —C(O)NH$_2$, —C(O)NH(C$_{1-3}$ alkyl), —C$_{1-3}$ aliphatic, —C$_{1-3}$ fluoroaliphatic, and optionally substituted aryl. In certain particular embodiments, Z$^a$ is a C$_{1-4}$ alkylene chain which is optionally substituted with zero, one or two groups selected from the group consisting of —F, —OH, C$_{1-3}$ aliphatic and optionally substituted aryl.

Z$^b$ is an optionally substituted C$_{2-6}$ alkylene chain, wherein the alkylene chain is optionally interrupted by —C(R$^{13}$)=C(R$^{13}$)—, —C≡C—, —O—, —S—, —N(R$^{13}$)—, —N(R$^{13}$)C(O)—, —N(R$^{13}$)CO$_2$—, —C(O)N(R$^{13}$)—, —C(O)—, —C(O)—C(O)—, —CO$_2$—, —OC(O)—, —OC(O)O—, —N(R$^{13}$)C(O)N(R$^{13}$)—, —N(R$^{13}$)N(R$^{13}$)—, —OC(O)N(R$^{13}$)—, —S(O)—, —S(O)$_2$—, —N(R$^{13}$)S(O)$_2$—, —S(O)$_2$N(R$^{13}$)—. In some embodiments, Z$^b$ is optionally substituted with one to four R$^x$ or R$^y$, wherein R$^x$ and R$^y$ are as defined above for formula (VI). Preferably, Z$^b$ is substituted with zero, one, or two substituents independently selected from the group consisting of —F, —OH, —O(C$_{1-3}$ alkyl), —CN, —N(R$^4$)$_2$, —C(O)(C$_{1-3}$ alkyl), —CO$_2$H, —CO$_2$(C$_{1-3}$ alkyl), —C(O)NH$_2$, —C(O)NH(C$_{1-3}$ alkyl), —C$_{1-3}$ aliphatic, —C$_{1-3}$ fluoroaliphatic, and optionally substituted aryl. In certain particular embodiments, Z$^b$ is a C$_{2-4}$ alkylene chain which is optionally substituted with zero, one or two groups selected from the group consisting of —F, —OH, C$_{1-3}$ aliphatic and optionally substituted aryl.

R$^{18}$ is an optionally substituted aryl, heteroaryl, heterocyclyl, or cycloaliphatic group.

R$^{19}$ is —C(R$^{14}$)=C(R$^{14}$)$_2$, —C≡C—R$^{14}$, —S(O)R$^{15}$, —SO$_2$R$^{15}$, —SO$_2$—N(R$^{16}$)$_2$, —C(R$^{14}$)=N—OR$^{14}$, —CO$_2$R$^{14}$, —C(O)—C(O)R$^{14}$, —C(O)R$^{14}$, —C(O)N(R$^{16}$)$_2$, —C(=NR$^{16}$)—N(R$^{16}$)$_2$, or —C(=NR$^{16}$)—OR$^{14}$.

R$^{20}$ is halo, —NO$_2$, —CN, —OR$^{14}$, SR$^{15}$—, —N(R$^{16}$)$_2$, —N(R$^{16}$)C(O)R$^{15}$, —N(R$^{16}$)C(O)N(R$^{16}$)$_2$, —N(R$^{16}$)CO$_2$R$^{14}$, —O—CO$_2$R$^{14}$, —OC(O)N(R$^{16}$)$_2$, —OC(O)R$^{14}$, —N(R$^{16}$)—N(R$^{16}$)$_2$, —N(R$^{16}$)S(O)$_2$R$^{15}$, or —N(R$^{16}$)SO$_2$—N(R$^{16}$)$_2$.

One embodiment of the invention relates to a compound of formula (VIII):

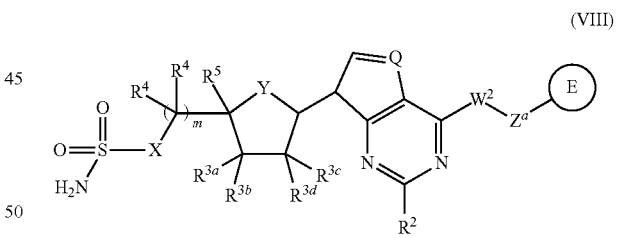

(VIII)

or a pharmaceutically acceptable salt thereof, wherein:
Ring E is a mono- or bicyclic aryl, heteroaryl, heterocyclyl, or cycloaliphatic group;
W$^2$ is —O—, —S—, or —N(R$^8$)—;
Z$^a$ is an optionally substituted C$_{1-6}$ alkylene chain, wherein the alkylene chain is optionally interrupted by —C(R$^{13}$)=C(R$^{13}$)—, —C≡C—, —O—, —S—, —N(R$^{13}$)—, —N(R$^{13}$)C(O)—, —N(R$^{13}$)CO$_2$—, —C(O)N(R$^{13}$)—, —C(O)—, —C(O)—C(O)—, —CO$_2$—, —OC(O)—, —OC(O)O—, —N(R$^{13}$)C(O)N(R$^{13}$)—, —N(R$^{13}$)N(R$^{13}$)—, —OC(O)N(R$^{13}$)—, —S(O)—, —S(O)$_2$—, —N(R$^{13}$)S(O)$_2$—, —S(O)$_2$N(R$^{13}$)—; and
the variables, Q, X, Y, R$^2$, R$^{3a}$, R$^{3b}$, R$^{3c}$, R$^{3d}$, R$^4$, R$^5$, R$^8$, and m have the values and preferred values described above for formulae (I) and (I-A).

In some such embodiments, Ring E is an optionally substituted furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, indolyl, isoindolyl, indazolyl, benzimidazolyl, benzthiazolyl, benzothienyl, benzofuranyl, purinyl, quinolyl, isoquinolyl, cinnolinyl, phthalazinyl, quinazolinyl, quinoxalinyl, naphthyridinyl, pteridinyl, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, quinuclidinyl, tetrahydroquinolinyl, tetrahydroisoquinolinyl, indanyl, phenanthridinyl, tetrahydronaphthyl, indolinyl, benzodioxanyl, and benzodioxolyl rings. In certain preferred embodiments, Ring E is an optionally substituted phenyl, naphthyl, indanyl, furanyl, thienyl, pyrrolyl, pyrrolidinyl, isoxazolyl, pyrazolyl, piperidinyl, piperazinyl, or morpholinyl ring.

Suitable substituents for Ring E include those described generally above for substituted aryl, heteroaryl, or heterocyclyl groups. Each substitutable ring nitrogen atom in Ring E is unsubstituted or substituted, preferably with —C(O)$R^{14}$, —C(O)N($R^{16}$)$_2$, —CO$_2R^{14}$, —SO$_2R^{15}$, —SO$_2$N($R^{16}$)$_2$, or an optionally substituted aliphatic. Substitutable ring carbon atoms in Ring E preferably are substituted with zero to four, preferably zero to two substituents independently selected from the group consisting of $C_{1-6}$ aliphatic, $C_{1-6}$ fluoroaliphatic, halo, —$R^{a18}$, —$R^{b18}$, —$Z^{18}$—$R^{a18}$, and —$Z^{18}$—$R^{b18}$. The variables $Z^{18}$, $R^{a18}$, and $R^{b18}$ have the values described below.

$Z^{18}$ is an optionally substituted $C_{1-6}$ alkylene chain, wherein the alkylene chain optionally is interrupted by —C($R^{14}$)=C($R^{14}$)—, —C≡C—, —O—, —S—, —S(O)—, —S(O)$_2$—, —SO$_2$N($R^{15}$)—, —N($R^{15}$)—, —N($R^{15}$)C(O)—, —$NR^{15}$C(O)N($R^{15}$)—, —N($R^{15}$)CO$_2$—, —N($R^{15}$)SO$_2$—, —C(O)N($R^{15}$)—, —C(O)—, —CO$_2$—, —OC(O)—, —OC(O)O—, or —OC(O)N($R^{15}$)—, and wherein $Z^{18}$ or a portion thereof optionally forms part of a 3-7 membered ring. In some embodiments, $Z^{18}$ is a $C_{1-6}$ or $C_{1-4}$ alkylene chain optionally substituted with one or two $R^x$ or $R^y$, wherein $R^x$ and $R^y$ have the values and preferred values described above.

Each $R^{a18}$ independently is an optionally substituted aryl, heteroaryl, heterocyclyl, or cycloaliphatic ring.

Each $R^{b18}$ independently is —NO$_2$, —CN, —C($R^{14}$)=C($R^{14}$)$_2$, —C≡C—$R^{14}$, —$OR^{14}$, —$SR^{15}$, —S(O)$R^{15}$, —SO$_2R^{15}$, —SO$_2$N($R^{16}$)$_2$), —N($R^{16}$)$_2$, —$NR^{16}$C(O)$R^{14}$, —$NR^{16}$C(O)N($R^{16}$)$_2$, —$NR^{16}$CO$_2R^{14}$, —O—CO$_2R^{14}$, —OC(O)N($R^{16}$)$_2$, —O—C(O)$R^{14}$, —CO$_2R^{14}$, —C(O)$R^{14}$, —C(O)N($R^{16}$)$_2$, —C(O)N($R^{16}$)C(=$NR^{16}$)—N($R^{16}$)$_2$, —C(=$NR^{16}$)—N($R^{16}$)$_2$, —C(=$NR^{16}$)—$OR^{14}$, —C($R^{14}$)=N—$OR^{14}$, —N($R^{16}$)C(=$NR^{16}$)—N($R^{16}$)$_2$, —N($R^{16}$)SO$_2R^{15}$, —N($R^{16}$)SO$_2$N($R^{16}$)$_2$. In some embodiments, each $R^{b18}$ independently is —CN, —N($R^4$)$_2$, —$NR^4$C(O)$R^5$, —$NR^4$—C(O)N($R^4$)$_2$, —$NR^4$CO$_2R^6$, —C(O)N($R^4$)$_2$, —CO$_2R^5$, or —$OR^5$.

In some embodiments, the substitutable ring carbon atoms in Ring E are substituted with zero, one, or two substituents independently selected from the group consisting of halo, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, —C(O)NH($C_{1-3}$ alkyl), —$C_{1-3}$ aliphatic, —$C_{1-3}$ fluoroaliphatic, —O($C_{1-3}$ fluoroaliphatic), optionally substituted aryl, and optionally substitued heteroaryl. Preferred halo substituents on Ring E include F and Cl.

In some embodiments, the invention relates to a compound of formula (VIII), wherein $R^8$ is hydrogen, $Z^a$ is $C_{1-3}$ alkylene, and Ring E is an optionally substituted phenyl, naphthyl, indanyl, furanyl, thienyl, pyrrolyl, pyrrolidinyl, isoxazolyl, pyrazolyl, piperidinyl, piperazinyl, pyrazinyl, morpholinyl, benzothiophenyl, or benzodioxolyl ring. In some such embodiments, the substitutable ring carbon atoms in Ring E are substituted with zero, one, or two substituents independently selected from the group consisting of fluoro, chloro, —OH, -methoxy, —CN, —O($C_{1-3}$ alkyl), -trifluoromethyl, and —$C_{1-3}$ fluoroaliphatic.

Subgenus definitions for $R^1$, $R^2$, $R^{3a}$, $R^{3b}$, $R^{3c}$, $R^{3d}$, $R^4$, and $R^5$ described for formulae (I) and (I-A) also apply to formulae (II)-(VII). Compounds embodying any combination of the preferred values for the variables described herein are within the scope of the present invention.

Representative examples of compounds of formula (I-A) are shown in Table 1.

TABLE 1

E1 activating enzyme inhibitors

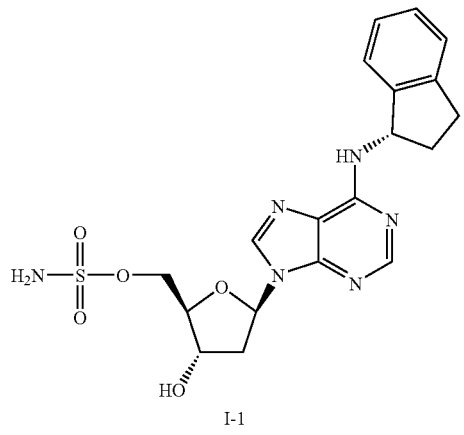

I-1

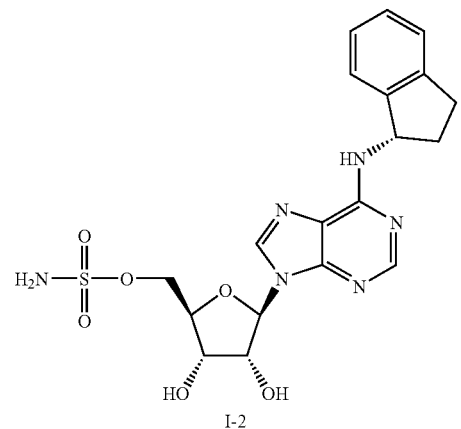

I-2

TABLE 1-continued
E1 activating enzyme inhibitors
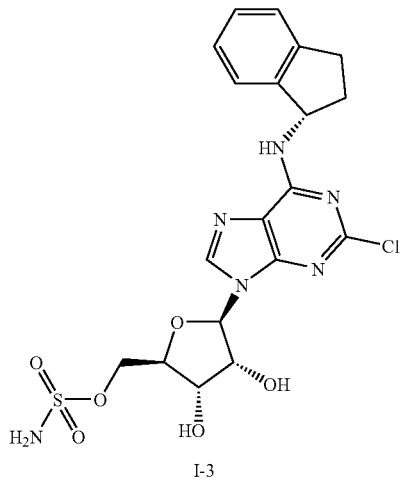
I-3
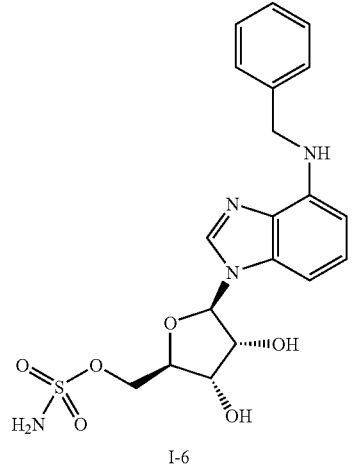
I-6
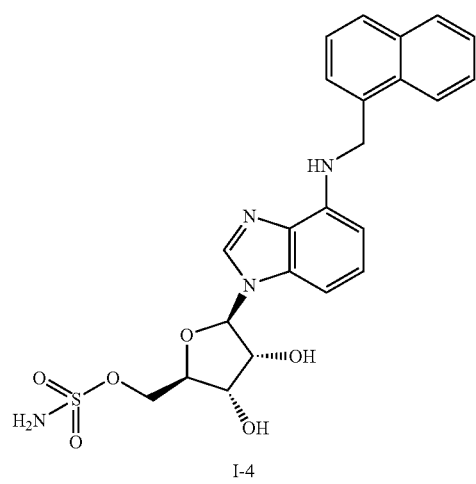
I-4
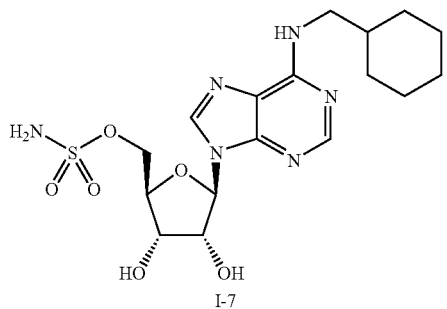
I-7
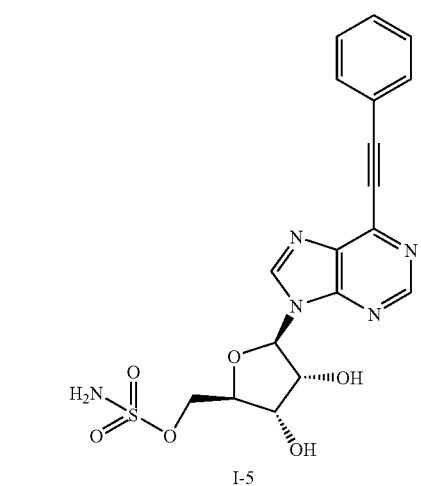
I-5
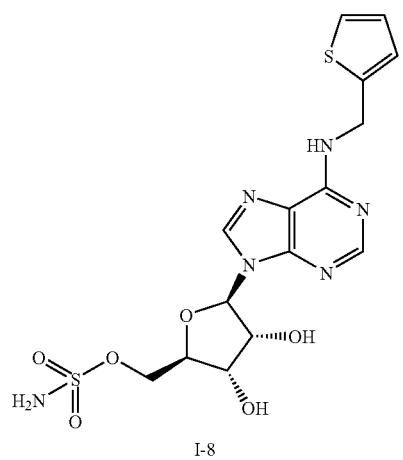
I-8

TABLE 1-continued
E1 activating enzyme inhibitors
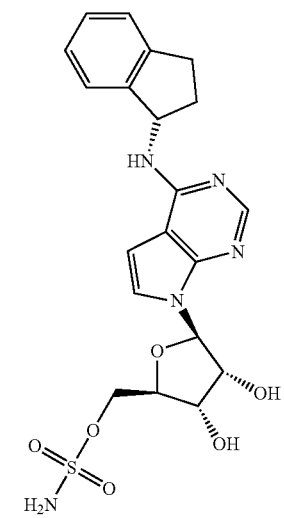
I-9
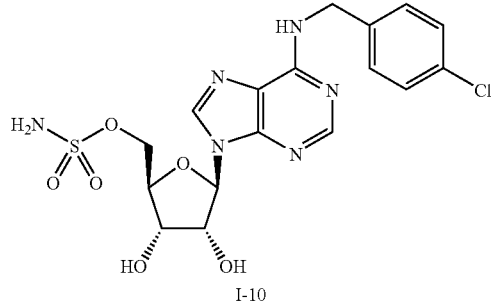
I-10
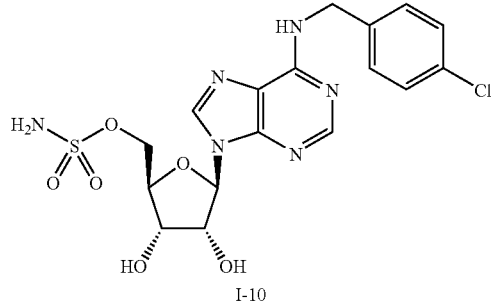
I-11
TABLE 1-continued
E1 activating enzyme inhibitors
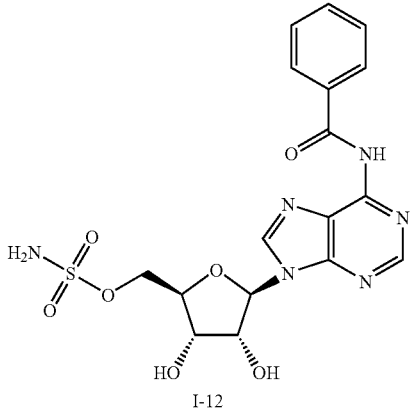
I-12
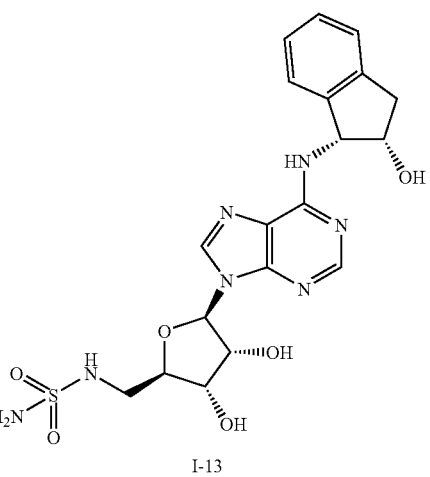
I-13
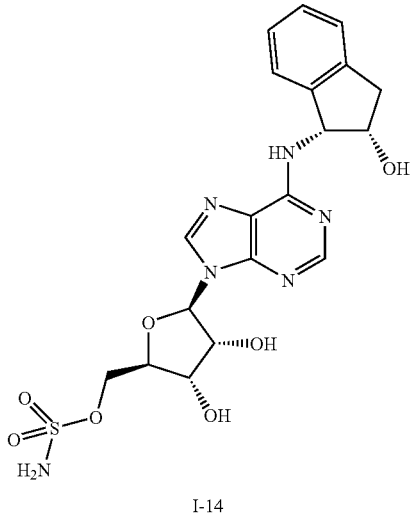
I-14

TABLE 1-continued
E1 activating enzyme inhibitors
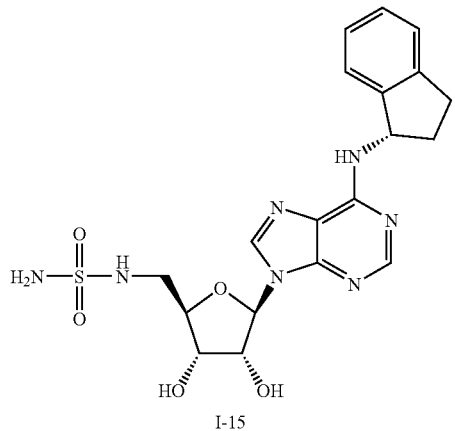
I-15
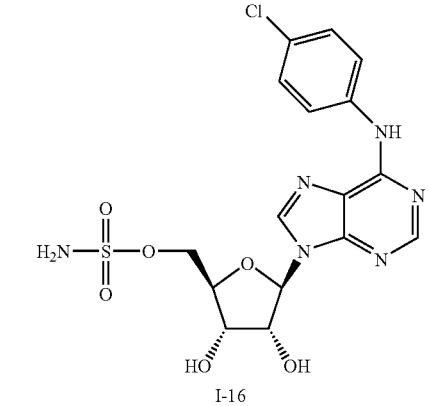
I-16
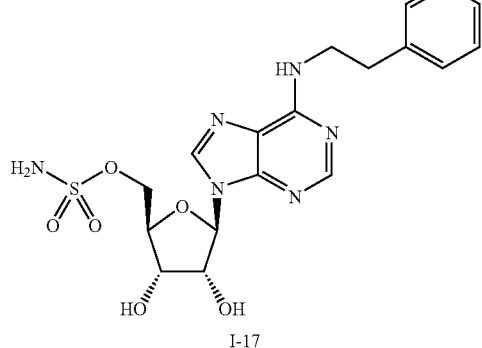
I-17
TABLE 1-continued
E1 activating enzyme inhibitors
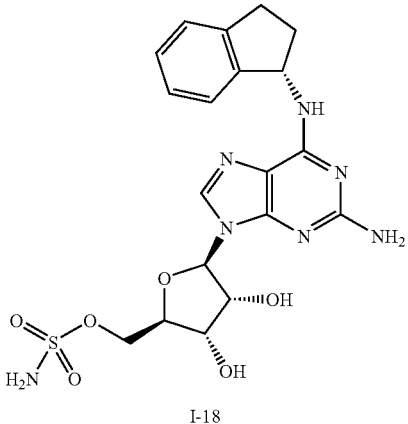
I-18
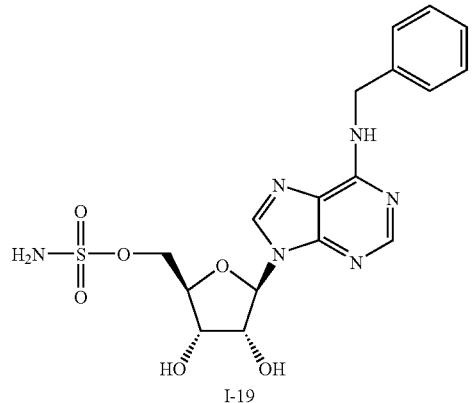
I-19
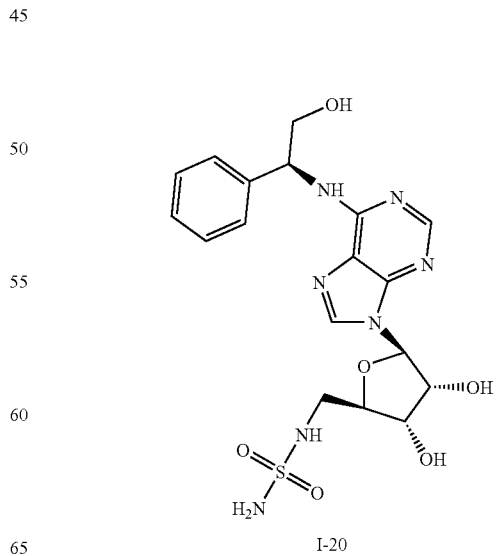
I-20

TABLE 1-continued
E1 activating enzyme inhibitors
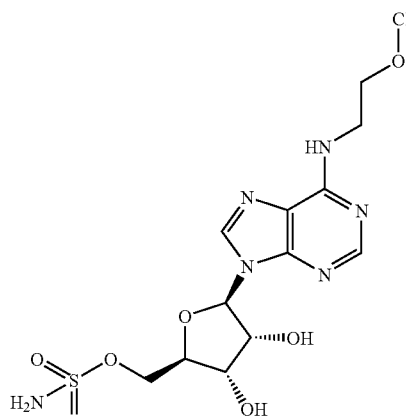
I-21
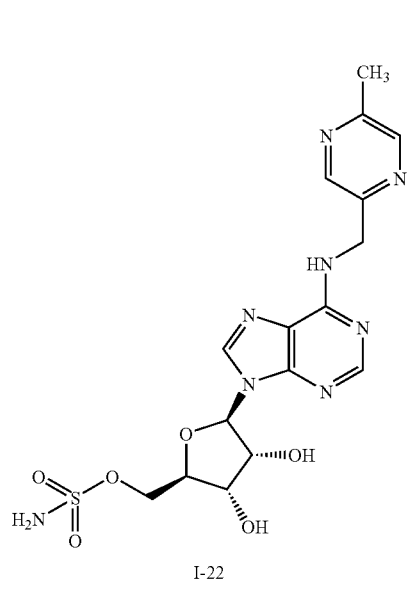
I-22
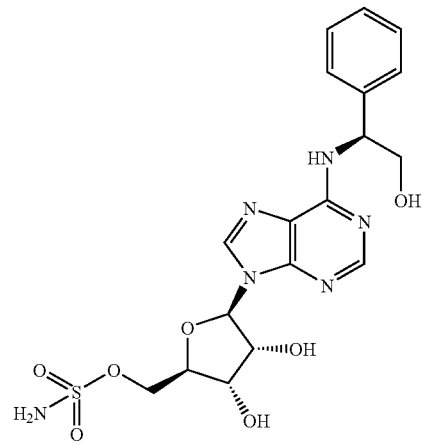
I-23
TABLE 1-continued
E1 activating enzyme inhibitors
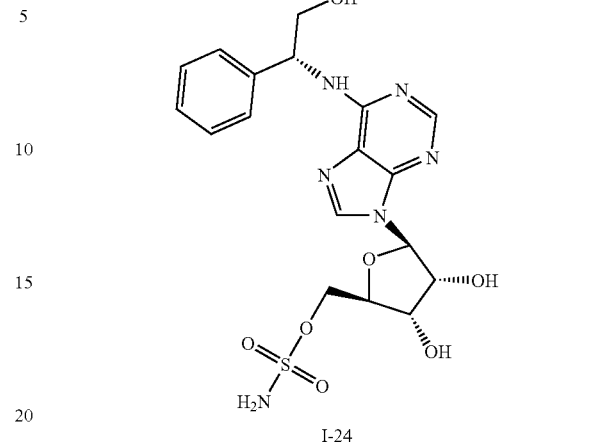
I-24
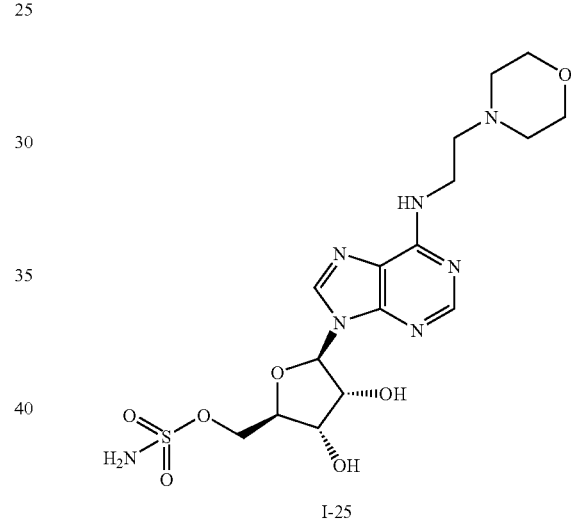
I-25
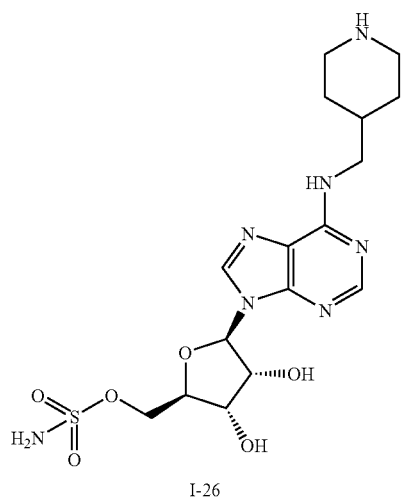
I-26

TABLE 1-continued
E1 activating enzyme inhibitors
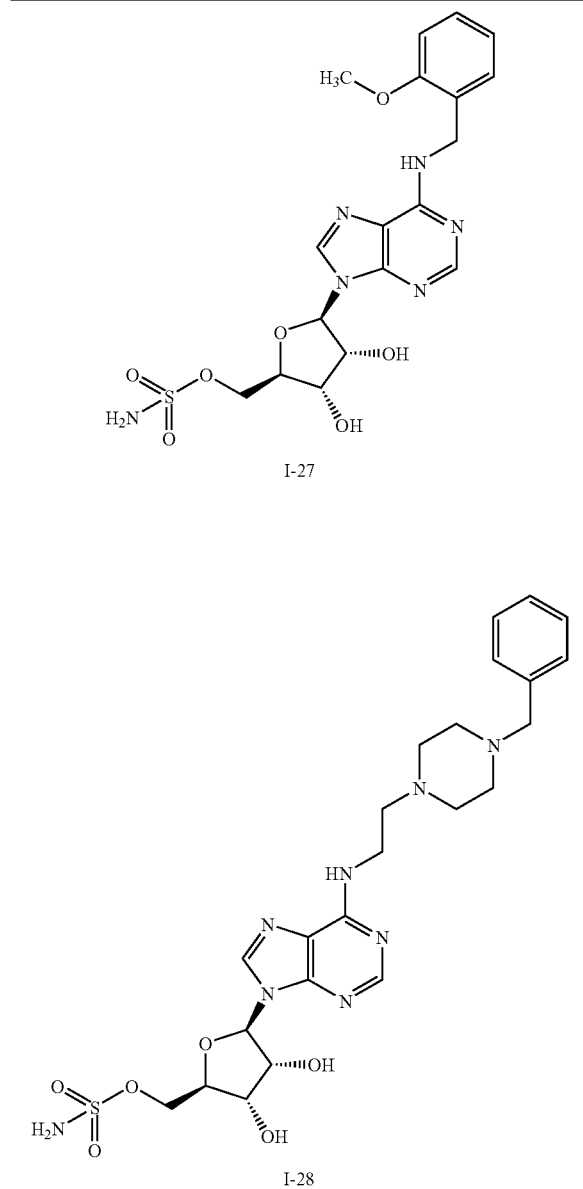
I-27
I-28
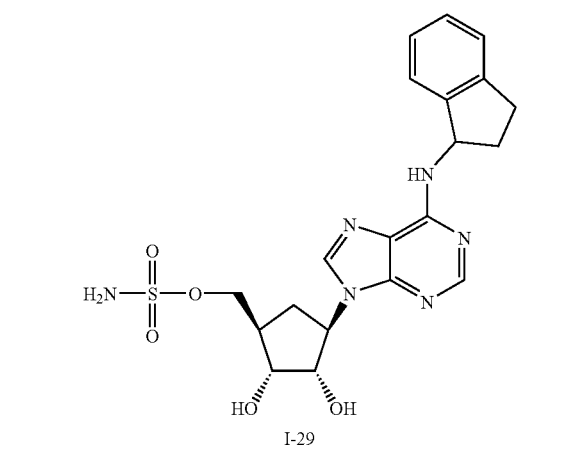
I-29
TABLE 1-continued
E1 activating enzyme inhibitors
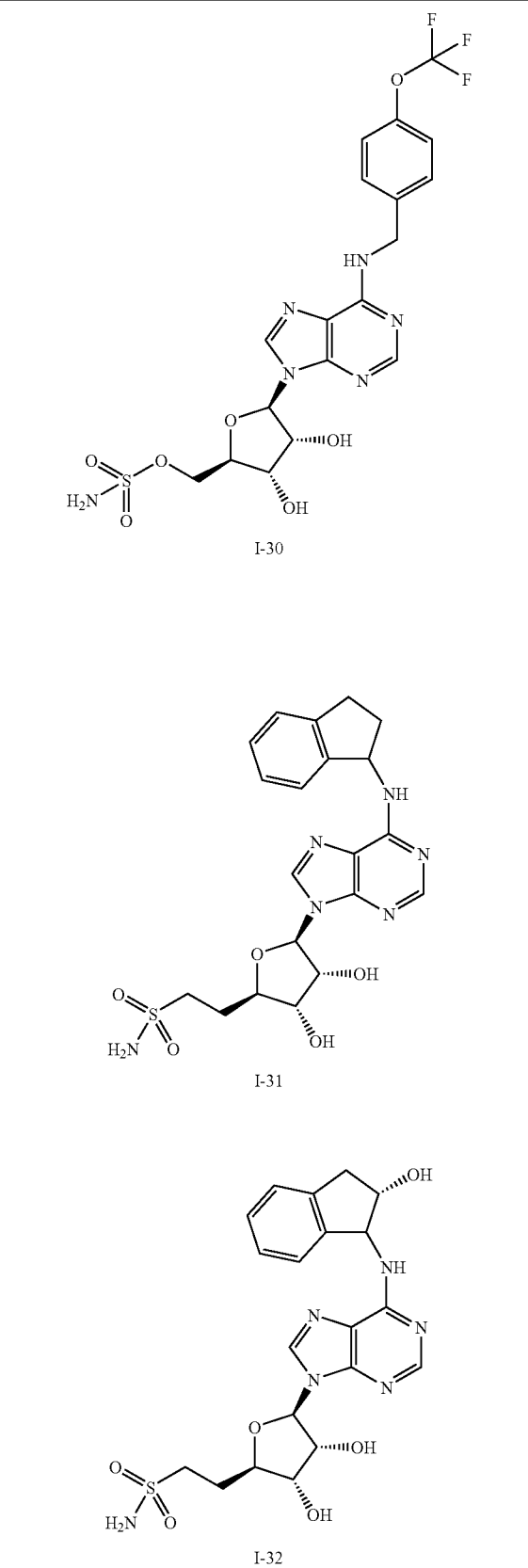
I-30
I-31
I-32

TABLE 1-continued
E1 activating enzyme inhibitors
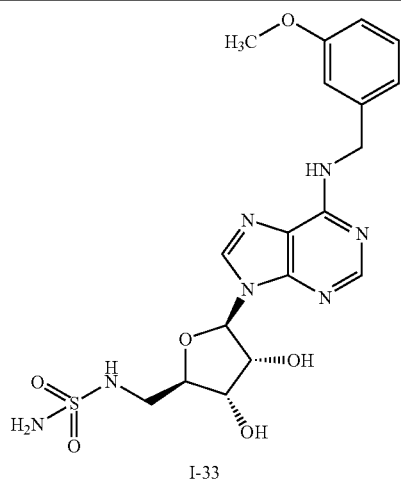
I-33
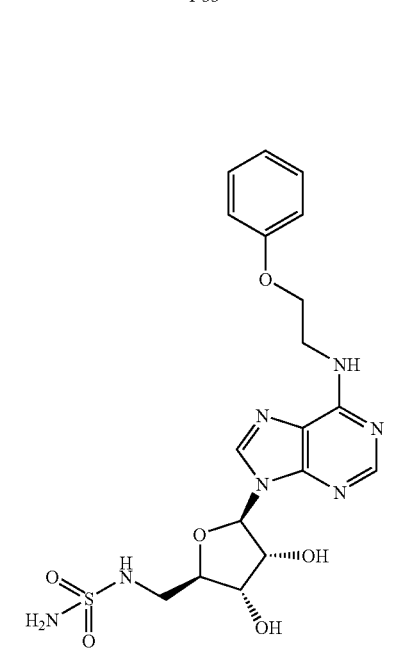
I-34
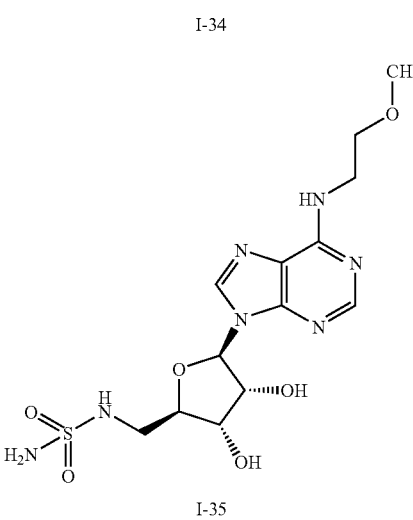
I-35
TABLE 1-continued
E1 activating enzyme inhibitors
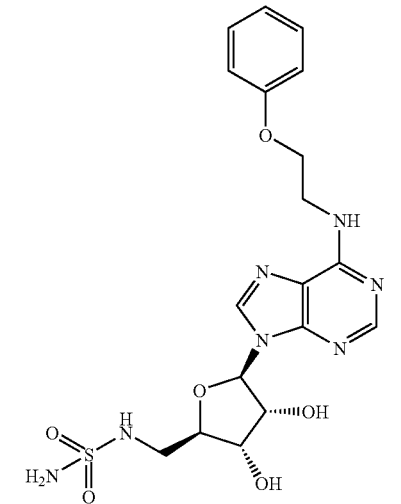
I-36
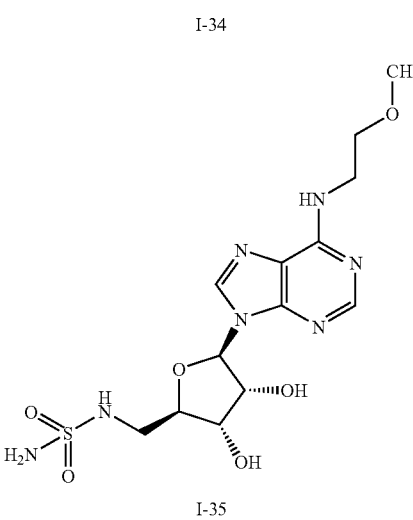
I-37
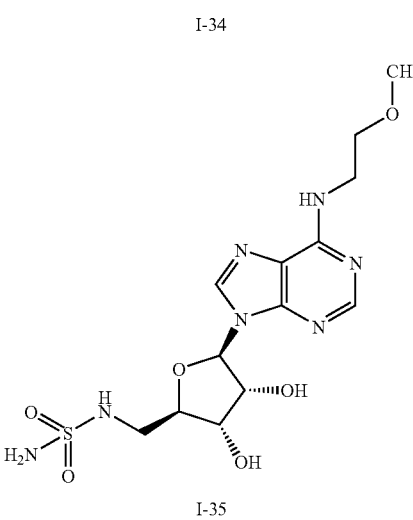
I-38

TABLE 1-continued
E1 activating enzyme inhibitors
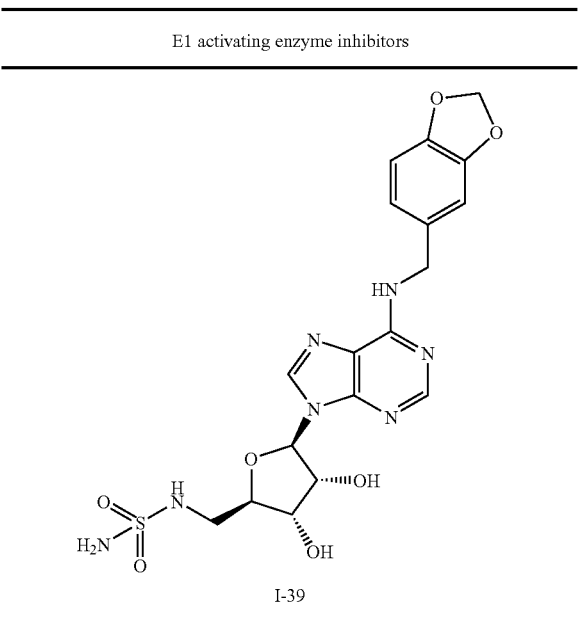
I-39
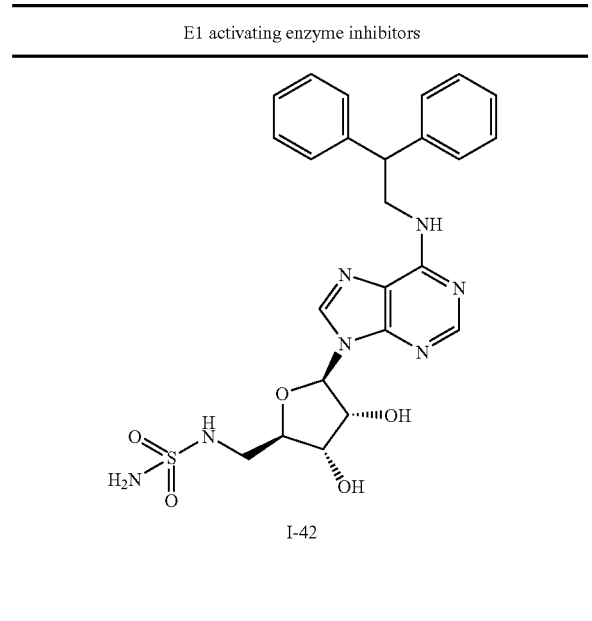
I-42
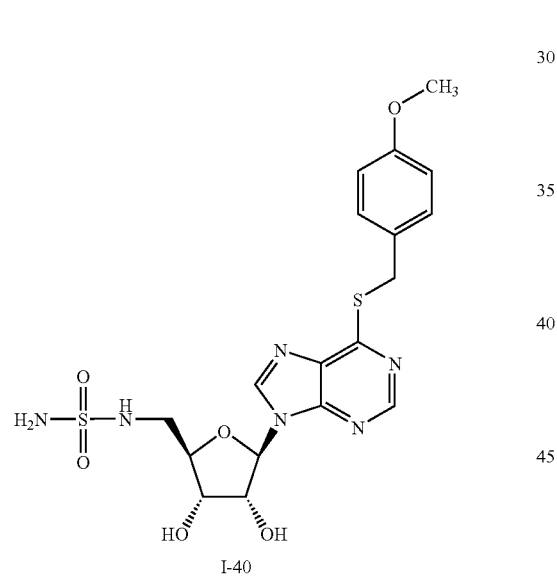
I-40
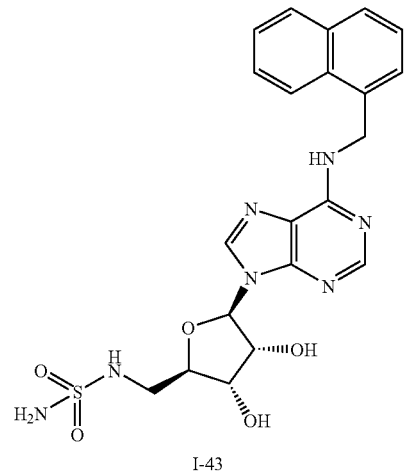
I-43
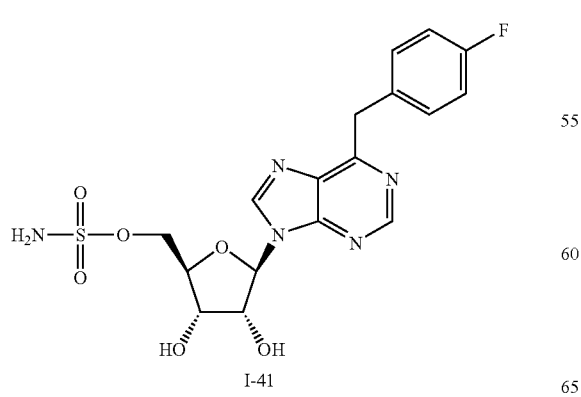
I-41
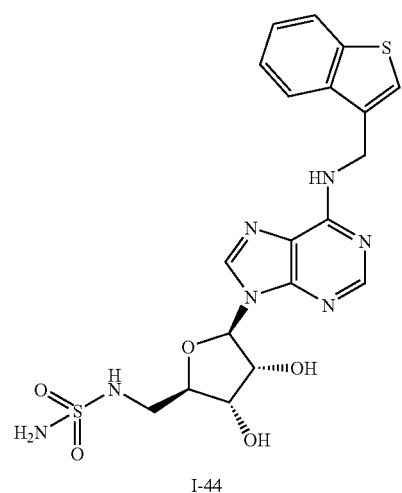
I-44

TABLE 1-continued
E1 activating enzyme inhibitors
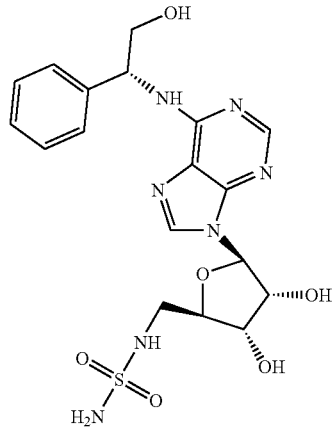
I-45
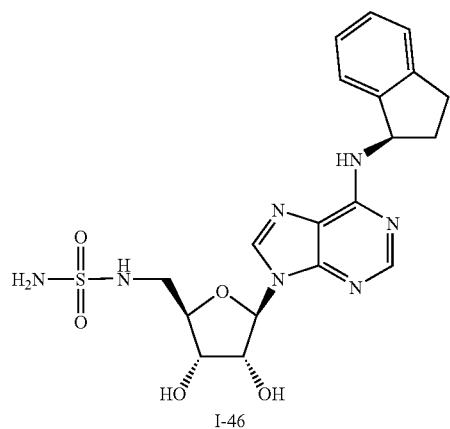
I-46
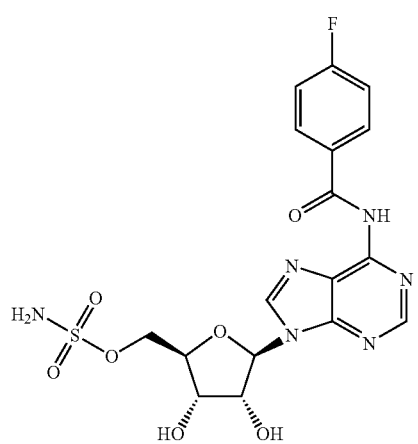
I-47
TABLE 1-continued
E1 activating enzyme inhibitors
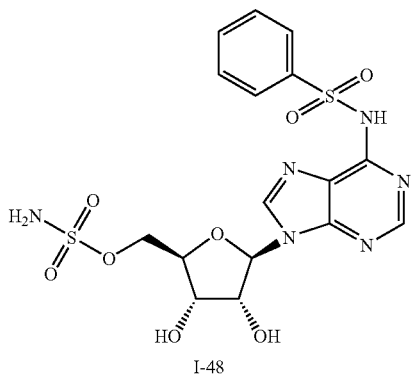
I-48
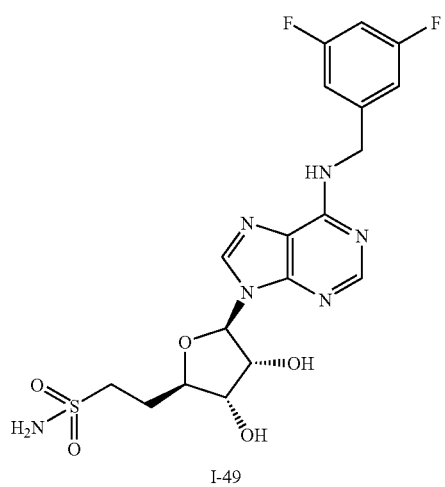
I-49
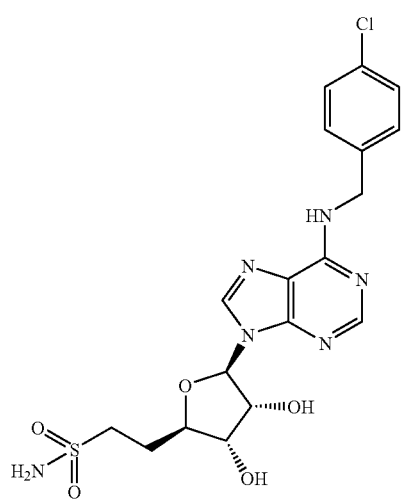
I-50

TABLE 1-continued
E1 activating enzyme inhibitors
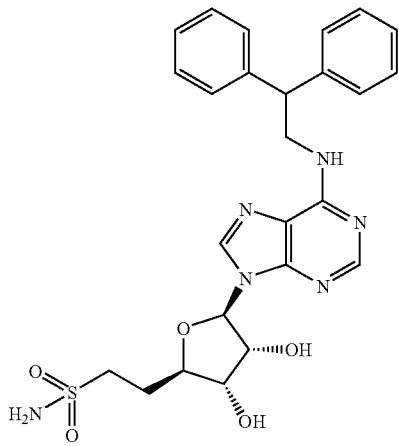
I-51
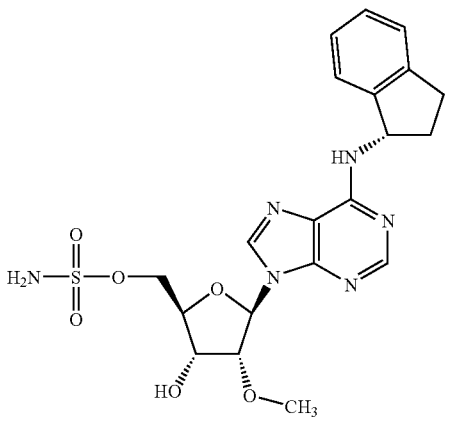
I-54
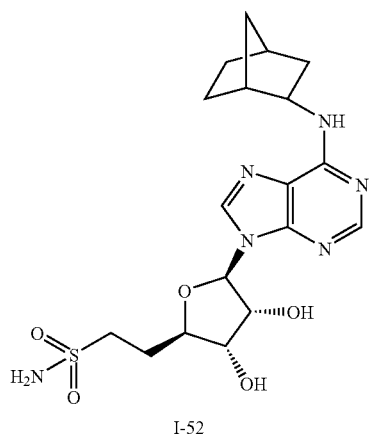
I-52
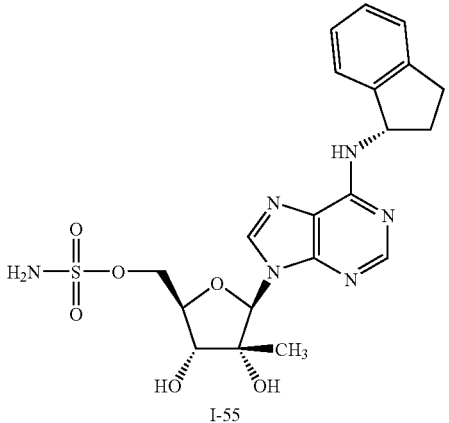
I-55
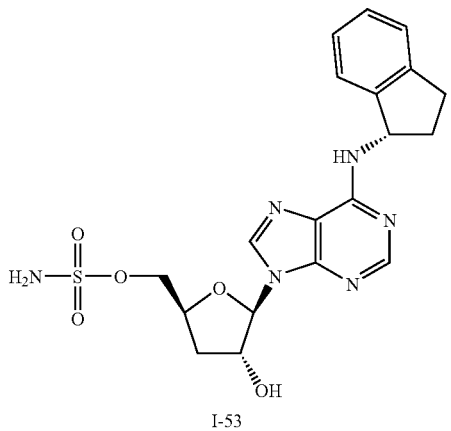
I-53
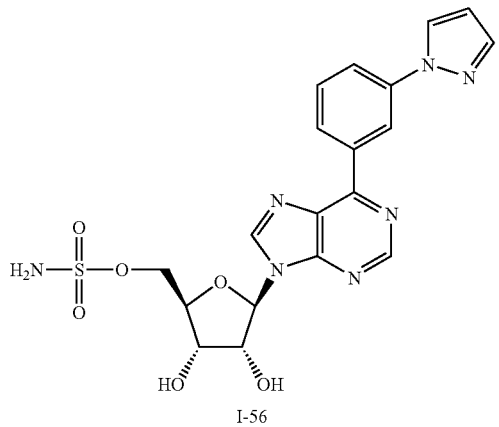
I-56

TABLE 1-continued
E1 activating enzyme inhibitors
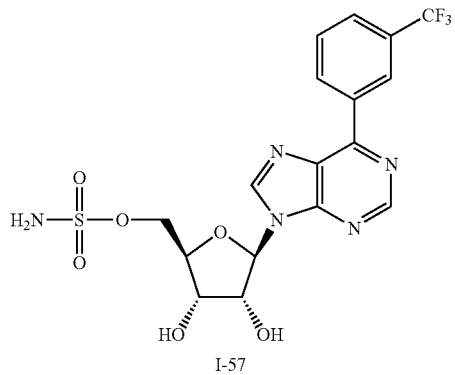
I-57
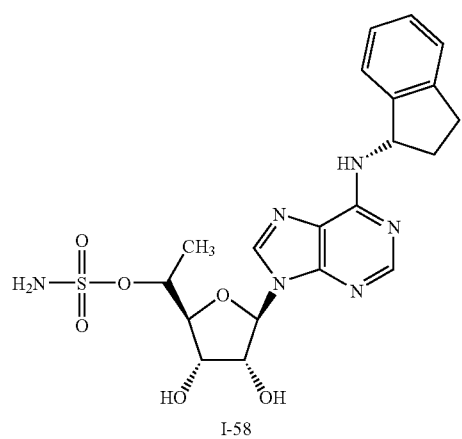
I-58
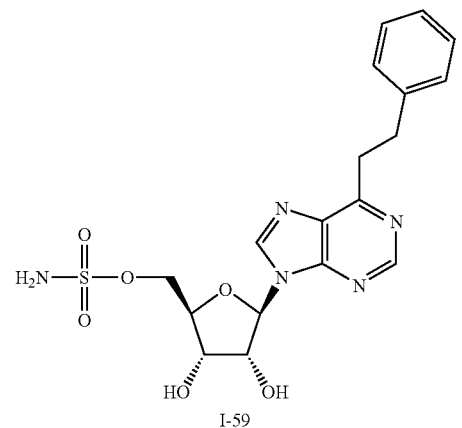
I-59
TABLE 1-continued
E1 activating enzyme inhibitors
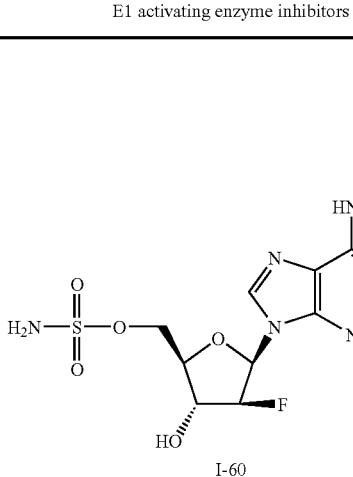
I-60
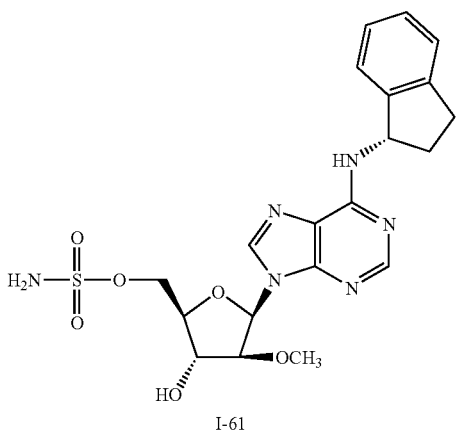
I-61
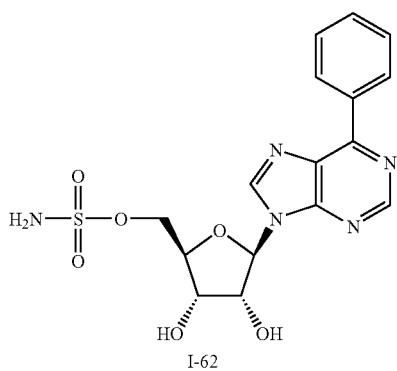
I-62

TABLE 1-continued
E1 activating enzyme inhibitors
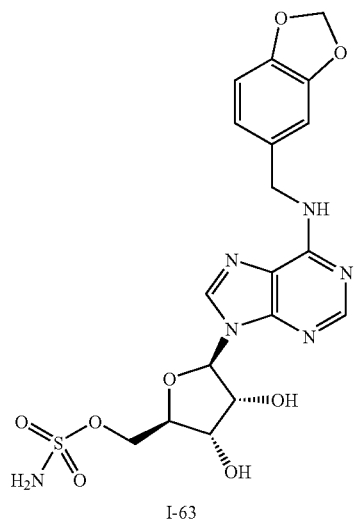
I-63
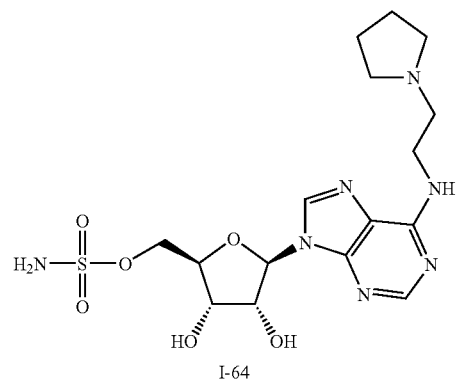
I-64
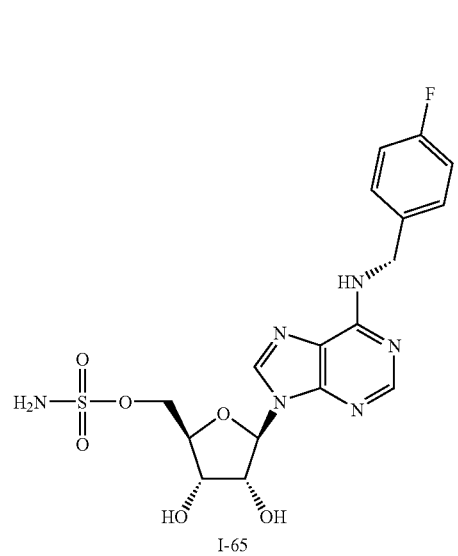
I-65
TABLE 1-continued
E1 activating enzyme inhibitors
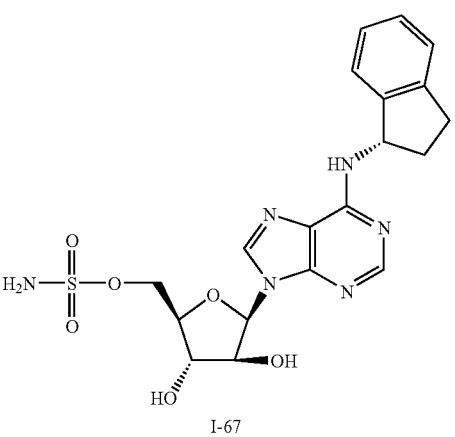
I-66
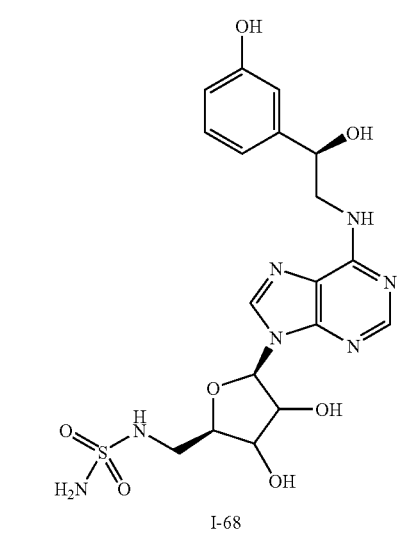
I-67
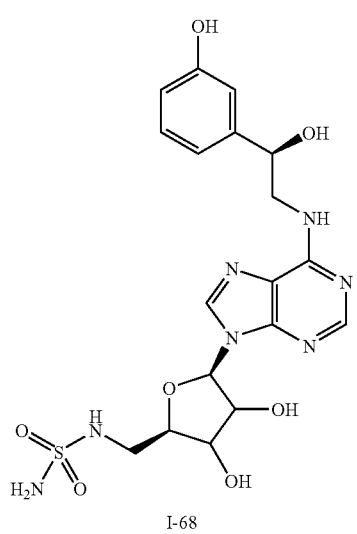
I-68

TABLE 1-continued
E1 activating enzyme inhibitors
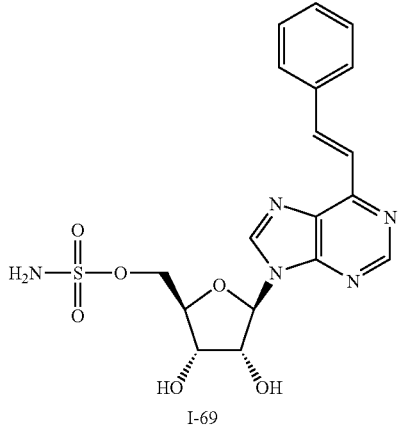
I-69
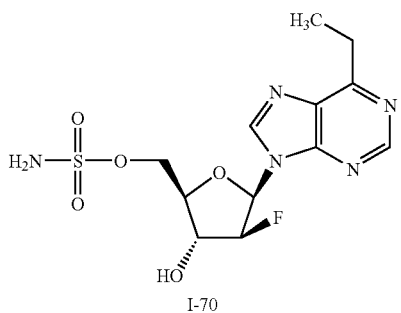
I-70
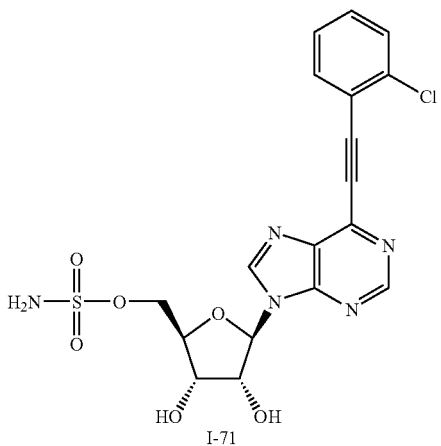
I-71
TABLE 1-continued
E1 activating enzyme inhibitors
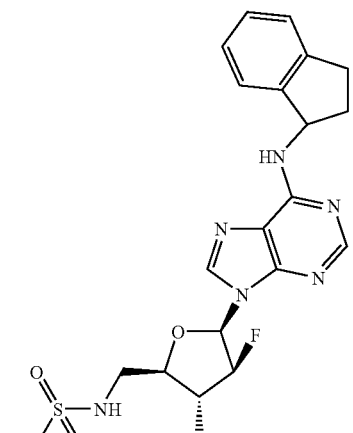
I-72
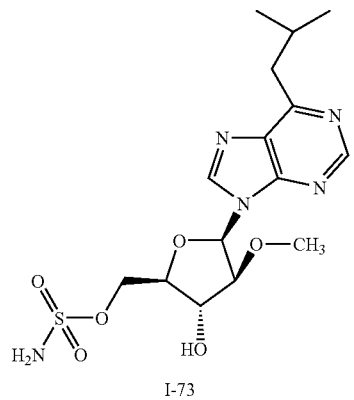
I-73
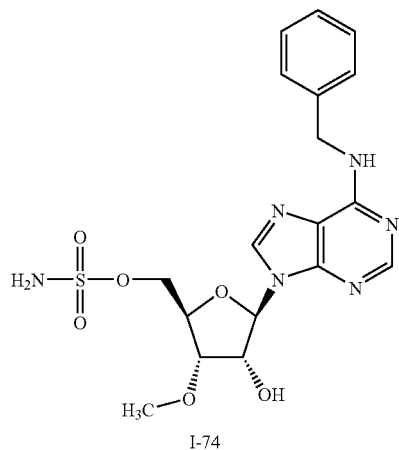
I-74

TABLE 1-continued
E1 activating enzyme inhibitors
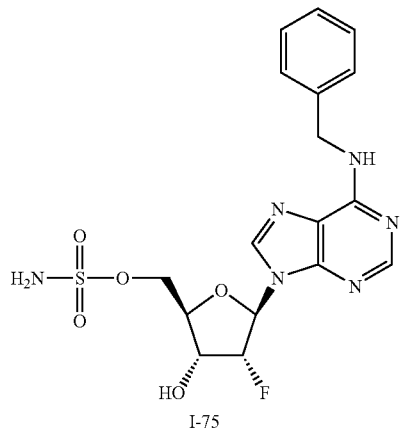
I-75
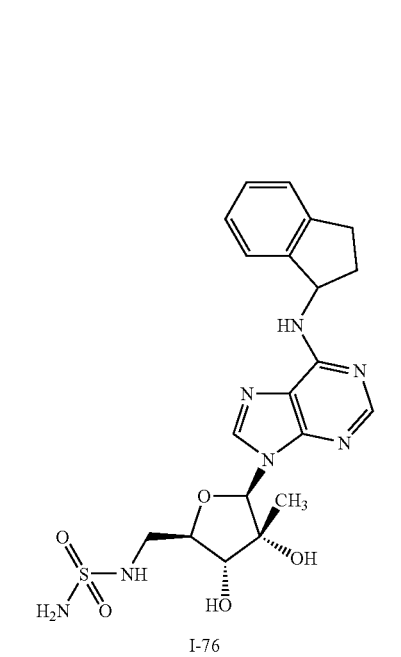
I-76
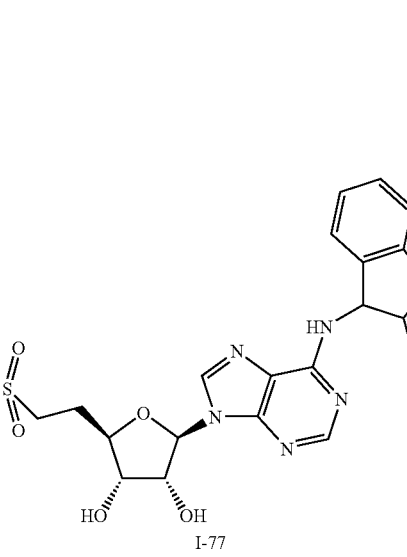
I-77
TABLE 1-continued
E1 activating enzyme inhibitors
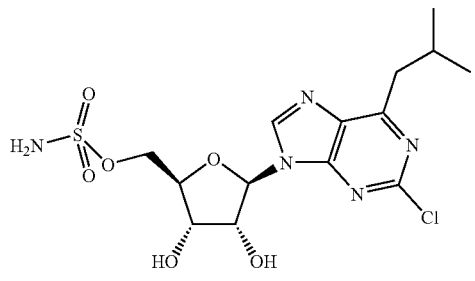
I-78
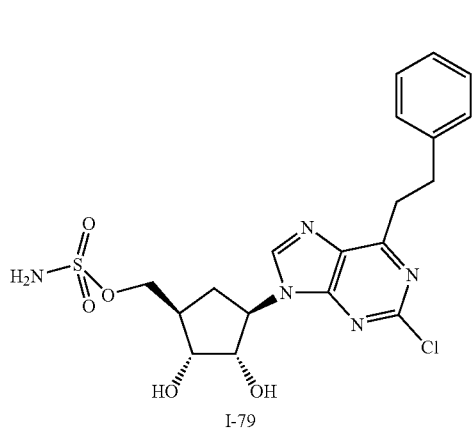
I-79
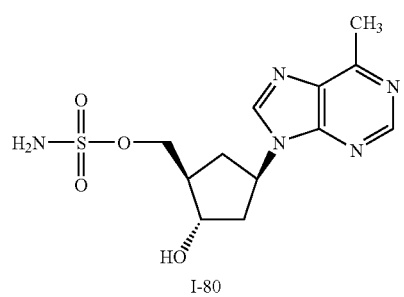
I-80
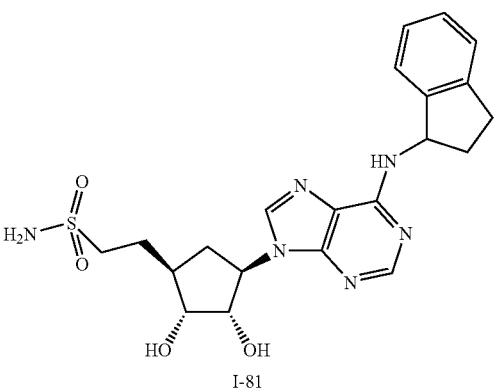
I-81

TABLE 1-continued
E1 activating enzyme inhibitors
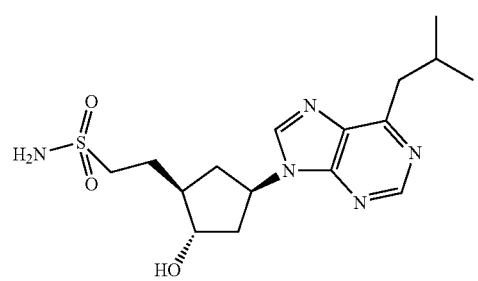
I-82
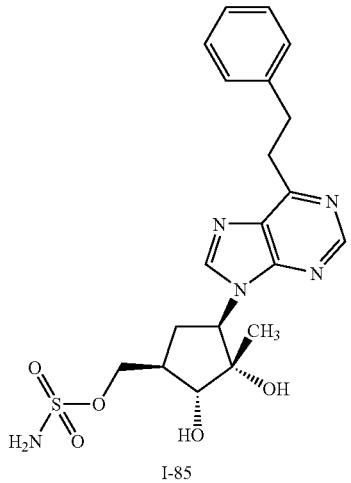
I-85
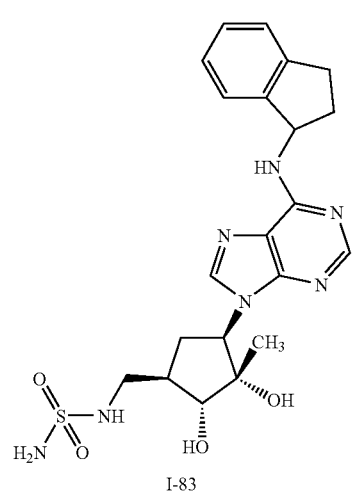
I-83
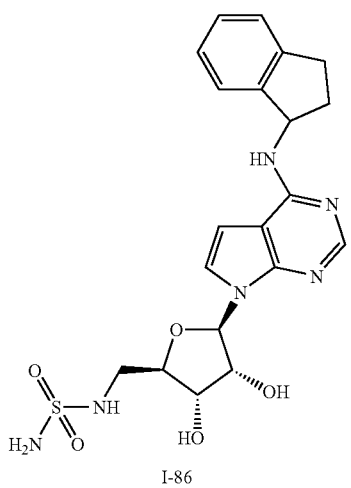
I-86
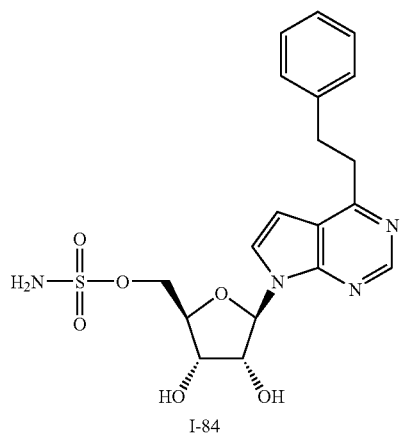
I-84
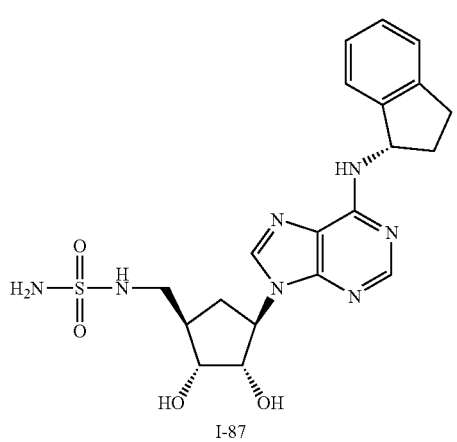
I-87

TABLE 1-continued
E1 activating enzyme inhibitors
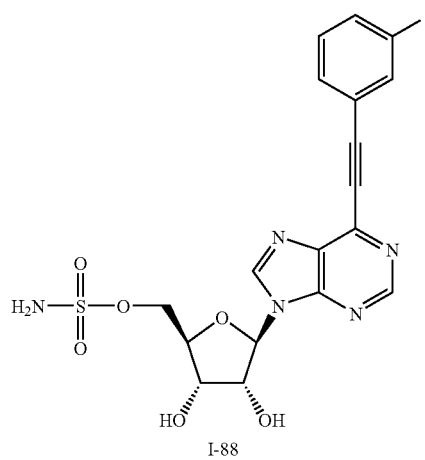
I-88
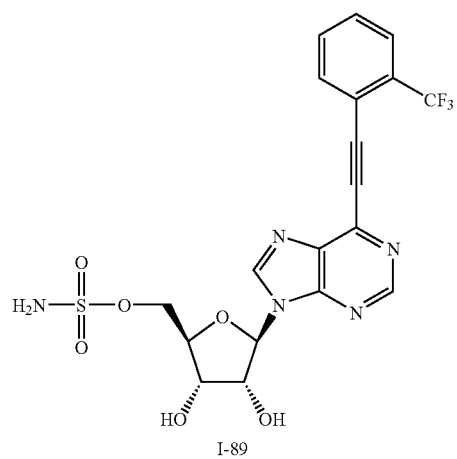
I-89
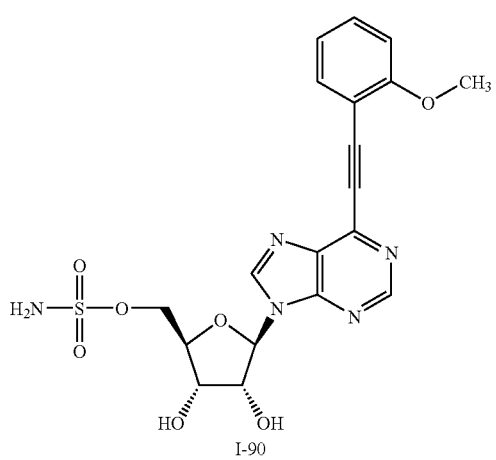
I-90
TABLE 1-continued
E1 activating enzyme inhibitors
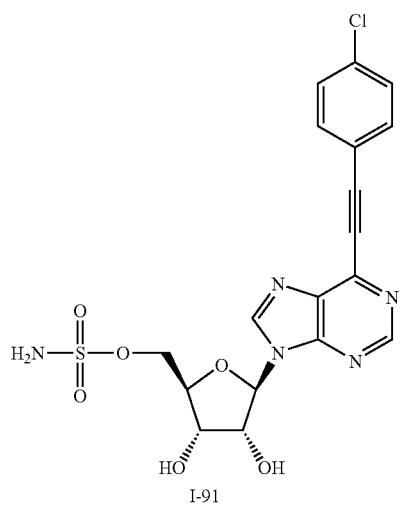
I-91
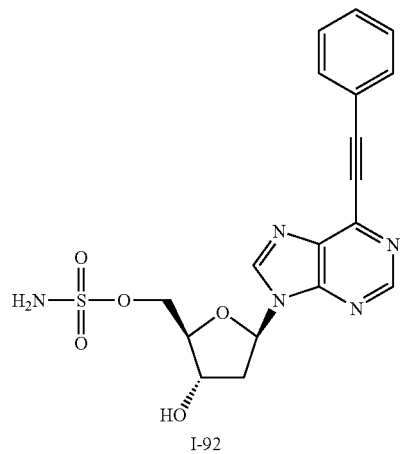
I-92
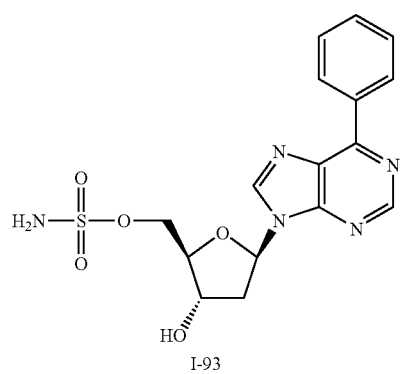
I-93

TABLE 1-continued
E1 activating enzyme inhibitors
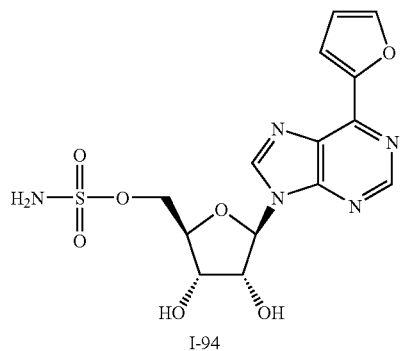
I-94
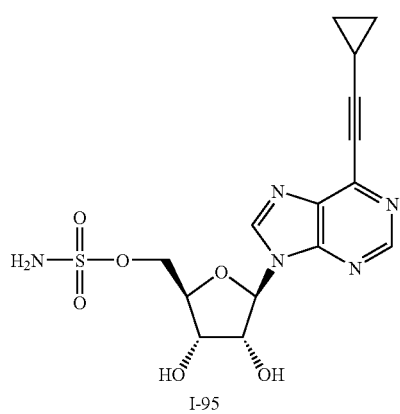
I-95
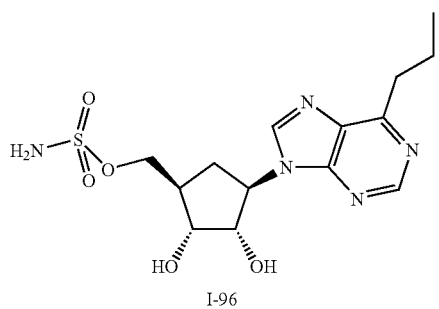
I-96
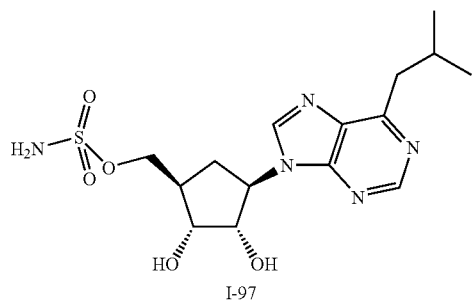
I-97
TABLE 1-continued
E1 activating enzyme inhibitors
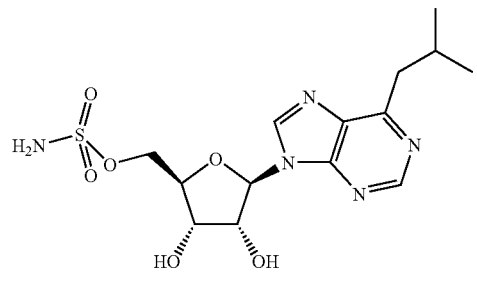
I-98
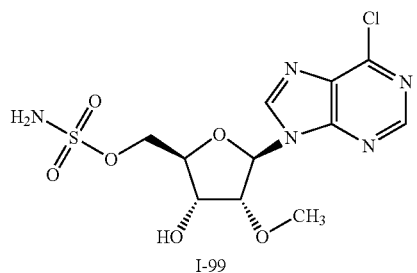
I-99
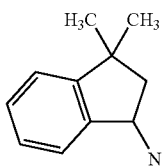
I-100
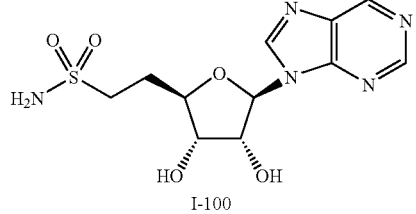
I-101

TABLE 1-continued
E1 activating enzyme inhibitors
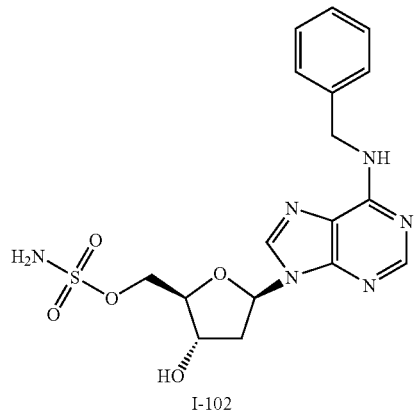
I-102
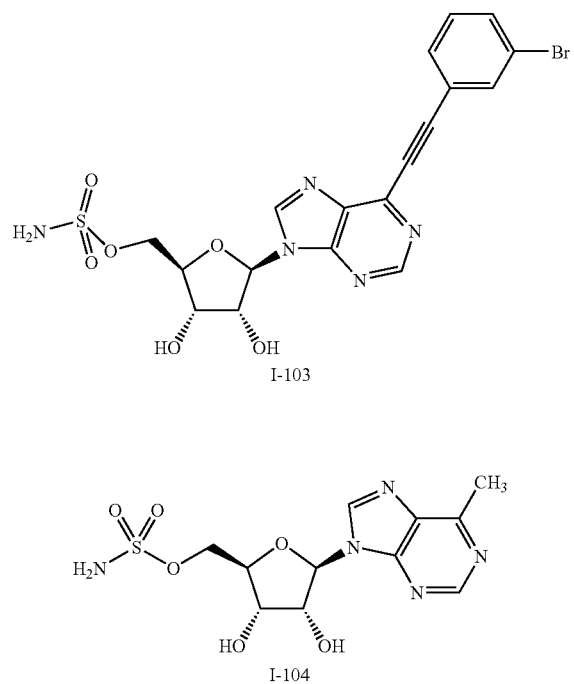
I-103
I-104
I-105
TABLE 1-continued
E1 activating enzyme inhibitors
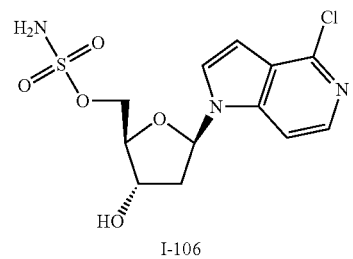
I-106
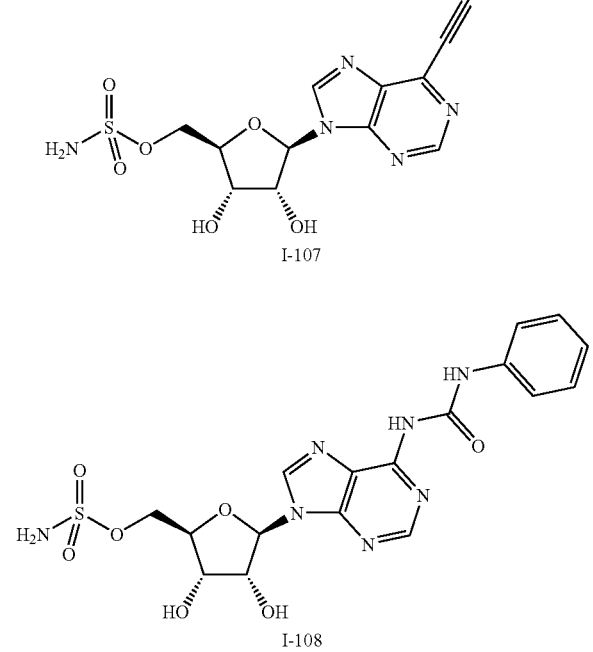
I-107
I-108
I-109

TABLE 1-continued
E1 activating enzyme inhibitors
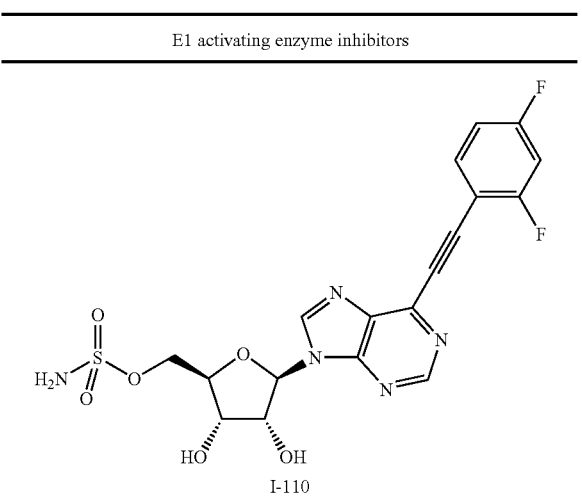
I-110
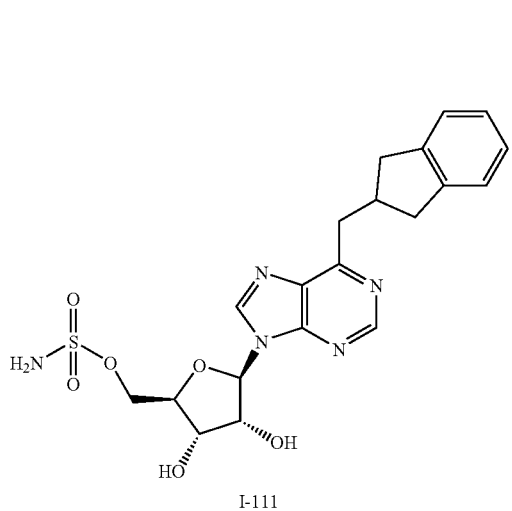
I-111
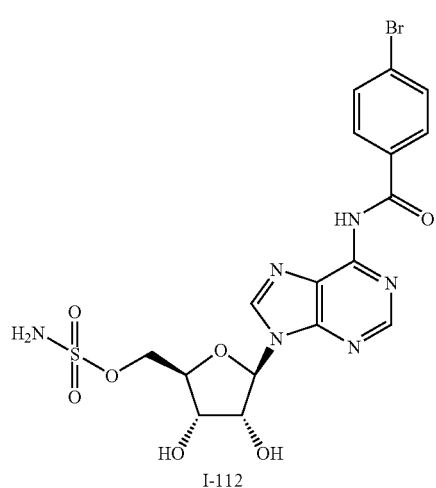
I-112
TABLE 1-continued
E1 activating enzyme inhibitors
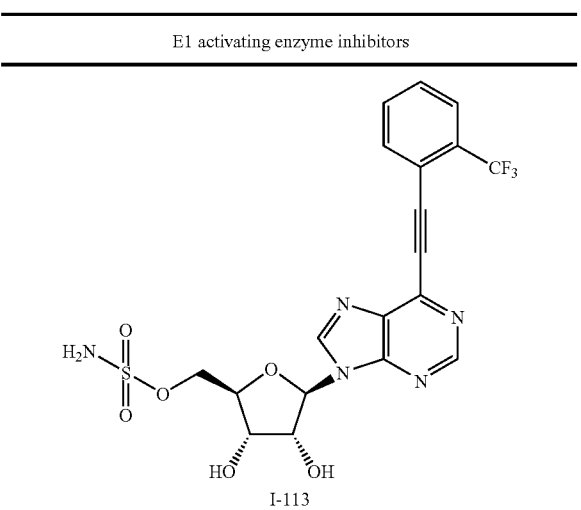
I-113
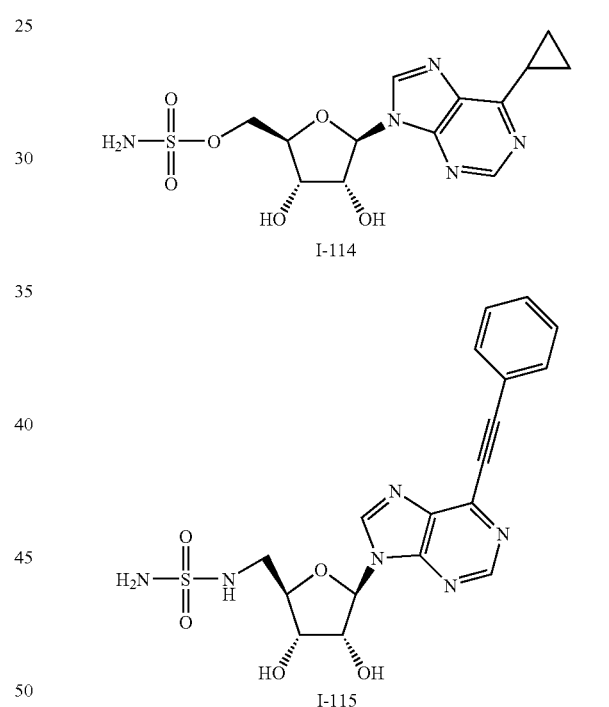
I-114
I-115
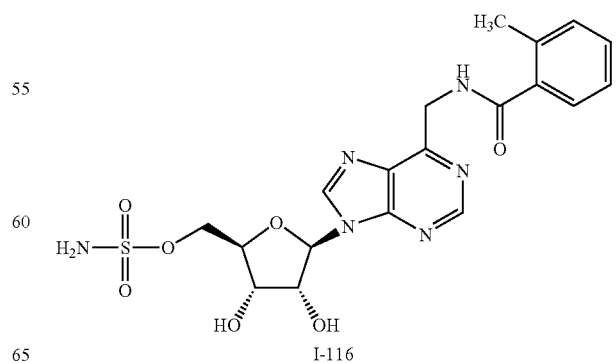
I-116

TABLE 1-continued
E1 activating enzyme inhibitors
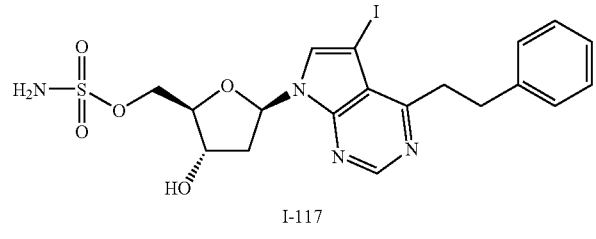
I-117
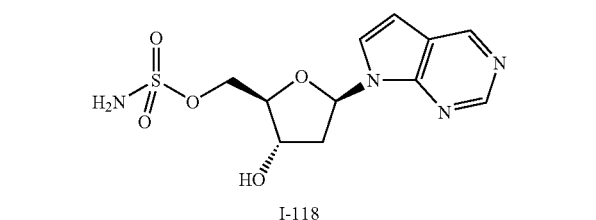
I-118
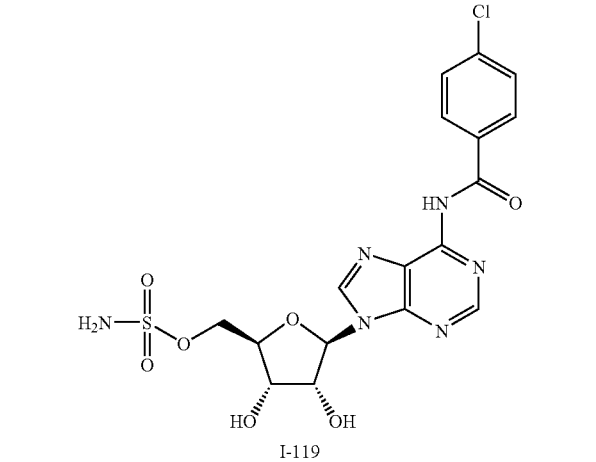
I-119
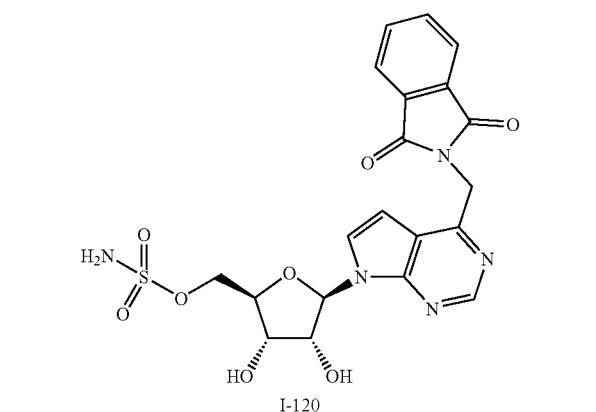
I-120
TABLE 1-continued
E1 activating enzyme inhibitors
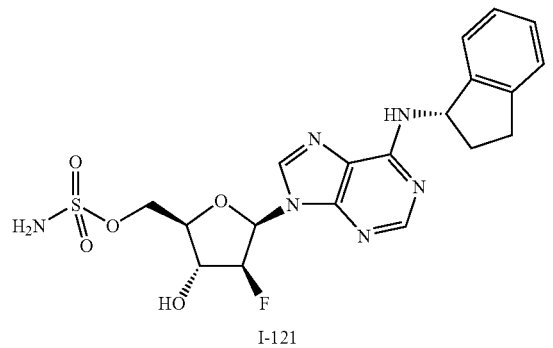
I-121
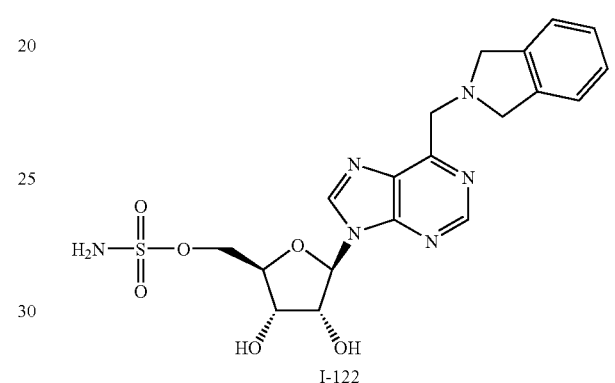
I-122
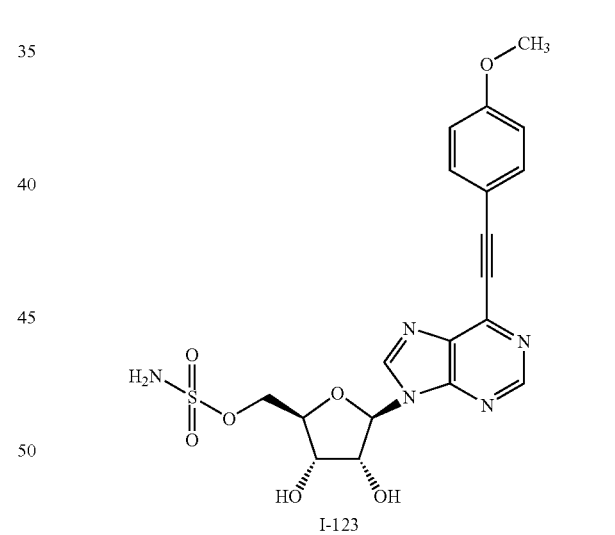
I-123
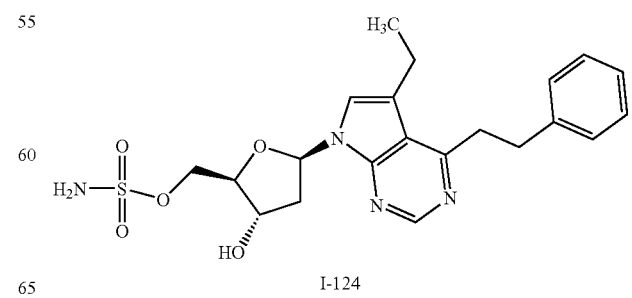
I-124

TABLE 1-continued
E1 activating enzyme inhibitors
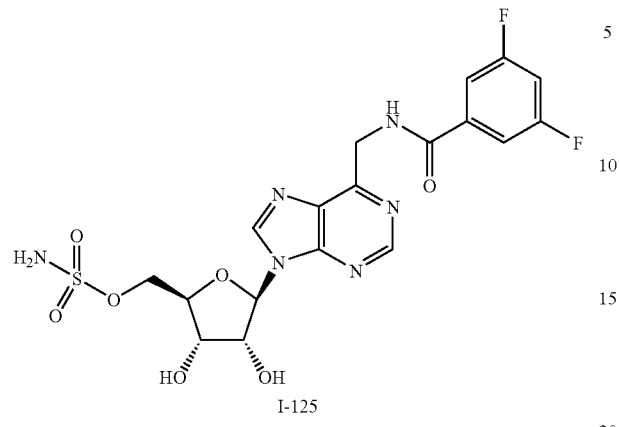
I-125
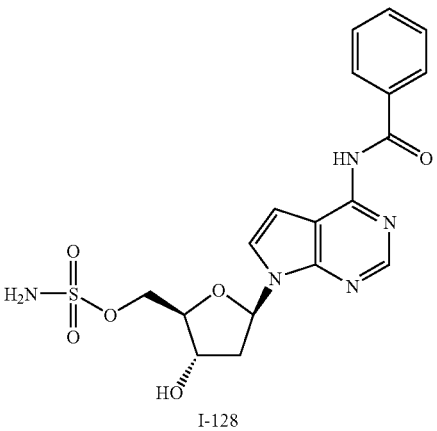
I-128
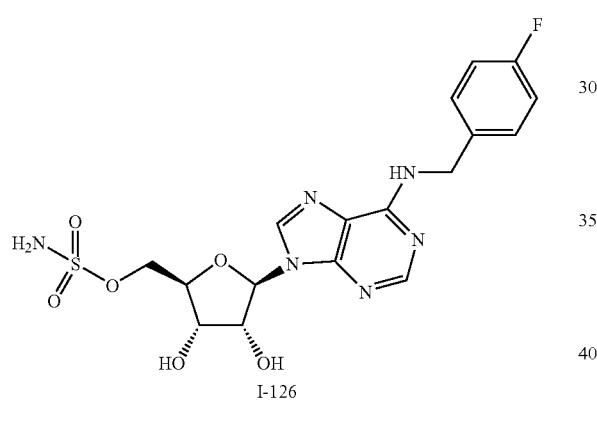
I-126
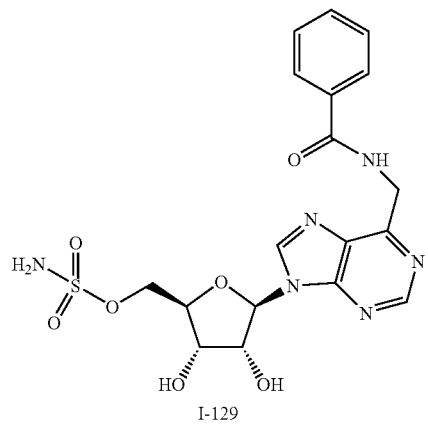
I-129
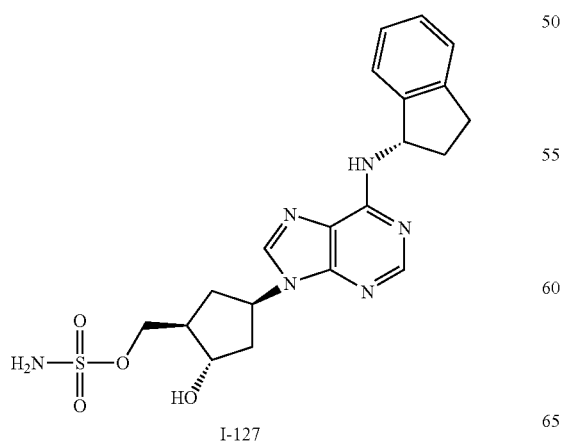
I-127
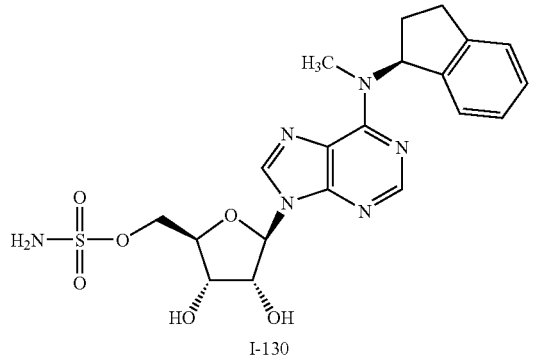
I-130

TABLE 1-continued
E1 activating enzyme inhibitors
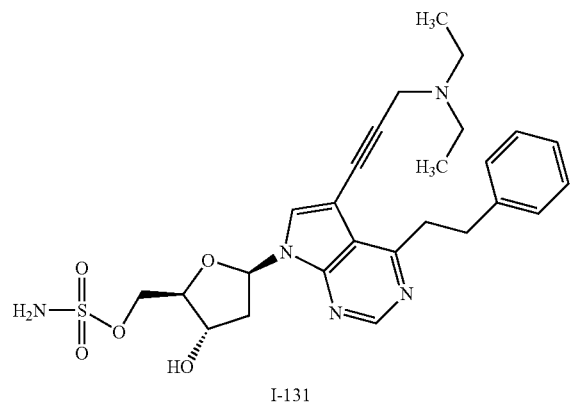
I-131
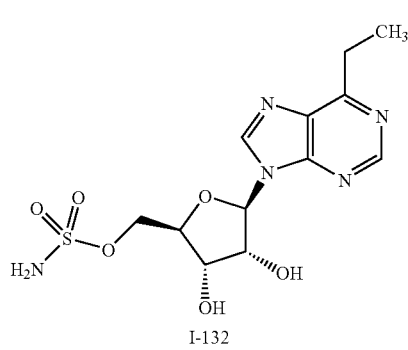
I-132
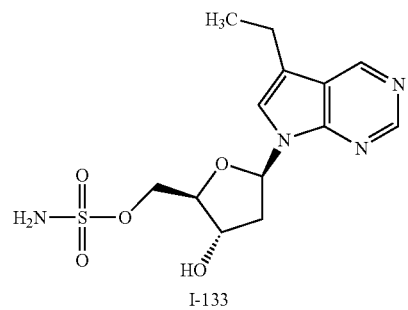
I-133
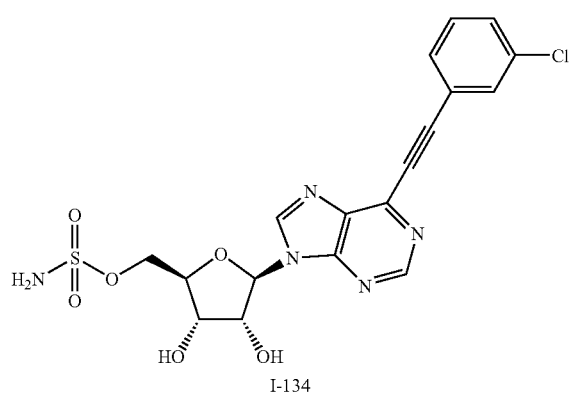
I-134
TABLE 1-continued
E1 activating enzyme inhibitors
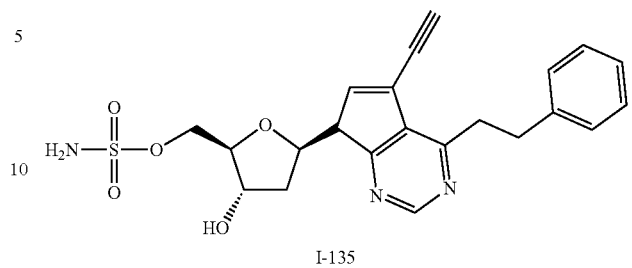
I-135
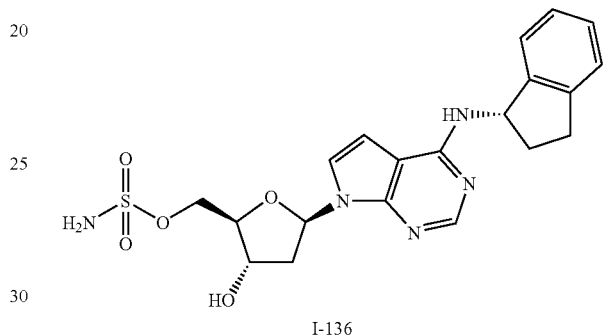
I-136
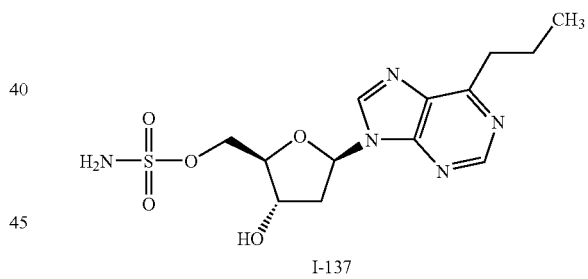
I-137
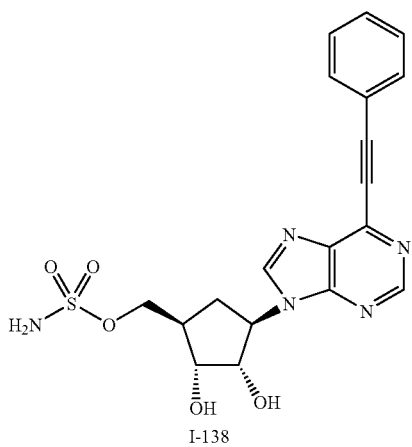
I-138

TABLE 1-continued

E1 activating enzyme inhibitors

I-139

I-140

I-141

I-142

I-143

I-144

I-145

I-146

TABLE 1-continued

E1 activating enzyme inhibitors

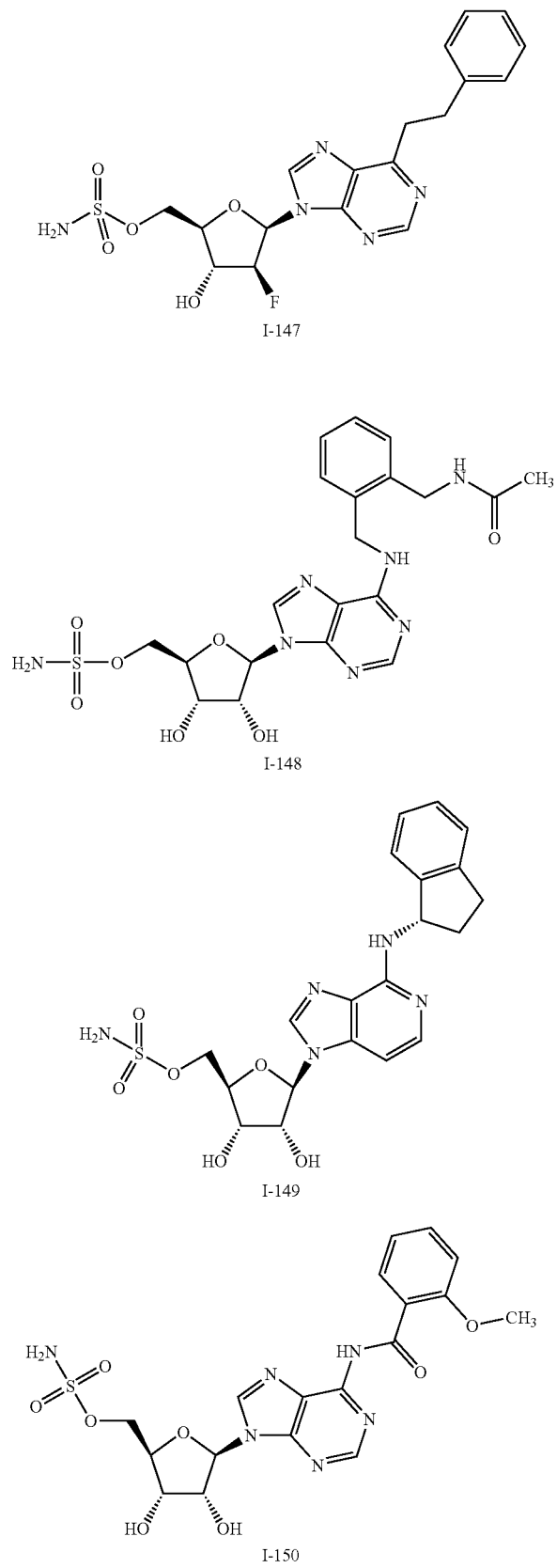

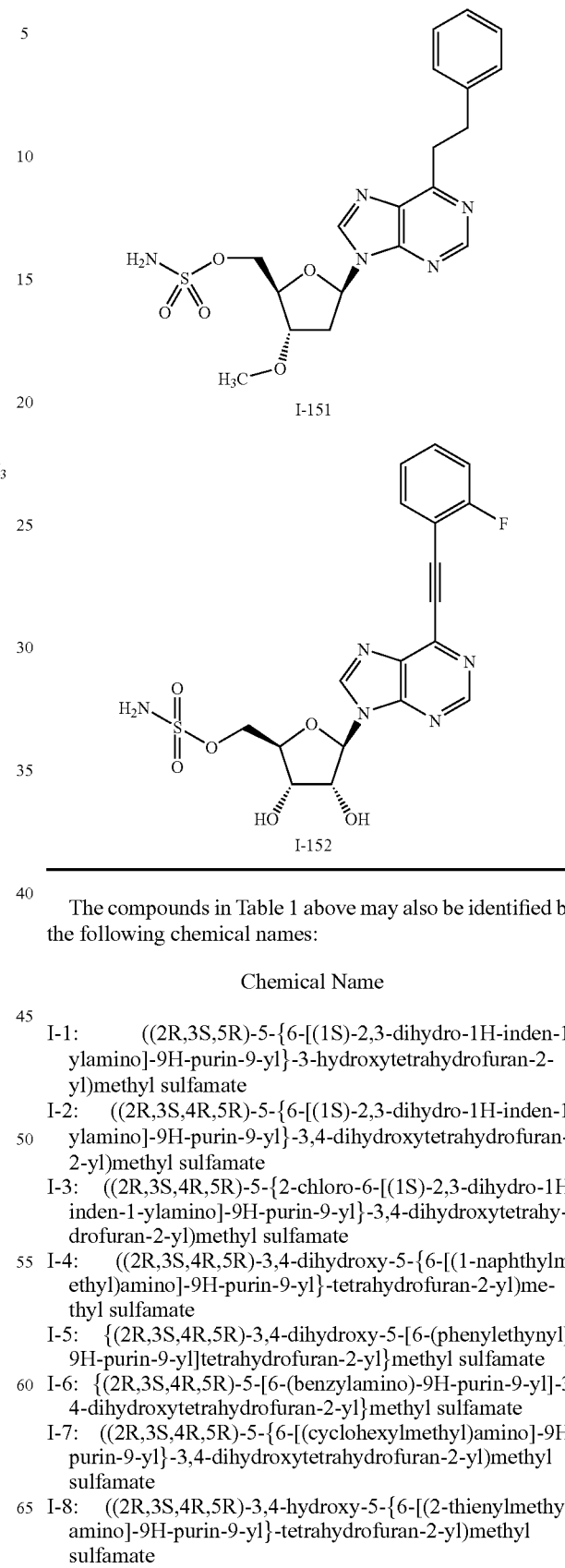

The compounds in Table 1 above may also be identified by the following chemical names:

Chemical Name

I-1: ((2R,3S,5R)-5-{6-[(1S)-2,3-dihydro-1H-inden-1-ylamino]-9H-purin-9-yl}-3-hydroxytetrahydrofuran-2-yl)methyl sulfamate I-2: ((2R,3S,4R,5R)-5-{6-[(1S)-2,3-dihydro-1H-inden-1-ylamino]-9H-purin-9-yl}-3,4-dihydroxytetrahydrofuran-2-yl)methyl sulfamate I-3: ((2R,3S,4R,5R)-5-{2-chloro-6-[(1S)-2,3-dihydro-1H-inden-1-ylamino]-9H-purin-9-yl}-3,4-dihydroxytetrahydrofuran-2-yl)methyl sulfamate I-4: ((2R,3S,4R,5R)-3,4-dihydroxy-5-{6-[(1-naphthylmethyl)amino]-9H-purin-9-yl}-tetrahydrofuran-2-yl)methyl sulfamate I-5: {(2R,3S,4R,5R)-3,4-dihydroxy-5-[6-(phenylethynyl)-9H-purin-9-yl]tetrahydrofuran-2-yl}methyl sulfamate I-6: {(2R,3S,4R,5R)-5-[6-(benzylamino)-9H-purin-9-yl]-3,4-dihydroxytetrahydrofuran-2-yl}methyl sulfamate I-7: ((2R,3S,4R,5R)-5-{6-[(cyclohexylmethyl)amino]-9H-purin-9-yl}-3,4-dihydroxytetrahydrofuran-2-yl)methyl sulfamate I-8: ((2R,3S,4R,5R)-3,4-hydroxy-5-{6-[(2-thienylmethyl)amino]-9H-purin-9-yl}-tetrahydrofuran-2-yl)methyl sulfamate I-9: ((2R,3S,4R,5R)-5-{4-[(1S)-2,3-dihydro-1H-inden-1-ylamino]-7H-pyrrolo[2,3-d]pyrimidin-7-yl}-3,4-dihydroxytetrahydrofuran-2-yl)methyl sulfamate I-10: ((2R,3S,4R,5R)-5-{6-[(4-chlorobenzyl)amino]-9H-purin-9-yl}-3,4-dihydroxytetrahydrofuran-2-yl)methyl sulfamate I-11: ((2R,3S,4R,5R)-3,4-dihydroxy-5-{6-[(3-methoxybenzyl)amino]-9H-purin-9-yl}-tetrahydrofuran-2-yl)methyl sulfamate I-12: {(2R,3S,4R,5R)-5-[6-(benzoylamino)-9H-purin-9-yl]-3,4-dihydroxytetrahydrofuran-2-yl}methyl sulfamate I-13: N-{[(2R,3S,4R,5R)-3,4-dihydroxy-5-(6-{[(1R,2S)-2-hydroxy-2,3-dihydro-1H-inden-1-yl]amino}-9H-purin-9-yl)tetrahydrofuran-2-yl]methyl}sulfamide I-14: [(2R,3S,4R,5R)-3,4-dihydroxy-5-(6-{[(1R,2S)-2-hydroxy-2,3-dihydro-1H-inden-1-yl]amino}-9H-purin-9-yl)tetrahydrofuran-2-yl]methyl sulfamate I-15: N-[((2R,3S,4R,5R)-5-{6-[(1S)-2,3-dihydro-1H-inden-1-ylamino]-9H-purin-9-yl}-3,4-dihydroxytetrahydrofuran-2-yl)methyl]sulfamide I-16: ((2R,3S,4R,5R)-5-{6-[(4-chlorophenyl)amino]-9H-purin-9-yl}-3,4-dihydroxytetrahydrofuran-2-yl)methyl sulfamate I-17: ((2R,3S,4R,5R)-3,4-dihydroxy-5-{6-[(2-phenylethyl)amino]-9H-purin-9-yl}-tetrahydrofuran-2-yl)methyl sulfamate I-18: ((2R,3S,4R,5R)-5-{2-amino-6-[(1S)-2,3-dihydro-1H-inden-1-ylamino]-9H-purin-9-yl}-3,4-dihydroxytetrahydrofuran-2-yl)methyl sulfamate I-19: N-({(2R,3S,4R,5R)-5-[6-(benzylamino)-9H-purin-9-yl]-3,4-dihydroxytetrahydrofuran-2-yl}methyl)sulfamide I-20: N-{[(2R,3S,4R,5R)-3,4-dihydroxy-5-(6-{[(1S)-2-hydroxy-1-phenylethyl]amino}-9H-purin-9-yl)tetrahydrofuran-2-yl]methyl}sulfamide I-21: ((2R,3S,4R,5R)-3,4-dihydroxy-5-{6-[(2-methoxyethyl)amino]-9H-purin-9-yl}-tetrahydrofuran-2-yl)methyl sulfamate I-22: [(2R,3S,4R,5R)-3,4-dihydroxy-5-(6-{[(5-methylpyrazin-2-yl)methyl]amino}-9H-purin-9-yl)tetrahydrofuran-2-yl]methyl sulfamate I-23: [(2R,3S,4R,5R)-3,4-dihydroxy-5-(6-{[(1S)-2-hydroxy-1-phenylethyl]amino}-9H-purin-9-yl)tetrahydrofuran-2-yl]methyl sulfamate I-24: [(2R,3S,4R,5R)-3,4-dihydroxy-5-(6-{[(1R)-2-hydroxy-1-phenylethyl]amino}-9H-purin-9-yl)tetrahydrofuran-2-yl]methyl sulfamate I-25: ((2R,3S,4R,5R)-3,4-dihydroxy-5-{(6-[(2-morpholin-4-ylethyl)amino]-9H-purin-9-yl}tetrahydrofuran-2-yl)methyl sulfamate I-26: ((2R,3S,4R,5R)-3,4-dihydroxy-5-{6-[(piperidin-4-ylmethyl)amino]-9H-purin-9-yl}-tetrahydrofuran-2-yl)methyl sulfamate I-27: ((2R,3S,4R,5R)-3,4-dihydroxy-5-{6-[(2-methoxybenzyl)amino]-9H-purin-9-yl}-tetrahydrofuran-2-yl)methyl sulfamate I-28: [(2R,3S,4R,5R)-5-(6-{[2-(4-benzylpiperazin-1-yl)ethyl]amino}-9H-purin-9-yl)-3,4-dihydroxytetrahydrofuran-2-yl]methyl sulfamate I-29: ((1R,2R,3S,4R)-4-{6-[(1S)-2,3-dihydro-1H-inden-1-ylamino]-9H-purin-9-yl}-2,3-dihydroxycyclopentyl)methyl sulfamate I-30: [(2R,3S,4R,5R)-3,4-dihydroxy-5-(6-{[4-(trifluoromethoxy)benzyl]amino}-9H-purin-9-yl)tetrahydrofuran-2-yl]methyl sulfamate I-31: 2-((2R,3S,4R,5R)-5-{6-[(1S)-2,3-dihydro-1H-inden-1-ylamino]-9H-purin-9-yl}-3,4-dihydroxytetrahydrofuran-2-yl)ethanesulfonamide I-32: 2-[(2R,3S,4R,5R)-3,4-dihydroxy-5-(6-{[(1R,2S)-2-hydroxy-2,3-dihydro-1H-inden-1-yl]amino}-9H-purin-9-yl)tetrahydrofuran-2-yl]ethanesulfonamide I-33: N-[((2R,3S,4R,5R)-3,4-dihydroxy-5-{6-[(3-methoxybenzyl)amino]-9H-purin-9-yl}-tetrahydrofuran-2-yl)methyl]sulfamide I-34: N-[((2R,3S,4R,5R)-3,4-dihydroxy-5-{6-[(2-phenoxyethyl)amino]-9H-purin-9-yl}-tetrahydrofuran-2-yl)methyl]sulfamide I-35: N-[((2R,3S,4R,5R)-3,4-dihydroxy-5-{6-[(2-methoxyethyl)amino]-9H-purin-9-yl}-tetrahydrofuran-2-yl)methyl]sulfamide I-36: N-{[(2R,3S,4R,5R)-3,4-dihydroxy-5-(6-{[(5-methylpyrazin-2-yl)methyl]amino}-9H-purin-9-yl)tetrahydrofuran-2-yl]methyl}sulfamide I-37: N-[((2R,3S,4R,5R)-3,4-dihydroxy-5-{6-[(2-thienylmethyl)amino]-9H-purin-9-yl}-tetrahydrofuran-2-yl)methyl]sulfamide I-38: N-{[(2R,3S,4R,5R)-3,4-dihydroxy-5-(6-{[(1-methyl-1H-pyrazol-4-yl)methyl]-amino}-9H-purin-9-yl)tetrahydrofuran-2-yl]methyl}sulfamide I-39: N-[((2R,3S,4R,5R)-5-{6-[(1,3-benzodioxol-5-ylmethyl)amino]-9H-purin-9-yl}-3,4-dihydroxytetrahydrofuran-2-yl)methyl]sulfamide I-40: N-[((2R,3S,4R,5R)-3,4-dihydroxy-5-{6-[(4-methoxybenzyl)sulfanyl]-9H-purin-9-yl}tetrahydrofuran-2-yl)methyl]sulfamide I-41: {(2R,3S,4R,5R)-5-[6-(4-fluorobenzyl)-9H-purin-9-yl]-3,4-dihydroxytetrahydrofuran-2-yl}methyl sulfamate I-42: N-[((2R,3S,4R,5R)-5-{6-[(2,2-diphenylethyl)amino]-9H-purin-9-yl}-3,4-dihydroxytetrahydrofuran-2-yl)methyl]sulfamide I-43: N-[((2R,3S,4R,5R)-3,4-dihydroxy-5-{6-[(1-naphthylmethyl)amino]-9H-purin-9-yl}-tetrahydrofuran-2-yl)methyl]sulfamide I-44: N-[((2R,3S,4R,5R)-5-{6-[(1-benzothien-3-ylmethyl)amino]-9H-purin-9-yl}-3,4-dihydroxytetrahydrofuran-2-yl)methyl]sulfamide I-45: N-{[(2R,3S,4R,5R)-3,4-dihydroxy-5-(6-{[(1R)-2-hydroxy-1-phenylethyl]amino}-9H-purin-9-yl)tetrahydrofuran-2-yl]methyl}sulfamide I-46: N-[((2R,3S,4R,5R)-5-{6-[(1R)-2,3-dihydro-1H-inden-1-ylamino]-9H-purin-9-yl}-3,4-dihydroxytetrahydrofuran-2-yl)methyl]sulfamide I-47: ((2R,3S,4R,5R)-5-{6-[(4-fluorobenzoyl)amino]-9H-purin-9-yl}-3,4-dihydroxytetrahydrofuran-2-yl)methyl sulfamate I-48: ((2R,3S,4R,5R)-3,4-dihydroxy-5-{6-[(phenylsulfonyl)amino]-9H-purin-9-yl}-tetrahydrofuran-2-yl)methyl sulfamate I-49: 2-((2R,3S,4R,5R)-5-{6-[(3,5-difluorobenzyl)amino]-9H-purin-9-yl}-3,4-dihydroxytetrahydrofuran-2-yl)ethanesulfonamide I-50: 2-((2R,3S,4R,5R)-5-{[(4-chlorobenzyl)amino]-9H-purin-9-yl}-3,4-dihydroxytetrahydrofuran-2-yl)ethanesulfonamide I-51: 2-((2R,3S,4R,5R)-5-{6-[(diphenylmethyl)amino]-9H-purin-9-yl}-3,4-dihydroxytetrahydrofuran-2-yl)ethanesulfonamide I-52: 2-{(2R,3S,4R,5R)-5-[6-(bicyclo[2.2.1]hept-2-ylamino)-9H-purin-9-yl]-3,4-dihydroxytetrahydrofuran-2-yl}ethanesulfonamide I-53: ((2S,4R,5R)-5-{6-[(1S)-2,3-dihydro-1H-inden-1-ylamino]-9H-purin-9-yl}-4-hydroxytetrahydrofuran-2-yl)methyl sulfamate I-54: ((2R,3R,4R,5R)-5-{6-[(1S)-2,3-dihydro-1H-inden-1-ylamino]-9H-purin-9-yl}-3-hydroxy-4-methoxytetrahydrofuran-2-yl)methyl sulfamate I-55: ((2R,3R,4R,5R)-5-(6-((S)-2,3-dihydro-1H-inden-1-ylamino)-9H-purin-9-yl)-3,4-dihydroxy-4-methyl-tetrahydrofuran-2-yl)methyl sulfamate I-56: ((2R,3S,4R,5R)-3,4-Dihydroxy-5-{6-[3-(1H-pyrazol-1-yl)phenyl]-9H-purin-9-yl}-tetrahydrofuran-2-yl)methyl sulfamate I-57: ((2R,3S,4R,5R)-3,4-Dihydroxy-5-{6-[3-(trifluoromethyl)phenyl]-9H-purin-9-yl}-tetrahydrofuran-2-yl)methyl sulfamate I-58: (R)-1-((2S,3S,4R,5R)-5-(6-((S)-2,3-dihydro-1H-inden-1-ylamino)-9H-purin-9-yl)-3,4-dihydroxy-tetrahydrofuran-2-yl)ethyl sulfamate I-59: {(2R,3S,4R,5R)-5-[6-phenethyl-9H-purin-9-yl]-3,4-dihydroxytetrahydrofuran-2-yl}methyl sulfamate I-60: (2R,3R,4S,5R)-4-fluoro-3-hydroxy-5-[6-((S)-indan-1-ylamino)-purin-9-yl]-tetrahydro-furan-2-ylmethyl-sulfamate I-61: ((2R,3R,4S,5R)-5-{6-[(1S)-2,3-dihydro-1H-inden-1-ylamino]-9H-purin-9-yl}-3-hydroxy-4-methoxytetrahydrofuran-2-yl)methyl sulfamate I-62: [(2R,3S,4R,5R)-3,4-Dihydroxy-5-(6-phenyl-9H-purin-9-yl)tetrahydro furan-2-yl]-methyl sulfamate I-63: ((2R,3S,4R,5R)-5-{6-[(1,3-benzodioxol-5-ylmethyl)amino]-9H-purin-9-yl}-3,4-dihydroxytetrahydrofuran-2-yl)methyl-sulfamate I-64: ((2R,3S,4R,5R)-3,4-dihydroxy-5-{6-[(2-pyrrolidin-1-ylethyl)amino]-9H-purin-9-yl}tetrahydrofuran-2-yl)methyl-sulfamate I-65: ((2R,3S,4R,5R)-5-{6-[(4-fluorobenzyl)amino]-9H-purin-9-yl}-3,4-dihydroxytetrahydrofuran-2-yl)methyl-sulfamate I-66: {(2R,3S,4R,5R)-5-[6-(3,5-Dimethylisoxazol-4-yl)-9H-purin-9-yl]-3,4-dihydroxytetrahydrofuran-2-yl}methyl sulfamate I-67: ((2R,3S,4S,5R)-5-{6-[(1S)-2,3-Dihydro-1H-inden-1-ylamino]-9H-purin-9-yl}-3,4-dihydroxytetrahydrofuran-2-yl)methyl sulfamate I-68: N-{[(2R,3S,4R,5R)-3,4-dihydroxy-5-(6-{[(2R)-2-hydroxy-2-(3-hydroxyphenyl)ethyl]amino}-9H-purin-9-yl)tetrahydrofuran-2-yl]methyl}-sulfamide I-69: ((2R,3S,4R,5R)-3,4-dihydroxy-5-{6-[(E)-2-phenylvinyl]-9H-purin-9-yl}tetrahydrofuran-2-yl)methyl sulfamate I-70: [(2R,3R,4S,5R)-5-(6-ethyl-9H-purin-9-yl)-4-fluoro-3-hydroxytetrahydrofuran-2-yl]methyl sulfamate I-71: ((2R,3S,4R,5R)-5-{6-[(2-chlorophenyl)ethynyl]-9H-purin-9-yl}-3,4-dihydroxytetrahydrofuran-2-yl)methyl sulfamate I-72: N-({(2R,3R,4S,5R)-5-[6-(2,3-dihydro-1H-inden-1-ylamino)-9H-purin-9-yl]-4-fluoro-3-hydroxytetrahydrofuran-2-yl}methyl)sulfamide I-73: [(2R,3R,4S,5R)-3-hydroxy-5-(6-isobutyl-9H-purin-9-yl)-4-methoxytetrahydrofuran-2-yl]methyl sulfamate I-74: {(2R,3S,4R,5R)-5-[6-(benzylamino)-9H-purin-9-yl]-4-hydroxy-3-methoxytetrahydrofuran-2-yl}methyl sulfamate I-75: {(2R,3R,4R,5R)-5-[enzylamino]-9H-purin-9-yl]-4-fluoro-3-hydroxytetrahydrofuran-2-yl}methyl sulfamate I-76: N-({(2R,3R,4R,5R)-5-[6-(2,3-dihydro-1H-inden-1-ylamino)-9H-purin-9-yl]-3,4-dihydroxy-4-methyltetrahydrofuran-2-yl}methyl)sulfamide I-77: 2-((2R,3S,4R,5R)-3,4-dihydroxy-5-{6-[(2-methoxy-2,3-dihydro-1H-inden-1-yl)amino]-9H-purin-9-yl}tetrahydrofuran-2-yl)ethanesulfonamide I-78: [(2R,3S,4R,5R)-5-(2-chloro-6-isobutyl-9H-purin-9-yl)-3,4-dihydroxytetrahydrofuran-2-yl]methyl sulfamate I-79: {(1R,2R,3S,4R)-2,3-dihydroxy-4-[6-(2-phenylethyl)-9H-purin-9-yl]cyclopentyl}-methyl sulfamate I-80: [(1R,2S,4R)-2-hydroxy-4-(6-methyl-9H-purin-9-yl)cyclopentyl]methyl sulfamate I-81: 2-[(1R,2S,4R)-2-hydroxy-4-(6-isobutyl-9H-purin-9-yl)cyclopentyl]-ethanesulfonamide I-82: 2-[(1R,2S,4R)-2-hydroxy-4-(6-isobutyl-9H-purin-9-yl)cyclopentyl]-ethanesulfonamide I-83: N-({(1R,2R,3S,4R)-4-[6-(2,3-dihydro-1H-inden-1-ylamino)-9H-purin-9-yl]-2,3-dihydroxy-3-methylcyclopentyl}methyl)sulfamide I-84: {(2R,3S,4R,5R)-3,4-dihydroxy-5-[4-(2-phenylethyl)-7H-pyrrolo[2,3-d]pyrimidin-7-yl]tetrahydrofuran-2-yl}methyl sulfamate I-85: {(1R,2R,3S,4R)-2,3-dihydroxy-3-methyl-4-[6-(2-phenylethyl)-9H-purin-9-yl]-cyclopentyl}methyl sulfamate I-86: N-({(2R,3S,4S,5R)-5-[4-(2,3-dihydro-1H-inden-1-ylamino)-7H-pyrrolo[2,3-d]pyrimidin-7-yl]-3,4-dihydroxytetrahydrofuran-2-yl}methyl)sulfamide I-87: N-[((1R,2R,3S,4R)-4-{6-[(1S)-2,3-dihydro-1H-inden-1-ylamino]-9H-purin-9-yl}-2,3-dihydroxycyclopentyl)methyl]sulfamide I-88: ((2R,3S,4R,5R)-5-{6-[(3-fluorophenyl)ethynyl]-9H-purin-9-yl}-3,4-dihydroxytetrahydrofuran-2-yl)methyl sulfamate I-89: ((2R,3S,4R,5R)-3,4-dihydroxy-5-{6-[(2-trifluoromethylphenyl)ethynyl]-9H-purin-9-yl}tetrahydrofuran-2-yl)methyl sulfamate I-90: ((2R,3S,4R,5R)-3,4-dihydroxy-5-{6-[(2-methoxyphenyl)ethynyl]-9H-purin-9-yl}-tetrahydrofuran-2-yl)methyl sulfamate I-91: ((2R,3S,4R,5R)-5-{6-[(4-chlorophenyl)ethynyl]-9H-purin-9-yl}-3,4-dihydroxytetrahydrofuran-2-yl)methyl sulfamate I-92: {(2R,3S,5R)-3-hydroxy-5-[6-(phenylethynyl)-9H-purin-9-yl]tetrahydrofuran-2-yl}-methyl sulfamate I-93: [(2R,3S,5R)-3-hydroxy-5-(6-phenyl-9H-purin-9-yl)tetrahydrofuran-2-yl]methyl sulfamate I-94: {(2R,3S,4R,5R)-5-[6-(2-furyl)-9H-purin-9-yl]-3,4-dihydroxytetrahydrofuran-2-yl}-methyl sulfamate I-95: {(2R,3S,4R,5R)-5-[6-(cyclopropylethynyl)-9H-purin-9-yl]-3,4-dihydroxytetrahydrofuran-2-yl}methyl sulfamate I-96: [(1R,2R,3S,4R)-2,3-dihydroxy-4-(6-propyl-9H-purin-9-yl)cyclopentyl]methyl sulfamate I-97: [(1R,2R,3S,4R)-2,3-dihydroxy-4-(6-isobutyl-9H-purin-9-yl)cyclopentyl]methyl sulfamate I-98: [(2R,3S,4R,5R)-3,4-dihydroxy-5-(6-isobutyl-9H-purin-9-yl)tetrahydrofuran-2-yl]-methyl sulfamate I-99: [(2R,3R,4S,5R)-5-(6-chloro-9H-purin-9-yl)-3-hydroxy-4-methoxytetrahydrofuran-2-yl]methyl sulfamate I-100: 2-((2R,3S,4R,5R)-5-{6-[(3,3-dimethyl-2,3-dihydro-1H-inden-1-yl)amino]-9H-purin-9-yl}-3,4-dihydroxytetrahydrofuran-2-yl)ethanesulfonamide I-101: ((2R,3S,4R,5R)-5-{6-[(4-bromophenyl)ethynyl]-9H-purin-9-yl}-3,4-dihydroxytetrahydrofuran-2-yl)methyl sulfamate I-102: {(2R,3S,5R)-5-[6-(benzylamino)-9H-purin-9-yl]-3-hydroxytetrahydrofuran-2-yl}methyl sulfamate I-103: ((2R,3S,4R,5R)-5-{6-[(3-bromophenyl)ethynyl]-9H-purin-9-yl}-3,4-dihydroxytetrahydrofuran-2-yl)methyl sulfamate I-104: [(2R,3S,4R,5R)-3,4-dihydroxy-5-(6-methyl-9H-purin-9-yl)tetrahydrofuran-2-yl]methyl sulfamate I-105: [(2R,3S,4R,5R)-3,4-dihydroxy-5-(6-{[(pyridin-3-ylcarbonyl)amino]methyl}-9H-purin-9-yl)tetrahydrofuran-2-yl]methyl sulfamate I-106: [(2R,3S,5R)-5-(4-chloro-1H-pyrrolo[3,2-c]pyridin-1-yl)-3-hydroxytetrahydrofuran-2-yl]methyl sulfamate I-107: ((2R,3S,4R,5R)-5-{6-[(4-fluorophenyl)ethynyl]-9H-purin-9-yl}-3,4-dihydroxytetrahydrofuran-2-yl)methyl sulfamate I-108: ((2R,3S,4R,5R)-5-{6-[(anilinocarbonyl)amino]-9H-purin-9-yl}-3,4-dihydroxytetrahydrofuran-2-yl)methyl sulfamate I-109: {(1R,2S,4R)-2-hydroxy-4-[6-(phenylethynyl)-9H-purin-9-yl]cyclopentyl}methyl sulfamate I-110: ((2R,3S,4R,5R)-5-{6-[(2,4-difluorophenyl)ethynyl]-9H-purin-9-yl}-3,4-dihydroxytetrahydrofuran-2-yl)methyl sulfamate I-111: {(2R,3S,4R,5R)-5-[6-(2,3-dihydro-1H-inden-2-ylmethyl)-9H-purin-9-yl]-3,4-dihydroxytetrahydrofuran-2-yl}methyl sulfamate I-112: ((2R,3S,4R,5R)-5-{6-[(4-bromobenzoyl)amino]-9H-purin-9-yl}-3,4-dihydroxytetrahydrofuran-2-yl)methyl sulfamate I-113: [(2R,3S,4R,5R)-3,4-dihydroxy-5-(6-{[2-(trifluoromethyl)phenyl]ethynyl}-9H-purin-9-yl)tetrahydrofuran-2-yl]methyl sulfamate I-114: [(2R,3S,4R,5R)-5-(6-cyclopropyl-9H-purin-9-yl)-3,4-dihydroxytetrahydrofuran-2-yl]methyl sulfamate I-115: N-({(2R,3S,4R,5R)-3,4-dihydroxy-5-[6-(phenylethynyl)-9H-purin-9-yl]tetrahydrofuran-2-yl}methyl)sulfamide I-116: [(2R,3S,4R,5R)-3,4-dihydroxy-5-{6-[(2-methoxybenzoyl)amino]methyl}-9H-purin-9-yl)tetrahydrofuran-2-yl]methyl sulfamate I-117: [(2R,3S,5R)-3-hydroxy-5-[5-iodo-4-(2-phenylethyl)-7H-pyrrolo[2,3-d]pyrimidin-7-yl]tetrahydrofuran-2-yl]methyl sulfamate I-118: [(2R,3S,5R)-3-hydroxy-5-(7H-pyrrolo[2,3-d]pyrimidin-7-yl)tetrahydrofuran-2-yl]methyl sulfamate I-119: ((2R,3S,4R,5R)-5-{6-[(4-chlorobenzoyl)amino]-9H-purin-9-yl}-3,4-dihydroxytetrahydrofuran-2-yl)methyl sulfamate I-120: ((2R,3S,4R,5R)-5-{6-[(1,3-dioxo-1,3-dihydro-2H-isoindol-2-yl)methyl]-9H-purin-9-yl}-3,4-dihydroxytetrahydrofuran-2-yl)methyl sulfamate I-121: ((2R,3R,4S,5R)-5-{6-[(1S)-2,3-dihydro-1H-inden-1-ylamino]-9H-purin-9-yl}-4-fluoro-3-hydroxytetrahydrofuran-2-yl)methyl sulfamate I-122: {(2R,3S,4R,5R)-5-[6-(1,3-dihydro-2H-isoindol-2-ylmethyl)-9H-purin-9-yl]-3,4-dihydroxytetrahydrofuran-2-yl}methyl sulfamate I-123: ((2R,3S,4R,5R)-3,4-dihydroxy-5-{6-[(4-methoxyphenyl)ethynyl]-9H-purin-9-yl}tetrahydrofuran-2-yl)methyl sulfamate I-124: {(2R,3S,5R)-5-[5-ethyl-4-(2-phenylethyl)-7H-pyrrolo[2,3-d]pyrimidin-7-yl]-3-hydroxytetrahydrofuran-2-yl}methyl sulfamate I-125: [(2R,3S,4R,5R)-5-(6-{[(3,5-difluorobenzoyl)amino]methyl}-9H-purin-9-yl)-3,4-dihydroxytetrahydrofuran-2-yl]methyl sulfamate I-126: N-[((2R,3S,4R,5R)-5-{6-[(4-fluorobenzyl)amino]-9H-purin-9-yl}-3,4-dihydroxytetrahydrofuran-2-yl)methyl]sulfamide I-127: ((1R,2S,4R)-4-{6-[(1S)-2,3-dihydro-1H-inden-1-ylamino]-9H-purin-9-yl}-2-hydroxycyclopentyl)methyl sulfamate I-128: {(2R,3S,5R)-5-[4-(benzoylamino)-7H-pyrrolo[2,3-d]pyrimidin-7-yl]-3-hydroxytetrahydrofuran-2-yl}methyl sulfamate I-129: ((2R,3S,4R,5R)-5-{6-[(benzoylamino)methyl]-9H-purin-9-yl}-3,4-dihydroxytetrahydrofuran-2-yl)methyl sulfamate I-130: ((2R,3S,4R,5R)-5-{6-[(1S)-2,3-dihydro-1H-inden-1-yl(methyl)amino]-9H-purin-9-yl}-3,4-dihydroxytetrahydrofuran-2-yl)methyl sulfamate I-131: {(2R,3S,5R)-5-[5-[3-(diethylamino)prop-1-yn-1-yl]-4-(2-phenylethyl)-7H-pyrrolo[2,3-d]pyrimidin-7-yl]-3-hydroxytetrahydrofuran-2-yl}methyl sulfamate I-132: [(2R,3S,4R,5R)-5-(6-ethyl-9H-purin-9-yl)-3,4-dihydroxytetrahydrofuran-2-yl]methyl sulfamate I-133: [(2R,3S,5R)-5-(5-ethyl-7H-pyrrolo[2,3-d]pyrimidin-7-yl)-3-hydroxytetrahydrofuran-2-yl]methyl sulfamate I-134: ((2R,3S,4R,5R)-5-{6-[(3-chlorophenyl)ethynyl]-9H-purin-9-yl}-3,4-dihydroxytetrahydrofuran-2-yl)methyl sulfamate I-135: {(2R,3S,5R)-5-[5-ethynyl-4-(2-phenylethyl)-7H-pyrrolo[2,3-d]pyrimidin-7-yl]-3-hydroxytetrahydrofuran-2-yl}methyl sulfamate I-136: ((2R,3S,5R)-5-{4-[(1S)-2,3-dihydro-1H-inden-1-ylamino]-7H-pyrrolo[2,3-d]pyrimidin-7-yl}-3-hydroxytetrahydrofuran-2-yl)methyl sulfamate I-137: {(2R,3S,4R,5R)-3,4-dihydroxy-5-[6-(2-methoxyethyl)-9H-purin-9-yl]tetrahydrofuran-2-yl}methyl sulfamate I-138: {(1R,2R,3S,4R)-2,3-dihydroxy-4-[6-(phenylethynyl)-9H-purin-9-yl]cyclopentyl}methyl sulfamate I-139: ((2R,3S,4R,5R)-5-{4-[(1S)-2,3-dihydro-1H-inden-1-ylamino]-1H-imidazo[4,5-d]pyridazin-1-yl}-3,4-dihydroxytetrahydrofuran-2-yl)methyl sulfamate I-140: ((2R,3S,4R,5R)-5-{6-[(2-bromophenyl)ethynyl]-9H-purin-9-yl}-3,4-dihydroxytetrahydrofuran-2-yl)methyl sulfamate I-141: ((1R,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate I-142: [(2R,3S,5R)-3-hydroxy-5-(1H-pyrrolo[3,2-c]pyridin-1-yl)tetrahydrofuran-2-yl]methyl sulfamate I-143: {(2R,3S,5R)-5-[4-(benzylamino)-1H-pyrrolo[3,2-c]pyridin-1-yl]-3-hydroxytetrahydrofuran-2-yl}methyl sulfamate I-144: [(2R,3S,5R)-3-hydroxy-5-(4-methoxy-7H-pyrrolo[2,3-d]pyrimidin-7-yl)tetrahydrofuran-2-yl]methyl sulfamate I-145: [(2R,3S,4R,5R)-3,4-dihydroxy-5-(6-{[3-(trifluoromethyl)phenyl]ethynyl}-9H-purin-9-yl)tetrahydrofuran-2-yl]methyl sulfamate I-146: ((2R,3S,4R,5R)-5-{6-[(3,5-difluorophenyl)ethynyl]-9H-purin-9-yl}-3,4-dihydroxytetrahydrofuran-2-yl)methyl sulfamate I-147: {(2R,3R,4S,5R)-4-fluoro-3-hydroxy-5-[6-(2-phenylethyl)-9H-purin-9-yl]-tetrahydrofuran-2-yl}methyl sulfamate I-148: {(2R,3S,4R,5R)-5-[6-({2-[(acetylamino)methyl]benzyl}amino)-9H-purin-9-yl]-3,4-dihydroxytetrahydrofuran-2-yl}methyl sulfamate I-149: ((2R,3S,4R,5R)-5-{4-[(1S)-2,3-dihydro-1H-inden-1-ylamino]-1H-imidazo[4,5-c]-pyridin-1-yl}-3,4-dihydroxytetrahydrofuran-2-yl)methyl sulfamate I-150: ((2R,3S,4R,5R)-3,4-dihydroxy-5-{6[(2-methoxybenzoyl)amino]-9H-purin-9-yl}tetrahydrofuran-2-yl)methyl sulfamate I-151: {(2R,3S,5R)-3-methoxy-5-[6-(2-phenylethyl)-9H-purin-9-yl]tetrahydrofuran-2-yl} methyl sulfamate I-152: ((2R,3S,4R,5R)-5-{6-[(2-fluorophenyl)ethynyl]-9H-purin-9-yl}-3,4-dihydroxytetrahydrofuran-2-yl)methyl sulfamate General Synthetic Methodology The compounds of this invention may be prepared by methods known to those skilled in the art for analogous compounds, as illustrated by the general schemes below, and by reference to the preparative examples shown below. In particular, the compounds of the invention may be prepared by various methods known in the art of organic chemistry and nucleoside and nucleotide analogue synthesis in particular. For example, general reviews of the preparation of nucleoside and nucleotide analogues are included in "Chemistry of Nucleosides and Nucleotides," Ed. L. B. Townsend, Plenum Press, 1991; and S. Simons, "Nucleoside Mimetics Their Chemistry and Biological Properties," Gordon and Breach Science Publishers, 2001.

example an amine nucleophile, is known and yields nucleoside analogues derivatized at the 6-position. Procedures have been adapted from those described by Golding (J. Chem. Soc. Perkin Trans 1, 1997, 185). For example, compound ii is produced by treatment with a primary amine, in the presence of a tertiary amine such as triethylamine and an appropriate solvent such as EtOH or water under conditions such as reflux or microwave (b). Compound iv may be produced by treatment of resulting compound ii with chlorosulfonamide in an appropriate solvent such as acetonitrile and a base such as triethylamine in an appropriate solvent such as N,N-dimethylformamide (c) followed by treatment with an acid, such as trifluoroacetic acid in an appropriate solvent such as water (d).

Scheme 1:

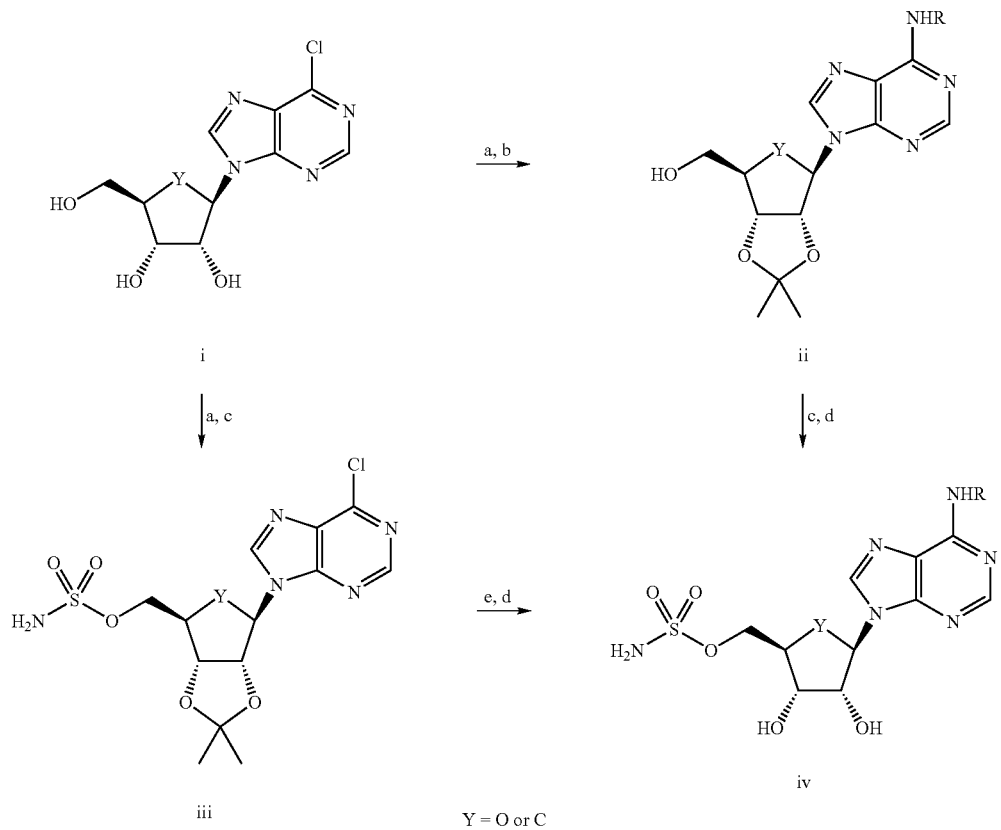

Reagents and conditions:
a: 2,2-Dimethoxypropane, pTsOH, Acetone;
b: amine, TEA, EtOH, reflux or microwave irradiation;
c: H$_2$NSO$_2$Cl, TEA, DMF, AcCN;
d: TFA-water;
e: Quinuclidine, EtOH, then amine.

Y = O or C

Scheme 1 above shows a general route to compounds of formula (IV-A). Starting materials for the syntheses are either available from commercial sources, are known, or may be prepared by routine techniques known in the art. Compound i (Y=O: commercially available; Y=C: Shealy, Y. F.; Clayton, J. D. *J. Am. Chem. Soc.* 1969, 91, 3075-308) is converted to compound ii or iii by treatment with 2,2-dimethoxypropane in the presence of an acid such as para-toluenesulfonic acid in an appropriate solvent, such as acetone (a). It will be understood that alternative protecting group strategies facilitating the derivatization of the primary alcohol (5'-position) of nucleosides may be utilized, and are known to those of ordinary skill in the art and taught by Greene 'Protective Groups in Organic Synthesis", John Wiley and Sons, 3$^{rd}$ Edition, 1999.

Following introduction of the protecting group, displacement of a leaving group from the 6-position of a purine, by for Alternatively, sulfamoylation can be effected prior to reaction with an amine nucleophile. Thus, following introduction of the protecting group, sulfamoylation of the unprotected alcohol can be achieved by reaction with chlorosulfonamide in an appropriate solvent such as acetonitrile and a base such as triethylamine in an appropriate solvent such as N,N-dimethylformamide (c) to afford compound iii. Compound iv may then be produced by addition of a primary amine to a solution of compound iii in an appropriate solvent, such as ethanol, in the presence of an appropriate base, such as quinuclidine (e), followed by treatment with an with an acid, such as trifluoroacetic acid and an appropriate solvent such as water (d).

Compounds of formula (I-A) wherein $R^1$ is an amide or sulfonamide substituent can be prepared by reaction of the 6-amino group of a suitably protected adenosine derivative with an appropriately activated carboxylic acid or sulfonyl chloride.

Some embodiments involve derivatization of the ribose moiety, in addition to sulfamoylation at the 5'-position. Examples include 2'-C-branched ribonucleosides, deoxy derivatives, fluoro-deoxy derivatives and O-alkylated compounds. Such compounds can be prepared by coupling a suitably protected ribose derivative to a purine base. Methods for effecting this coupling reaction are known to those of ordinary skill in the art, for example the method taught by Vorbruggen H. et. al. "Handbook of Nucleoside Synthesis", John Wiley and Sons, 2001. Suitable protecting groups are also known to those of ordinary skill in the art, and may be found described for example, in Greene "Protective Groups in Organic Synthesis", John Wiley and Sons, 3$^{rd}$ Edition, 1999. In a particular embodiment, 2'-C-methylated derivatives can be prepared following the procedures described in Franchetti (J. Med. Chem. 1998, 41, 1708) and Wolfe (J. Org. Chem. 1997, 62, 1754).

Some embodiments involve derivatization of the purine moiety, in addition to sulfamoylation at the 5'-position. Examples include rings A-ii, A-iii, A-iv, A-v, A-vi, and A-vii. Such compounds can be prepared by coupling a suitably protected ribose derivative to these bases. Methods for effecting this coupling reaction are known to those of ordinary skill in the art, for example the method taught by Vorbruggen H. et. al. "Handbook of Nucleoside Synthesis", John Wiley and Sons, 2001. Suitable protecting groups are also known to those of ordinary skill in the art, and may be found described for example, in Greene "Protective Groups in Organic Synthesis", John Wiley and Sons, 3$^{rd}$ Edition, 1999. In a particular embodiment, 2'-deoxy-ribose analogs can be prepared by coupling 1-α-chloro-2-deoxy-3,5-bis(p-toluoyl)-α-D-ribofuranosyl chloride with a variety of nucleoside base analogs following the procedures described in Robins (J. Am. Chem. Soc 1984, 106, 6379).

Scheme 2:

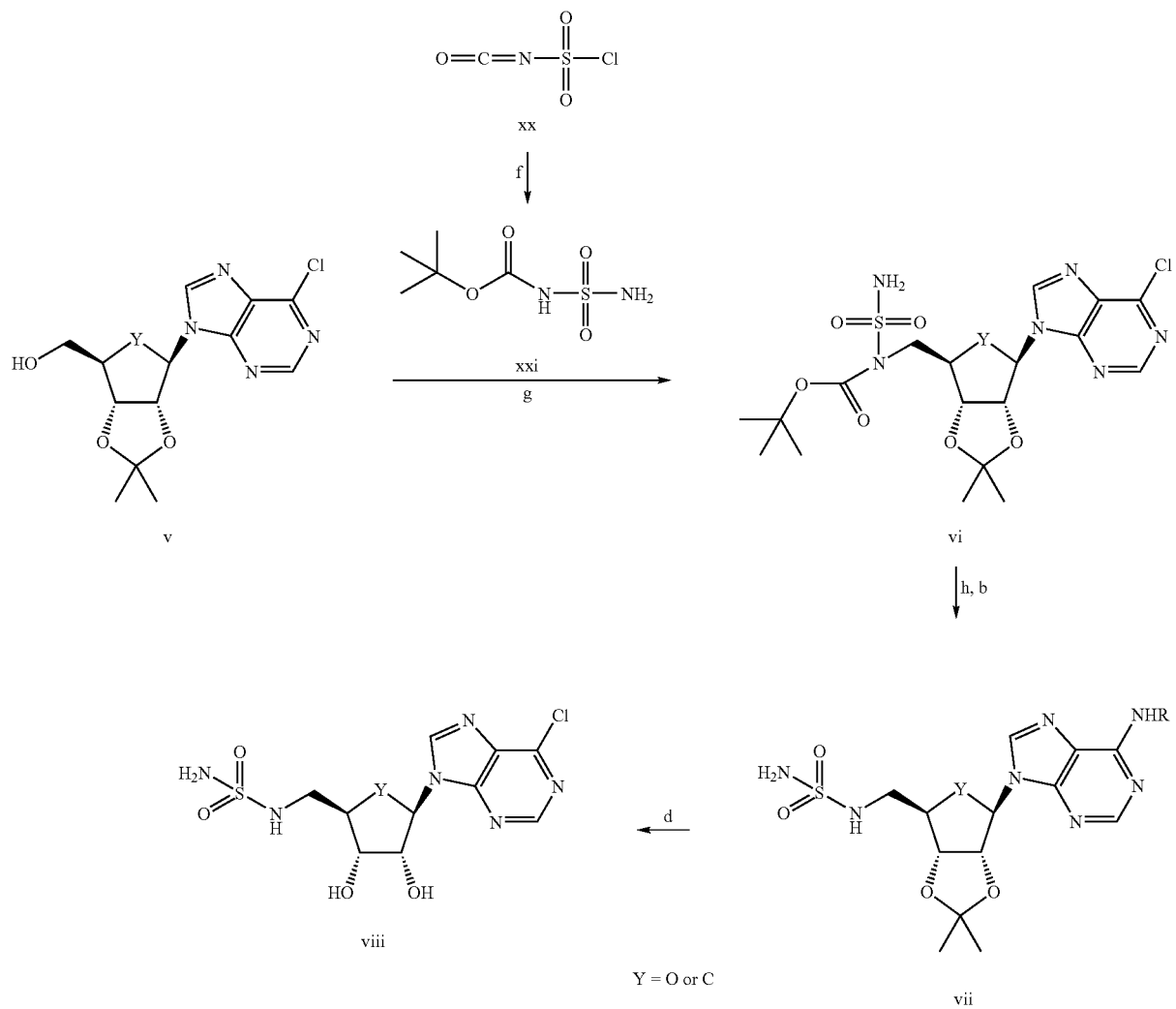

Reagents and conditions:
f) tert-BuOH, NH$_3$;
g) Ph$_3$P, DIAD, EtOAc;
h) TFA, DCM;
b) amine, TEA, EtOH, reflux, or microwave irradiation;
d) TFA-water.

In an analogous fashion to the preparation of sulfamate derivatives of compound (IV-A) described in scheme 1, sulfamide derivatives can be prepared at the 5'-position. Scheme 2 above shows a general route to synthesis of compounds of formula (II-A).

For example, compound v, prepared according to step (a) of scheme I above, can be treated with tert-butyl(aminosulfonyl) carbamate (compound xxi), in the presence of triphenylphosphine and an azodicarboxylate (g) to form the sulfamide compound vi. Sulfamide deprotection by treatment with an acid such as trifluoroacetic acid in an appropriate solvent, such as dichloromethane (h), followed by treatment with a primary amine in the presence of a tertiary amine, such as triethylamine and an appropriate solvent such as EtOH or water under conditions such as reflux or microwave (b) then affords compound vii. Compound vii is then treated with an acid, such as trifluoroacetic acid in an appropriate solvent such as water (d) to form compound viii.

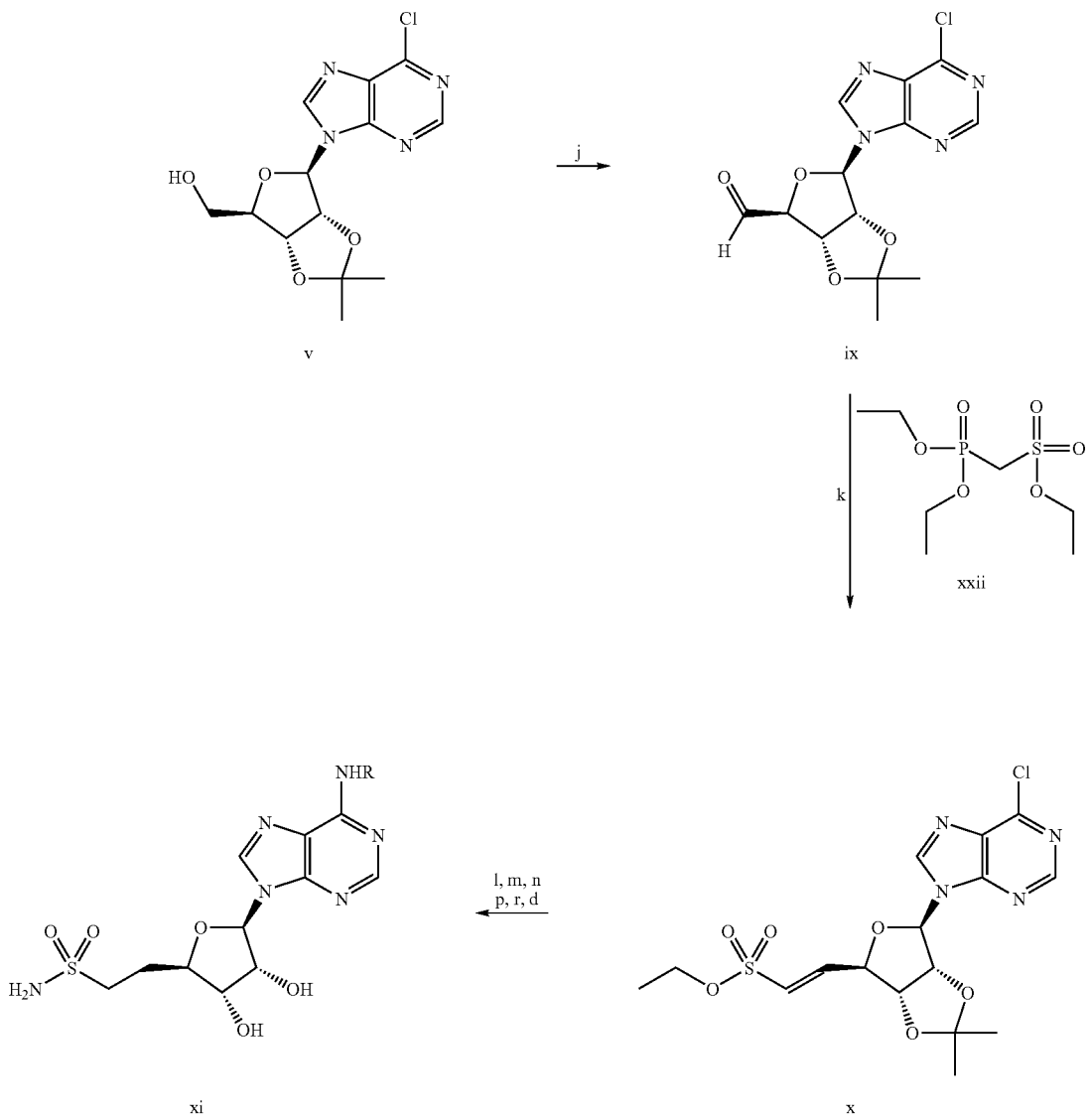

Scheme 3

Reagents and conditions:
j) Dess-Martin periodinane, DCM;
k) n-BuLi, THF;
l) NaBH$_4$, EtOH;
m) Bu$_4$NI, acetoe, reflux;
n) SO$_2$Cl$_2$, DCM, DMF;
p) NH$_3$, MeOH;
r) amine, DIPEA, EtOH, reflux or microwave irradiation;
d) TFA-water.

Furthermore, analogous to the preparation of sulfamate derivatives of compound (IV-A) described in scheme I, sulfonamide derivatives can be prepared at the 5'-position. Scheme 3 above shows a general route to synthesis of compounds of formula (III-A)

Thus, oxidation of the alcohol of compound v (prepared as in step (a) of Scheme 1) with a standard oxidizing agent, such as Dess-Martin periodinane, and dichloromethane (j) affords aldehyde ix. Treatment of compound ix with a phosphoryl methane sulfonic acid ester (xxii) and n-butyllithium in an appropriate solvent, such as tetrahydrofuran (k) produces the alkene compound x. Reduction and subsequent functional group interconversion of compound x, for example under steps, (l), (m), (n), (p), (r), and (d), gives the sulfonamide compound xi.

Scheme 4 step (s)). Synthetic procedures are known in the art and can be adapted as applicable. For example procedures described herein were adapted from those described in, e.g., Lakshman (J. Am. Chem. Soc. 2001, 123, 7779); Hocek (Collect. Czech. Commun., 2001, 66, 483; Robins (Org. Lett., 2004, 6, 2917). For a review of palladium assisted routes to nucleoside analogues see Agrofoglio (Chem. Rev., 2003, 103, 1875).

Treatment of resulting compound xiii with ammonia in methanol, followed by steps (c) and (d) as described above as in Scheme 1, results in synthesis of the 5'-sulfamoylated compound xv.

While Scheme 4 depicts synthesis of formula (IV-A), procedures may be readily adapted for synthesis of compounds of formulae (II-A), (III-A), (II-B), (III-B), and (IV-B) using

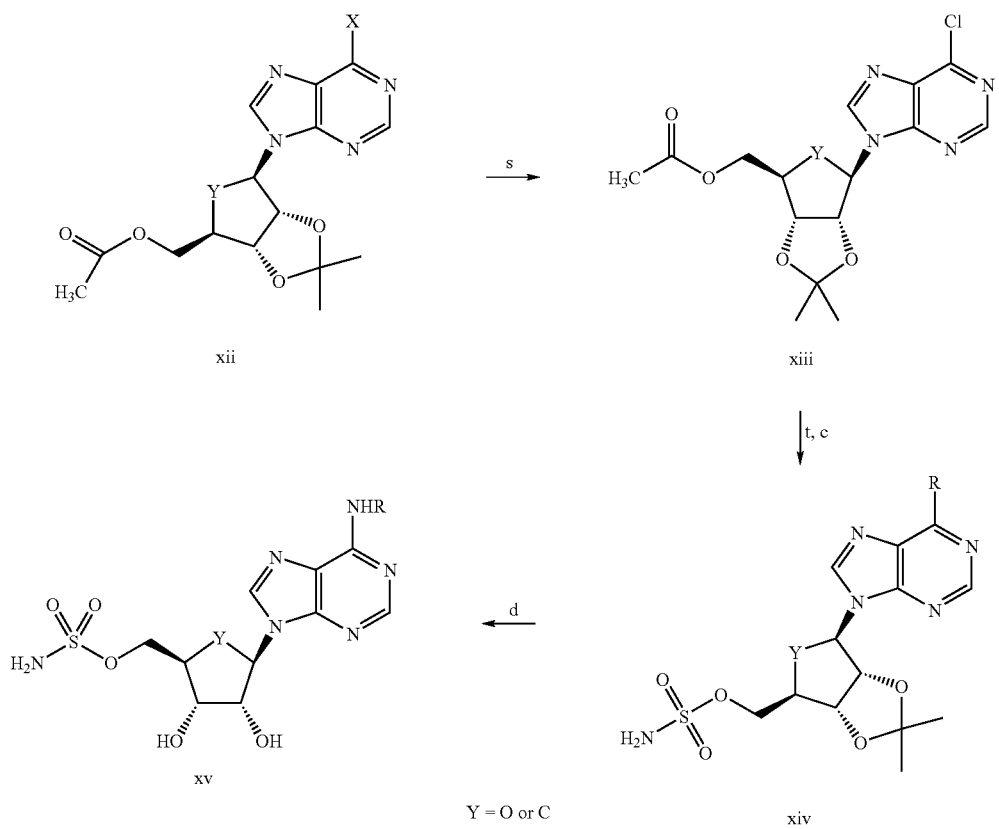

Scheme 4

Y = O or C

Reagents and conditions:
s) when X = Cl, and R = alkyl, then (PPh$_3$)$_4$Pd, RZncL, THF heat; or
   when X = Br, and R = aryl, then Ar—B(OH)$_2$, Pd(dppf)Cl$_2$, DCM, K$_3$PO, dioxane, heat; or
   when X = Br, and R = acetylene, then RC≡CH, Pd(PPh$_3$)$_2$Cl$_2$, CuI, DIPEA, DMF, heat; or
   when X = I, and R = acetylene then RC≡CH, Pd(PPh$_3$)$_2$Cl$_2$, CuI, DIPEA, DMF;
t) NH$_3$/MeOH;
c) H$_2$NSO$_2$Cl, TEA, DMF, AcCN;
d) TFA, water.

Scheme 4 above shows a general synthesis of compounds of formula (IV-A), wherein R$^1$ is an optionally substituted aliphatic, aryl or heteroaryl group. Compound xii can be prepared by reaction of compound v (prepared as described above in Scheme 2) with pyridine, dimethylaminopyridine and acetic anhydride in methylene chloride.

Compounds xiii can be produced by introduction of a variety of alkyl or aryl functionality at the 6-position of the purine ring through a palladium catalyzed coupling with a suitable organometallic reagent, aryl boronic acid, or alkyne (e.g., analogous procedures provided throughout the general schemes and examples, as well as application of alternate synthesis routes known in the art.

One of ordinary skill in the art will recognize that numerous variations in reaction conditions including variations in solvent, reagents, catalysts, reaction temperatures and times are possible for each of the reactions described. Alternative synthetic routes are also possible.

Uses of Compounds of the Invention

The compounds of this invention are useful inhibitors of E1 enzyme activity. In particular, the compounds are designed to be inhibitors of NAE, UAE, and/or SAE. Inhibitors are meant to include compounds which reduce the promoting effects of E1 enzymes in ubl conjugation to target proteins (e.g., reduction of ubiquitination, neddylation, sumoylation), reduce intracellular signaling mediated by ubl conjugation, and/or reduce proteolysis mediated by ubl conjugation (e.g., inhibition of cullin-dependent ubiquitination and proteolysis (e.g., the ubiquitin-proteasome pathway)). Thus, the compounds of this invention may be assayed for their ability to inhibit the E1 enzyme in vitro or in vivo, or in cells or animal models according to methods provided in further detail herein, or methods known in the art. The compounds may be assessed for their ability to bind or mediate E1 enzyme activity directly. Alternatively, the activity of compounds may be assessed through indirect cellular assays, or assays of downstream effects of E1 activation to assess inhibition of downstream effects of E1 inhibition (e.g., inhibition of cullin-dependent ubiquitination and proteolysis). For example, activity may be assessed by detection of ubl-conjugated substrates (e.g., ubl-conjugated E2s, neddylated cullins, ubiquitinated substrates, sumoylated substrates); detection of downstream protein substrate stabilization (e.g., stabilization of p27, stabilization of IκB); detection of inhibition of UPP activity; detection of downstream effects of protein E1 inhibition and substrate stabilization (e.g., reporter assays, e.g., NFκB reporter assays, p27 reporter assays). Assays for assessing activities are described below in the Experimental section and/or are known in the art.

One embodiment of this invention relates to a composition comprising a compound of this invention or a pharmaceutically acceptable salt thereof, and a pharmaceutically acceptable carrier. It will be appreciated that the compounds of this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the present compounds, similar to the metabolically labile esters or carbamates, which are capable of producing the parent compounds described herein in vivo, are within the scope of this invention.

If pharmaceutically acceptable salts of the compounds of the invention are utilized in these compositions, the salts preferably are derived from inorganic or organic acids and bases. For reviews of suitable salts, see, e.g., Berge et al, *J. Pharm. Sci.* 66:1-19 (1977) and Remington: The Science and Practice of Pharmacy, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

In certain particular embodiments, the invention relates to a base addition salt of a compound of formula I formed by deprotonation of the sulfamate (X=O) moiety, the sulfamide (X=NH) moiety, or the sulfonamide (X=CH$_2$) moiety, as applicable. In some such embodiments, the invention relates to a sodium or potassium salt of a compound of formula I.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutical formulations may be prepared as liquid suspensions or solutions using a liquid, such as, but not limited to, an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Pharmaceutically acceptable carriers that may be used in these compositions include, but are not limited to, ion exchangers, alumina, aluminum stearate, lecithin, serum proteins, such as human serum albumin, buffer substances such as phosphates and carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to disorders as described herein (e.g., proliferation disorders, e.g., cancers, inflammatory, neurodegenerative disorders). Preferably, the composition is formulated for administration to a patient having or at risk of developing or experiencing a recurrence of the relevant disorder being treated. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In certain embodiments, the pharmaceutical composition of the invention may further comprise another therapeutic agent. Preferably, such other therapeutic agent is one normally administered to patients with the disorder, disease or condition being treated.

By "therapeutically effective amount" is meant an amount of compound or composition sufficient, upon single or multiple dose administration, to cause a detectable decrease in E1 enzyme activity and/or the severity of the disorder or disease state being treated. "Therapeutically effective amount" is also intended to include an amount sufficient to treat a cell, prolong or prevent advancement of the disorder or disease state being treated (e.g., prevent additional tumor growth of a cancer, prevent additional inflammatory response), ameliorate, alleviate, relieve, or improve a subject's symptoms of the a disorder beyond that expected in the absence of such treatment. The amount of E1 enzyme inhibitor required will depend on the particular compound of the composition given, the type of disorder being treated, the route of administration, and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. In certain aspects where the inhibitor is administered in combination with another agent, the amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

One embodiment of the invention relates to a method of inhibiting or decreasing E1 enzyme activity in a sample comprising contacting the sample with a compound of this invention, or composition comprising a compound of the invention. The sample, as used herein, includes, without limitation, sample comprising purified or partially purified E1 enzyme, cultured cells or extracts of cell cultures; biopsied cells or fluid obtained from a mammal, or extracts thereof; and body fluid (e.g., blood, serum, saliva, urine, feces, semen, tears) or extracts thereof. Inhibition of E1 enzyme activity in a sample may be carried out in vitro or in vivo, in cellulo, or in situ.

In another embodiment, the invention provides a method for treating a patient having a disorder, a symptom of a disorder, at risk of developing or experiencing a recurrence of a disorder, comprises administering to the patient a compound or pharmaceutical composition according to the invention. Treating can be to cure, heal, alleviate, relieve, alter, remedy, ameliorate, palliate, improve or affect the disorder, the symptoms of the disorder or the predisposition toward the disorder. While not wishing to be bound by theory, treating is believed to cause the inhibition of growth, ablation, or killing of a cell or tissue in vitro or in vivo, or otherwise reduce capacity of a cell or tissue (e.g., an aberrant cell, a diseased tissue) to mediate a disorder, e.g., a disorder as described herein (e.g., a proliferative disorder, e.g., a cancer, inflammatory disorder). As used herein, "inhibiting the growth" or "inhibition of growth" of a cell or tissue (e.g., a proliferative cell, tumor tissue) refers to slowing, interrupting, arresting or stopping its growth and metastases and does not necessarily indicate a total elimination of growth.

Disease applications include those disorders in which inhibition of E1 enzyme activity is detrimental to survival and/or expansion of diseased cells or tissue (e.g., cells are sensitive to E1 inhibition; inhibition of E1 activity disrupts disease mechanisms; reduction of E1 activity stabilizes protein which are inhibitors of disease mechanisms; reduction of E1 activity results in inhibition of proteins which are activators of disease mechanisms). Disease applications are also intended to include any disorder, disease or condition which requires effective cullin and/or ubiquitination activity, which activity can be regulated by diminishing E1 enzyme activity (e.g., NAE, UAE activity).

For example, methods of the invention are useful in treatment of disorders involving cellular proliferation, including, but not limited to, disorders which require an effective cullin-dependent ubiquitination and proteolysis pathway (e.g., the ubiquitin proteasome pathway) for maintenance and/or progression of the disease state. The methods of the invention are useful in treatment of disorders mediated via proteins (e.g., NFκB activation, $p27^{Kip}$ activation, $p21^{MAF/CIP1}$ activation, p53 activation) which are regulated by E1 activity (e.g., NAE activity, UAE activity, SAE activity). Relevant disorders include proliferative disorders, most notably cancers and inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis), vascular proliferative disorders (e.g., atherosclerosis, restenosis) autoimmune diseases (e.g., multiple sclerosis, tissue and organ rejection)); as well as inflammation associated with infection (e.g., immune responses), neurodegenerative disorders (e.g., Alzheimer's disease, Parkinson's disease, motor neurone disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies)).

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

In some embodiments, the cancer is a solid tumor. Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the compound or composition of the invention is used to treat a patient having or at risk of developing or experiencing a recurrence in a cancer selected from the group consisting of colorectal cancer, ovarian cancer, lung cancer, breast cancer, gastric cancer, prostate cancer, and pancreatic cancer. In certain preferred embodiments, the cancer is selected from the group consisting of lung cancer, colorectal cancer, ovarian cancer and a hematologic cancer.

Depending on the particular disorder or condition to be treated, in some embodiments, the E1 enzyme inhibitor of the invention is administered in conjunction with additional therapeutic agent or agents. In some embodiments, the additional therapeutic agent(s) is one that is normally administered to patients with the disorder or condition being treated. As used herein, additional therapeutic agents that are normally administered to treat a particular disorder or condition are known as "appropriate for the disorder or condition being treated."

The E1 inhibitor of the invention may be administered with the other therapeutic agent in a single dosage form or as a separate dosage form. When administered as a separate dosage form, the other therapeutic agent may be administered prior to, at the same time as, or following administration of the E1 inhibitor of the invention.

In some embodiments, the E1 enzyme inhibitor of the invention is administered in conjunction with a therapeutic agent selected from the group consisting of cytotoxic agents, radiotherapy, and immunotherapy appropriate for treatment of proliferative disorders and cancer. Non-limiting examples of cytotoxic agents suitable for use in combination with the E1 enzyme inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; including, e.g., CC-5013 and CC-4047; protein tyrosine kinase inhibitors, including, e.g., imatinib mesylate and gefitinib; proteasome inhibitors, including, e.g., bortezomib, thalidomide and related analogs; antibodies, including, e.g., trastuzumab, rituximab, cetuximab, and bevacizumab; mitoxantrone; dexamethasone; prednisone; and temozolomide.

Other examples of agents the inhibitors of the invention may be combined with include anti-inflammatory agents such as corticosteroids, TNF blockers, Il-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, methotrexate, and sulfasalazine; antibacterial and antiviral agents; and agents for Alzheimer's treatment such as donepezil, galantamine, memantine and rivastigmine.

In order that this invention be more fully understood, the following preparative and testing examples are set forth. These examples are for the purpose of illustration only and are not to be construed as limiting the scope of the invention in any way.

EXAMPLES

Abbreviations
AcCN acetonitrile
AcOH acetic acid
aq aqueous
ATP adenosine triphosphate
DIPEA diisopropylethylamine
DMAP 4-dimethylaminopyridine
DMF N,N-dimethylformamide
DCM dichloromethane
DMSO dimethylsulfoxide
eq equivalents
EtOAc ethyl acetate
EtOH ethanol
ES+ electrospray +ve mode
ES− electrospray −ve mode
FRET fluorescence resonance energy transfer
h hours
HPLC high pressure liquid chromatography
LCMS liquid chromatography mass spectrum
MeOH methanol
MHz megahertz
min minutes
mL milliliter
mM millimolar
mm millimeter
MS mass spectrum
nM nanomolar
NMR nuclear magnetic resonance
pTsOH para-toluenesulfonic acid
r.t. room temperature
R.t. retention time
s seconds
SDS sodium dodecyl sulfate
TEA triethylamine
TFA trifluoroacetic acid
THF tetrahydrofuran The following analytical methods were utilized in the preparation and analysis of the compounds as specified in the Examples below:

LCMS: compounds were analyzed on a Phenomenex Luna column [C18, 30×4.6 mm, 5 μm], flow rate 2.5 mL/min.
  Formic acid method: mobile phase A consisting of 5% acetonitrile/water/0.1% formic acid and mobile phase B of 99% acetonitrile/water/0.1% formic acid.
  Ammonium acetate method: mobile phase A consisting of 1% acetonitrile/10 mM ammonium acetate aqueous and mobile phase B of 95% acetonitrile/10 mM ammonium acetate aqueous. The 5 min cycle consisted of a gradient of 5% to 100% B in 3.5 min; 100% B for 1 min; 100% B to 100% A in 0.1 min; then re-equilibration with mobile phase A for 0.49 min.
  NMR: proton spectra were recorded on a Bruker 300 or 400 MHz ultrashield spectrometer. Chemical shifts are reported relative to methanol ($\delta$ 3.31) or dimethyl sulfoxide ($\delta$ 2.50).
  Microwave: All microwave reactions were carried out using a Personal Chemistry 'Creator' system operating a single mode cavity at 2450 MHz with a maximum power of 300 W. The chemistry was carried out in sealed tubes with a capacity of 0.5 to 8 mL and a pressure cut out of 22 bar.

Example 1

((2R,3S,4R,5R)-5-{6-[(1S)-2,3-dihydro-1H-inden-1-ylamino]9H-purin-9-yl}-3,4-dihydroxytetrahydrofuran-2-yl)methyl sulfamate (I-2)

Step a: [(3aR,4R,6R,6aR)-6-(6-chloro-9H-purin-9-yl)-2,2-dimethyltetrahydrofuro-[3,4-d][1,3]dioxol-4-yl]methanol 6-Chloro-β-ribofuranosylpurine (8.17 g, 28.5 mmol), p-toluenesulfonic acid monohydrate (5.42 g, 28.5 mmol) and 2,2-dimethoxypropane (17.5 mL, 142.5 mmol) were mixed in acetone (500 mL). The reaction mixture was stirred at room temperature for 16 hours. Saturated aqueous $NaHCO_3$ solution (400 mL) was then added and the mixture was evaporated under reduced pressure to remove most of the acetone. The remaining aqueous residue was then extracted with chloroform (4×200 mL). The combined organics were dried over $Na_2SO_4$, and then evaporated to yield the product as a white amorphous solid (9.22 g, 99%).

LCMS: R.t. 1.22 min ES+ 327 (formic acid).

Step b: ((3aR,4R,6R,6aR)-6-{6-[(1S)-2,3-dihydro-1H-inden-1-ylamino]-9H-purin-9-yl}-2,2-dimethyltetrahydrofuro[3,4-d][1,3]dioxol-4-yl)methanol

[(3aR,4R,6R,6aR)-6-(6-chloro-9H-purin-9-yl)-2,2-dimethyltetrahydrofuro[3,4-d][1,3]dioxol-4-yl]methanol (736 mg, 2.26 mmol), (S)-(+)-1-aminoindane (360 mg, 2.71 mmol) and triethylamine (380 μL, 2.71 mmol) were added to ethanol (2.5 mL) and the mixture was heated at 140° C. for 10 minutes using microwave irradiation. The cooled mixture was diluted with diethyl ether (5 mL) and the precipitated product isolated by filtration. Further product was isolated from the filtrates by evaporation, followed by recrystallization from ethanol/ether. Total yield was 630 mg, 66%.

LCMS: R.t. 1.64 min ES+ 424 (formic acid).

Step c: ((3aR,4R,6R,6aR)-6-{6-[(1S)-2,3-dihydro-1H-inden-1-ylamino]-9H-purin-9-yl}-2,2-dimethyltetrahydrofuro[3,4-d][1,3]dioxol-4-yl)methyl sulfamate A 2M solution of chlorosulfonamide in acetonitrile was prepared as follows:

Formic acid (2.3 mL, 60 mmol) was added dropwise, with stirring to Chlorosulfonyl isocyanate (5.2 mL, 60 mmol) under nitrogen at 0° C. After the addition was complete and the mixture had solidified, acetonitrile (30 mL) was added. The resulting solution was left to stand under a vented source of nitrogen overnight at room temperature.

((3aR,4R,6R,6aR)-6-{6-[(1S)-2,3-Dihydro-1H-inden-1-ylamino]-9H-purin-9-yl}-2,2-dimethyltetrahydrofuro[3,4-d][1,3]dioxol-4-yl)methanol (525 mg, 1.24 mmol) and triethylamine (260 μL, 1.86 mmol) were dissolved in N,N-dimethylformamide (3 mL) under nitrogen. The solution was cooled to 0° C. and freshly prepared chlorosulfonamide solution (2M) (0.93 mL, 1.86 mmol) was added dropwise. The mixture was stirred for 1 hour at 0° C., until complete by LCMS. The mixture was allowed to warm to room temperature, diluted with dichloromethane (20 mL) and the organic phase was washed with brine (2×10 mL), water (10 mL) and evaporated to give a crude product, 445 mg (71%). This was used without further purification.

LCMS: R.t. 1.62 min ES+ 503 (formic acid).

Step d: ((2R,3S,4R,5R)-5-{6-[(1S)-2,3-dihydro-1H-inden-1-ylamino]9H-purin-9-yl}-3,4-dihydroxytetrahydrofuran-2-yl)methyl sulfamate (I-2)

((3aR,4R,6R,6aR)-6-{6-[(1S)-2,3-Dihydro-1H-inden-1-ylamino]-9H-purin-9-yl}-2,2-dimethyltetrahydrofuro[3,4-d][1,3]dioxol-4-yl)methyl sulfamate (400 mg, 0.80 mmol) was dissolved in a preformed mixture of trifluoroacetic acid (1.8 mL) and water (0.2 mL). The solution was allowed to stand at room temperature for 10 minutes and evaporated to dryness. This was twice evaporated from methanol and the residue was purified by reverse phase HPLC to yield 248 mg (67%) of final compound.

LCMS: R.t. 1.27 min ES+ 463 (formic acid).
$^1$H-NMR (300 MHz, $d_6$-DMSO): δ 8.31 (s, 1H), 8.28 (br, 1H), 8.16 (br, 1H), 7.60 (s, 2H), 7.19 (m, 4H), 5.97 (m, 2H), 5.67 (br, 1H), 5.47 (br, 1H), 4.63 (t, 1H, J=4.9 Hz), 4.22 (m, 4H), 3.01 (m, 1H), 2.83 (m, 1H), 2.10 (br, 1H)

Example 2

((2R,3S,4R,5R)-5-{6-[(4-chlorobenzyl)amino]-9H-purin-9-yl}-3,4dihydroxytetrahydrofuran-2-yl)methyl sulfamate (I-10)

The title compound was prepared following the procedure described in Example 1, steps b-d, using 4-Chloro-benzylamine in step b.

LCMS: R.t. 1.23 min ES+ 471 (formic acid).
$^1$H-NMR (300 MHz, $d_6$-DMSO): δ 8.34 (s, 1H), 8.21 (s, 1H), 7.35 (s, 4H), 5.94 (d, 1H, J=5.3 Hz), 4.63 (m, 1H), 4.31-4.11 (m, 4H).

Example 3

((2R,3S,4R,5R)-5-{6-[(cyclohexylmethyl)amino]-9H-purin-9-yl}-3,4-dihydroxytetrahydrofuran-2-yl)methyl sulfamate (I-7)

The title compound was prepared following the procedure described in Example 1, steps b-d, using cyclohexyl-methylamine in step b.

LCMS: R.t. 1.15 min ES+ 443 (formic acid).
$^1$H-NMR (300 MHz, $d_6$-DMSO): δ 8.28 (s, 1H), 8.21 (s, 1H), 7.84 (br s, 1H), 7.59 (s, 2H), 5.93 (d, 1H, J=5.3 Hz), 4.62 (m, 1H), 4.31-4.11 (m, 4H), 1.68 (m, 6H), 1.15 (m, 3H), 0.94 (m, 2H).

Example 4

((2R,3S,4R,5R)-5-{6-[(4-Chlorophenyl)amino]-9H-purin-9-yl}-3,4dihydroxytetrahydrofuran-2-yl)methyl sulfamate (I-16)

The title compound was prepared following the procedure described in Example 1, steps b-d, using 4-chloroaniline in step b.

LCMS: R.t. 1.39 min ES+ 457 (formic acid).
$^1$H-NMR (300 MHz, $d_6$-DMSO): δ 8.47 (s, 1H), 8.40 (s, 1H), 7.98 (d, 2H, J=8.9 Hz), 7.34 (d, 2H, J=8.9 Hz), 5.97 (d, 1H, J=5.2 Hz), 4.62 (t, 1H, J=5.1 Hz), 4.21 (m, 4H).

Example 5

((2R,3S,4R,5R)-3,4-Dihydroxy-5-{6-[(2-phenyl-ethyl)amino]-9H-purin-9-yl}-tetrahydrofuran-2-yl)methyl sulfamate (I-17)

The title compound was prepared following the procedure described in Example 1, steps b-d, using phenethylamine in step b.

LCMS: R.t. 1.10 min ES+ 451 (formic acid).

$^1$H-NMR (300 MHz, $d_6$-DMSO): δ 8.29 (s, 1H), 8.24 (s, 1H), 7.88 (br s, 1H), 7.57 (s, 2H), 7.31-7.18 (m, 5H), 5.94 (d, 1H, J=5.3 Hz), 5.59 (d, 1H, J=5.8 Hz), 5.42 (d, 1H, J=5.5 Hz), 4.61 (dd, 1H, J=5.5 Hz, J=11.0 Hz), 4.30-4.11 (m, 4H), 3.71 (br s, 2H), 2.91 (t, 2H, J=8.2 Hz).

Example 6

((2R,3S,4R,5R)-3,4-Dihydroxy-5-{6-[(3-methoxy-benzyl)amino]-9H-purin-9-yl}-tetrahydrofuran-2-yl)methyl-sulfamate (I-11)

Step a: Sulfamic acid 6-(6-chloro-purin-9-yl)-2,2-dimethyl-tetrahydro-furo[3,4-d][1,3]-dioxol4-yl methyl ester

[6-(6-Chloro-purin-9-yl)-2,2-dimethyl-tetrahydro-furo[3,4-d][1,3]dioxol-4-yl]-methanol (6.53 g, 20 mmol) and triethylamine (4.17 mL, 30 mmol) were dissolved in DMF (30 mL) under nitrogen and cooled on an ice bath. Chlorosulfonamide solution (10 mL, 20 mmol) was then added over 5 minutes and the mixture stirred for 90 minutes. Two further portions of chlorosulfonamide (5 mL, 10 mmol) were added with the reaction mixture stirred for a 60 minutes after each addition. The mixture was then evaporated under vacuum at 50° C. and the residue was purified by column chromatography on silica (120 g) using ethyl acetate gradient 0 to 100% in hexane to give the desired product, as a foam (6.88 g, 85%).

Step b: 1-[9-(2,2-Dimethyl-6-sulfamoyloxymethyl-tetrahydro-furo[3,4-d][1,3]-dioxol-4-yl)-9Hpurin-6-yl]-1-azonia-bicylo[2.2.2]octane chloride Quinuclidine (785 mg, 7.06 mmol) was dissolved in ethanol (39 mL) and 1.5 mL (0.2716 mmol) of the solution was added to sulfamic acid 6-(6-chloro-purin-9-yl)-2,2-dimethyltetrahydrofuro[3,4-d][1,3]dioxol-4-yl methyl ester (100 mg, 0.246 mmol) in a 10 mL vial. The reaction vial was sealed and agitated for 1 hour, then evaporated to dryness to yield crude product, which was used directly in the next step.

Step c: ((2R,3S,4R,5R)-3,4-Dihydroxy-5-{6-[(3-methoxybenzyl)amino]-9H-purin-9-yl}-tetrahydro-furan-2-yl)methyl-sulfamate (I-11)

3-Methoxybenzylamine (4.0 eq, 0.986 mmol) was dissolved in EtOH (1.5 mL) and added to the crude product described above (0.246 mmol). The reaction mixture was agitated overnight, and then evaporated to dryness. The resulting residue was treated with 1 mL of TFA/water (9:1) for 20 minutes. The solution was evaporated and the product purified by preparative HPLC.

LCMS: R.t. 1.35 min, ES+ 467 (formic acid).

$^1$H-NMR (300 MHz, $d_6$-DMSO): δ 8.36 (s, 1H), 8.25 (s, 1H), 7.23 (t, 1H, J=7.9 Hz), 6.95 (s, 2H), 6.81 (d, 1H, J=7.1 Hz), 5.98 (d, 1H, J=5.2 Hz), 5.68 (br, 1H), 5.50 (br, 1H), 4.68 (dd, 2H, J=7.8 Hz, J=13.6 Hz), 4.26 (m, 4H), 3.73 (s, 3H).

Example 7

((2R,3S,4R,5R)-3,4-Dihydroxy-5-{6-[(2-thienylmethyl)amino]-9H-purin-9-yl}-tetrahydrofuran-2-yl)methyl-sulfamate (I-8)

The title compound was prepared as described in Example 6, step c, using 2-methylaminothiophene.

LCMS: R.t. 1.31 min, ES+ 443 (formic acid).

$^1$H-NMR (300 MHz, $d_6$-DMSO): δ 8.36 (s, 1H), 8.31 (s, 1H), 7.62 (s, 2H), 7.36 (d, 1H, J=4.9 Hz), 7.05 (d, 1H, J=3.3 Hz), 6.96 (dd, 1H, J=3.5 Hz, J=5.0 Hz), 5.98 (d, 1H, J=5.3 Hz), 5.65 (d, 1H, J=5.9 Hz), 5.47 (d, 1H, J=5.3 Hz), 4.88 (br, 2H), 4.66 (m, 1H), 4.24 (m, 4H).

Example 8

[(2R,3S,4R,5R)-3,4-Dihydroxy-5-(6-{[(5-methylpyrazin-2-yl)methyl]amino}-9H-purin-9-yl)tetrahydrofuran-2-yl]methyl-sulfamate (I-22)

The title compound was prepared as described in Example 6, step c, using 3-methyl-5-methylaminopyrazine LCMS: R.t. 1.06 min, ES+ 453 (formic acid).

$^1$H-NMR (300 MHz, $d_6$-DMSO): δ 8.50 (br, 2H), 8.40 (s, 1H), 8.26 (s, 1H), 7.64 (s, 2H), 6.00 (d, 1H, J=5.3 Hz), 5.55 (br, 2H), 4.86 (br, 2H), 4.68 (t, 1H, J=5.1 Hz), 4.27 (m, 4H), 2.49 (s, 3H).

Example 9

[(2R,3S,4R,5R)-3,4-Dihydroxy-5-(6-{[(1S)-2-hydroxy-1-phenylethyl]amino}-9H-purin-9-yl)tetrahydrofuran-2-yl]methyl-sulfamate (I-23)

The title compound was prepared as described in Example 6, step c, using (S)-alpha-hydroxymethyl benzylamine.

LCMS: R.t. 1.19 min, ES+ 467 (formic acid).

$^1$H-NMR (300 MHz, $d_6$-DMSO): δ 7.58 (br, 2H), 7.42 (d, 2H, J=7.6 Hz), 7.28 (t, 1H, J=7.3 Hz), 7.19 (t, 1H, J=7.2 Hz), 5.93 (d, 1H, J=5.2 Hz), 5.62 (br, 1H), 5.40 (br, 2H), 4.60 (q, 1H, J=7.0 Hz), 4.20 (m, 4H), 3.76 (td, 2H, J=11.1 Hz, J=15.9 Hz).

Example 10

[(2R,3S,4R,5R)-3,4-Dihydroxy-5-(6-{[(1R)-2-hydroxy-1-phenylethyl]amino}-9H-purin-9-yl)tetrahydrofuran-2-yl]methyl-sulfamate (I-24)

The title compound was prepared as described in Example 6, step c, using (R)-alpha-hydroxymethylbenzylamine LCMS: R.t. 1.23 min, ES+ 467 (formic acid).

$^1$H-NMR (300 MHz, $d_6$-DMSO): δ 8.38 (s, 1H), 8.20 (s, 1H), 8.09 (d, 1H, J=8.5 Hz), 7.61 (s, 2H), 7.46 (d, 2H, J=7.4 Hz), 7.32 (t, 2H, J=7.4 Hz), 7.22 (t, 1H, J=7.2 Hz), 5.97 (d, 1H, J=5.2 Hz), 5.63 (br, 1H), 5.45 (br, 1H), 4.98 (br, 1H), 4.24 (m, 4H), 4.64 (br, 1H), 3.79 (td, 2H, J=10.5 Hz, J=15.6 Hz).

Example 11

((2R,3S,4R,5R)-5-{6-[(1,3-Benzodioxol-5-ylmethyl) amino]-9H-purin-9-yl}-3,4-dihydroxytetrahydrofuran-2-yl)methyl-sulfamate (I-63)

The title compound was prepared as described in Example 6, step c, using 3,4-methylenedioxybenzylamine LCMS: R.t. 1.32 min, ES+ 481 (formic acid).

$^1$H-NMR (300 MHz, $d_6$-DMSO): δ 8.35 (s, 1H), 8.25 (s, 1H), 7.62 (s, 2H), 6.95 (s, 1H), 6.85 (d, 2H, J=0.5 Hz), 5.98 (m, 3H), 5.64 (d, 1H, J=5.9 Hz), 5.46 (d, 1H, J=5.3 Hz), 4.66 (dd, 2H, J=5.3 Hz, J=10.7 Hz), 4.25 (m, 4H).

Example 12

((2R,3S,4R,5R)-3,4-Dihydroxy-5-{6-[(2-methoxyethyl)amino]-9H-purin-9-yl}-tetrahydrofuran2-yl) methyl-sulfamate (I-21)

The title compound was prepared as described in Example 6, step c, using O-methyl ethanolamine.

LCMS: R.t. 0.95 min, ES+ 405 (formic acid).

$^1$H-NMR (300 MHz, $CD_3OD$): δ 8.39 (br, 2H), 6.20 (d, 1H, J=5.0 Hz), 4.78 (t, 1H, J=5.1 Hz), 4.48 (m, 4H), 3.91 (br, 2H), 3.77 (t, 1H, J=5.4 Hz), 3.52 (m, 3H).

Example 13

((2R,3S,4R,5R)-3,4-Dihydroxy-5-{6-[(2-pyrrolidin-1-ylethyl)amino]-9H-purin-9-yl}tetrahydrofuran-2-yl)methyl-sulfamate (I-64)

The title compound was prepared as described in Example 6, step c, using N-ethylamino-tetrahydropyrrole and isolated as the formate salt.

LCMS: R.t. 0.92 min, ES+ 444 (formic acid).

$^1$H-NMR (300 MHz, $d_6$-DMSO): δ 8.41 (s, 1H), 8.34 (s, 1H), 7.64 (s, 2H), 6.00 (d, 1H, J=5.3 Hz), 4.67 (t, 1H, J=5.2 Hz), 4.25 (m, 4H), 3.86 (br, 2H), 3.68 (br, 2H), 3.45 (d, 2H, J=4.9 Hz), 3.10 (br, 2H), 1.95 (br, 4H).

Example 14

((2R,3S,4R,5R)-5-{6-[(4-Fluorobenzyl)amino]-9H-purin-9-yl}-3,4-dihydroxytetrahydrofuran-2-yl)methyl-sulfamate (I-65)

The title compound was prepared as described in Example 6, step c, using 4-fluorobenzylamine.

LCMS: R.t. 1.38 min, ES+ 455 (formic acid).

$^1$H-NMR (300 MHz, $d_6$-DMSO): δ 8.35 (s, 1H), 8.25 (s, 1H), 7.61 (s, 2H), 7.40 (dd, 2H, J=5.7 Hz, J=8.5 Hz), 7.13 (t, 2H, J=8.9 Hz), 5.97 (d, 1H, J=5.3 Hz), 5.64 (d, 1H, J=5.9 Hz), 5.46 (d, 1H, J=5.3 Hz), 4.68 (m, 2H), 4.24 (m, 4H).

Example 15

((2R,3S,4R,5R)-3,4-Dihydroxy-5-{6-[(2-morpholin-4-ylethyl)amino]-9H-purin-9-yl}tetrahydrofuran-2-yl)methyl-sulfamate (I-25)

The title compound was prepared as described in Example 6, step c, using N-ethylamino-morpholine LCMS: R.t. 1.05 min, ES+ 460 (formic acid).

$^1$H-NMR (300 MHz, $d_6$-DMSO): δ 8.41 (s, 1H), 8.34 (s, 1H), 7.64 (s, 2H), 6.00 (d, 1H, J=5.3 Hz), 4.26 (m, 4H), 5.57 (br, 2H), 4.67 (t, 1H, J=5.2 Hz), 3.88 (br, 8H), 3.42 (br, 4H).

Example 16

((2R,3S,4R,5R)-3,4-Dihydroxy-5-{6-[(1-naphthylmethyl)amino]-9H-purin-9-yl}tetrahydrofuran-2-yl) methyl-sulfamate (I-4)

The title compound was prepared as described in Example 6, step c, using 1-methylamino naphthalene.

LCMS: R.t. 1.42 min, ES+ 487 (formic acid).

$^1$H-NMR (300 MHz, $d_6$-DMSO): δ 8.46 (s, 1H), 8.33 (s, 1H), 8.23 (s, 2H), 7.94 (dd, 1H, J=2.7 Hz, J=6.7 Hz), 7.81 (dd, 1H, J=1.8 Hz, J=7.3 Hz), 7.57 (m, 4H), 7.43 (t, 1H, J=6.3 Hz), 5.95 (d, 1H, J=5.3 Hz), 5.61 (d, 1H, J=5.9 Hz), 5.44 (d, 1H, J=5.3 Hz), 5.18 (br, 2H), 4.64 (dd, 1H, J=5.0 Hz, J=10.3 Hz), 4.21 (m, 4H).

Example 17

((2R,3S,4R,5R)-3,4-Dihydroxy-5-{6-[(piperidin-4-ylmethyl)amino]-9H-purin-9-yl}tetrahydrofuran-2-yl)methyl-sulfamate (I-26)

The title compound was prepared as described in Example 6, step c, using 4-methylamino piperidine and isolated as the formate salt.

LCMS: R.t. 1.88 min, ES+ 444 (formic acid).

$^1$H-NMR (300 MHz, $d_6$-DMSO): δ 8.35 (s, 1H), 8.27 (s, 1H), 7.64 (s, 2H), 5.98 (d, 1H, J=5.3 Hz), 4.66 (t, 1H, J=5.1 Hz), 4.25 (m, 4H), 3.36 (m, 4H), 2.86 (dd, 2H, J=11.6 Hz, J=23.0 Hz), 1.99 (br, 1H), 1.85 (d, 1H, J=14.5 Hz), 1.37 (dd, 2H, J=13.1 Hz, J=24.6 Hz).

Example 18

((2R,3S,4R,5R)-3,4-Dihydroxy-5-{6-[(2-methoxybenzyl)amino]-9H-purin-9-yl}-tetrahydrofuran-2-yl) methyl sulfamate (I-27)

The title compound was prepared as described in Example 6, step c, using 2-methoxybenzylamine.

LCMS: R.t. 1.35 min, ES+ 467 (formic acid).

$^1$H-NMR (300 MHz, $d_6$-DMSO): δ 8.37 (s, 1H), 8.22 (s, 1H), 7.62 (s, 2H), 7.24 (t, 1H, J=7.7 Hz), 7.13 (d, 1H, J=7.4 Hz), 7.01 (d, 1H, J=8.1 Hz), 6.87 (t, 1H, J=7.4 Hz), 5.98 (d, 1H, J=5.3 Hz), 5.65 (d, 1H, J=5.9 Hz), 5.47 (d, 1H, J=5.3 Hz), 4.69 (br, 2H), 4.26 (m, 4H), 3.87 (s, 3H).

Example 19

[(2R,3S,4R,5R)-5-(6-{[2-(4-Benzylpiperazin-1-yl) ethyl]amino}-9H-purin-9-yl)-3,4-dihydroxytetrahydrofuran-2-yl]methyl-sulfamate (I-28)

The title compound was prepared as described in Example 6, step c, using 1-N-ethylamino(4-N-benzyl)piperazine, and isolated as the formate salt.

LCMS: R.t. 0.94 min, ES+ 549 (formic acid).

$^1$H-NMR (300 MHz, d$_6$-DMSO): δ 8.30 (s, 1H), 7.97 (s, 1H), 7.64 (s, 2H), 7.45 (m, 5H), 5.99 (d, 1H, J=5.3 Hz), 5.59 (br, 2H), 4.66 (t, 1H, J=5.1 Hz), 4.25 (m, 4H), 3.82 (br, 4H), 3.09 (br, 10H).

Example 20

[(2R,3S,4R,5R)-3,4-Dihydroxy-5-(6-{[4-(trifluoromethoxy)benzyl]amino}-9H-purin-9-yl)tetrahydrofuran-2-yl]methyl-sulfamate (I-30)

The title compound was prepared as described in Example 6, step c, using 4-trifluoromethoxybenzylamine.

LCMS: R.t. 1.49 min, ES+ 521 (formic acid).

$^1$H-NMR (300 MHz, d$_6$-DMSO): δ 8.38 (s, 1H), 8.27 (s, 1H), 7.63 (s, 2H), 7.49 (d, 2H, J=8.6 Hz), 7.33 (d, 2H, J=8.0 Hz), 5.99 (d, 1H, J=5.3 Hz), 5.65 (d, 1H, J=5.9 Hz), 5.48 (d, 1H, J=5.4 Hz), 4.77 (br, 2H), 4.67 (dd, 1H, J=5.5 Hz, J=10.9 Hz), 4.26 (m, 4H).

Example 21

{(2R,3S,4R,5R)-5-[6-(Benzylamino)-9H-purin-9-yl]-3,4-dihydroxytetrahydrofuran-2-yl}methyl sulfamate (I-6)

The title compound was prepared as described in Example 6, step c, using benzylamine.

LCMS: R.t. 1.16 min, ES+ 437 (formic acid).

$^1$H-NMR (300 MHz, CD$_3$OD): δ 8.25 (m, 2H) ppm 7.30 (m, 5H) ppm 6.06 (d, 1H, J=4.9 Hz) ppm 4.64 (dd, 1H, J=4.3 Hz, J=9.1 Hz) ppm 4.36 (m, 4H)

Example 22

N-[((2R,3S,4R,5R)-5-{6-[(1S)-2,3-Dihydro-1H-inden-1-ylamino]-9H-purin-9-yl}-3,4-dihydroxytetrahydrofuran-2-yl)methyl]sulfamide (I-15)

Step a: tert-Butyl(aminosulfonyl) carbamate

A solution of tert-butyl alcohol (5.930 g, 0.080 mol) in ethyl acetate (100 mL) was cooled in an acetonitrile/dry ice bath under nitrogen and chlorosulfonyl isocyanate (6.964 mL, 0.080 mol) was added dropwise. The clear solution was stirred at about −40° C. under nitrogen for 2 h. The cooling bath was changed for a chloroform/dry ice bath, the reaction flask was topped with a cold finger containing acetone/dry ice, and ammonia was condensed in the reaction for 20 min to lead to the rapid formation of a white solid. The reaction was stirred at about −60° C. for 3 h. The cold finger and the cooling bath were removed and the reaction allowed to warm to room temperature under a stream of nitrogen. Water (100 mL) was added. The phases were separated and the aqueous washed once with EtOAc (50 mL). The aqueous was cooled in ice/water bath and acidified to pH-2 by adding 20% aq H$_2$SO$_4$ dropwise to obtain a white precipitate, which was isolated by filtration and washed with water. The product was dried overnight in vacuum oven at 40° C. and obtained as a white solid (9.440 g, 60%).

LCMS: R.t. 1.07 min ES-195 (formic acid).

Step b: tert-Butyl(aminosulfonyl){[(3aR,4R,6R,6aR)-6-(6-chloro-9H-purin-9-yl)-2,2-dimethyltetrahydrofuro[3,4-d][1,3]dioxol-4-yl]methyl}carbamate (2R,3R,4S,5R)-2-(6-chloro-9H-purin-9-yl)-5-(hydroxymethyl)tetrahydrofuran-3,4-diol (6.352 g, 0.01944 mol), N-Boc-sulfamide (5.717 g, 0.02913 mol) and triphenylphosphine (6.119 g, 0.02333 mol) were dissolved in ethyl acetate (200 mL) under nitrogen and diisopropyl azodicarboxylate (5.742 mL, 0.02916 mol) was added dropwise. The solution was stirred for 2 h, and then concentrated in vacuo. The residue was purified by flash chromatography (Hex/EtOAc 25% to 65%) to afford 5.460 g of product as a white solid and 1.40 g of product with triphenylphosphine oxide impurity. This second batch was purified by flash chromatography (Hex/EtOAc 20% to 60%). The product was obtained as a white solid (6.160 g, 63%).

LCMS: R.t. 1.66 min ES+ 505 (formic acid).

Step c: N-[((3aR,4R,6R,6aR)-6-(6-chloro-9H-purin-9-yl)-2,2-dimethyltetrahydrofuro[3,4-d][1,3]dioxol-4-yl)methyl]sulfamide tert-Butyl(aminosulfonyl){[(3aR,4R,6R,6aR)-6-(6-chloro-9H-purin-9-yl)-2,2-dimethyltetrahydrofuro[3,4-d][1,3]dioxol-4-yl]methyl}carbamate (6.160 g, 0.01220 mol) was treated with trifluoroacetic acid/methylene chloride 1:2 (60 mL) for 30 min. Toluene was added and the solution was concentrated to dryness to obtain a white solid which was purified by flash chromatography (MeOH/DCM 1% to 6%). The product was obtained as a white solid (4.939 g, 83%).

LCMS: R.t. 1.18 min ES+ 405 (formic acid).

Step d: N-[((3aR,4R,6R,6aR)-6-{6-[(1S)-2,3-dihydro-1H-inden-1-ylamino]-9H-purin-9-yl}-2,2-dimethyltetrahydrofuro[3,4-d][1,3]dioxol-4-yl)methyl]sulfamide N-[((3aR,4R,6R,6aR)-6-(6-Chloro-9H-purin-9-yl)-2,2-dimethyltetrahydrofuro[3,4-d][1,3]dioxol-4-yl)methyl]sulfamide (4.100 g, 0.01013 mol), (S)-(+)-1-aminoindane (1.624 mL, 0.01266 mol) and triethylamine (3.529 mL, 0.02532 mol) were refluxed in ethanol (100 mL) overnight. The reaction mixture was concentrated in vacuo, and the residue was purified by flash chromatography DCM/EtOAc 25% to 60%). The product was obtained as a white solid (4.185 g, 82%).

LCMS: R.t. 1.56 min ES+ 502 (formic acid).

Step e: N-[((2R,3S,4R,5R)-5-{6-[(1S)-2,3-Dihydro-1H-inden-1-ylamino]-9H-purin-9-yl}-3,4-dihydroxytetrahydrofuran-2-yl)methyl]sulfamide (I-15)

N-[((3aR,4R,6R,6aR)-6-{6-[(1S)-2,3-Dihydro-1H-inden-1-ylamino]-9H-purin-9-yl}-2,2-dimethyltetrahydrofuro[3,4-d][1,3]dioxol-4-yl)methyl]sulfamide (4.185 g, 0.008344 mol) was treated with trifluoroacetic acid/water 9:1 (50 mL) at room temperature for 15 min. The pinkish solution was concentrated in vacuo and the residue precipitated from methanol/ether. The product was obtained as an off-white solid (3.434 g, 89%).

LCMS: R.t. 1.31 min ES+ 463 (formic acid).

$^1$H-NMR (300 MHz, d$_6$-DMSO+D$_2$O): δ 8.40 (br s, 1H), 8.33 (s, 1H), 7.29-7.11 (m, 4H), 5.86 (m, 1H), 5.17 (m,1H), 4.68 (m, 1H), 4.13 (m, 2H), 3.18 (m, 2H), 3.02 (m, 1H), 2.85 (m, 1H), 2.09 (m, 1H).

Example 23

N-{[(2R,3S,4R,5R)-3,4-Dihydroxy-5-(6-{[(1R,2S)-2-hydroxy-2,3-dihydro-1H-inden-1-yl]amino}-9H-purin-9-yl)tetrahydrofuran-2-yl]methyl}sulfamide (I-13)

The title compound was prepared as described in Example 22, step d, and example 22, step e, using (1R,2S)-2-hydroxy-2,3-dihydro-1H-inden-1-yl amine, and purified by preparative HPLC.

LCMS: R.t. 0.98 min ES+ 478 (formic acid).
$^1$H-NMR (300 MHz, d$_6$-DMSO+D$_2$O): δ 8.33 (s, 1H), 8.30 (br s, 1H), 7.28-7.13 (m, 4H), 5.85 (d, 1H, J=7.0 Hz), 5.68 (br s, 1H), 4.72 (dd, 1H, J=6.9 Hz, J=4.9 Hz), 4.57 (m, 1H), 4.14 (m, 2H), 3.26-3.10 (m, 3H), 2.88 (d, 1H, J=15.5 Hz).

Example 24

N-[((2R,3S,4R,5R)-5-{6-[(1R)-2,3-Dihydro-1H-inden-1-ylamino]-9H-purin-9-yl}-3,4-dihydroxytetrahydrofuran-2-yl)methyl]sulfamide (I-46)

The title compound was prepared as described in Example 22, step d, and example 22, step e, using (R)-(−)-1-aminoindane, and purified by preparative HPLC.
LCMS: R.t. 1.25 min ES+ 462.5 (formic acid).
$^1$H-NMR (300 MHz, d$_6$-DMSO): δ 8.34 (s, 1H), 8.28 (s, 1H), 8.21 (m, 1H), 7.61 (m, 1H), 7.28-7.09 (m, 4H), 6.62 (s, 2H), 5.95 (m, 1H), 5.86 (d, 1H, J=6.9 Hz), 5.46 (m, 1H), 5.27 (m, 1H), 4.77 (m, 1H), 4.17-4.11 (m, 2H), 3.27-3.10 (m, 2H), 3.03 (m, 1H), 2.84 (m, 1H), 2.16 (m, 1H).

Example 25

N-{[(2R,3S,4R,5R)-3,4-Dihydroxy-5-{6-[(1-methyl-1H-pyrazol-4-yl)methyl]-amino}-9H-purin-9-yl)tetrahydrofuran-2-yl]methyl}sulfamide (I-38)

The title compound was prepared as described in Example 22, step d, and example 22, step e, using 1-methyl-1H-pyrazol-4-yl methylamine, and purified by preparative HPLC.
LCMS: R.t. 0.74 min ES+ 440 (formic acid).
$^1$H-NMR (300 MHz, d$_6$-DMSO): δ 8.33 (s, 1H), 8.26 (m, 2H), 8.02 (d, 1H, J=7.0 Hz), 7.57 (m, 2H), 7.35 (s, 1H), 6.60 (s, 2H), 5.84 (d, 1H, J=6.9 Hz), 5.44 (d, 1H, J=6.4 Hz), 4.74 (dd, 1H, J=6.6 Hz, J=5.4 Hz), 4.51 (m, 2H), 4.16-4.06 (m, 2H), 3.75 (s, 3H), 3.26-3.10 (m, 2H).

Example 26

N-[((2R,3S,4R,5R)-3,4-Dihydroxy-5-{6-[(1-naphthylmethyl)amino]-9H-purin-9-yl}tetrahydrofuran-2-yl)methyl]sulfamide (I-43)

The title compound was prepared as described in Example 22, step d, and example 22, step e, using 1-naphthylmethyl amine, and purified by preparative HPLC.
LCMS: R.t. 1.28 min ES+ 486 (formic acid).
$^1$H-NMR (300 MHz, d$_6$-DMSO): δ 8.53 (m, 1H), 8.36 (s, 1H), 8.26 (m, 1H), 8.22 (s, 1H), 7.95 (m, 1H), 7.81 (m, 1H), 7.56 (m, 3H), 7.45 (m, 2H), 6.60 (s, 2H), 5.85 (d, 1H, J=6.6 Hz), 5.45 (d, 1H, J=6.0 Hz), 5.26 (m, 1H), 5.19 (m, 1H), 4.75 (dd, 1H, J=11.3 Hz, J=5.6 Hz), 4.31 (m, 1H), 4.16-4.10 (m, 2H), 3.26-3.09 (m, 2H).

Example 27

N-[((2R,3S,4R,5R)-5-{6-[(2,2-Diphenylethyl)amino]-9H-purin-9-yl}-3,4-dihydroxytetrahydrofuran-2-yl)methyl]sulfamide (I-42)

The title compound was prepared as described in Example 22, step d, and example 22, step e, using α-phenylbenzylamine, and purified by preparative HPLC.
LCMS: R.t. 1.39 min ES+ 526 (formic acid).
$^1$H-NMR (300 MHz, d$_6$-DMSO): δ 8.29 (s, 1H), 8.27 (m, 1H), 7.90 (m, 1H), 7.53 (m, 1H), 7.34-7.26 (m, 8H), 7.20-7.15 (m, 2H), 6.60 (s, 2H), 5.81 (d, 1H, J=6.9 Hz), 4.72 (m, 1H), 4.60 (m, 1H), 4.14-4.10 (m, 4H), 3.25-3.08 (m, 2H).

Example 28

N-[((2R,3S,4R,5R)-5-{6-[(1-Benzothien-3-ylmethyl)amino]-9H-purin-9-yl}-3,4-dihydroxytetrahydrofuran-2-yl)methyl]sulfamide (I-44)

The title compound was prepared as described in Example 22, step d, and example 22, step e, using 1-benzothien-3-ylmethylamine, and purified by preparative HPLC.
LCMS: R.t. 1.27 min ES+ 492 (formic acid).
$^1$H-NMR (300 MHz, d$_6$-DMSO): δ 8.51 (m, 1H), 8.35 (s, 1H), 8.26 (s, 1H), 8.02 (d, 1H, J=7.0 Hz), 7.97 (m, 1H), 7.55 (dd, 1H, J=8.2 Hz, J=4.5 Hz), 7.52 (s, 1H), 7.39 (m, 2H), 6.60 (s, 2H), 5.84 (d, 1H, J=7.0 Hz), 5.44 (d, 1H, J=6.4 Hz), 5.26 (d, 1H, J=4.3 Hz), 4.75 (dd, 1H, J=11.6 Hz, J=6.4 Hz), 4.16-4.06 (m, 4H), 3.23-3.09 (m, 2H).

Example 29

N-[((2R,3S,4R,5R)-3,4-Dihydroxy-5-{6-[(3-methoxybenzyl)amino]-9H-purin-9-yl}tetrahydrofuran-2-yl)methyl]sulfamide (I-33)

The title compound was prepared as described in Example 22, step d, and example 22, step e, using 3-methoxybenzylamine, and purified by preparative HPLC.
LCMS: R.t. 1.08 min ES+ 466 (formic acid).
$^1$H-NMR (300 MHz, d$_6$-DMSO): δ 8.45 (br s, 1H), 8.35 (s, 1H), 8.21 (s, 1H), 7.55 (m, 1H), 7.20 (m, 1H), 6.90 (m, 2H), 6.78 (m, 1H), 6.59 (s, 2H), 5.84 (d, 1H, J=6.9 Hz), 5.44 (m, 1H), 5.25 (m, 1H), 4.75 (m, 1H), 4.18-4.05 (m, 4H), 3.70 (s, 3H), 3.26-3.08 (m, 2H).

Example 30

N-[((2R,3S,4R,5R)-3,4-Dihydroxy-5-{6-[(2-thienylmethyl)amino]-9H-purin-9-yl}tetrahydrofuran-2-yl)methyl]sulfamide (I-37)

The title compound was prepared as described in Example 22, step d, and example 22, step e, using 2-thienylmethylamine, and purified by preparative HPLC.
LCMS: R.t. 1.03 min ES+ 442 (formic acid).
$^1$H-NMR (300 MHz, d$_6$-DMSO): δ 8.54 (br s, 1H), 8.36 (s, 1H), 8.27 (br s, 1H), 7.54 (m, 1H), 7.33 (dd, 1H, J=5.1 Hz, J=1.3 Hz), 7.03 (dd, 1H, J=3.5 Hz, J=1.1 Hz), 6.93 (dd, 1H, J=5.1 Hz, J=3.4 Hz), 6.61 (s, 2H), 5.85 (d, 1H, J=7.0 Hz), 4.86 (m, 2H), 4.75 (dd, 1H, J=6.8 Hz, J=5.2 Hz), 4.16-4.10 (m, 2H), 3.26-3.10 (m, 2H).

Example 31

N-{([(2R,3S,4R,5R)-3,4-Dihydroxy-5-(6{[(2R)-2-hydroxy-2-(3-hydroxyphenyl)-ethyl]amino}-9H-purin-9-yl)tetrahydrofuran-2-yl]methyl}sulfamide (I-68)

The title compound was prepared as described in Example 22, step d, and example 22, step e, using (2R)-2-hydroxy-2-(3-hydroxyphenyl)ethylamine, and purified by preparative HPLC.
LCMS: R.t. 0.81 min ES+ 482 (formic acid).
$^1$H-NMR (300 MHz, d$_6$-DMSO): δ 8.33 (s, 1H), 8.25 (s, 1H), 7.63 (m, 1H), 7.56 (m, 1H), 7.11 (t, 1H, J=7.8 Hz), 6.83

(m, 2H), 6.63 (m, 1H), 6.60 (s, 2H), 5.84 (d, 1H, J=6.8 Hz) 5.49 (m, 1H), 5.45 (d, 1H, J=6.4 Hz), 5.25 (d, 1H, J=3.7 Hz), 4.76 (m, 2H), 4.15-4.06 (m, 2H), 3.71 (m, 1H), 3.53 (m, 1H), 3.26-3.10 (m, 2H).

Example 32

N-[((2R,3S,4R,5R)-5-{6-[(1,3-Benzodioxol-5-ylmethyl)amino]-9H-purin-9-yl}-3,4-dihydroxytetrahydrofuran-2-yl)methyl]sulfamide (I-39)

The title compound was prepared as described in Example 22, step d, and example 22, step e, using 1-(1,3-benzodioxol-5-yl)methanamine, and purified by preparative HPLC.
LCMS: R.t. 1.06 min ES+ 480 (formic acid).
$^1$H-NMR (300 MHz, $d_6$-DMSO): δ 8.43 (m, 1H), 8.35 (s, 1H), 8.22 (s, 1H), 7.55 (m, 1H), 6.92 (s, 1H), 6.78 (m,1H), 6.82 (m, 2H) 6.60 (s, 2H), 5.95 (s, 2H), 5.84 (d, 1H, J=6.7 Hz), 4.74 (dd, 1H, J=6.5 Hz, J=6.5 Hz), 4.60 (m, 2H), 4.16-4.10 (m, 2H), 3.26-3.10 (m, 2H).

Example 33

N-[((2R,3S,4R,5R)-3,4-Dihydroxy-5-{6-[(2-methoxyethyl)amino]-9H-purin-9-yl}tetrahydrofuran-2-yl)methyl]sulfamide (I-35)

The title compound was prepared as described in Example 22, step d, and example 22, step e, using 2-methoxyethylamine, and purified by preparative HPLC.
LCMS: R.t. 0.68 min ES+ 404 (formic acid).
$^1$H-NMR (300 MHz, $d_6$-DMSO): δ 8.34 (s, 1H), 8.23 (s, 1H), 7.85 (m, 1H), 7.54 (m, 1H), 6.60 (s, 2H), 5.84 (d, 1H, J=7.0 Hz), 4.73 (dd, 1H, J=6.7 Hz, J=5.2 Hz), 4.16-4.10 (m, 2H), 3.65 (m, 2H), 3.52 (t, 2H, J=5.7 Hz), 3.26 (s, 3H), 3.25-3.10 (m, 2H).

Example 34

N-{[(2R,3S,4R,5R)-3,4-Dihydroxy-5-(6-{[(1R)-2-hydroxy-1-phenylethyl]-amino}-9H-purin-9-yl)tetrahydrofuran-2-yl]methyl}sulfamide (I-45)

The title compound was prepared as described in Example 22, step d, and example 22, step e, using (1R)-2-hydroxy-1-phenylethyl]amino, and purified by preparative HPLC.
LCMS: R.t. 0.94 min ES+ 466 (formic acid).
$^1$H-NMR (300 MHz, $d_6$-DMSO): δ 8.36 (s, 1H), 8.16 (s, 1H), 8.12 (d, 1H, J=8.5 Hz), 7.53 (m, 1H), 7.43 (m, 2H), 7.29 (m, 2H), 7.20 (m, 1H), 6.59 (s, 2H), 5.83 (d, 1H, J=6.7 Hz) 5.42 (m, 2H), 5.25 (m, 1H), 4.95 (m, 1H), 4.72 (m, 1H), 4.15-4.09 (m, 2H), 3.84-3.68 (m, 2H), 3.26-3.10 (m, 2H).

Example 35

N-{[(2R,3S,4R,5R)-3,4-Dihydroxy-5-(6-{[(5-methylpyrazin-2-yl)methyl]amino}-9H-purin-9-yl)tetrahydrofuran-2-yl]methyl}sulfamide (I-36)

The title compound was prepared as described in Example 22, step d, and example 22, step e, using 5-methylpyrazin-2-yl-methylamine, and purified by preparative HPLC.
LCMS: R.t. 0.79 min ES+ 452 (formic acid).
$^1$H-NMR (300 MHz, $d_6$-DMSO): δ 8.50 (m, 1H), 8.45 (m, 2H), 8.38 (s, 1H), 8.20 (s, 1H), 7.50 (m, 1H), 6.59 (s, 2H), 5.85 (d, 1H, J=6.9 Hz), 4.80 (m, 2H), 4.74 (dd, 1H, J=6.6 Hz, J=5.4 Hz), 4.16-4.09 (m, 2H), 3.26-3.10 (m, 2H), 2.45 (s, 3H).

Example 36

N-({(2R,3S,4R,5R)-5-[6-(Benzylamino)-9H-purin-9-yl]-3,4-dihydroxytetrahydrofuran-2-yl}methyl)sulfamide (I-19)

The title compound was prepared as described in Example 22, step d, and example 22, step e, using benzylamine, and purified by preparative HPLC.
LCMS: R.t. 1.02 min ES+ 436 (formic acid).
$^1$H-NMR (300 MHz, $d_6$-DMSO): δ 8.48 (m, 1H), 8.35 (s, 1H), 8.21 (s, 1H), 7.56 (dd, 1H, J=7.8 Hz, J=3.7 Hz), 7.36-7.18 (m, 5H), 6.60 (s, 2H), 5.85 (d, 1H, J=6.7 Hz), 5.45 (d, 1H, J=6.4 Hz), 5.26 (m, 1H), 4.74 (m, 3H), 4.14 (m, 2H), 3.27-3.09 (m, 2H).

Example 37

N-[((2R,3S,4R,5R)-3,4-Dihydroxy-5-{6-[(2-phenoxyethyl)amino]-9H-purin-9-yl}tetrahydrofuran-2-yl)methyl]sulfamide (I-34)

The title compound was prepared as described in Example 22, step d, and example 22, step e, using 2-phenoxyethylamine, and purified by preparative HPLC.
LCMS: R.t. 1.11 min ES+ 466 (formic acid).
$^1$H-NMR (300 MHz, $d_6$-DMSO): δ 8.35 (s, 1H), 8.26 (br s, 1H), 8.04 (br s, 1H), 7.53 (m, 1H), 7.27 (dd, 2H, J=8.9 Hz, J=7.1 Hz), 6.93 (m, 3H), 6.60 (s, 2H), 5.85 (d, 1H, J=6.8 Hz), 5.44 (d, 1H, J=6.4 Hz), 5.25 (d, 1H, J=4.3 Hz), 4.74 (dd, 1H, J=11.7 Hz, J=6.4 Hz), 4.19-4.09 (m, 4H), 3.87 (m, 2H), 3.27-3.09 (m, 2H).

Example 38

N-{[(2R,3S,4R,5R)-3,4-Dihydroxy-5-(6-{[(1S)-2-hydroxy-1-phenylethyl]amino}-9H-purin-9-yl)tetrahydrofuran-2-yl]methyl}sulfamide (I-20)

The title compound was prepared as described in Example 22, step d, and example 22, step e, using (S)-2-amino-2-phenylethanol, and purified by preparative HPLC.
LCMS: R.t. 0.90 min ES+ 466 (formic acid).
$^1$H-NMR (300 MHz, $d_6$-DMSO): δ 8.36 (s, 1H), 8.16 (s, 1H), 8.12 (d, 1H, J=8.5 Hz), 7.53 (m, 1H), 7.43 (m, 2H), 7.29 (m, 2H), 7.20 (m, 1H), 6.59 (s, 2H), 5.83 (d, 1H, J=6.7 Hz) 5.42 (m, 2H), 5.25 (m, 1H), 4.95 (m, 1H), 4.72 (m, 1H), 4.15-4.09 (m, 2H), 3.84-3.68 (m, 2H), 3.26-3.10 (m, 2H).

Example 39

((2R,3S,4R,5R)-5-{4-[(1S)-2,3-Dihydro-1H-inden-1-ylamino]-7H-pyrrolo[2,3-d]pyrimidin-7-yl}-3,4-dihydroxytetrahydrofuran-2-yl)methyl sulfamate (I-9)

Step a: [(3aR,4R,6R,6aR)-6-(4-Chloro-pyrrolo[2,3-d]pyrimidin-7-yl)-2,2-dimethyltetrahydrofuro[3,4-d][1,3]dioxol-4-yl]-methanol To a suspension of (2R,3R,4S,5R)-2-(4-chloro-pyrrolo[2,3-d]pyrimidin-7-yl)-5-hydroxymethyl-tetrahydro-furan-3,4-diol (0.5 g, 1.75 mmol) and 2,2-dimethoxypropane (1.12 mL, 8.75 mmol) in acetone (40 mL) was added 333 mg (1.75 mmol) p-TsOH monohydrate. The resulting clear solution was stirred for 13 hours and then saturated aq NaHCO₃ was added. Approximately half the solvent was removed in vacuo and the resulting suspension was diluted with water and extracted with CH₂Cl₂ (4×). The combined organic layers were washed with brine, dried over Na₂SO₄, filtered, and concentrated in vacuo. The crude product was used without further purification.

LCMS: R.t. 1.49 min, ES+ 326 (formic acid).

Step b {(3aR,4R,6R,6aR)-6-[4-((S)-Indan-1-ylamino)-pyrrolo[2,3-d]pyrimdin-7-yl]-2,2-dimethyltetrahydro-furo[3,4-d][1,3]dioxol-4-yl}-methanol A solution of [(3aR,4R,6R,6aR)-6-(4-Chloro-pyrrolo[2,3-d]pyrimidin-7-yl)-2,2-dimethyl-tetrahydro-furo[3,4-d][1,3]dioxol-4-yl]-methanol (574 mg, 1.76 mmol), diisopropylethylamine (1.2 mL, 7.04 mmol) and (S)-(+)-1-aminoindane (680 µL, 5.27 mmol) in n-butanol 3.3 mL) was divided into two portions and each portion was microwave irradiated at 190° C. for 900 s. The solvent was removed in vacuo and the combined crude portions were purified by silica gel chromatography (0 to 5% MeOH/CH₂Cl₂) to afford 460 mg (62% over two steps) of the title compound.

LCMS: R.t. 1.31 min, ES+ 423 (formic acid).

Step c: Sulfamic acid (3aR,4R,6R,6aR)-6-[4-((S)-indan-1-ylamino)-pyrrolo[2,3-d]pyrimidin-7-yl]-2,2-dimethyl-tetrahydro-furo[3,4-d][1,3]dioxol-4-ylmethyl ester To a solution of the alcohol formed in Example 39, step b (349 mg, 0.83 mmol), and triethylamine (231 µL, 1.66 mmol) in DMF (14 mL) was added dropwise 620 µL of a 2M solution of the chlorosulfonamide in acetonitrile and the cloudy solution was stirred for 50 minutes. The reaction was diluted with EtOAc and water/brine, the layers were separated, and the aqueous layer was extracted with EtOAc (1×). The combined organic layers were washed with brine, dried over Na₂SO₄, filtered, and concentrated in vacuo. The crude material was purified by silica gel chromatography (0 to 5% MeOH/ CH₂Cl₂) to afford 233 mg (56%) of the title compound.

LCMS: R.t. 1.48 min, ES+ 502 (formic acid).

Step d: ((2R,3S,4R,5R)-5-{4-[(1S)-2,3-Dihydro-1H-inden-1-ylamino]-7H-pyrrolo[2,3-d]pyrimidin-7-yl}-3,4-dihydroxytetrahydrofuran-2-yl)methyl sulfamate (I-9)

The isopropylidene protected diol described in Example 39, step c (100 mg) was dissolved in approximately 3 mL of 10% water in TFA. After 18 minutes the solvent was removed in vacuo and the crude product was purified by HPLC to obtain 26 mg (28%) of product.

LCMS: R.t. 1.08 min, ES+ 462 (formic acid).

¹H-NMR (400 MHz, CD₃OD): δ (s, 1H); 7.39 (d, J=3.8 Hz, 1H); 7.33-7.20 (m, 4H); 6.76 (d, J=3.7 Hz, 1H); 6.31 (d, J=5.6 Hz, 1H); 5.92 (t, J=7.7 Hz, 1H); 5.55 (s, 1H); 4.51 (t, J=5.4 Hz, 1H); 4.44-4.31 (m, 3H); 3.16-3.09 (m, 1H); 3.03-2.95 (m, 1H); 2.74-2.66 (m, 1H); 2.13-2.04 (m, 1H).

Example 40

((2R,3S,4R,5R)-5-{4-[(1S)-2,3-Dihydro-1H-inden-1-ylamino]-7H-pyrrolo[2,3-d]pyrimidin-7-yl}-3,4-dihydroxytetrahydrofuran-2-yl)methyl sulfamate (I-1)

Step a: (2R,3S,5R)-5-(6-amino-9H-purin-9-yl)-2-({[tert-butyl(dimethyl)silyl]oxy}methyl)-tetrahydrofuran-3-ol To a solution of (2R,3S,5R)-5-(6-amino-9H-purin-9-yl)-2-(hydroxymethyl)-tetrahydrofuran-3-ol (3.78 g, 15.04 mmol) and imidazole (2.46 g, 36.10 mmol) in DMF (20 mL) was added tert-butyldimethylsilylchloride (2.38 g, 15.80 mmol) and the solution was stirred at room temperature for approximately 4 hours. The reaction mixture was diluted with water, and extracted three times with EtOAc. The combined organics were dried over Na₂SO₄ and concentrated in vacuo. The product was isolated as a white solid (4.138 g, 75%) and was used without further purification.

LCMS: R.t. 1.31 min, ES+ 366 (formic acid).

Step b: (2R,3S,5R)-5-(6-Amino-9H-purin-9-yl)-2-({[tert-butyl(dimethyl)silyl]oxy}methyl)-tetrahydrofuran-3-yl acetate A solution of (2R,3S,5R)-5-(6-amino-9H-purin-9-yl)-2-({[tert-butyl(dimethyl)silyl]oxy}methyl)tetrahydrofuran-3-ol (4.138 g, 11.32 mmol) and catalytic amount of DMAP in pyridine was cooled with an ice bath. Acetic anhydride (1.124 mL, 11.89 mmol) was added slowly and the reaction mixture was stirred while warming to room temperature for approximately 5 hours. The reaction was quenched with 1N HCl solution and extracted three times with EtOAc. The combined organic phases were washed with aqueous CuSO₄ solution and dried over Na₂SO₄. A white solid was isolated upon removing the solvent (4.143 g, 90%) and the crude material was used without further purification.

LCMS: R.t. 1.61 min, ES+ 409 (formic acid).

Step c: (2R,3S,5R)-5-(6-bromo-9H-purin-9-yl)-2-({[tert-butyl(dimethyl)silyl]oxy}methyl)-tetrahydrofuran-3-yl acetate To a solution of (2R,3S,5R)-5-(6-amino-9H-purin-9-yl)-2-({[tert-butyl(dimethyl)silyl]oxy}methyl)tetrahydrofuran-3-yl acetate (2.00 g, 4.91 mmol) in dibromomethane (98.2 mL) were added trimethylsilylbromide (0.717 mL, 5.55 mmol) then t-butylnitrite (3.98 mL, 33.44 mmol). The reaction mixture was stirred at room temperature for approximately 3 hours before being slowly poured into a 1:1 mixture of saturated NaHCO₃:CH₂Cl₂. The organics were washed with water then brine. After drying over Na₂SO₄, the solvent was removed in vacuo. The crude product was purified by flash chromatography (0% to 30% EtOAc/Hex) to obtain the title compound as a yellow oil (1.26 g, 55%).

LCMS: R.t. 2.16 min, ES+ 473 (formic acid).

Step d (2R,3S,5R)-2-({[tert-Butyl(dimethyl)silyl]oxy}methyl)-5-{6-[(1S)-2,3-dihydro-1H-inden-1-ylamino]-9H-purin-9-yl}tetrahydrofuran-3-yl acetate A solution of (2R,3S,5R)-5-(6-bromo-9H-purin-9-yl)-2-({[tert-butyl(dimethyl)-silyl]oxy}methyl)tetrahydrofuran-3-yl acetate (359 mg, 0.76 mmol), diisopropylethylamine (265 µL, 1.52 mmol) and (S)-(+)-1-aminoindane (146 µL, 1.14 mmol) in ethanol (13 mL) was heated to reflux for 17 h. The solvent was removed in vacuo and the residue purified by silica gel chromatography (10 to 50% EtOAc/hexanes) to afford 322 mg (81%) of product.

LCMS: R.t. 2.31 min, ES+ 525 (formic acid).

Step e: (2R,3S,5R)-5-{6-[(1S)-2,3-Dihydro-1H-inden-1-ylamino]-9H-purin-9-yl}-2-(hydroxymethyl) tetrahydrofuran-3-yl acetate To a solution of (2R,3S,5R)-2-({[tert-butyl(dimethyl)silyl] oxy}methyl)-5-{6-[(1S)-2,3-dihydro-1H-inden-1-ylamino]-9H-purin-9-yl}tetrahydrofuran-3-yl acetate (440 mg, 0.84 mmol) in pyridine/tetrahydrofuran (1:1, 3.4 mL) was added approximately 20 drops of hydrofluoric acid in pyridine (2.0 M). After stirring for 17 h, the reaction was quenched with saturated aqueous NaHCO₃ and extracted with dichloromethane. The combined organic layers were washed with brine, dried over Na₂SO₄, filtered, and concentrated in vacuo. Purification via flash chromatography (40 to 100% EtOAc/hexanes) afforded 314 mg (91%) of the title compound.

LCMS: R.t. 1.39 min, ES+ 410 (formic acid).

Step f: (2R,3S,5R)-2-{[(Aminosulfonyl)oxy]methyl}-5-{6-[(1S)-2,3-dihydro-1H-inden-1-ylamino]-9H-purin-9-yl}tetrahydrofuran-3-yl acetate (2R,3S,5R)-5-{6-[(1S)-2,3-Dihydro-1H-inden-1-ylamino]-9H-purin-9-yl}-2-(hydroxymethyl)tetrahydrofuran-3-yl acetate (199 mg, 0.29 mmol) was treated with chlorosulfonamide as described in Example 39, step c. The product was purified by flash chromatography (0 to 5% MeOH/CH₂Cl₂) to afford 105 mg (74%) of the title compound.

LCMS: R.t. 1.52 min, ES+ 489 (formic acid).

Step g: ((2R,3S,4R,5R)-5-{4-[(1S)-2,3-Dihydro-1H-inden-1-ylamino]-7H-pyrrolo[2,3-d]pyrimidin-7-yl}-3,4-dihydroxytetrahydrofuran-2-yl)methyl sulfamate (I-1)

(2R,3S,5R)-2-{[(Aminosulfonyl)oxy]methyl}-5-{6-[(1S)-2,3-dihydro-1H-inden-1-ylamino]-9H-purin-9-yl}tetrahydrofuran-3-yl acetate (96 mg, 0.20 mmol) was dissolved in 2.6 mL of 7M NH₃/MeOH and stirred for one hour. Approximately 1 mL tetrahydrofuran was added, and the resulting solution was stirred for 3 hours. The solvent was removed in vacuo and the residue purified by silica gel chromatography (0% to 10% MeOH/CH₂Cl₂) to afford 59 mg (66%) of the title compound.

LCMS: R.t. 1.30 min, ES+ 447 (formic acid).

¹H NMR (400 MHz, CD₃OD): δ 8.31 (s, 1H); 8.25 (s, 1H); 7.29-7.13 (m, 4H); 6.49 (t, J=6.8 Hz, 1H); 5.87 (bs, 1H); 4.64-4.61 (m, 1H); 4.39-4.29 (m, 2H); 4.25-4.21 (m, 1H); 3.32-3.31(m, 1H); 3.12-3.03 (m, 1H); 2.98-2.87 (m, 1H); 2.85-2.76 (m, 1H); 2.72-2.62 (m, 1H); 2.54-2.46 (m, 1H); 2.08-1.95 (m, 1H).

Example 41

((2R,3S,4R,5R)-5-{4-[(1S)-2,3-Dihydro-1H-inden-1-ylamino]-7H-pyrrolo[2,3-d]pyrimidin-7-yl}-3,4-dihydroxytetrahydrofuran-2-yl)methyl sulfamate (I-53)

Step a: (2R,3R,5S)-2-(6-Chloro-purin-9-yl)-5-(tert-butyl-dimethyl-silanyloxymethyl)-tetrahydro-furan-3-yl acetate To a solution of (2R,3R,5S)-2-(6-amino-purin-9-yl)-5-(tert-butyl-dimethylsilanyloxymethyl)tetrahydrofuran-3-ol (727 mg, 1.99 mmol) (Norbeck, D. W.; Kramer, J. B. *J. Am. Chem. Soc.* 1988, 110, 7217-7218) in pyridine (10 mL) at 0° C. was added dropwise acetic anhydride (207 μL, 2.19 mmol). After stirring for two hours, the solution was warmed to room temperature and a few crystals of DMAP were added. After one hour, the reaction was quenched with saturated aqueous NaHCO₃ and poured into water/1 N HCl/EtOAc. The layers were separated and the aqueous layer was extracted with EtOAc (2×). The combined organics were washed once with brine, dried over Na₂SO₄, filtered, and the solvent removed in vacuo. The crude product was purified by silica gel chromatography (20 to 70% EtOAc/hexanes) to afford 610 mg (75%) of the acylated compound.

LCMS: R.t. 1.66 min, ES+ 408 (formic acid).

Of this material, 394 mg (0.97 mmol) was dissolved in CH₂Cl₂ (29 mL) and cooled to 0° C. To this was added trimethylsilylchloride (1.1 mL, 8.73 mmol) dropwise, followed by a solution of tert-butylnitrite (692 μL, 5.82 mmol) in CH₂Cl₂ (10 mL). After stirring for 30 minutes the solution was warmed to room temperature. After stirring for one hour, the solution was quenched with saturated aqueous NaHCO₃ and extracted with EtOAc. The combined organics were washed once with brine, dried over Na₂SO₄, filtered, and the solvent removed in vacuo. The crude product was purified by silica gel chromatography (5 to 30% EtOAc/hexanes) to afford 136 mg (33%) of the title compound.

LCMS: R.t. 2.23 min, ES+ 427 (formic acid standard).

Step b: (2R,3R,5S)-5-(tert-Butyl-dimethyl-silanyloxymethyl)-2-[6-((S)-indan-1-ylamino)-purin-9-yl] tetrahydro-furan-3-yl acetate A solution of (2R,3R,5S)-2-(6-chloro-purin-9-yl)-5-(tert-butyldimethylsilanyloxymethyl)tetrahydrofuran-3-yl acetate (167 mg, 0.39 mmol), diisopropylethylamine (109 μL, 0.78 mmol) and (S)-(+)-1-aminoindane (75 μL, 0.59 mmol) in ethanol (6.3 mL) was heated to reflux for 15 hours. The solvent was removed in vacuo and the residue purified by silica gel chromatography (0 to 5% MeOH/CH₂Cl₂) to afford 109 mg (53%) of product.

LCMS: R.t. 2.43 min, ES+ 524 (formic acid).

Step c: (2R,3R,5S)-5-Hydroxymethyl-2-[6-((S)-indan-1-ylamino)-purin-9-yl]tetrahydrofuran-3-yl acetate To a solution of (2R,3R,5S)-5-(tert-butyl-dimethyl-silanyloxymethyl)-2-[6-((S)-indan-1-ylamino)purin-9-yl]tetrahydrofuran-3-yl acetate (109 mg, 0.20 mmol) in pyridine/tetrahydrofuran (1:1, 2 mL) was added approximately 6 drops of hydrofluoric acid in pyridine (2.0 M). After stirring for 5 h the reaction was quenched with saturated aqueous NaHCO₃ and extracted with EtOAc. The combined organic layers were washed with brine, dried over Na₂SO₄, filtered, and concentrated in vacuo to afford a quantitative amount of the crude product.

LCMS: R.t. 1.45 min, ES+ 410 (formic acid).

Step d: (2R,3R,5S)-2-[6-((S)-Indan-1-ylamino)-purin-9-yl]-5-sulfamoyloxymethyl-tetrahydrofuran-3-yl acetate To a solution of (2R,3R,5S)-5-hydroxymethyl-2-[6-((S)-indan-1-ylamino)-purin-9-yl]tetrahydrofuran-3-yl acetate (0.20 mmol) and triethylamine (56 μL, 0.0.40 mmol) in DMF (3.3 mL) was added dropwise 150 μL of a 2M solution of the chlorosulfonamide in acetonitrile and the cloudy solution was stirred. Identical amounts of triethylamine and the chlorosulfonamide solution were added after 2.5 and 4 hours. The reaction was diluted with EtOAc and water, the layers were separated, and the aqueous layer was extracted with EtOAc (1×). The combined organic layers were washed with brine, dried over $Na_2SO_4$, filtered, and concentrated in vacuo. The crude material was purified by silica gel chromatography (0% to 10% $MeOH/CH_2Cl_2$) to afford 51 mg (52%) of the title compound.

LCMS: R.t. 1.52 min, ES+ 489 (formic acid).

Step e: ((2R,3S,4R,5R)-5-{4-[(1S)-2,3-Dihydro-1H-inden-1-ylamino]-7H-pyrrolo[2,3-d]pyrimidin-7-yl}-3,4-dihydroxytetrahydrofuran-2-yl)methyl sulfamate (I-53)

(2R,3R,5S)-2-[6-((S)-Indan-1-ylamino)-purin-9-yl]-5-sulfamoyloxymethyl-tetrahydrofuran-3-yl acetate (50 mg, 0.10 mmol) was dissolved in 1.3 mL of 7M $NH_3$/MeOH and stirred for one hour. Approximately 1 mL methanol was added, and the resulting solution was stirred for 1.5 hours. The solvent was removed in vacuo and the residue purified by silica gel chromatography (0 to 10% $MeOH/CH_2Cl_2$) to afford 34 mg (76%) of product.

LCMS: R.t. 1.33 min, ES+ 447 (formic acid).
$^1$H NMR (400 MHz, $CD_3OD$): δ 8.38 (bs, 1H); 8.31 (s, 1H); 7.35-7.20(m, 4H); 6.11(m, 1H); 5.95 (bs, 1H); 4.81-4.78 (m, 2H); 4.52-4.49 (m, 1H); 4.36 (dd, J=4.2, 11.1 Hz, 1H); 3.41 (s, 2H); 3.18-3.11 (m, 1H); 3.04-2.96 (m, 1H); 2.77-2.69 (m, 1H); 2.47-2.40 (m, 1H); 2.23-2.18 (m, 1H); 2.13-2.04 (m, 1H).

Example 42

((2R,3R,4S,5R)-5-{6-[(1S)-2,3-Dihydro-1H-inden-1-ylamino]-9H-purin-9-yl}-3-hydroxy-4-methoxytetrahydrofuran-2-yl)methyl sulfamate (I-61)

Step a: 6-chloro-9-[(6aR,8R,9S,9aR)-2,2,4,4-Tetraisopropyl-9-methoxytetrahydro-6H-furo-[3,2-f][1,3,5,2,4]trioxadisilocin-8-yl]-9H-purine To a suspension of (6aR,8R,9S,9aS)-8-(6-chloro-9H-purin-9-yl)-2,2,4,4-tetraisopropyltetrahydro-6H-furo[3,2-f][1,3,5,2,4]trioxadisilocin-9-ol (300 mg, 0.57 mmol) and $Cs_2CO_3$ (1.86 g, 5.7 mmol) in DMF (5.7 mL) at 0° C. was added MeI (350 µL, 5.7 mmol) dropwise. The suspension was stirred for 3 hours, quenched with saturated aqueous $NH_4Cl$ and $CH_2Cl_2$. The layers were separated and the aqueous layer was extracted with $CH_2Cl_2$ (2×). The combined organic layers were dried over $Na_2SO_4$, filtered, and concentrated in vacuo. The crude material was purified by silica gel chromatography (0 to 20% EtOAc/hexanes) to afford 221 mg (71%) of the title compound.

LCMS: R.t. 3.12 min, ES+ 543 (formic acid standard).

Step b: N-[(1S)-2,3-Dihydro-H-inden-1-yl]-9-[(6aR, 8R,9S,9aR)-2,2,4,4-tetraisopropyl-9-methoxytetrahydro-6H-furo[3,2-f][1,3,5,2,4]trioxadisilocin-8-yl]-9H-purin-6-amine A solution of 6-chloro-9-[(6aR,8R,9S,9aR)-2,2,4,4-tetraisopropyl-9-methoxytetrahydro-6H-furo[3,2-1][1,3,5,2,4]trioxadisilocin-8-yl]-9H-purine (221 mg, 0.41 mmol), diisopropylethylamine (114 µL, 0.82 mmol) and (S)-(+)-1-aminoindane (78 µL, 0.61 mmol) in ethanol (7 mL) was heated to reflux for 24 hours. The solvent was removed in vacuo and the residue purified by silica gel chromatography (10 to 30% EtOAc/hexanes) to afford 239 mg (91%) of the title compound.

LCMS: R.t. 3.20 min, ES+ 641 (formic acid standard).

Step c: 3-{[(2R,3R,4S,5R)-5-{6-[(1S)-2,3-Dihydro-1H-inden-1-ylamino]-9H-purin-9-yl}-2-(hydroxymethyl)-4-methoxytetrahydrofuran-3-yl]oxy}-1,1,3,3-tetraisopropyldisiloxan-1-ol To a solution of N-[(1S)-2,3-dihydro-1H-inden-1-yl]-9-[(6aR,8R,9S,9aR)-2,2,4,4-tetraisopropyl-9-methoxytetrahydro-6H-furo[3,2-f][1,3,5,2,4]trioxadisilocin-8-yl]-9H-purin-6-amine (238 mg, 0.37 mmol) in methanol/dioxane (1:4, 8 mL) was added 3.2 mL 0.2N HCl. After stirring for two hours the solvent was removed in vacuo and the residue purified by silica gel chromatography (10 to 50% EtOAc/hexanes) to afford 32 mg (13%) of the title compound.

LCMS: R.t. 2.31 min, ES+ 659 (formic acid standard).

Step d: {(2R,3R,4S,5R)-5-{6-[(1S)-2,3-Dihydro-1H-inden-1-ylamino]-9H-purin-9-yl}-3-[(3-hydroxy-1,1,3,3-tetraisopropyldisiloxanyl)oxy]-4-methoxytetrahydrofuran-2-yl}-methyl sulfamate 3-{[(2R,3R,4S,5R)-5-{6-[(1S)-2,3-Dihydro-1H-inden-1-ylamino]-9H-purin-9-yl}-2-(hydroxymethyl)-4-methoxytetrahydrofuran-3-yl]oxy}-1,1,3,3-tetraisopropyldisiloxan-1-ol was reacted with chlorosulfonamide as described in Example 41, step d. The crude product was reacted directly.

LCMS: R.t. 2.62 min, ES+ 737 (formic acid standard).

Step e: ((2R,3R,4S,5R)-5-{6-[(1S)-2,3-Dihydro-1H-inden-1-ylamino]-9H-purin-9-yl}-3-hydroxy-4-methoxytetrahydrofuran-2-yl)methyl sulfamate (I-61)

{(2R,3R,4S,5R)-5-{6-[(1S)-2,3-Dihydro-1H-inden-1-ylamino]-9H-purin-9-yl}-3-[(3-hydroxy-1,1,3,3-tetraisopropyldisiloxanyl)oxy]-4-methoxytetrahydrofuran-2-yl}methyl sulfamate was reacted with hydrofluoric acid in pyridine (2.0 M) essentially as described in Example 41, step c. The product was purified by flash chromatography (0 to 10% $MeOH/CH_2Cl_2$) affording 17 mg (74%)

LCMS: R.t. 1.35 min, ES+ 477 (formic acid standard).
$^1$H NMR (400 MHz, $CD_3OD$): δ 8.38 (s, 1H); 8.25 (s, 1H); 7.38-7.21 (m, 4H); 6.62-6.60 (d, J=5.1 Hz, 1H); 5.98-5.93 (m, 1H); 5.50 (s, 2H); 4.52-4.43 (m, 3H); 4.25-4.10 (m, 2H); 3.31 (s, 3H); 3.21-3.08 (m, 1H); 3.05-2.95 (m, 1H); 2.79-2.69 (m, 1H); 2.15-2.03 (m, 1H).

Example 43

((2R,3S,4S,5R)-5-{6-[(1S)-2,3-Dihydro-1H-inden-1-ylamino]-9H-purin-9-yl}-3,4-dihydroxytetrahydrofuran-2-yl)methyl sulfamate (I-67)

Step a: (2R,3S,4S,5R)-2-(6-Amino-9H-purin-9-yl)-5-{[(triisopropylsilyl)oxy]methyl}-tetrahydrofuran-3,4-diol Adenine 9-β-D-arabinofuranoside (0.25 g, 0.936 mmol) was stirred in DMF (2.5 mL) and cooled to 0° C. Imidazole (0.143 g, 2.1 mmol) was added followed by the dropwise addition of triisopropylsilyl chloride (2.89 g, 1.49 mmol). The reaction was stirred for seven hours then diluted with water and extracted using ethyl acetate (3×). The organic layer was dried (Na$_2$SO$_4$), filtered and concentrated. The clear oil was placed on high vacuum overnight and used as is (0.780 g, 98%) based on two (0.25 g) reactions.

LCMS: R.t. 1.53 min ES+ 424 (formic acid standard)

Step b: (2R,3S,4R,5R)-2-(6-Amino-9H-purin-9-yl)-5-{[(triisopropylsilyl)oxy]methyl}-tetrahydrofuran-3,4-diyl diacetate (2R,3S,4S,5R)-2-(6-Amino-9H-purin-9-yl)-5-{[(triisopropylsilyl)oxy]methyl}-tetrahydrofuran-3,4-diol (0.858 g, 2.03 mmol) was stirred in pyridine (6 mL) and cooled to 0° C. Acetic anhydride (0.456 g, 0.42 mL) was added dropwise followed by a catalytic amount of dimethylaminopyridine. The reaction was stirred for two hours, poured into saturated sodium bicarbonate and extracted with ethyl acetate (3×). The organic layer was washed with water, dried (Na$_2$SO$_4$), filtered and concentrated. The clear oil was purified by flash chromatography (25-100% ethyl acetate/hexanes) to give product (0.605 g, 59%).

LCMS: R.t. 1.94 min ES+ 508 (formic acid)

Step c: (2R,3S,4R,5R)-2-(6-Bromo-9H-purin-9-yl)-5-{[(triisopropylsilyl)oxy]methyl}-tetrahydrofuran-3,4-diyl diacetate (2R,3S,4R,5R)-2-(6Amino-9H-purin-9-yl)-5-{[(triisopropylsilyl)oxy]methyl}-tetrahydrofuran-3,4-diyl diacetate (0.605 g, 1.19 mmol) was dissolved in dibromomethane (24 mL). Trimethylsilyl bromide (0.17 mL, 1.35 mmol) was added dropwise followed by tert-butylnitrite (0.97 mL, 8.12 mmol). The orange solution was stirred for 2.5 hours then slowly poured into a 1:1 mixture of saturated sodium bicarbonate and dichloromethane and extracted. The pale yellow organic layer was washed with water and brine, dried (Na$_2$SO$_4$), filtered and concentrated. The yellow solid was purified by flash chromatography eluting with 25% ethyl acetate/hexanes to give the title compound as a yellow solid (0.402 g, 52%).

LCMS: R.t. 2.53 min ES+ 572 (formic acid)

Step d: (2R,3S,4R,5R)-2-{6-[(1S)-2,3-Dihydro-1H-inden-1-ylamino]-9H-purin-9-yl}-5-{[(triisopropylsilyl)oxy]methyl}tetrahydrofuran-3,4-diyl diacetate (2R,3S,4R,5R)-2-(6-Bromo-9H-purin-9-yl)-5-{[(triisopropylsilyl)oxy]methyl}-tetrahydrofuran-3,4-diyl diacetate (0.402 g, 0.703 mmol) was stirred in ethanol (10 mL) and S-(+)-1-aminoindan (0.14 mL, 1.06 mmol) was added followed by triethylamine (0.2 mL, 1.41 mmol). The reaction mixture was heated at overnight. The brown solution was concentrated and purified by flash chromatography, eluting with 10 to 35% ethyl acetate/hexanes to give the title compound as a white solid (0.142 g) and deacylated product (0.161 g, 37%).

LCMS: R.t. 2.61 min ES+ 624 (formic acid)

Step e: (2R,3S,4R,5R)-2-{6-[(1S)-2,3-Dihydro-1H-inden-1-ylamino]-9H-purin-9-yl}-5-(hydroxymethyl)tetrahydrofuran-3,4-diyl diacetate (2R,3S,4R,5R)-2-{6-[(1S)-2,3-Dihydro-1H-inden-1-ylamino]-9H-purin-9-yl}-5-{[(triisopropylsilyl)oxy]methyl}tetrahydrofuran-3,4-diyl diacetate (0.305 g, 0.49 mmol) was stirred in pyridine (2 mL) and tetrahydrofuran (2 mL). Hydrofluoric acid in pyridine (2.0 M) was added (15 drops) and the reaction was stirred at room temperature for thirty minutes. The reaction was quenched using saturated sodium bicarbonate then extracted using ethyl acetate (3×10 mL). The organic layer was dried (Na$_2$SO$_4$), filtered and concentrated. The brown residue was purified by column chromatography (30-50% ethyl acetate/hexanes followed by ethyl acetate) to give the title compound as a white solid (0.188 g, 82%).

LCMS: R.t. 1.49 min ES+ 468 (formic acid standard)

Step f: (2R,3R,4S,5R)-2-{[(Aminosulfonyl)oxy]methyl}-5-{6-[(1S)-2,3-dihydro-1H-inden-1-ylamino]-9H-purin-9-yl}tetrahydrofuran-3,4-diyl diacetate (2R,3S,4R,5R)-2-{6-[(1S)-2,3-Dihydro-1H-inden-1-ylamino]-9H-purin-9-yl}-5-(hydroxymethyl)tetrahydrofuran-3,4-diyl diacetate (0.188 g, 0.40 mmol) was stirred in anhydrous methylene chloride (0.6 mL) cooled to 0° C. Triethylamine (0.081 mL, 0.80 mmol) was added followed by the dropwise addition of a 2 N solution of chlorosulfonamide in acetonitrile (0.6 mL). The yellow solution was concentrated after one hour. The residue was purified by column chromatography using 0-5% methanol/methylene chloride concentrated to give the title compound as a yellow solid (0.104 g, 48%).

LCMS: R.t. 1.49 min ES+ 547 (formic acid)

Step g: ((2R,3S,4S,5R)-5-{6-[(1S)-2,3-Dihydro-1H-inden-1-ylamino]-9H-purin-9-yl}-3,4-dihydroxytetrahydrofuran-2-yl)methyl sulfamate (I-67)

(2R,3R,4S,5R)-2-{[(Aminosulfonyl)oxy]methyl}-5-{6-[(1S)-2,3-dihydro-1H-inden-1-ylamino]-9H-purin-9-yl}tetrahydrofuran-3,4-diyl diacetate (0.104 g, 0.19 mmol) was stirred in a 7 N solution of ammonia/methanol as described in Example 41, step e. The product was purified on a prep plate using 10% methanol/methylene chloride as developing solvent (0.018 g, 20%).

LCMS: R.t. 1.38 min ES+ 463 (formic acid)
$^1$H-NMR (300 MHz, d$_6$-DMSO): δ 8.28 (bs, 1H); 8.18-8.06 (bs, 2H); 7.59 (bs, 1H); 7.30-7.07 (m, 4H); 5.95 (bs, 1H); 5.80 (bs, 1H); 5.75 (bs, 1H); 4.38-4.26 (m, 4H); 4.18 (bs, 2H); 4.05 (bs, 1H); 3.87 (q, J=7.0 Hz, 1H); 3.10-2.97 (m, 1H); 2.91-2.78 (m, 1H).

Example 44

((2R,3S,4R,5R)-3,4-Dihydroxy-5-{6-[3-(1H-pyrazol-1-yl)phenyl]-9H-purin-9-yl}tetrahydrofuran-2-yl)methyl sulfamate (I-56)

Step a: [(3aR,4R,6R,6aR)-6-(6-Amino-9H-purin-9-yl)-2,2-dimethyltetrahydrofuro[3,4-d][1,3]dioxol-4-yl]methyl acetate Using essentially the same procedure as described in 43, step b, 2',3'-isopropylidene adenine (10 g 32.5 mmol)) was reacted with acetic anhydride to give the product as a white solid (7.65 g, 67%).

LCMS: R.t. 1.03 min ES+ 350 (formic acid standard)

Step b: [(3aR,4R,6R,6aR)-6-(6-Bromo-9H-purin-9-yl)-2,2-dimethyltetrahydrofuro[3,4-d][1,3]dioxol-4-yl]methyl acetate The title compound was prepared using essentially the same procedure as described in Example 43, step c. The product was purified by flash chromatography (25-50% ethyl acetate/hexanes) to give a yellow foam (1.621 g, 69%).
LCMS: R.t. 1.50 min ES+ 413, 415 (formic acid)

Step c: ((3aR,4R,6R,6aR)-2,2-Dimethyl-6-{6-[3-(1H-pyrazol-1-yl)phenyl]-9H-purin-9-yl}-tetrahydrofuro[3,4-d][1,3]dioxol-4-yl)methyl acetate

[(3aR,4R,6R,6aR)-6-(6-Bromo-9H-purin-9-yl)-2,2-dimethyltetrahydrofuro[3,4-d][1,3]dioxol-4-yl]methyl acetate (0.1 g, 0.242 mmol), 3-(1-H-pyrazole-1-yl)phenylboronic acid (0.137 g, 0.726 mmol), potassium phosphate (0.154 g, 0.726 mmol), and [1,1'-bis(diphenylphosphino)ferrocene]dichloropalladium(II), complex dichloromethane (1:1) (0.040 g, 0.048 mmol) were placed in an oven-dried microwave vial and degassed with argon. Anhydrous dioxane (1.5 mL) was added and the reaction was heated to 150° C. for ten minutes in the microwave. The mixture was filtered through a pad of Celite washing with dichloromethane then concentrated. The residue was taken up in dichloromethane and purified on a prep plate using 60% ethyl acetate/hexanes as developing solvent to give the title compound as a yellow solid (0.061 g 53%).
LCMS: R.t. 1.84 min ES+ 477 (formic acid)

Step d: ((3aR,4R,6R,6aR)-2,2-Dimethyl-6-{6-[3-(1H-pyrazol-1-yl)phenyl]-9H-purin-9-yl}-tetrahydrofuro[3,4-d][1,3]dioxol-4-yl)methanol Using essentially the same procedure as Example 43, step g, ((3aR,4R,6R,6aR)-2,2-dimethyl-6-{6-[3-(1H-pyrazol-1-yl)phenyl]-9H-purin-9-yl}tetrahydrofuro[3,4-d][1,3]-dioxol-4-yl)methyl acetate (0.217 g, 0.46 mmol) was deprotected and purified by flash chromatography (30-65% ethyl acetate/hexanes) to give the title compound as a white solid (0.209 g).
LCMS: R.t. 1.67 min ES+ 435 (formic acid)

Step e: ((3aR,4R,6R,6aR)-2,2-Dimethyl-6-{6-[3-(1H-pyrazol-1-yl)phenyl]-9H-purin-9-yl}-tetrahydrofuro[3,4-d][1,3]dioxol-4-yl)methyl sulfamate Using essentially the same procedure as Example 43, step f, ((3aR,4R,6R,6aR)-2,2-dimethyl-6-{6-[3-(1H-pyrazol-1-yl)phenyl]-9H-purin-9-yl}tetrahydrofuro[3,4-d][1,3]dioxol-4-yl)methanol (0.2 g, 0.46 mmol) was reacted with chlorosulfonamide, as described in Example 43, step f, and the product was purified by flash chromatography using 40-75% ethyl acetate/hexanes to give the title compound as a yellow solid (0.208, 88%).
LCMS: R.t. 1.63 min ES+ 514 (formic acid)

Step f: ((2R,3S,4R,5R)-3,4-Dihydroxy-5-{6-[3-(1H-pyrazol-1-yl)phenyl]-9H-purin-9-yl}-tetrahydrofuran-2-yl)methyl sulfamate (I-56)

((3aR,4R,6R,6aR)-2,2-Dimethyl-6-{6-[3-(1H-pyrazol-1-yl)phenyl]-9H-purin-9-yl}tetrahydrofuro[3,4-d][1,3]dioxol-4-yl)methyl sulfamate (0.207 g, 0.439 mmol) was stirred in trifluoroacetic acid/water (9:1, 3 mL) for 1.5 hours then concentrated. The residue was taken up in methanol and purified on a prep plate using 10% methanol/methylene chloride as developing solvent to give the product as a pale yellow solid (0.093 g, 45%).
LCMS: R.t. 1.30 min ES+ 474 (formic acid)
$^1$H-NMR (300 MHz, d$_6$-DMSO): δ 9.28 (s, 1H); 9.04 (s, 1H); 8.84 (s, 1H); 8.76 (d, J=8.2 Hz, 1H); 8.55 (ds, J=2.4 Hz, 1H); 8.01 (dd, J=1.5 Hz, J=9.5 Hz, 1H); 7.79 (ds, J=1.5 Hz 1H); 7.78 (t, J=8.0 Hz, 1H); 7.60 (s, 2H); 6.57 (t, J=2.3 Hz, 1H); 6.35 (bs, 1H); 6.12 (d, J=5.1 Hz, 1H); 4.68 (t, J=4.9 Hz, 1H); 4.32-4.17 (m, 4H).

Example 45

((2R,3S,4R,5R)-3,4-Dihydroxy-5-{6-[3-(trifluoromethyl)phenyl]-9H-purin-9-yl}tetrahydrofuran-2-yl) methyl sulfamate (I-57)

Step a: ((3aR,4R,6R,6aR)-2,2-Dimethyl-6-{6-[3-(trifluoromethyl)phenyl]-9H-purin-9-yl}-tetrahydrofuro[3,4-d][1,3]dioxol-4-yl)methyl acetate

[(3aR,4R,6R,6aR)-6-(6-Bromo-9H-purin-9-yl)-2,2-dimethyltetrahydrofuro[3,4-d][1,3]dioxol-4-yl]methyl acetate (0.60 g, 1.45 mmol), 3-(trifluoromethyl)phenylboronic acid (0.414 g, 2.18 mmol), palladium(II)acetate (0.033 g, 0.145 mmol), racemic-2,2'-bis(diphenylphosphino)-1,1'-binaphthyl (0.136 g, 0.218 mmol), and potassium phosphate (0.617 g, 2.91 mmol) were placed in an oven dried flask and degassed using argon. Anhydrous dioxane (9 mL) was added and the reaction was heated to 90° C. overnight. The mixture was filtered through a pad of Celite washing with methylene chloride. The filtrate was concentrated and purified by flash chromatography using 25-40% ethyl acetate/hexanes. Relevant fractions were collected and concentrated to give the product (0.224 g, 32%).
LCMS: R.t. 2.05 min ES+ 479 (formic acid)

Step b: ((2R,3S,4R,5R)-3,4-Dihydroxy-5-{6-[3-(trifluoromethyl)phenyl]-9H-purin-9-yl}-tetrahydrofuran-2-yl)methyl sulfamate (I-57)

The product was prepared following the procedure described in Example 44, steps d-f.
LCMS: R.t. 1.56 min ES+ 476 (formic acid)
$^1$H-NMR (300 MHz, d$_6$-DMSO): δ 9.19 (s, 1H); 9.11 (d, J=7.9 Hz, 1H); 9.09 (s, 1H); 8.89 (s, 1H); 7.97 (d, J=7.9 Hz, 1H); 7.88 (t, J=7.8 Hz, 1H); 7.60 (bs, 1H); 6.15 (d, J=5.1 Hz, 1H); 5.71 (d, J=5.8 Hz, 1H); 5.51 (bs, 1H); 4.70 (t, J=4.7 Hz, 1H); 4.35-4.23 (m, 4H).

Example 46

[(2R,3S,4R,5R)-3,4-Dihydroxy-5-(6-phenyl-9H-purin-9-yl)tetrahydro furan-2-yl]methyl sulfamate (I-62)

Step a: [(3aR,4R,6R,6aR)-2,2-Dimethyl-6-(6-phenyl-9H-purin-9-yl)tetrahydro furo[3,4-d][1,3]dioxol-4-yl]methyl acetate Using essentially the same procedure as Example 45, step a, [(3aR,4R,6R,6aR)-6-(6-bromo-9H-purin-9-yl)-2,2-dimethyltetrahydrofuro[3,4-d][1,3]dioxol-4-yl]methyl acetate (0.60 g, 1.45 mmol) was reacted with phenylboronic acid (0.22 g, 1.8 mmol) and the product was purified by flash chromatography (20-50% ethyl acetate/hexanes) (0.322 g, 44%).
LCMS: R.t. 1.79 min ES+ 411 (formic acid)

Step b: [(2R,3S,4R,5R)-3,4-Dihydroxy-5-(6-phenyl-9H-purin-9-yl)tetrahydro furan-2-yl]-methyl sulfamate (I-62)

The product was prepared following the procedure described in Example 44, steps d-f.
LCMS: R.t. 1.20 min ES+ 408 (formic acid)
$^1$H-NMR (300 MHz, d$_6$-DMSO): δ 9.02 (s, 1H); 8.82-8.84 (m, 3H); 7.65-7.57 (m, 4H); 6.15 (d, J=5.2 Hz, 1H); 5.71 (d, J=5.8 Hz, 1H); 5.49 (bs, 1H); 4.72 (q, J=5.2 Hz, 1H); 4.34-4.19(m, 4H).

Example 47

{(2R,3S,4R,5R)-5-[6-(3,5-Dimethylisoxazol-4-yl)-9H-purin-9-yl]-3,4-dihydroxytetrahydrofuran-2-yl}methyl sulfamate (I-66)

Step a: {(3aR,4R,6R,6aR)-6-[6-(3,5-Dimethylisoxazol-4-yl)-9H-purin-9-yl]-2,2-dimethyltetrahydro-furo[3,4-d][1,3]dioxol-4-yl}methyl acetate Using essentially the same procedure as Example 45, step a, [(3aR,4R,6R,6aR)-6-(6-bromo-9H-purin-9-yl)-2,2-dimethyltetrahydrofuro[3,4-d][1,3]dioxol-4-yl]methyl acetate (0.60 g, 1.45 mmol) was reacted with 3,5-dimethylisoxazol-4-boronic acid (0.25 g, 1.88 mmol) at 90° C. for 2.5 days and the product was purified by flash chromatography (10-40% ethyl acetate/hexanes) (0.180 g, 22%).
LCMS: R.t. 1.50 min ES+ 430 (formic acid)

Step b: {(2R,3S,4R,5R)-5-[6-(3,5-Dimethylisoxazol-4-yl)-9H-purin-9-yl]-3,4-dihydroxytetrahydrofuran-2-yl}methyl sulfamate (I-66)

The product was prepared following the procedures described in Example 44, steps d-f.
LCMS: R.t. 1.09 min ES+ 427 (formic acid)
$^1$H NMR (400 MHz, CD$_3$OD): δ 9.00 (s, 1H); 8.67 (s, 1H); 6.26 (d, J=5.0 Hz, 1H); 4.54-4.36 (m, 4H); 3.36 (s, 1H); 2.63 (s, 3H): 2.46 (s, 3H).

Example 48

((2R,3R,4R,5R)-5-{6-[(1S)-2,3-Dihydro-1H-inden-1-ylamino]-9H-purin-9-yl}-3-hydroxy-4-methoxytetrahydrofuran-2-yl)methyl sulfamate (I-54)

The product was prepared following an analogous sequence of reactions as described in Example 42.
LCMS: R.t. 1.38 min ES+ 477 (formic acid)
$^1$H NMR (300 MHz, CDCl$_3$): δ 8.42 (bs, 1H); 7.93 (s, 1H); 7.76 (bs, 1H); 7.58 (s, 1H); 6.17 (bs, 1H); 6.01 (d, J=3.6 Hz, 1H); 5.93 (bs, 1H); 5.49 (bs, 2H); 4.61-4.44 (m, 3H); 3.49 (m, 1H); 3.10 (s, 1H); 3.08-2.89 (m, 2H); 2.54 (m, 1H); 2.03-1.93 (m, 1H).

Example 49

2-((2R,3S,4R,5R)-5-{6-[(1S)-2,3-Dihydro-1H-inden-1-ylamino]-9H-purin-9-yl}-3,4-dihydroxytetrahydrofuran-2-yl)ethanesulfonamide (I-31)

Step a: [(3aR,4R,6R,6aR)-6-(6-Chloro-9H-purin-9-yl)-2,2-dimethyltetrahydrofuro[3,4-d][1,3]dioxol-4-carbaldehyde To a suspension of Dess-Martin periodinane (16.42 g, 0.03872 mol) in anhydrous methylene chloride (88.0 mL) cooled in an ice/water bath was added [(3aR,4R,6R,6aR)-6-(6-chloro-9H-purin-9-yl)-2,2-dimethyltetrahydrofuro[3,4-d][1,3]dioxol-4-yl]methanol (11.50 g, 0.03520 mol) in methylene chloride (200 mL). The reaction was stirred under an atmosphere of nitrogen and allowed to warm to ambient temperature. After 2 hours, a further portion of Dess-Martin periodinane (1.00 g, 0.00236 mol) was added. After 3 hours, a solution (200 mL) of sodium thiosulfate (50 g in 200 mL of saturated aqueous sodium bicarbonate) was added and the mixture stirred for 10 min. The aqueous was extracted 2×250 mL methylene chloride and 8×50 mL of chloroform. The combined organics were washed with water and dried over magnesium sulfate and concentrated in vacuo to dryness. The residue was taken up in dry toluene (200 mL) and concentrated in vacuo, and then taken up in dry methylene chloride and concentrated in vacuo to yield the product as a foam (9.83 g, 86%).

Step b: (Diethoxyphosphoryl)-methanesulfonic acid ethyl ester

To a solution of methanesulfonic acid, ethyl ester (11.00 mL, 0.1068 mol) in THF (200.0 mL, 2.466 mol) at −78° C. was added 2.500 M of n-butyllithium in hexane (50.00 mL) over 15 minutes and the mixture was stirred for 20 minutes. Phosphorochloridic acid, diethyl ester (10.0 mL, 0.0694 mol) was added to the mixture at −78° C. The mixture was stirred for 3.5 hours, allowing to warm to 0° C. The reaction was quenched with 5M ammonium chloride in water (100 mL) and the mixture was concentrated in vacuo to remove THF. The aqueous was extracted with EtOAc (2×150 mL) and the organics were combined and concentrated in vacuo. The product was purified by flash chromatography (0 to 100% EtOAc/Hexanes) to yield the product as an oil (9.07 g, 50%+ 10.4 g of a mixed fraction).

Step c: Ethyl 2-[(3aR,4R,6R,6aR)-6-(6-chloro-9H-purin-9-yl)-2,2-dimethyltetrahydrofuro[3,4-d][1,3]dioxol-4-yl]ethenesulfonate To a solution of (diethoxy-phosphoryl)-methanesulfonic acid ethyl ester (7.991 g, 0.03070 mol) in THF (100 mL), at −78° C. under an atmosphere of nitrogen, was added dropwise 2.5M n-butyllithium in hexane (13 mL), and the solution was stirred for 30 minutes. Freshly prepared 6-(6-chloro-purin-9-yl)-2,2-dimethyl-tetrahydro-furo[3,4-d][1,3]-dioxole-4-carbaldehyde (13.10 g, 0.03026 mol) in THF (100 mL) was added over 15 min at −78° C. The reaction was allowed to slowly warm to −10° C. over 4 hours with stirring. The reaction was quenched with water (400 mL) and 5M ammonium chloride in water (100 mL) and extracted with methylene chloride (600 mL). The organic phase was concentrated in vacuo and the residue was purified by flash chromatography (30 to 100% EtOAc:hexanes) to yield the product as a foam (10.5 g, 81%).

Step d: Ethyl 2-[(3aR,4R,6R,6aR)-6-(6-chloro-9H-purin-9-yl)-2,2-dimethyltetrahydrofuro[3,4-d][1,3]dioxol-4-yl]ethanesulfonate Ethyl 2-[(3aR,4R,6R,6aR)-6-(6-chloro-9H-purin-9-yl)-2,2-dimethyltetrahydrofuro[3,4-d][1,3]dioxol-4-yl]ethenesulfonate (10.500 g, 0.024370 mol) was dissolved in ethanol (200 mL, 3 mol) in a 1-necked round-bottom flask. Sodium borohydride (507.1 mg, 0.01340 mol) was added in 2 portions, 10 min apart. The reaction was stirred for a further 15 min at 25° C. The reaction was diluted with water (400 mL)

and 5M ammonium chloride in water (50 mL) and was concentrated in vacuo to remove most of the ethanol. The aqueous residue was extracted with methylene chloride (2×250 mL) and the organic phase was concentrated in vacuo to yield crude product (9.83 g).

Step e: Tetrabutyl-ammonium 2-[(3aR,4R,6R,6aR)-6-(6-chloro-purin-9-yl)-2,2-dimethyltetrahydro-furo[3,4-d][1,3]dioxol-4-yl]-ethanesulfonate Ethyl 2-[(3aR,4R,6R,6aR)-6-(6-chloro-9H-purin-9-yl)-2,2-dimethyltetrahydro-furo[3,4-d][1,3]dioxol-4-yl]ethanesulfonate (1.8900 g, 0.0043661 mol) and tetra-n-butylammonium iodide (1.613 g, 0.004366 mol) were dissolved in acetone (70.00 mL) and heated to reflux for 26 h. The reaction mixture was cooled and concentrated in vacuo to dryness to yield crude product (2.84 g).

Step f: 2-[(3aR,4R,6R,6aR)-6-(6-Chloro-9H-purin-9-yl)-2,2-dimethyltetrahydrofuro[3,4-d][1,3]dioxol-4-yl]ethanesulfonyl chloride Tetrabutyl-ammonium 2-[(3aR,4R,6R,6aR)-6-(6-chloro-purin-9-yl)-2,2-dimethyl-tetrahydro-furo[3,4-d][1,3]dioxol-4-yl]-ethanesulfonate (250.0 mg, 0.0003481 mol) was dissolved in methylene chloride (5.00 mL, 0.0780 mol) and N,N-dimethylformamide (100.0 μL, 0.001292 mol). Thionyl chloride (228 μL, 0.00313 mol) was added and the reaction was stirred at 0° C. for 45 minutes, concentrated in vacuo to dryness and followed by azeotroping with toluene. The residue was purified by flash chromatography (10% THF in DCM) to yield product (115 mg, 78%).

Step g: 2-[(3aR,4R,6R,6aR)-6-(6-Chloro-purin-9-yl)-2,2-dimethyltetrahydrofuro[3,4-d][1,3]dioxol-4-yl]-ethanesulfonamide 2-[(3aR,4R,6R,6aR)-6-(6-chloro-9H-purin-9-yl)-2,2-dimethyltetrahydrofuro[3,4-d][1,3]dioxol-4-yl]ethanesulfonyl chloride (100.0 mg, 0.0002362 mol) was dissolved in N,N-Dimethylformamide (2.0 mL). 7.00 M of Ammonia in Methanol (0.500 mL) was added at 0° C. and the mixture was stirred for 30 minutes, allowing to warm to room temperature. The reaction was concentrated in vacuo and the residue was diluted with brine and extracted with EtOAc. The organic phase was brine washed, water washed and evaporated. The residue was purified by flash chromatography (0 to 100% EtOAc/Hexanes) to yield the product (40 mg, 42%).

Step h: 2-[(3aR,4R,6R,6aR)-6-(6-(Indan-1-ylamino)-purin-9-yl)-2,2-dimethyltetrahydro-furo[3,4-d][1,3]dioxol-4-yl]-ethanesulfonamide 2-[(3aR,4R,6R,6aR)-6-(6-Chloro-purin-9-yl)-2,2-dimethyltetrahydrofuro[3,4-d][1,3]dioxol-4-yl]-ethanesulfonamide (45.0 mg, 0.000111 mol), (S)-(+)-1-aminoindane (20.0 μL, 0.000156 mol) and N,N-diisopropylethylamine (24.0 μL, 0.000138 mol) were dissolved in ethanol (1.25 mL, 0.0214 mol) and reacted in a microwave at 140° C. for 10 minutes. The mixture was then concentrated in vacuo and used crude in the next step.

Step i: 2-((2R,3S,4R,5R)-5-{6-[(1S)-2,3-Dihydro-1H-inden-1-ylamino]-9H-purin-9-yl}-3,4-dihydroxytetrahydrofuran-2-yl)ethanesulfonamide (I-31)

Trifluoroacetic acid (3.60 mL, 0.0467 mol) was added to water (0.40 mL, 0.022 mol) and the mixture was added to 2-[(3aR,4R,6R,6aR)-6-(6-(indan-1-ylamino)-purin-9-yl)-2,2-dimethyltetrahydrofuro[3,4-d][1,3]dioxol-4-yl]-ethanesulfonamide (crude, 0.000111 mol). The reaction was left to stand (with occasional shaking) for 25 minutes. The reaction was concentrated in vacuo to dryness and the residue purified by preparative HPLC to yield the title compound 23 mg.

LCMS: R.t. 1.31 min ES+ 461 (formic acid)
$^1$H-NMR (300 MHz, CD$_3$OD): δ 8.45 (s, 1H), 8.32 (s, 1H), 7.35 (m, 4H), 6.10 (d, 1H, J=4.6 Hz), 4.93 (m, 1H), 4.41 (t, 1H, J=5.3 Hz), 4.26 (dd, 1H, J=6.2 Hz, J=12.2 Hz), 3.35 (td, 2H, J=6.8 Hz, J=13.8 Hz), 3.22 (ddd, 1H, J=3.8 Hz, J=8.7 Hz, J=15.9 Hz), 3.07 (td, 1H, J=8.2 Hz, J=16.1 Hz), 2.81 (m, 1H), 2.43 (dd, 2H, J=7.2 Hz, J=15.2 Hz), 2.15 (ddd, 1H, J=8.4 Hz, J=12.7 Hz, J=16.1 Hz).

Example 50

2-((2R,3S,4R,5R)-5-{6-[(4-Chlorobenzyl)amino]-9H-purin-9-yl}-3,4-dihydroxytetrahydrofuran-2-yl)ethanesulfonamide (I-50)

2-[(3aR,4R,6R,6aR)-6-(6-Chloro-purin-9-yl)-2,2-dimethyltetrahydrofuro[3,4-d][1,3]dioxol-4-yl]-ethanesulfonamide was reacted with 4-chlorobenzylamine as described in Example 43, step h, and deprotected as described in 43, step i.

LCMS: R.t. 1.25 min ES+ 469 (formic acid standard)
$^1$H-NMR (300 MHz, d$_6$-DMSO): δ 8.47 (br, 1H), 8.36 (1H), 8.20 (s, 1H), 7.35 (br, 4H), 6.78 (br, 2H), 5.86 (d, 1H, J=4.6 Hz), 4.65 (m, 2H), 4.14 (t, 1H, J=4.7 Hz), 3.95 (dd, 1H, J=6.0 Hz, J=11.3 Hz), 3.16 (d, 1H, J=0.7 Hz), 3.03 (dd, 2H, J=5.5 Hz, J=9.8 Hz), 2.09 (m, 2H).

Example 51

2-((2R,3S,4R,5R)-5-{6-[(3,5-Difluorobenzyl)amino]-9H-purin-9-yl}-3,4-dihydroxytetrahydrofuran-2-yl)ethanesulfonamide (I-49)

2-[(3aR,4R,6R,6aR)-6-(6-Chloro-purin-9-yl)-2,2-dimethyltetrahydrofuro[3,4-d][1,3]dioxol-4-yl]-ethanesulfonamide was reacted with 3,5-difluorobenzylamine as described in Example 43, step h, and deprotected as described in 43, step i.

LCMS: R.t. 1.22 min ES+ 471 (formic acid)
$^1$H-NMR (300 MHz, d$_6$-DMSO): δ 8.50 (br, 1H), 8.39 (s, 1H), 8.22 (s, 1H), 7.06 (ddd, 3H, J=2.5 Hz, J=5.8 Hz, J=12.2 Hz), 6.77 (s, 2H), 5.87 (d, 1H, J=4.8 Hz), 4.72 (m, 2H), 4.66 (t, 1H, J=5.0 Hz), 4.14 (t, 1H, J=5.0 Hz), 3.96 (dd, 1H, J=6.2 Hz, J=11.5 Hz), 3.04 (t, 2H, J=4.8 Hz), 2.10 (td, 2H, J=4.8 Hz, J=9.6 Hz).

Example 52

2-((2R,3S,4R,5R)-5-{6-[(Diphenylmethyl)amino]-9H-purin-9-yl}-3,4-dihydroxytetrahydrofuran-2-yl)ethanesulfonamide (I-51)

2-[(3aR,4R,6R,6aR)-6-(6-Chloro-purin-9-yl)-2,2-dimethyltetrahydrofuro[3,4-d][1,3]dioxol-4-yl]ethanesulfonamide was reacted with α-phenylbenzylamine as described in Example 49, step h, and deprotected as described in Example 49, step i.

LCMS: R.t. 1.42 min ES+ 511 (formic acid)
$^1$H-NMR (300 MHz, d$_6$-DMSO): δ 8.73 (br, 1H), 8.40 (s, 1H), 8.24 (s, 1H), 7.43 (d, 4H, J=7.4 Hz), 7.32 (t, 4H, J=7.4 Hz), 7.23 (t, 2H, J=7.1 Hz), 6.78 (s, 2H), 5.87 (d, 1H, J=4.8

Hz), 4.66 (dd, 1H, J=4.3 Hz, J=8.8 Hz), 4.14 (m, 1H), 3.95 (dd, 1H, J=6.2 Hz, J=11.4 Hz), 3.03 (dd, 2H, J=5.4 Hz, J=9.9 Hz), 2.09 (m, 2H).

Example 53

2-[(2R,3S,4R,5R)-3,4-Dihydroxy-5-(6-{[(1R,2S)-2-hydroxy-2,3-dihydro-1H-inden-1-yl]amino}-9H-purin-9-yl)tetrahydrofuran-2-yl]ethanesulfonamide (I-32)

2-[(3aR,4R,6R,6aR)-6-(6-Chloro-purin-9-yl)-2,2-dimethyltetrahydrofuro[3,4-d][1,3]dioxol-4-yl]-ethanesulfonamide was reacted with (1R,2S) 1-amino-2-hydroxyindane as described in Example 49, step h, and deprotected as described in 49, step i.

LCMS: R.t. 1.03 min ES+ 477 (formic acid)
$^1$H-NMR (300 MHz, d$_6$-DMSO): δ 8.43 (s, 1H), 8.35 (s, 1H), 7.21 (m, 4H), 6.80 (s, 2), 5.91 (d, 1H, J=4.7 Hz), 4.68 (t, 1H, J=5.0 Hz), 4.59 (d, 1H, J=4.5 Hz), 4.17 (d, 1H, J=4.3 Hz), 3.99 (dd, 1H, J=6.1 Hz, J=11.3 Hz), 3.16 (m, 1H), 3.06 (dd, 2H, J=5.3 Hz, J=9.6 Hz), 2.91 (d, 1H, J=16.0 Hz), 2.12 (m, 2H).

Example 54

2-{(2R,3S,4R,5R)-5-[6-(Bicyclo[2.2.1]hept-2-ylamino)-9H-purin-9-yl]-3,4-dihydroxytetrahydrofuran-2-yl}ethanesulfonamide (I-52)

2-[(3aR,4R,6R,6aR)-6-(6-Chloro-purin-9-yl)-2,2-dimethyltetrahydrofuro[3,4-d][1,3]dioxol-4-yl]-ethanesulfonamide was reacted with (exo)-1-amino norbornane as described in Example 49, step h, and deprotected as described in 49, step i.

LCMS: R.t. 1.06 min ES+ 439 (formic acid)
$^1$H-NMR (300 MHz, d$_6$-DMSO): δ 8.41 (s, 1H), 8.27 (s, 1H), 6.78 (br, 2H), 5.88 (d, 1H, J=4.6 Hz), 4.65 (q, 1H, J=4.3 Hz), 4.14 (t, 1H, J=3.5 Hz), 3.97 (dd, 2H, J=5.8 Hz, J=11.2 Hz), 3.04 (dd, 2H, J=5.1 Hz, J=9.3 Hz), 2.24 (m, 2H), 2.10 (m, 2H), 1.66 (m, 3H), 1.47 (q, 2H, J=8.1 Hz), 1.27 (t, 1H, J=10.6 Hz), 1.12 (dd, 2H, J=7.9 Hz, J=14.9 Hz).

Example 55

[(2R,3S,4R,5R)-3,4-Dihydroxy-5-(6-{[(1R,2S)-2-hydroxy-2,3-dihydro-1H-inden-1-yl]amino}-9H-purin-9-yl)tetrahydrofuran-2-yl]methyl sulfamate (I-14)

Step a: (2R,3R,4R,5R)-2-(6-{[(1R,2S)-2-(Acetyloxy)-2,3-dihydro-1H-inden-1-yl]amino}-9H-purin-9-yl)-5-(hydroxymethyl)tetrahydrofuran-3,4-diyl diacetate To a suspension of 6-chloro-β-D-ribofuranosylpurine (0.573 g, 0.002 mol) in ethanol (20 mL) was added (1R,2S)-1-amino-2-indanol (0.33 g, 0.0022 mol) and diisopropylethylamine (0.38 mL, 0.0022 mol) and the reaction mixture heated to reflux for 4 h. The mixture was collected and concentrated in vacuo to dryness and dissolved in pyridine (20 mL). 4,4'-dimethoxytrityl chloride (0.74 g, 0.0022 mol) was added and the reaction stirred overnight.

The reaction mixture was cooled (ice bath) and acetic anhydride (0.8 mL, 0.008 mol) added dropwise. The reaction was stirred for 90 min allowing to warm to room temperature. The reaction was concentrated in vacuo, taken up in ethyl acetate (50 mL), washed with water (2×25 mL), dried and concentrated in vacuo to dryness.

The residue was taken up in methylene chloride (100 mL) and triisopropylsilane (3.0 mL, 0.015 mol) was added followed by trifluoroacetic acid (1.0 mL, 0.013 mol) and the reaction stirred for 10 min and concentrated in vacuo.

Flash chromatography (methylene chloride:ethyl acetate 30 to 70%) gave product (0.25 g) contaminated with over acylated material.

LCMS: R.t. 1.75 min ES+ 526 (ammonium acetate).

Step b: (2R,3R,4R,5R)-2-(6-{[(1R,2S)-2-(acetyloxy)-2,3-dihydro-1H-inden-1-yl]amino}-9H-purin-9-yl)-5-{[(aminosulfonyl)oxy]methyl}tetrahydrofuran-3,4-diyl diacetate (2R,3R,4R,5R)-2-(6-{[(1R,2S)-2-(acetyloxy)-2,3-dihydro-1H-inden-1-yl]amino}-9H-purin-9-yl)-5-(hydroxymethyl)tetrahydrofuran-3,4-diyl diacetate (0.225 g, 0.0003 mol) was reacted with chlorosulfonamide as described in Example 43 step f. The product was purified by flash chromatography (methylene chloride:ethyl acetate 20 to 60%) (0.11 g, 60%).

LCMS: R.t. 1.64 min ES+ 605 (ammonium acetate).

Step c: [(2R,3S,4R,5R)-3,4-Dihydroxy-5-(6-{[(1R,2S)-2-hydroxy-2,3-dihydro-1H-inden-1-yl]amino}-9H-purin-9-yl)tetrahydrofuran-2-yl]methyl sulfamate (I-14)

(2R,3R,4R,5R)-2-(6-{[(1R,2S)-2-(acetyloxy)-2,3-dihydro-1H-inden-1-yl]amino}-9H-purin-9-yl)-5-{[(aminosulfonyl)oxy]methyl}tetrahydrofuran-3,4-diyl diacetate was stirred in 7M ammonia in methanol (2 mL) for 8 hours and the reaction concentrated in vacuo. The product was purified by HPLC to give 0.024 g, 30% yield.

LCMS: R.t. 1.21 min ES+ 479 (ammonium acetate).
$^1$H-NMR (300 MHz, CD$_3$OD): δ 8.46 (s, 1H), 8.37 (s, 1H), 7.38-7.45 (m, 4H), 6.23 (m, 1H), 5.91 (br), 4.71-4.91 (m, 3H), 4.41-4.60 (m, 4H), 3.30 (m, 1H), 3.07-3.17 (m, 2H), 2.90 (m, 1H).

Example 56

((2R,3R,4R,5R)-5-(6-((S)-2,3-Dihydro-1H-inden-1-ylamino)-9H-purin-9-yl)-3,4-dihydroxy-4-methyl-tetrahydrofuran-2-yl)methyl sulfamate (I-55)

Step a: (2R,3R,4R,5R)-2-(6-((S)-2,3-Dihydro-1H-inden-1-ylamino)-9H-purin-9-yl)-5-(hydroxymethyl)-3-methyl-tetrahydrofuran-3,4-diol (2R,3R,4R,5R)-5-[(Benzoyloxy)methyl]-2-(6-chloro-9H-purin-9-yl)-3-methyltetrahydrofuran-3,4-diyl dibenzoate was prepared according to the method described by M. Wolfe, *J. Org. Chem.* (1997), 62:1754 and P. Franchetti, *J. Med. Chem.* (1998), 41:1708.

A solution of (2R,3R,4R,5R)-5-[(benzoyloxy)methyl]-2-(6-chloro-9H-purin-9-yl)-3-methyltetrahydrofuran-3,4-diyl dibenzoate (0.35 g, 0.57 mmol), (S)-(+)-1-aminoindane (0.32 g, 2.3 mmol), N,N-diisopropylethylamine (0.20 mL, 1.1 mmol) in ethanol (3 mL, 0.05 mol) was reacted in a microwave at 150° C. for 15 min.

The reaction mixture was transferred to a pressure tube and the solvent removed by bubbling nitrogen through. The residue was taken up in methanolic ammonia (7M) (10.0 mL) and the reaction mixture was heated for 5 h at 45° C. The reaction mixture was cooled and concentrated in vacuo. Flash chromatography (6% methanol in chloroform) gave product, 0.22 g, 97%.

LCMS: R.t. 1.3 min ES+ 369 (ammonium acetate).

Step b: ((3aR,4R,6R,6aR)-6-(6-((S)-2,3-Dihydro-1H-inden-1-ylamino)-9H-purin-9-yl)-2,2,6a-trimethyl-tetrahydrofuro[3,4-d][1,3]dioxol-4-yl)methanol A solution of (2R,3R,4R,5R)-2-(6-((S)-2,3-dihydro-1H-inden-1-ylamino)-9H-purin-9-yl)-5-(hydroxymethyl)-3-methyl-tetrahydrofuran-3,4-diol (0.21 g, 0.53 mmol), p-toluenesulfonic acid monohydrate (0.10 g, 0.53 mmol), 2,2-dimethoxypropane (1.0 mL, 8.1 mmol) in acetone (5 mL) was stirred for 8 h. The reaction mixture was concentrated in vacuo and partitioned between ethyl acetate (25 mL) and saturated sodium bicarbonate (15 mL), the aqueous was extracted with ethyl acetate and the organic phases combined, dried ($MgSO_4$) and concentrated in vacuo. Flash chromatography (2% methanol in chloroform) gave the title compound 0.155 g, 67% yield.

LCMS: R.t. 1.74 ES+ 438 (ammonium acetate).

Step c: ((2R,3R,4R,5R)-5-(6-((S)-2,3-Dihydro-1H-inden-1-ylamino)-9H-purin-9-yl)-3,4-dihydroxy-4-methyl-tetrahydrofuran-2-yl)methyl sulfamate (I-55)

To a solution of ((3aR,4R,6R,6aR)-6-(6-((S)-2,3-Dihydro-1H-inden-1-ylamino)-9H-purin-9-yl)-2,2,6a-trimethyl-tetrahydrofuro[3,4-d][1,3]dioxol-4-yl)methanol (0.12 g, 0.27 mmol), N,N-diisopropylethylamine (100 µL, 0.8 mmol) in acetonitrile (2.0 mL) was added a solution of chlorosulfonamide in acetonitrile (2.0 M) (0.4 mL) dropwise. The reaction was stirred for 3 h and evaporated to dryness.

Flash chromatography (4% methanol in methylene chloride) gave the protected sulfamate 70 mg.

LCMS: R.t. 1.75 ES+ 517 (ammonium acetate).

The protected sulfamate was dissolved in a solution of trifluoroacetic acid in water (9:1, 3.0 mL) and stirred for 20 min. The reaction mixture was concentrated in vacuo and methanol added and again concentrated in vacuo. The product was purified by HPLC.

LCMS: R.t. 1.39 min ES+ 477 (ammonium acetate).
$^1$H-NMR (300 MHz, $CD_3OD$): δ 8.28 (s, 1 h), 8.19 (s, 1H), 7.11-7.25 (m, 4H), 6.08 (s, 1H), 4.52 (dd J 11.2 Hz, 2.0 Hz, 1H) 4.42 (dd J 11.2, 3.3 Hz, 1H), 4.15-4.21 (m, 2H), 2.98-3.07 (m, 1H), 2.83-2.93 (m, 1H), 2.56-2.66 (m, 1H), 1.90-2.03 (m, 1H), 0.90 (s, 3H).

Example 57

((2R,3S,4R,5R)-5-{2-Chloro [(1S)-2,3-dihydro-1H-inden-1-ylamino]-9H-purin-9-yl}-3,4-dihydroxytetrahydrofuran-2-yl)methyl sulfamate (I-3)

Step a: (2-Chloro-9H-purin-6-yl)-(S)-indan-1-ylamine (S)-(+)-1-Aminoindane (266.0 mg, 2.0 mmol), 2,6-dichloropurine (380 mg, 2.0 mmol) and N,N-diisopropylethylamine (380 µL, 2.2 mmol), were dissolved in Ethanol (4.0 mL) and reacted in a microwave at 120° C. for 600 s. A yellow solid formed which was filtered, washed with ethanol (20 mL) and dried to give the title compound 0.455 g, 80% yield.

LCMS: R.t. 1.77 ES+ 286, 288 (ammonium acetate).

Step b: (2S,3R,4R,5R)-2,4-Diacetoxy-5-sulfamoyloxymethyl-tetrahydro-furan-3-yl acetate The title compound was prepared from (2S,3R,4R,5R)-2,4-diacetoxy-5-hydroxymethyl-tetrahydro-furan-3-yl acetate by reaction with chlorosulfonamide following a procedure analogous to that described in Example 43, step f.

Step c: (2R,3R,4R,5R)-2-{[(Aminosulfonyl)oxy]methyl}-5-{2-chloro-6-[(1S)-2,3-dihydro-1H-inden-1-ylamino]-9H-purin-9-yl}tetrahydrofuran-3,4-diyl diacetate To a suspension of (2S,3R,4R,5R)-2,4-diacetoxy-5-sulfamoyloxymethyl-tetrahydro-furan-3-yl acetate (200 mg, 0.6 mmol), (2-chloro-9H-purin-6-yl)-(S)-indan-1-ylamine (180 mg, 0.62 mmol), 1,8-diazabicyclo[5.4.0]undec-7-ene (420 µL, 2.8 mmol) in acetonitrile (8 mL) cooled by an ice/water bath was added trimethylsilyl trifluoromethanesulfonate (610 µL, 3.4 mmol) dropwise. The reaction became clear and after 5 min the reaction was heated to 60° C. for 4 h. The reaction was allowed to cool, diluted with ethyl acetate (30 mL) and washed with saturated sodium bicarbonate solution, HCl aq (0.05M), and brine. The organic was dried ($MgSO_4$) and concentrated in vacuo.

Flash chromatography (2% MeOH in methylene chloride) gave the product, 105 mg, 30% yield.

Step d: ((2R,3R,4R,5R)-5-(6-((S)-2,3-Dihydro-1H-inden-1-ylamino)-9H-purin-9-yl)-3,4-dihydroxy-4-methyl-tetrahydrofuran-2-yl)methyl sulfamate (I-55)

To a solution of (2R,3R,4R,5R)-2-{[(aminosulfonyl)oxy]methyl}-5-{2-chloro-6-[(1S)-2,3-dihydro-1H-inden-1-ylamino]-9H-purin-9-yl}tetrahydrofuran-3,4-diyl diacetate (90 mg, 2.2 mmol) in methanol (2.0 mL) was added a solution of ammonia in methanol (7M), (2.0 mL) and the reaction mixture was stirred for 30 min. LCMS showed complete reaction. The reaction was concentrated in vacuo to dryness. Purification by preparative HPLC gave product, 23 mg, 30% yield.

LCMS: R.t. 1.76 ES+ 497, 499 (ammonium acetate).
$^1$H-NMR (300 MHz, $d_6$-DMSO): δ 8.75 (d, J=8.6 Hz, 1H, exchange $D_2O$), 8.33 (s, 1H), 7.60 (br.s, 1H, exchange $D_2O$), 7.11-7.27 (m, 4H), 5.90 (d J 5.3 Hz, 1H), 5.76-5.86 (m, 1H), 5.70 (br.s, 1H, exchange $D_2O$), 5.51 (br.s, 1H, exchange $D_2O$), 4.46-4.57 (m, 1H), 4.17-4.30 (m, 4H), 3.25-3.30(m, 1H), 2.73-2.92 (m, 1H), 2.03-2.22 (m, 1H).

Example 58

(R)-1-((2S,3S,4R,5R)-5-(6-((S)-2,3-Dihydro-1H-inden-1-ylamino)-9H-purin-9-yl)-3,4-dihydroxy-tetrahydrofuran-2-yl)ethyl sulfamate (I-58)

Step a: 1-((3aR,4R,6R,6aR)-6-(6-Chloro-9H-purin-9-yl)-2,2-dimethyl-tetrahydrofuro[3,4-d][1,3]dioxol-4-yl)ethanol To a suspension of Dess-Martin periodinane (1.4 g, 3.3 mmol) in methylene chloride (8 mL), cooled in an ice/water bath, was added dropwise a solution of ((3aR,4R,6R,6aR)-6-(6-chloro-9H-purin-9-yl)-2,2-dimethyl-tetrahydrofuro[3,4- d][1,3]dioxol-4-yl)methanol (0.978 g, 3.0 mmol) in methylene chloride (10 mL). The reaction was allowed to warm to ambient temperature while stirring for 2 h.

A solution of sodium thiosulfate (25%) in sat. sodium bicarbonate (25 mL) was added and the mixture stirred for 15 min and extracted with methylene chloride (3×15 mL). The organic was dried (MgSO$_4$) and evaporated to give a colorless foam, 0.66 g.

To a solution of the aldehyde (0.65 g, 2.0 mmol) in anhydrous THF (20 mL) at −78° C. was added dropwise a 3.0 M solution of methylmagnesium bromide in diethylether (1.2 mL, 4.0 mmol) and the reaction was allowed to warm to −20° C. over 2 h while being stirred under a stream of nitrogen.

The reaction was quenched with saturated ammonium chloride solution (20 mL) containing acetic acid (0.5 mL) and extracted with ethyl acetate (3×50 mL).

Flash chromatography (3:2 methylenechloride:EtOAc) gave the title compound (0.32 g, 27% yield).

LCMS: R.t. 1.36 ES+ 339, 341 (ammonium acetate).

Step b: (R)-1-((3aR,4R,6R,6aR)-6-(6-((S)-2,3-Dihydro-1H-inden-1-ylamino)-9H-purin-9-yl)-2,2-dimethyl-tetrahydrofuro[3,4-d][1,3]dioxol-4-yl)ethanol (S)-(+)-1-Aminoindane (40.0 mg, 0.3 mmol), 1-((3aR,4R,6R,6aR)-6-(6-chloro-9H-purin-9-yl)-2,2-dimethyl-tetrahydrofuro[3,4-d][1,3]dioxol-4-yl)ethanol (68 mg, 0.2 mmol) and triethylamine (40 μL, 0.3 mmol), were dissolved in ethanol (2.0 mL) and reacted in a microwave at 140° C. for 600 s. The reaction mixture was concentrated in vacuo.

Flash chromatography (4:1 to 2:1 methylene chloride:EtOAc) gave product, 73 mg, 83% yield.

LCMS: R.t. 1.83 ES+ 438 (ammonium acetate).

Step c: (R)-1-((2S,3S,4R,5R)-5-(6-((S)-2,3-Dihydro-1H-inden-1-ylamino)-9H-purin-9-yl)-3,4-dihydroxy-tetrahydrofuran-2-yl)ethyl sulfamate (I-58)

To a stirred solution of (R)-1-((3aR,4R,6R,6aR)-6-(6-((S)-2,3-dihydro-1H-inden-1-ylamino)-9H-purin-9-yl)-2,2-dimethyl-tetrahydrofuro[3,4-d][1,3]dioxol-4-yl)ethanol (60 mg, 0.136 mmol) and triethylamine (0.03 mL) in DMF at 0° C. was added a solution of chlorosulfonamide (2.0 M in MeCN) dropwise (0.1 mL) and the reaction was allowed to warm to ambient temperature while being stirred under an inert atmosphere. A further aliquot of chlorosulfonamide solution (0.1 mL) and triethylamine (0.03 mL) were added and the reaction stirred for 30 min.

The reaction mixture was filtered, the precipitate washed with methylene chloride and the organics combined and concentrated in vacuo.

Flash chromatography (1:2 methylene chloride:EtOAc) gave the protected sulfamate 35 mg, 83% yield.

LCMS: R.t. 1.81 ES+ 517 (ammonium acetate).

The protected sulfamate (33 mg 0.06 mmol) was dissolved in cold (ice/water bath) TFA:water 9:1 (2 mL) and the reaction allowed to warm to ambient temperature. After 15 min the mixture was concentrated in vacuo, the residue taken up in dry methylene chloride (10 mL) and concentrated in vacuo. This was repeated 3 times to give the title compound as a mixture of diastereomers in approx. 3:1 ratio, 30 mg, 98%.

LCMS: R.t. 1.42 ES+ 477 (ammonium acetate).

$^1$H-NMR (300 MHz, CD$_3$OD): δ 8.4-8.6 (br. m, 2H,), 7.15-7.38 (m, 4H), 6.05-6.25 (m, 1H), 4.75-4.85 (m, 1H), 4.60-4.70 (m, 1H), 4.45-4.55 (m, 1H), 4.05-4.15 (m, 1H), 3.28-3.35 (m, 1H), 3.07-3.20 (m, 1H), 2.90-3.05 (m, 1H), 2.62-2.80 (br., 1H), 2.08-2.20(m, 1H), 1.45-1.55 (m, 3H).

Example 59

N-[((2R,3S,4R,5R)-3,4-Dihydroxy-5-{6-[(4-methoxybenzyl)sulfanyl]-9H-purin-9-yl}tetrahydrofuran-2-yl)methyl]sulfamide (I-40)

Step a: (2R,3R,4R,5R)-2-(6-Chloro-9H-purin-9-yl)-5-(hydroxyethyl)tetrahydrofuran-3,4-diyl di-acetate 6-Chloro-9-β-D-ribofuranosylpurine (1.147 g, 0.0040 mol) and 4,4'-dimethoxytrityl chloride (1.423 g, 0.0042 mol) were stirred in pyridine (20 mL) at room temperature for 60 h. Acetic anhydride (1.510 mL, 0.01600 mol) and 4-dimethylaminopyridine (97.7 mg, 0.000800 mol) were added and the reaction stirred at room temperature for 3 h. The reaction was concentrated in vacuo and the residue taken up in methylene chloride. The solution was washed twice with HCl (1N) and once with water, dried over Na$_2$SO$_4$ and concentrated in vacuo to obtain an oil. The product was treated with methylene chloride/trifluoroacetic acid/triisopropylsilane 100:2:2 (104 mL) for 20 min. The solution was concentrated in vacuo and the residue purified by flash chromatography (DCM/EtOAc 10% to 80%) to obtain the product as a white solid (447 mg, 30%).

LCMS: R.t. 1.12 min ES+ 371 (formic acid)

Step b: (2R,3R,4R,5R)-2-{[(Aminosulfonyl)(tert-butoxycarbonyl)amino]methyl}-5-(6-chloro-9H-purin-9-yl)tetrahydrofuran-3,4-diyl diacetate (2R,3R,4R,5R)-2-(6-chloro-9H-purin-9-yl)-5-(hydroxymethyl)tetrahydrofuran-3,4-diyl di-acetate (425.0 mg, 0.001146 mol), N-Boc-sulfamide (337.4 mg, 0.001720 mol) and triphenylphosphine (360.8 mg, 0.001376 mol) were dissolved in ethyl acetate (10 mL) under nitrogen and diisopropyl azodicarboxylate (338.6 μL, 0.001720 mol) was added dropwise as a solution in ethyl acetate (2 mL). The solution was stirred at room temperature under nitrogen for 3 h. The solution was concentrated in vacuo and the residue purified by flash chromatography (DCM/EtOAc 10% to 50%) to give product, contaminated with triphenylphosphine oxide (502 mg).

LCMS: R.t. 1.49 min ES+ 549 (formic acid)

Step c: (2R,3R,4R,5R)-2-{[(Aminosulfonyl)amino]methyl}-5-(6-chloro-9H-purin-9-yl)-tetrahydrofuran-3,4-diyl di-acetate (2R,3R,4R,5R)-2-{[(Aminosulfonyl)(tert-butoxycarbonyl)amino]methyl}-5-(6-chloro-9H-purin-9-yl) tetrahydrofuran-3,4-diyl di-acetate (502 mg, 0.000914 mol) was treated with trifluoroacetic acid/methylene chloride 1:2 (9 mL) for 45 min. The solution was concentrated in vacuo and the residue purified by flash chromatography (DCM/EtOAc 30% to 80%) to obtain the product as a white solid (251 mg, 61%).

LCMS: R.t. 1.07 min ES+ 449 (formic acid)

Step d: N-[((2R,3S,4R,5R)-3,4-Dihydroxy-5-{6-[(4-methoxybenzyl)sulfanyl]-9H-purin-9-yl}tetrahydrofuran-2-yl)methyl]sulfamide (I-40)

2-{[(Aminosulfonyl)amino]methyl}-5-(6-chloro-9H-purin-9-yl)tetrahydrofuran-3,4-diyl di-acetate (120.0 mg, 0.2674 mmol), p-methoxy-α-toluenethiol (149.0 μL, 1.069 mmol) and triethylamine (149.0 µL, 0.001069 mol) were refluxed in ethanol (10 mL, 0.2 mol) overnight. After 14 h, the reaction was concentrated in vacuo. The residue was treated with ammonia 7N in MeOH (3 mL) at room temperature. After 1 h, the solution was concentrated in vacuo and the residue purified by HPLC to obtain the product as a lyophilized powder (66 mg, 51%).

LCMS: R.t. 1.27 min ES+ 483 (formic acid)

$^1$H-NMR (300 MHz, $d_6$-DMSO): δ 8.77 (s, 1H), 8.68 (s, 1H), 7.38 (d, 2H, J=8.6 Hz), 7.08 (br s, 1H), 6.87 (d, 2H, J=8.6 Hz), 6.61 (br s, 2H), 5.95 (d, 1H, J=6.8 Hz), 4.73 (m, 1H), 4.61 (s, 2H), 4.18 (m, 1H), 4.10 (m, 1H), 3.72 (s, 3H), 3.28-3.10 (m, 2H).

Example 60

{(2R,3S,4R,5R)-5-[6-(4-Fluorobenzyl)-9H-purin-9-yl]-3,4-dihydroxytetrahydrofuran-2-yl}methyl sulfamate (I-41)

Step a: [(3aR,4R,6R,6aR)-6-(6-Chloro-9H-purin-9-yl)-2,2-dimethyltetrahydrofuro[3,4-d][1,3]dioxol-4-yl]methyl acetate

[(3aR,4R,6R,6aR)-6-(6-Chloro-9H-purin-9-yl)-2,2-dimethyltetrahydrofuro[3,4-d][1,3]dioxol-4-yl]methanol (1.000 g, 0.003060 mol), pyridine (495.1 µL, 0.006121 mol), 4-dimethylaminopyridine (0.0748 g, 0.000612 mol) and acetic anhydride (577.5 µL, 0.006121 mol) were stirred in methylene chloride (20 mL) at room temperature for 1 h. The solution was diluted with Methylene chloride, extracted with HCl 1N, dried over $NA_2SO_4$ and concentrated in vacuo. The residue was purified by flash chromatography (EtOAc/DCM 0% to 25%) to obtain the product (1.129 g, 84%) as an oil.

LCMS: R.t. 1.38 ES+ 477 (formic acid).

Step b: {(3aR,4R,6R,6aR)-6-[6-(4-Fluorobenzyl)-9H-purin-9-yl]-2,2-dimethyltetrahydrofuro[3,4-d][1,3]dioxol-4-yl}methyl acetate

[(3aR,4R,6R,6aR)-6-(6-Chloro-9H-purin-9-yl)-2,2-dimethyltetrahydrofuro[3,4-d][1,3]dioxol-4-yl]methyl acetate (369 mg, 0.00100 mol) and tetrakis(triphenylphosphine)palladium(0) (58 mg, 0.000050 mol) were dissolved in tetrahydrofuran (10 mL) at room temperature under nitrogen. 0.5 M of 4-fluorobenzylzinc chloride in tetrahydrofuran (3 mL) was added dropwise over 10 min. The solution was stirred under nitrogen at room temperature for 15 min then heated at 60° C. for 3 h. The reaction was allowed to cool to r.t then poured on saturated $NH_4Cl$ (10 mL). Saturated $Na_2EDTA$ (10 mL) was added and the solution extracted three times with EtOAc. The organics were pooled and extracted twice with saturated $Na_2EDTA$ then once with brine, dried over $Na_2SO_4$ and concentrated in vacuo. The residue was purified by flash chromatography (DCM/EtOAc 10% to 50%) to obtain the product (322 mg, 73%) as an oil.

LCMS: R.t. 1.63 ES+ 443(formic acid).

Step c: {(3aR,4R,6R,6aR)-6-[6-(4-Fluorobenzyl)-9H-purin-9-yl]-2,2-dimethyltetradrofuro[3,4-d][1,3]dioxol-4-yl}methanol {(3aR,4R,6R,6aR)-6-[6-(4-Fluorobenzyl)-9H-purin-9-yl]-2,2-dimethyltetrahydrofuro[3,4-d][1,3]dioxol-4-yl}methyl acetate (307 mg, 0.000694 mol) was treated with 7M ammonia in methanol (5 mL) at room temperature for 2 h.

The solution was concentrated and the residue purified by flash chromatography (DCM/EtOAc 10% to 80%) to give the product as an oil (260 mg, 94%).

LCMS: R.t. 1.43 ES+ 401 (formic acid).

Step d: {(3aR,4R,6R,6aR)-6-[6-(4-Fluorobenzyl)-9H-purin-9-yl]-2,2-dimethyltetrahydrofuro[3,4-d][1,3]dioxol-4-yl}methyl sulfamate {(3aR,4R,6R,6aR)-6-[6-(4-Fluorobenzyl)-9H-purin-9-yl]-2,2-dimethyltetrahydrofuro[3,4-d][1,3]dioxol-4-yl}methanol (249 mg, 0.000622 mol) and triethylamine (173.4 µL, 0.001244 mol) were dissolved in dry N,N-dimethylformamide (10 mL) under nitrogen and the solution was cooled in a water/ice bath. A 2M solution of chlorosulfonamide in acetonitrile (0.0012 mol, 600 µL) was added dropwise. After 1.5 h, the reaction was quenched with methanol, concentrated in vacuo and the residue was purified by flash chromatography (DCM/EtOAc 30% to 80%) to obtain the product as an oil (262 mg, 88%).

LCMS: R.t. 1.49 ES+ 480(formic acid).

Step e: {(2R,3S,4R,5R)-5-[6-(4-Fluorobenzyl)-9H-purin-9-yl]-3,4-dihydroxytetrahydrofuran-2-yl}methyl sulfamate (I-41)

{(3aR,4R,6R,6aR)-6-[6-(4-Fluorobenzyl)-9H-purin-9-yl]-2,2-dimethyltetrahydrofuro[3,4-d][1,3]dioxol-4-yl}methyl sulfamate (252 mg, 0.000526 mol) was treated with trifluoroacetic acid/water 4:1 (5 mL) for 15 min at room temperature The solution was concentrated to dryness and the residue purified by HPLC to give the product as a lyophilized powder (106 mg, 46%).

LCMS: R.t. 1.15 ES+ 440 (formic acid).

$^1$H-NMR (300 MHz, $d_6$-DMSO+$D_2O$): δ 8.85 (s, 1H), 8.73 (s, 1H), 7.40 (dd, 2H, J=8.8 Hz, J=5.6 Hz), 7.10 (dd, 2H, J=8.8 Hz, J=8.8 Hz), 6.06 (d, 1H, J=5.5 Hz), 4.68 (dd, 1H, J=5.1 Hz, J=5.1 Hz), 4.43 (s, 2H), 4.31-4.18 (m, 4H).

Example 61

{(2R,3S,4R,5R)-5-[6-Phenethyl-9H-purin-9-yl]-3,4-dihydroxytetrahydrofuran-2-yl}methyl sulfamate (I-59)

Step a: {(3aR,4R,6R,6aR)-6-[6-Phenethyl-9H-purin-9-yl]-2,2-dimethyltetrahydrofuro[3,4-d][1,3]dioxol-4-yl}methyl acetate

[(3aR,4R,6R,6aR)-6-(6-Chloro-9H-purin-9-yl)-2,2-dimethyltetrahydrofuro[3,4-d][1,3]dioxol-4-yl]methyl acetate (775 mg, 0.00210 mol) and tetrakis(triphenylphosphine)palladium(0) (120 mg, 0.00010 mol) were dissolved in tetrahydrofuran (20 mL) at room temperature under nitrogen. 0.5M Phenethylzinc bromide in tetrahydrofuran (5 mL) was added dropwise over 5 min. The solution was stirred under nitrogen for 30 min at room temperature then heated to 60° C. for 30 min. The reaction was poured on sat $NH_4Cl$ (20 mL). Saturated $Na_2EDTA$ (20 mL) was added and the solution extracted three times with EtOAc. The pooled organics were washed with saturated $Na_2EDTA$, brine, dried over $Na_2SO_4$ and concentrated in vacuo. The residue was purified by flash chromatography (DCM/EtOAc 10% to 50%) to obtain the product as an oil (643 mg, 70%).

LCMS: R.t. 1.66, ES+ 439.6 (formic acid).

Step b: {(3aR,4R,6R,6aR)-6-[6-Phenethyl-9H-purin-9-yl]-2,2-dimethyltetrahydrofuro[3,4-d][1,3]dioxol-4-yl}methanol {(3aR,4R,6R,6aR)-6-[6-Phenethyl-9H-purin-9-yl]-2,2-dimethyltetrahydrofuro[3,4-d][1,3]dioxol-4-yl}methyl acetate (643 mg, 0.00147 mol) was treated with 7M ammonia in methanol (10 mL) at room temperature for 1 h. The solution was concentrated and the residue purified by flash chromatography (DCM/EtOAc 10% to 50%) to give the product as an oil (473 mg, 81%).

LCMS: R.t. 1.52, ES+ 397 (formic acid).

Step c: {(3aR,4R,6R,6aR)-6-[6-Phenethyl-9H-purin-9-yl]-2,2-dimethyltetrahydrofuro[3,4-d][1,3]dioxol-4-yl}methyl sulfamate {(3aR,4R,6R,6aR)-6-[6-Phenethyl-9H-purin-9-yl]-2,2-dimethyltetrahydrofuro[3,4-d][1,3]dioxol-4-yl}methanol (464 mg, 0.00117 mol) and triethylamine (489 µL, 0.00351 mol) were dissolved in dry N,N-dimethylformamide (10 mL) under nitrogen and the solution cooled in an ice/water bath. A 2M solution of chlorosulfonamide in acetonitrile previously prepared (800 µL) was added dropwise and the reaction stirred under nitrogen at 0-5° C. After 30 min, 2M chlorosulfonamide in acetonitrile (800 µL) was added. After 2 h, the reaction was quenched with methanol and concentrated. The residue was purified by flash chromatography (DCM/EtOAc 10% to 60%) to yield the product as an oil (435 mg, 78%).

LCMS: R.t. 1.52, ES+ 476.5 (formic acid).

Step d: {(2R,3S,4R,5R)-5-[6-Phenethyl-9H-purin-9-yl]-3,4-dihydroxytetrahydrofuran-2-yl}methyl sulfamate (I-59)

{(3aR,4R,6R,6aR)-6-[6-phenethyl-9H-purin-9-yl]-2,2-dimethyltetrahydrofuro[3,4-d][1,3]dioxol-4-yl}methyl sulfamate (435 mg, 0.000915 mol) was treated with trifluoroacetic acid/water 9:1 (5 mL) for 20 min. The solution was concentrated to dryness and the residue purified by HPLC to give the product as a lyophilized powder (240 mg, 60%).

LCMS: R.t. 1.22, ES+ 436 (formic acid).

$^1$H-NMR (300 MHz, $d_6$-DMSO): δ 8.87 (s, 1H), 8.68 (s, 1H), 7.61 (s, 2H), 7.26 (m, 4H), 7.17 (m, 1H), 6.06 (d, 1H, J=5.2 Hz), 5.70 (m, 1H), 5.52 (m, 1H), 4.68 (m, 1H), 4.32-4.18 (m, 4H), 3.41 (m, 2H), 3.18 (m, 2H).

Example 62

{(2R,3S,4R,5R)-5-[6-(Benzoylamino)-9H-purin-9-yl]-3,4-dihydroxytetrahydrofuran-2-yl}methyl sulfamate (I-12)

Step a: N-{9-[(2R,3R,4S,5R)-3,4-Dihydroxy-5-(hydroxymethyl)tetrahydrofuran-2-yl]-9H-purin-6-yl}benzamide (−)-Adenosine (0.668 g, 2.5 mmol) was dried by co-evaporation with pyridine three times and dissolved in dry pyridine (12.5 mL). Trimethylsilyl chloride (1.90 mL, 12.5 mmol) was added and the solution stirred for 15 minutes before adding benzoyl chloride (1.45 mL, 12.5 mmol). The reaction mixture was stirred at room temperature for an additional 2 hours. The mixture was cooled to 0° C. and stirred together with 2.7 mL of water for 5 minutes. Aqueous NH$_3$ (5.05 mL of 29%) was added and the mixture was stirred at room temperature for 30 minutes and evaporated to near dryness. The residue was dissolved in 39 mL of water and washed with 13 mL of EtOAc. The product precipitated from the aqueous layer and was isolated by filtration to give 0.643 g 69% yield.

LCMS: R.t. 1.09 min, ES+ 372.5 (formic acid).

Step b: N-[9-((3aR,4R,6R,6aR)-6-Hydroxymethyl-2,2-dimethyl-tetrahydrofuro[3,4-d][1,3]dioxol-4-yl)-9H-purin-6-yl]-benzamide N-{9-[(2R,3R,4S,5R)-3,4-Dihydroxy-5-(hydroxymethyl)tetrahydrofuran-2-yl]-9H-purin-6-yl}benzamide (0.643 g, 1.73 mmol), 2,2-dimethoxypropane (1.06 mL, 8.66 mmol), and para-toluenesulfonic acid monohydrate (0.333 g, 1.73 mmol) were dissolved in acetone (43 mL). The solution was stirred at room temperature overnight and then heated to 40° C. for 3 hours. Once cooled to room temperature, saturated sodium bicarbonate solution was added to the reaction mixture and then approximately half the solvent was removed in vacuo. The resulting solution was diluted with water and extracted four times with CH$_2$Cl$_2$. Combined organics were washed with brine and dried over Na$_2$SO$_4$. The crude material was purified by silica gel chromatography (0 to 5% MeOH/CH$_2$Cl$_2$) to isolate the title compound (0.419 g, 59%)

LCMS: R.t. 1.47 min, ES+ 412.6 (formic acid).

Step c: {(3aR,4R,6R,6aR)-6-[6-(Benzoylamino)-9H-purin-9-yl]-2,2-dimethyltetrahydrofuro[3,4-d][1,3]dioxol-4-yl}methyl sulfamate A solution of N-{9-[(3aR,4R,6R,6aR)-6-(hydroxymethyl)-2,2-dimethyltetrahydrofuro[3,4-d][1,3]dioxol-4-yl]-9H-purin-6-yl}benzamide (0.419 g, 1.02 mmol) and TEA (0.284 mL, 2.04 mmol) in 3.4 mL of dry DMF was cooled with an ice bath. A 1M solution of chlorosulfonamide (1.53 mL) in acetonitrile was added slowly. The resulting cloudy solution was stirred while warming to room temperature for approximately 6 hours. The reaction mixture was concentrated and the residue was dissolved in CH$_2$Cl$_2$ and washed with water. The aqueous layer was extracted three times with CH$_2$Cl$_2$. The combined organics were washed with brine and dried over Na$_2$SO$_4$. The crude product was purified by silica gel chromatography (1% to 5% MeOH/CH$_2$Cl$_2$) to collect the title compound as a white solid (0.315 g, 63%)

LCMS: R.t. 1.57 min, ES+ 491.6 (formic acid).

Step d: {(2R,3S,4R,5R)-5-[6-(Benzoylamino)-9H-purin-9-yl]-3,4-dihydroxytetrahydrofuran-2-yl}methyl sulfamate (I-12)

Approximately 3 mL of 90% TFA/H$_2$O was added to {(3aR,4R,6R,6aR)-6-[6-(benzoylamino)-9H-purin-9-yl]-2,2-dimethyltetrahydrofuro[3,4-d][1,3]dioxol-4-yl}methyl sulfamate (0.315 g, 0.642 mmol) and stirred together for 20 minutes at room temperature. The solvent was removed and the product was purified by HPLC (0.113 g, 39%).

LCMS: R.t. 1.20 min, ES+ 451.5 (formic acid).

$^1$H-NMR (300 MHz, $d_6$-DMSO): δ 11.18 (s, 1H); 8.76 (s, 1H); 8.63 (s, 1H); 8.06 (d, J=7.162 Hz, 2); 7.67-7.63 (m, 1H); 7.60-7.52 (m, 4H); 6.08 (d, J=5.41 Hz, 1H); 4.70 (t, J=5.26 Hz, 1H); 4.33-4.19 (m, 4H).

Example 63

((3aR,4R,6R,6aR)-6-{6-[(4-Fluorobenzoyl)amino]-9H-purin-9-yl}-2,2-dimethyltetrahydrofuro[3,4-d][1,3]dioxol-4-yl)methyl sulfamate (I-47)

The product was prepared as described in Example 62, steps a-d, using 4-fluorobenzoyl chloride in step a.

LCMS: R.t. 1.12 min, ES+ 469 (formic acid).
$^1$H-NMR (400 MHz, d$_6$-DMSO): δ 8.76 (s, 1H), 8.63 (s, 1H); 8.12 (m, 1H); 7.61 (br, 2H); 7.39 (t, J=9.0, 8.8 Hz, 2H); 6.09 (d, J=5.3 Hz, 1H); 5.71 (d, J=5.8 Hz, 1H); 5.49 (d, J=5.02 Hz, 1H); 4.70 (q, J=5.3, 5.5 Hz, 1H); 4.33-4.19 (m, 4).

Example 64

((2R,3S,4R,5R)-3,4-dihydroxy-5-{6-[(phenylsulfonyl)amino]-9H-purin-9-yl}-tetrahydrofuran-2-yl)methyl sulfamate (I-48)

Step a: [(3aR,4R,6R,6aR)-6-(6-amino-9H-purin-9-yl)-2,2-dimethyltetrahydrofuro[3,4-d][1,3]dioxol-4-yl]methyl acetate

[(3aR,4R,6R,6aR)-6-(6-Chloro-9H-purin-9-yl)-2,2-dimethyltetrahydrofuro[3,4-d][1,3]dioxol-4-yl]methanol (0.500 g, 1.63 mmol) was dissolved in pyridine (12.5 mL) and cooled with an ice bath. Acetic anhydride (0.154 mL, 1.63 mmol) was added slowly and the reaction was warmed to room temperature then stirred overnight. The reaction mixture was then poured over ice and extracted three times with CH$_2$Cl$_2$. Combined organics were washed with CuSO$_4$ (aq) solution, dried over Na$_2$SO$_4$, and concentrated. The crude material was purified by flash chromatography (70% to 100% EtOAc/Hex) to afford product 0.336 g (59%).

LCMS: R.t. 1.41 min, ES+ 350.5 (formic acid).

Step b: (3aR,4R,6R,6aR)-6-(6-Benzenesulfonylamino-purin-9-yl)-2,2-dimethyl-tetrahydrofuro[3,4-d][1,3]dioxol-4-ylmethyl acetate

[(3 aR,4R,6R,6aR)-6-(6-Amino-9H-purin-9-yl)-2,2-dimethyltetrahydrofuro[3,4-d][1,3]dioxol-4-yl]methyl acetate (0.738 g, 2.11 mmol) and benzene sulfonyl chloride (0.942 mL, 7.39 mmol) were dissolved in dry pyridine (21 mL) and stirred at 80° C. After 22 hours, extra benzenesulfonyl chloride (0.942 mL, 7.39 mmol) was added and the reaction mixture was stirred at 80° C. for 6 additional hours. The solvent was then removed in vacuo, and the residue was dissolved in CH$_2$Cl$_2$. The organics were washed with water, then brine, dried over Na$_2$SO$_4$, and concentrated. The dark orange crude oil was purified by flash column chromatography (70% to 100% EtOAc/Hex) to obtain product (0.600 g, 58%).

LCMS: R.t. 1.66 min, ES+ 490.5 (formic acid).

Step c: N-{9-[(3aR,4R,6R,6aR)-6-(Hydroxymethyl)-2,2-dimethyltetrahydrofuro[3,4-d][1,3]dioxol-4-yl]-9H-purin-6-yl}benzenesulfonamide (3aR,4R,6R,6aR)-6-(6-Benzenesulfonylamino-purin-9-yl)-2,2-dimethyltetrahydro-furo[3,4-d][1,3]dioxol-4-ylmethyl acetate (0.600 g, 1.23 mmol) was dissolved in approximately 3 mL of 7N NH$_3$/MeOH solution and stirred at room temperature overnight. The reaction mixture was then concentrated in vacuo and the crude product was purified by flash chromatography (0% to 5% MeOH/CH$_2$Cl$_2$) to afford a white solid (0.330 g, 60%).

LCMS: R.t. 1.34 min, ES+ 448 (formic acid).

Step d: ((3aR,4R,6R,6aR)-2,2-Dimethyl-6-{6-[(phenylsulfonyl)amino]-9H-purin-9-yl}-tetrahydrofuro[3,4-d][1,3]dioxol-4-yl)methyl sulfamate N-{9-[(3aR,4R,6R,6aR)-6-(Hydroxymethyl)-2,2-dimethyltetrahydrofuro[3,4-d][1,3]dioxol-4-yl}-9H-purin-6-yl]benzenesulfonamide (0.293 g, 0.655 mmol) was treated with chlorosulfonamide as described in Example 62, step c, with a reaction time of 2 hours. The crude product was purified by silica gel chromatography (0% to 1% MeOH/EtOAc) to give a foam (0.142 g, 41%).

LCMS: R.t. 1.55 min, ES+ 527.5 (formic acid).

Step e: ((2R,3S,4R,5R)-3,4-dihydroxy-5-{6-[(phenylsulfonyl)amino]-9H-purin-9-yl}-tetrahydrofuran-2-yl)methyl sulfamate (I-48)

Approximately 3 mL of 90% TFA/H$_2$O was added to ((3aR,4R,6R,6aR)-2,2-dimethyl-6-{6-[(phenylsulfonyl)amino]-9H-purin-9-yl}tetrahydrofuro[3,4-d][1,3]dioxol-4-yl)methyl sulfamate (0.142 g, 0.270 mmol) and the mixture was stirred for 30 minutes at room temperature. The solvent was removed and the product was purified by HPLC (0.0727 g, 55%).

LCMS: R.t. 1.25 min, ES+ 487.5 (formic acid).
$^1$H-NMR (400 MHz, d$_6$-DMSO): δ 12.93 (bs, 1H); 8.46 (bs, 1H); 8.37 (s, 1H); 7.98 (bs, 2H); 7.62-7.54 (m, 5H); 5.96 (d, J=5.3, 2H); 5.66, (d, J=5.5, 1H); 5.45 (d, J=5.3, 1H); 4.56 (m, 1H); 4.29-4.15 (m, 3H).

Example 65

((2R,3S,4R,5R)-5-{2-Amino-6-[(1S)-2,3-dihydro-1H-inden-1-ylamino]-9H-purin-9-yl}-3,4-dihydroxytetrahydrofuran-2-yl)methyl sulfamate (I-18)

The title compound was prepared following the procedure described in Example 1 using 2-amino-6-chloropurine riboside as starting material and (S)-(+)-1-aminoindane in step b.

LCMS: R.t. 1.31 min, ES+ 478 (ammonium acetate).
$^1$H-NMR (300 MHz, CD$_3$OD): δ 8.00 (s, 1H), 7.33 (m, 4H), 6.00 (d, 1H, J=5.4 Hz), 5.93 (br, 1H), 4.76 (t, 1H, J=5.3 Hz), 4.49 (ddd, 2H, J=3.7 Hz, J=10.0 Hz, J=11.0 Hz), 4.47 (m, 1H), 4.38 (dd, 1H, J=3.8 Hz, J=7.5 Hz), 3.16 (ddd, 1H, J=3.4 Hz, J=8.7 Hz, J=15.9 Hz), 2.99 (td, 1H, J=6.0 Hz, J=19.8 Hz), 2.74 (dtd, 1H, J=4.0 Hz, J=7.8 Hz, J=15.8 Hz), 2.06 (tt, 1H, J=5.7 Hz, J=15.8 Hz)

Example 66

((1R,2R,3S,4R)-4-{6-[(1S)-2,3-Dihydro-1H-inden-1-ylamino]-9H-purin-9-yl}-2,3-dihydroxycyclopentyl)methyl sulfamate (I-29)

Step a: (1R,2S,3R,5R)-3-[(5-Amino-6-chloropyrimidin-4-yl)amino]-5-(hydroxymethyl)-cyclopentane-1,2-diol (1R,2S,3R,4R)-2,3-Dihydroxy-4-(hydroxymethyl)-1-aminocyclopentane hydrochloride (250.0 mg, 0.001361 mol) and 5-amino-4,6-dichloropyrimidine (240.0 mg, 0.001463 mol) and Triethylamine (395.0 µL, 0.002834 mol) in 1-Butanol (4.0 mL, 0.044 mol) were reacted in a microwave at 180° C. for 20 minutes. The reaction was concentrated in vacuo to dryness, redissolved in EtOH and pre-adsorbed onto silica. This was then eluted through a silica plug with EtOAc to recover starting pyrimidine. Elution with 20% EtOH/EtOAc gave product (285 mg, 76%).

LCMS: R.t. 0.96 min, ES+ 275 (ammonium acetate).

Step b: [(3aR,4R,6R,6aS)-6-(6-Chloro-9H-purin-9-yl)-2,2-dimethyltetrahydro-3aH-cyclopenta[d][1,3]dioxol-4-yl]methanol (1R,2S,3R,5R)-3-[(5-Amino-6-chloropyrimidin-4-yl)amino]-5-(hydroxymethyl)cyclopentane-1,2-diol (335.0 mg, 0.001219 mol) and p-toluenesulfonic acid monohydrate (280 mg, 0.0015 mol) was dissolved in N,N-dimethylformamide (5.00 mL) and trimethoxymethane (10.0 mL, 0.0914 mol) under an atmosphere of nitrogen at 25° C. The reaction was stirred overnight, concentrated in vacuo, diluted with water and concentrated in vacuo again. The residue was then twice concentrated in vacuo from toluene. The residue was taken up in acetone (15.0 mL, 0.204 mol) and 2,2-dimethoxypropane (5.0 mL, 0.041 mol) and stirred for 2 hours, until complete by LCMS. The mixture was basified with sodium bicarbonate solution (20 mL), and concentrated in vacuo to remove organic solvent. The aqueous residue was extracted with DCM (4×20 mL) and the combined organic phase was concentrated in vacuo. Flash chromatography (0-100% EtOAc/DCM) gave the desired product (210 mg, 53%)

LCMS: R.t. 1.65 min, ES+ 325 (ammonium acetate).

Step c: ((3aR,4R,6R,6aS)-6-{6-[(1S)-2,3-Dihydro-1H-inden-1-ylamino]-9H-purin-9-yl}-2,2-dimethyltetrahydro-3aH-cyclopenta[d][1,3]dioxol-4-yl)methanol

[(3aR,4R,6R,6aS)-6-(6-Chloro-9H-purin-9-yl)-2,2-dimethyltetrahydro-3aH-cyclopenta[d][1,3]dioxol-4-yl]methanol (210.0 mg, 0.0006466 mol) and (S)-(+)-1-aminoindane (103.7 µL, 0.0008083 mol) was dissolved in ethanol (3.0 mL, 0.051 mol) and triethylamine (135.2 µL, 0.0009699 mol). The reaction was microwaved at 150° C. for 11 minutes. The reaction was concentrated in vacuo and the residue purified by flash chromatography (0 to 100% EtOAc/methylene chloride) to yield the product (175 mg, 64%).

LCMS: R.t. 2.17 min, ES+ 422 (ammonium acetate).

Step d: ((3aR,4R,6R,6aS)-6-{6-[(1S)-2,3-Dihydro-1H-inden-1-ylamino]-9H-purin-9-yl}-2,2-dimethyltetrahydro-3aH-cyclopenta[d][1,3]dioxol-4-yl) methyl sulfamate 6-[6-(Indan-1-ylamino)-purin-9-yl]-2,2-dimethyl-tetrahydro-cyclopenta[1,3]-dioxol-4-yl-methanol (170.0 mg, 0.0004033 mol) was dissolved in methylene chloride (4 mL, 0.06 mol) and triethylamine (85 µL, 0.00061 mol) under an atmosphere of nitrogen. The reaction was cooled on an ice bath. 2.0 M of chlorosulfonamide in acetonitrile (0.30 mL, 0.00060 mol) was added and the mixture was stirred for 90 minutes at 0° C. The reaction was quenched with diluted sodium bicarbonate solution (20 mL) and extracted with DCM (3×20 mL). The organics were evaporated, taken up in EtOAc and filtered through a pad of silica, eluting with EtOAc. The filtrates were concentrated and dried under vacuum to yield the product (160 mg, 79%)

LCMS: R.t. 1.59 min, ES+ 501 (ammonium acetate).

Step e: ((1R,2R,3S,4R)-4-{6-[(1S)-2,3-Dihydro-1H-inden-1-ylamino]-9H-purin-9-yl}-2,3-dihydroxycyclopentyl)methyl sulfamate (I-29)

((3aR,4R,6R,6aS)-6-{6-[(1S)-2,3-Dihydro-1H-inden-1-ylamino]-9H-purin-9-yl}-2,2-dimethyltetrahydro-3aH-cyclopenta[d][1,3]dioxol-4-yl)methyl sulfamate (160 mg, 0.00032 mol) was dissolved in TFA/H$_2$O 9:1 (10.0 mL) and was stirred for 10 minutes The reaction was concentrated in vacuo to dryness and concentrated in vacuo twice from MeOH. The crude residue was purified by reverse phase HPLC to give the product (65 mg, 44%)

LCMS: R.t. 1.24 min, ES+ 461 (ammonium acetate).
$^1$H-NMR (400 MHz, CD$_3$OD): δ 7.73 (s, 1H), 7.57 (s, 1H), 6.66 (m, 4H), 5.31 (br, 1H), 3.96 (dd, 1H, J=5.6 Hz, J=8.6 Hz), 3.72 (dq, 2H, J=5.8 Hz, J=9.9 Hz), 3.53 (dd, 1H, J=3.3 Hz, J=5.5 Hz), 2.78 (m, 2H), 2.51 (ddd, 1H, J=3.6 Hz, J=8.6 Hz, J=15.8 Hz), 2.37 (td, 1H, J=8.1 Hz, J=15.9 Hz), 2.11 (dtd, 1H, J=3.7 Hz, J=7.7 Hz, J=12.6 Hz), 1.93 (m, 2H), 1.44 (m, 2H)

Example 67

{(2R,3S,4R,5R)-3,4-Dihydroxy-5-[6-(phenylethynyl)-9H-purin-9-yl]tetrahydrofuran-2-yl}methyl sulfamate (I-5)

Step a: {(3aR,4R,6R,6aR)-6-(6-Amino-9H-purin-9-yl)-2,2-dimethyltetrahydrofuro[3,4-d][1,3]dioxol-4-yl}methyl acetate

[(3aR,4R,6R,6aR)-6-(6-amino-9H-purin-9-yl)-2,2-dimethyltetrahydrofuro[3,4-d][1,3]dioxol-4-yl]methanol (4.071 g, 0.01325 mol) was dissolved in pyridine (50 mL, 0.6 mol) and acetic anhydride (1500 µL, 0.016 mol) was added. The solution was stirred at room temperature for 15 h, and more acetic anhydride (250 µL) was added. After 5 h, ethanol (10 mL) was added and the solution stirred for 10 min then concentrated in vacuo. The residue was taken up in chloroform and the solution washed twice with saturated NaHCO$_3$ then twice with saturated CuSO$_4$, dried over Na$_2$SO$_4$ and concentrated in vacuo to dryness. The residue was purified by flash chromatography (DCM/MeOH 1% to 4%) to obtain the product as an oil (3.774 g, 82%). LCMS: R.t. 1.03 min, ES+ 350 (formic acid).

Step b: [(3aR,4R,6R,6aR)-6-(6-Bromo-9H-purin-9-yl)-2,2-dimethyltetrahydrofuro[3,4-d][1,3]dioxol-4-yl]methyl acetate

[(3aR,4R,6R,6aR)-6-(6-Amino-9H-purin-9-yl)-2,2-dimethyltetrahydrofuro[3,4-d][1,3]dioxol-4-yl]methyl acetate (3.77 g, 0.0108 mol) was dissolved in dibromomethane (150 mL, 2.2 mol) and cooled in an ice/water bath under nitrogen. tert-Butyl nitrite (25.7 mL, 0.216 mol) and then bromotrimethylsilane (4.28 mL, 0.0324 mol) were added dropwise. After 6 h, the reaction was added dropwise to cooled saturated NaHCO$_3$/DCM 1:1 (500 mL). The organic was washed with water then brine, dried over Na$_2$SO$_4$ and concentrated in vacuo. The residue was purified by flash chromatography (DCM/EtOAc 20% to 40%) to obtain the product as a white solid (3.79 g, 85%).

LCMS: R.t. 1.44 min, ES+ 415 (formic acid).

Step c: {(3aR,4R,6R,6aR)-2,2-Dimethyl-6-[6-(phenylethynyl)-9H-purin-9-yl]tetrahydrofuro[3,4-d][1,3]dioxol-4-yl}methyl acetate

[(3aR,4R,6R,6aR)-6-(6-Bromo-9H-purin-9-yl)-2,2-dimethyltetrahydrofuro[3,4-d][1,3]dioxol-4-yl]methyl acetate (749 mg, 0.00181 mol), copper(I) iodide (69.0 mg, 0.000362 mol) and bis(triphenylphosphine)palladium(II) chloride (127 mg, 0.000181 mol) were dissolved in dry N,N-dimethylformamide (37 mL, 0.48 mol) under nitrogen. Dry N,N-diisopropylethylamine (631 µL, 0.00362 mol) then phenylacetylene (798 µL, 0.00725 mol) were added. The yellow solution was heated at 75° C. for 1 h then concentrated in vacuo. The residue was taken in DCM and the solution washed three times with saturated $Na_2EDTA$, dried over $Na_2SO_4$ and concentrated in vacuo. The residue was purified by flash chromatography (hexane/EtOAc 20% to 60%) to obtain compound as a foam (659 mg, 84%) which was used without further purification.

LCMS: R.t. 1.76 min, ES+ 435 (formic acid).

Step d: {(3aR,4R,6R,6aR)-2,2-Dimethyl-6-[6-(phenylethynyl)-9H-purin-9-yl]tetrahydrofuro[3,4-d][1,3]dioxol-4-yl}methanol {(3aR,4R,6R,6aR)-2,2-Dimethyl-6-[6-(phenylethynyl)-9H-purin-9-yl]-tetrahydrofuro[3,4-d][1,3]dioxol-4-yl}methyl acetate (650 mg, 0.0015 mol) was treated with 7M ammonia in methanol (10 mL) at room temperature for 1 h. The solution was concentrated in vacuo and the residue purified by flash chromatography (DCM/EtOAc 20% to 60%) to obtain the product (465 mg, 79%) as a white solid.

LCMS: R.t. 1.56 min, ES+ 393 (formic acid).

Step e: {(3aR,4R,6R,6aR)-2,2-Dimethyl-6-[6-(phenylethynyl)-9H-purin-9-yl]tetrahydrofuro[3,4-d][1,3]dioxol-4-yl}methyl sulfamate {(3aR,4R,6R,6aR)-2,2-Dimethyl-6-[6-(phenylethynyl)-9H-purin-9-yl]-tetrahydrofuro[3,4-d][1,3]dioxol-4-yl}methanol (463 mg, 0.00118 mol) and triethylamine (329 µL, 0.00236 mol) were dissolved in dry acetonitrile (10 mL, 0.2 mol) under nitrogen. The solution was cooled in an ice bath and 2M chlorosulfonamide in acetonitrile (800 µL) was added dropwise. After 1 h, more triethylamine (300 µL) and 2M chlorosulfonamide in acetonitrile (800 µL) were added. After 30 min, the reaction was quenched with MeOH concentrated in vacuo and the residue was purified by flash chromatography (DCM/EtOAc 10% to 40%) to obtain the product as a white solid (378 mg, 68%).

LCMS: R.t. 1.62 min, ES+ 472 (formic acid).

Step f: {(2R,3S,4R,5R)-3,4-Dihydroxy-5-[6-(phenylethynyl)-9H-purin-9-yl]tetrahydrofuran-2-yl}methyl sulfamate (I-5)

{(3aR,4R,6R,6aR)-2,2-Dimethyl-6-[6-(phenylethynyl)-9H-purin-9-yl]-tetrahydrofuro[3,4-d][1,3]dioxol-4-yl}methyl sulfamate (370 mg, 0.00078 mol) was treated with trifluoroacetic acid/water 9:1 (5 mL) for 30 min. The solution was concentrated in vacuo and the residue taken in methanol to obtain the product as a white solid (234 mg, 69%) which was isolated by filtration.

LCMS: R.t. 1.26 min, ES+ 432 (formic acid).

$^1$H-NMR (300 MHz, $d_6$-DMSO): δ 8.95 (s, 1H), 8.78 (s, 1H), 7.72 (m, 2H), 7.62 (s, 2H), 7.54 (m, 3H), 6.08 (d, 1H, J=4.9 Hz), 4.68 (dd, 1H, J=4.8 Hz, J=4.8 Hz), 4.35-4.20 (m, 4H).

Example 68

((2R,3R,4S,5R)-5-{6-[(1S)-2,3-Dihydro-1H-inden-1-ylamino]-9H-purin-9-yl}-4-fluoro-3-hydroxytetrahydrofuran-2-yl)methyl sulfamate (I-60)

Step a: (2R,3R,4S,5R)-2-(6-Chloro-9H-purin-9-yl)-5-[(trityloxy)methyl]tetrahydrofuran-3,4-diol To a solution of 6-chloro-9-β-D-ribofuranosylpurine (5.00 g, 17.4 mmol) and triphenylmethyl chloride (9.72 g, 34.8 mmol) in DMF (60 mL) was added DIPEA (2.7 mL, 19.1 mmol) dropwise. The reaction was heated to 40° C. overnight, cooled to r.t. and filtered. The yellow filtrate was diluted with chloroform and washed with water, 0.5 N HCl, and water. The organic layer was dried ($Na_2SO_4$), filtered and concentrated. The yellow foam was purified by flash chromatography (0 to 4% MeOH/$CHCl_3$) to yield the product as a pale yellow foam (5.99 g, 65%).

LCMS: R.t. 1.93 min ES+ 529, 531 (formic acid).

Step b: (2R,3S,4R,5R)-5-(6-Chloro-9H-purin-9-yl)-4-hydroxy-2-[(trityloxy)methyl]-tetrahydrofuran-3-yl benzoate To a solution of (2R,3R,4S,5R)-2-(6-chloro-9H-purin-9-yl)-5-[(trityloxy)methyl]tetrahydrofuran-3,4-diol (5.99 g, 11.3 mmol) in pyridine (20 mL) at 0° C. was added benzoyl chloride (1.45 mL, 12.5 mmol) dropwise. After stirring for six hours the yellow solution was diluted with methylene chloride, washed with saturated aq sodium bicarbonate (3×), saturated aq copper sulfate (3×) and water (4×). The organic layer was dried ($Na_2SO_4$), filtered and concentrated. The brown foam was purified by flash chromatography (0 to 1% MeOH/$CHCl_3$) to give a mixture of regioisomers. The mixture was re-purified in 1 g batches by flash chromatography (0 to 2% MeOH/$CHCl_3$) to yield the product as a white solid (1.505 g, 21%).

LCMS: R.t. 2.29 min ES+ 633, 635 (formic acid).

Step c: (2R,3R,4S,5R)-5-(6-Chloro-9H-purin-9-yl)-4-fluoro-2-[(trityloxy)methyl]tetrahydrofuran-3-yl benzoate To a solution of (2R,3S,4R,5R)-5-(6-chloro-9H-purin-9-yl)-4-hydroxy-2-[(trityloxy)methyl]tetrahydrofuran-3-yl benzoate (0.905 g, 1.43 mmol) and pyridine (0.7 mL, 8.58 mmol) in DCM (40 mL) at 0° C. was added diethylaminosulfur trifluoride (0.75 mL, 5.72 mmol) dropwise. The reaction was stirred at 0° C. for one hour, warmed to r.t., and heated at reflux overnight. The reaction was cooled to r.t., quenched with 5% aq sodium bicarbonate and diluted with DCM. The organic layer was washed with saturated aq copper sulfate (2×), water (4×), dried ($MgSO_4$), filtered, and concentrated.

The yellow oil was purified by flash chromatography (0 to 2% MeOH/CHCl$_3$) to yield the product as a yellow foam (0.781 g, 86
LCMS: R.t. 2.42 min ES+ 635, 637 (formic acid).

Step d: (2R,3R,4S,5R)-5-{6-[(1S)-2,3-Dihydro-1H-inden-1-ylamino]-9H-purin-9-yl}-4-fluoro-2-[(trityloxy)methyl]tetrahydrofuran-3-yl benzoate A solution of (2R,3R,4S,5R)-5-(6-chloro-9H-purin-9-yl)-4-fluoro-2-[(trityloxy)methyl]tetrahydrofuran-3-yl benzoate (0.781 g, 1.23 mmol), (S)-(+)-1-aminoindan (0.316 mL, 2.46 mmol) and Et$_3$N (0.343 mL, 2.46 mmol) in ethanol (25 mL) was heated at reflux overnight. The brown mixture was cooled to r.t. and concentrated. The residue was purified by flash chromatography (0 to 2% MeOH/CHCl$_3$) to yield the product (0.705 g, 79%).
LCMS: R.t. 2.57 min ES+ 732 (formic acid).

Step e: (2R,3R,4S,5R)-5-{6-[(1S)-2,3-Dihydro-1H-inden-1-ylamino]-9H-purin-9-yl}-4-fluoro-2-(hydroxymethyl)tetrahydrofuran-3-yl benzoate To a solution of (2R,3R,4S,5R)-5-{6-[(1S)-2,3-Dihydro-1H-inden-1-ylamino]-9H-purin-9-yl}-4-fluoro-2-[(trityloxy)methyl]tetrahydrofuran-3-yl benzoate (0.715 g, 0.98 mmol) in ether (9 mL) was added formic acid (6 mL) and the reaction was stirred for four hours. The solution was diluted with ether and washed with saturated aq sodium bicarbonate to quench. The organic layer was dried (Na$_2$SO$_4$), filtered and concentrated. The beige foam was purified by flash chromatography (0 to 2% MeOH/CHCl$_3$) to yield the product (0.468 g, 98%).
LCMS: R.t. 1.87 min ES+ 490 (formic acid).

Step f: (2R,3R,4S,5R)-2-{[(Aminosulfonyl)oxy]methyl}-5-{6-[(1S)-2,3-dihydro-1H-inden-1-ylamino]-9H-purin-9-yl}-4-fluorotetrahydrofuran-3-yl benzoate The title compound was prepared following the procedure described in Example 67 step e using DMF as the solvent.
LCMS: R.t. 1.83 min ES+ 569 (formic acid).

Step g: ((2R,3R,4S,5R)-5-{6-[(1S)-2,3-Dihydro-1H-inden-1-ylamino]-9H-purin-9-yl}-4-fluoro-3-hydroxytetrahydrofuran-2-yl)methyl sulfamate (I-60)

The title compound was prepared following the procedure described in Example 67 step d using (2R,3R,4S,5R)-2-{[(aminosulfonyl)oxy]methyl}-5-{6-[(1S)-2,3-dihydro-H-inden-1-ylamino]-9H-purin-9-yl}-4-fluorotetrahydrofuran-3-yl benzoate. LCMS: R.t. 1.46 min ES+ 465 (formic acid).
$^1$H-NMR (400 MHz, CD$_3$OD): δ 8.34 (bs, 1H); 8.22 (d, J=2.4 Hz, 1H); 7.36-7.12 (m, 4H); 6.56 (dd, J=3.7 Hz, 17.9 Hz, 1H); 5.90 (bs, 1H); 5.25-5.08 (dt, J=3.1 Hz, 51.7 Hz, 1H); 4.57 (dt, J=3.2 Hz, 16.5 Hz, 1H); 4.40 (d, J=5.1 Hz, 2H); 4.26 (q, J=4.5 Hz, 1H); 3.17-3.03 (m, 1H); 3.02-2.63 (m, 1H); 2.75-2.63 (m, 1H); 2.11-1.98 (m, 1H).

Example 69

{(2R,3S,4R,5R)-5-[6-(2-furyl)-9H-purin-9-yl]-3,4-dihydroxytetrahydrofuran-2-yl}methyl sulfamate (I-94)

Step a: (3aR,4R,6R,6aR)-6-[6-(2-furyl)-9H-purin-9-yl]-2,2-dimethyltetrahydrofuro[3,4-d][1,3]dioxol-4-yl)methyl acetate

[(3aR,4R,6R,6aR)-6-(6-Bromo-9H-purin-9-yl)-2,2-dimethyltetrahydrofuro[3,4-d][1,3]dioxol-4-yl]methyl acetate (0.10 g, 0.242 mmol), 2-(tributylstannyl)furan (0.08 mL, 0.242 mmol) and bis(triphenylphosphine)palladium(II) chloride (0.008 g, 0.012 mmol) were stirred in DMF (1 mL) under an atmosphere of argon for 4 hours. The mixture was filtered through a pad of Celite and then concentrated. The residue was purified by preparative plate chromatography (50% EtOAc/hexanes) to give the title compound as a yellow foam (0.076 g, 78%).
LCMS: R.t. 2.45 min ES+ 401 (formic acid).

Step b: {(2R,3S,4R,5R)-5-[6-(2-furyl)-9H-purin-9-yl]-3,4-dihydroxytetrahydrofuran-2-yl}-methyl sulfamate (I-94)

The title compound was prepared following the procedure described in Example 67, steps d-f using DCM as the solvent in step e.
LCMS: R.t. 1.02 min ES+ 398 (formic acid).
$^1$H-NMR (300 MHz, d$_6$-DMSO): δ 8.91 (s, 1H); 8.77 (s, 1H), 8.08 (bs, 1H); 7.85 (d, J=3.4 Hz, 1H); 7.50 (bs, 1H); 6.85-6.79 (m, 1H); 6.09 (d, J=5.1 Hz, 1H); 5.74 (bs, 1H); 5.54 (bs, 1H); 4.69 (bs, 1H); 4.37-4.16 (m, 4H).

Example 70

((2R,3S,4R,5R)-5-{6-[(2-Chlorophenyl)ethynyl]-9H-purin-9-yl}-3,4-dihydroxytetrahydrofuran-2-yl)methyl sulfamate (I-71)

The title compound was prepared following the procedure described in Example 67, steps c-f using 1-chloro-2-ethynyl-benzene in step c and DCM as the solvent in step e.
LCMS: R.t. 1.42 min ES+ 466 (formic acid
$^1$H-NMR (300 MHz, CD$_3$OD): δ 8.92 (s, 1H); 8.73 (s, 1H); 7.84 (d, J=7.6 Hz, 1H); 7.58-7.33 (m, 3H); 6.21 (d, J=4.9 Hz, 1H); 4.76 (t, J=4.9 Hz, 1H); 4.48-4.29 (m, 4H).

Example 71

((2R,3S,4R,5R)-5-{6-[(3-Fluorophenyl)ethynyl]-9H-purin-9-yl}-3,4-dihydroxytetrahydrofuran-2-yl)methyl sulfamate (I-88)

The title compound was prepared following the procedure described in Example 67, steps c-f using 1-fluoro-3-ethynyl-benzene in step c and DCM as the solvent in step e.
LCMS: R.t. 1.35 min ES+ 450 (formic acid).
$^1$H-NMR (300 MHz, CD$_3$OD): δ 8.92 (s, 1H); 8.76 (s, 1H); 7.63-7.42 (m, 3H); 7.25 (dt, J=2.4 Hz, J=10.5 Hz, 1H); 6.20 (d, J=4.8 Hz, 1H); 4.76 (t, J=4.9 Hz, 1H); 4.47-4.27 (m, 4H).

Example 72

((2R,3S,4R,5R)-3,4-Dihydroxy-5-{6-[(2-methoxyphenyl)ethynyl]-9H-purin-9-yl}tetrahydrofuran-2-yl)methyl sulfamate (I-90)

The title compound was prepared following the procedure described in Example 67, steps c-f using 1-ethynyl-2-methoxy benzene in step c and DCM as the solvent in step e.
LCMS: R.t. 1.23 min ES+ 462 (formic acid).
$^1$H-NMR (400 MHz, d$_6$-DMSO): δ 8.95 (s, 1H); 8.80 (s, 1H); 7.66-7.45 (m, 4H); 7.17 (d, J=8.4 Hz, 1H): 7.06 (t, J=7.4 Hz, 1H); 6.09 (d, J=5.0 Hz, 1H); 5.70 (s, 1H); 5.49 (s, 1H); 4.68 (s, 1H); 4.38-4.14 (m, 1H); 3.91 (s, 3H)

Example 73

((2R,3S,4R,5R)-5-{6-[(4-Bromophenyl)ethynyl]-9H-purin-9-yl}-3,4-dihydroxytetrahydrofuran-2-yl)methyl sulfamate (I-150)

The title compound was prepared following the procedure described in Example 67, steps c-f using 1-bromo-4-ethynylbenzene in step c and DCM as the solvent in step e.
LCMS: R.t. 1.49 min ES+ 509, 511 (formic acid)
$^1$H-NMR (400 MHz, $d_6$-DMSO): δ 8.93 (s, 1H); 8.73 (s, 1H); 7.81-7.57 (m, 4H); 6.06 (d, J=5.0 Hz, 1H); 4.67 (t, J=4.9 Hz, 1H); 4.36-4.15 (m, 4H).

Example 74

[(2R,3S,4R,5R)-3,4-Dihydroxy-5-(6-{[3-(trifluoromethyl)phenyl]ethynyl}-9H-purin-9-yl)tetrahydrofuran-2-yl]methyl sulfamate (I-108)

The title compound was prepared following the procedure described in Example 67, steps c-f using 1-ethynyl-3-(trifluoromethyl)benzene in step c and DCM as the solvent in step e.
LCMS: R.t. 1.52 min ES+ 501 (formic acid)
$^1$H-NMR (400 MHz, $d_6$-DMSO): δ 9.00 (s, 1H); 8.85 (s, 1H); 8.08-8.01 (m, 2H); 7.92 (d, J=7.9 Hz, 1H); 7.78 (t, J=7.7 Hz, 1H); 7.60 (s, 2H); 6.10 (d, J=5.1 Hz, 1H); 5.72 (d, J=5.7 Hz, 1H); 5.50 (d, J=5.4 Hz, 1H); 4.69 (q, J=5.3 Hz, 1H); 4.37-4.15 (m, 4H).

Example 75

((2R,3S,4R,5R)-5-{6-[(4-Fluorophenyl)ethynyl]-9H-purin-9-yl}-3,4-dihydroxytetrahydrofuran-2-yl)methyl sulfamate (I-144)

The title compound was prepared following the procedure described in Example 67, steps c-f using 1-ethynyl-4-fluorobenzene in step c and DCM as the solvent in step e.
LCMS: R.t. 1.34 min ES+ 450 (formic acid)
$^1$H-NMR (300 MHz, $d_6$-DMSO): δ 8.96 (s, 1H); 8.82 (s, 1H); 7.79 (t, J=5.4 Hz, 2H); 7.61 (bs, 2H); 7.37 (t, J=8.9 Hz, 2H); 6.09 (d, J=5.0 Hz, 1H); 4.69 (t, J=4.9 Hz, 1H); 4.37-4.17 (m, 4H).

Example 76

((1S,2S,4R)-4-{4-[(1S)-2,3-Dihydro-1H-inden-1-ylamino]-7H-pyrrolo[2,3-d]-pyrimidin-7-yl}-2-hydroxycyclopentyl)methyl sulfamate

Step a: (1R,2R,3S,5S)-3-(Hydroxymethyl)-6-oxabicyclo[3.1.0]hexan-2-ol

To a solution of (1S,5S)-5-(hydroxymethyl)cyclopent-2-en-1-ol (3.19 g, 27.9 mmol) (An, G.-I.; Rhee, H. *Nucleosides Nucleotides* 2002, 21, 65-72) in DCM (143 mL) at 0° C. was added 3-chloroperbenzoic acid (7.52 g, 33.5 mmol) and the mixture was stirred at room temperature for 4 hours. Silica gel (20 g) was added, the mixture was concentrated to dryness and was purified via flash chromatography (0 to 100% EtOAc/DCM) to afford the title compound (2.75 g, 76%).
LCMS: R.t. 0.37 min ES+ 131 (ammonium acetate).

Step b: (1aS,1bR,5aS,6aS)-3-(4-Methoxyphenyl)hexahydrooxireno[4,5]cyclopenta[1,2-d][1,3]dioxine To a solution of (1R,2R,3S,5S)-3-(hydroxymethyl)-6-oxabicyclo[3.1.0]hexan-2-ol (3.65 g, 21.0 mol) in DCM (121 mL) at 0° C. was added 1-(dimethoxymethyl)-4-methoxybenzene (10.7 mL, 63.1 mmol) followed by pyridinium p-toluenesulfonate (530. mg, 2.11 mmol). The mixture was stirred at room temperature overnight. The reaction mixture was concentrated and the residue was purified by flash chromatography (0 to 50% EtOAc/hexanes) to afford the title compound (4.10 g, 78%).
LCMS: R.t 1.68 min ES+ 249 (ammonium acetate).

Step c: N-[(1S)-2,3-Dihydro-1H-inden-1-yl]-7H-pyrrolo[2,3-d]pyrimidin-4-amine A solution of 4-chloro-1H-pyrrolo[2,3-d]pyrimidine (2.10 g, 13.6 mmol), DIPEA (3.57 mL, 20.5 mmol) and (S)-(+)-1-aminoindan (1.93 mL, 15.0 mmol) in 1-butanol (60.0 mL) and was heated to reflux for 60 hours, cooled down to room temperature and concentrated. The residue was purified by flash chromatography (0 to 100% EtOAc/DCM) to afford the title compound (2.72 g, 80%).
LCMS: R.t 1.42 min ES+ 251 (ammonium acetate).

Step d: (4aS,6R,7S,7aR)-6-{4-[(1S)-2,3-Dihydro-1H-inden-1-ylamino]-7H-pyrrolo[2,3-d]pyrimidin-7-yl}-2-(4-methoxyphenyl)hexahydrocyclopenta[d][1,3]dioxin-7-ol To a solution of N-[(1S)-2,3-Dihydro-1H-inden-1-yl]-7H-pyrrolo[2,3-d]pyrimidin-4-amine (3.70 g, 14.8 mmol) in DMF (49.4 mL) under an atmosphere of nitrogen was added NaH (60% by weight in mineral oil, 546 mg, 13.6 mmol) and the suspension was stirred at 70° C. for 10 minutes. To this was added (1aS,1bR,5aS,6aS)-3-(4-Methoxyphenyl)hexahydrooxireno[4,5]cyclopenta[1,2-d][1,3]dioxine (2.82 g, 11.4 mmol) in DMF (35.3 mL) and the reaction was stirred at 110° C. for 2 hours. The reaction mixture was cooled, quenched with brine (30 mL), extracted with ethyl acetate (3×50 mL), dried (MgSO$_4$), filtered, and concentrated. The residue was purified by flash chromatography (30 to 100% EtOAc/hexanes) to afford the title compound (3.90 g, 69%).
LCMS: R.t 1.86 min ES+ 500 (ammonium acetate).

Step e: O-[(4aS,6R,7S,7aR)-6-{4-[(1S)-2,3-Dihydro-1H-inden-1-ylamino]-7H-pyrrolo[2,3-d]pyrimidin-7-yl}-2-(4-methoxyphenyl)hexahydrocyclopenta[d][1,3]dioxin-7-yl]O-phenyl thiocarbonate To a solution of (4aS,6R,7S,7aR)-6-{4-[(1S)-2,3-dihydro-1H-inden-1-ylamino]-7H-pyrrolo[2,3-d]pyrimidin-7-yl}-2-(4-methoxyphenyl)hexahydrocyclopenta[d][1,3]dioxin-7-ol (4.00 g, 8.02 mmol) in DCM (169 mL) under an atmosphere of Ar was added DMAP (2.94 g, 24.1 mmol) followed by phenyl chlorothionocarbonate (2.22 mL, 16.0 mmol). The mixture was stirred at room temperature for 1 hour. The solvent was concentrated and purified by flash chromatography (20 to 100% EtOAc/hexanes, column pre-treated with 1% Et$_3$N/hexanes) to afford the title compound (5.00 g, 99%).
LCMS: R.t 2.34 min ES+ 636 (ammonium acetate).

Step f: N-[(1S)-2,3-Dihydro-1H-inden-1-yl]-7-[(4aS,6R,7aS)-2-(4-methoxyphenyl)-hexahydrocyclopenta[d][1,3]dioxin-6-yl]-7H-pyrrolo[2,3-d]pyrimidin-4-amine To a solution of O-[(4aS,6R,7S,7aR)-6-{4-[(1S)-2,3-dihydro-1H-inden-1-ylamino]-7H-pyrrolo[2,3-d]pyrimidin-7-yl}-2-(4-methoxyphenyl)hexahydrocyclopenta[d][1,3]dioxin-7-yl]O-phenyl thiocarbonate (5.00 g, 7.88 mmol) in toluene (150. mL) under an atmosphere of nitrogen was added Bu₃SnH (4.24 mL, 15.8 mmol) followed by 2,2'-azo-bis-isobutyronitrile (259 mg, 1.58 mmol). The solution was heated to reflux for 30 minutes, the mixture was cooled, concentrated to 30 mL and the residue was purified by flash chromatography (30 to 100% EtOAc/hexanes) to afford the title compound (3.00 g, 79%).

LCMS: R.t 2.12 min ES+ 483 (ammonium acetate).

Step g: (1S,2S,4R)-4-{4-[(1S)-2,3-Dihydro-1H-inden-1-ylamino]-7H-pyrrolo[2,3-d]pyrimidin-7-yl}-2-(hydroxymethyl)cyclopentanol A solution of N-[(1S)-2,3-dihydro-1H-inden-1-yl]-7-[(4aS,6R,7aS)-2-(4-methoxyphenyl)hexahydrocyclopenta[d][1,3]dioxin-6-yl]-7H-pyrrolo[2,3-d]pyrimidin-4-amine (3.00 g, 5.90 mmol) in THF (11.6 mL), water (11.6 mL) and AcOH (34.9 mL, 614 mmol) was stirred at room temperature under an atmosphere of argon for 60 hours. The mixture was concentrated and the residue was purified via flash chromatography (0 to 10% MeOH/DCM) to afford the title compound (2.10 g, 98%).

LCMS: R.t 1.46 min ES+ 365 (ammonium acetate).

Step h: ((1S,2S,4R)-4-{4-[(1S)-2,3-Dihydro-1H-inden-1-ylamino]-7H-pyrrolo[2,3-d]pyrimidin-7-yl}-2-hydroxycyclopentyl)methyl sulfamate The title compound was prepared following the procedure described in Example 40 steps a-b and steps e-g using CH₃CN as the solvent in step f.

LCMS: R.t 1.54 min ES+ 444 (ammonium acetate).

¹H-NMR (400 MHz, CD₃OD): δ 8.16 (s, 1H), 7.26-7.12 (m, 5H), 6.63 (d, J=3.6 Hz, 1H), 5.85 (dd, J=7.6, 7.6 Hz, 1H), 5.46-5.40 (m, 1H), 4.50-4.47 (m, 1H), 4.37 (d, J=7.6, 9.6 Hz, 1H), 4.19 (dd, J=7.4, 9.6 Hz, 1H), 3.08-3.02 (m, 1H), 2.96-2.87 (m, 1H), 2.85-2.75 (m, 1H), 2.67-2.59 (m, 1H), 2.37-2.20 (m, 3H), 2.07-1.97 (m, 2H) ppm.

Example 77

[(1S,2S,4R)-2-Hydroxy-4-(4-{[(1R,2S)-2-methoxy-2,3-dihydro-1H-inden-1-yl]-amino}-7H-pyrrolo[2,3-d]pyrimidin-7-yl)cyclopentyl]methyl sulfamate The title compound was prepared following the procedures described in Example 76 steps a-g using (1R,2S)-2-methoxy-indan-1-amine (Maruyama, Y.; Hirabayashi, K.; Hori, K. PCT Int. Appl. WO03037862A1, 2003) in step c and Example 86 steps g-h.

LCMS: R.t. 1.46 min ES+ 474 (ammonium acetate).

¹H-NMR (400 MHz, CD₃OD): δ 8.20 (s, 1H), 7.27-7.14 (m, 5), 6.67 (d, J=3.6 Hz, 1H), 5.90 (d, J=5.2 Hz, 1H), 4.49 (t, J=3.5 Hz, 1H), 4.37 (dd, J=7.6, 9.7 Hz, 1H), 4.31-4.28 (m, 1H), 4.20 (dd, J=7.3, 9.7 Hz, 1H), 3.31-3.29 (m, 4H) 3.19-3.05 (m, 2H), 2.85-2.77 (m, 1H), 2.37-2.20 (m, 3H), 2.08-2.00 (m, 1H).

Example 78

[(1R,2R,3S,4R)-2,3-dihydroxy-4-(6-isobutyl-9H-purin-9-yl)cyclopentyl]methyl sulfamate (I-97)

Step a: [(3aR,4R,6R,6aS)-6-(6-chloro-9H-purin-9-yl)-2,2-dimethyltetrahydro-3aH-cyclopenta[d][1,3]dioxol-4-yl]methyl acetate To a solution of ((3aR,4R,6R,6aS)-[6-(6-chloro-purin-9-yl)-2,2-dimethyltetrahydro-cyclopenta[1,3]dioxol-4-yl]-methanol (2.3 g, 6.4 mmol) in DCM (20 mL) and pyridine (1.03 mL, 0.0127 mol) was added acetic anhydride (1.20 mL, 12.7 mmol) and N,N-dimethylaminopyridine (20 mg, 0.10 mmol). The reaction was stirred for 2 hours, diluted with DCM, and washed with water. The organic phase was concentrated and the residue was purified by flash chromatography (0 to 100% EtOAc/hexanes) to yield the product (1.83 g, 78%).

LCMS: R.t. 2.20 min ES+ 367 (formic acid).

Step b: [(3aR,4R,6R,6aS)-6-(6-isobutyl-9H-purin-9-yl)-2,2-dimethyltetrahydro-3aH-cyclopenta[d][1,3]dioxol-4-yl]methyl acetate To a solution of [(3aR,4R,6R,6aS)-6-(6-chloro-9H-purin-9-yl)-2,2-dimethyltetrahydro-3aH-cyclopenta[d][1,3]dioxol-4-yl]methyl acetate (250.0 mg, 0.68 mmol) in degassed THF (6 mL) under nitrogen was added Pd(PPh₃)₄ (44 mg, 0.038 mmol) followed by 0.5 M of isobutylzinc bromide in tetrahydrofuran (2.04 mL) dropwise over 15 min. The reaction was heated at 60° C. for 1 hour. The reaction was cooled then quenched with saturated aq NH₄Cl, extracted with EtOAc and the organic phase was washed with saturated aq EDTA.Na₂ solution then water. The organic phase was concentrated and the residue purified by flash chromatography (0 to 100% EtOAc/DCM) to provide the title compound (120 mg, 45%).

LCMS: R.t. 1.60 min ES+ 389 (formic acid).

Step c: [(1R,2R,3S,4R)-2,3-dihydroxy-4-(6-isobutyl-9H-purin-9-yl)cyclopentyl]methyl sulfamate (I-97)

The title compound was prepared following the procedure described in Example 67, steps d-f.

LCMS: R.t. 1.08 min ES+ 386 (formic acid).

¹H-NMR (400 MHz, d₆-DMSO): δ 8.87 (s, 1H); 8.66 (s, 1H); 7.52 (bs, 2H); 4.86 (dd, J=9.3, 18.1 Hz, 1H); 4.41 (dd, J=5.3, 9.0 Hz, 1H); 4.17 (dd, J=6.8, 9.8 Hz, 1H,); 4.08 (dd, J=6.3, 9.8 Hz, 1H); 3.88 (dd, J=2.8, 5.2 Hz, 1H,); 2.98 (d, J=7.2 Hz, 1H); 2.40-2.27 (m, 3H); 1.87-1.78 (m, 1H); 0.92 (d, J=6.7 Hz, 6H).

Example 79

[(1R,2R,3S,4R)-2,3-dihydroxy-4-(6-propyl-9H-purin-9-yl)cyclopentyl]methyl sulfamate (I-96)

The title compound was prepared following the procedure described in Example 78, steps b-c using n-propylzincbromide in step b.

LCMS: R.t. 0.98 min ES+ 372 (formic acid).

¹H-NMR (300 MHz, d₆-DMSO): δ 8.85 (s, 1H); 8.66 (s, 1H); 7.52 (bs, 2H); 4.86 (dd, J=9.3, 18.1 Hz, 1H); 4.41 (dd, J=5.3, 9.0 Hz, 1H); 4.17 (dd, J=6.8, 9.8 Hz, 1H); 4.08 (dd, J=6.3, 9.8 Hz, 1H); 3.88 (dd, J=2.7, 5.2 Hz, 1H); 3.09-3.05 (m, 2H); 2.40-2.25 (m, 2H); 1.90.1.79 (m, 3H); 0.93 (t, J=7.4 Hz, 3H).

Example 80

{(1R,2R,3S,4R)-2,3-dihydroxy-4-[6-(2-phenyl-ethyl)-9H-purin-9-yl]-cyclopentyl}methyl sulfamate (I-79)

The title compound was prepared following the procedure described in Example 78, steps b-c using phenethylzincbromide in step b.

LCMS: R.t. 1.26 min ES+ 434 (formic acid).

$^1$H-NMR (400 MHz, d$_6$-DMSO): δ 8.85 (s, 1H); 8.65 (s, 1H); 7.52 (bs, 2H); 7.30-7.24 (m, 4H); 7.19-7.13 (m, 1H); 4.86 (dd, J=9.3, 18.0 Hz, 1H); 4.41 (dd, J=5.3, 9.0 Hz, 1H); 4.17 (dd, J=6.8, 9.8 Hz, 1H); 4.08 (dd, J=6.3, 9.8 Hz, 1H); 3.88 (dd, J=2.7, 5.2 Hz, 1H); 3.40 (dd, J=6.5, 9.3 Hz, 2H); 3.17 (dd, J=6.6, 9.3 Hz, 2H); 2.40-2.26 (m, 2H); 1.88-1.78 (m, 1H).

Example 81

{(1R,2R,3S,4R)-2,3-dihydroxy-4-[6-(phenylethynyl)-9H-purin-9-yl]cyclopentyl}methyl sulfamate (I-138)

Step a: [(3aR,4R,6R,6aS)-6-(6-iodo-9H-purin-9-yl)-2,2-dimethyltetrahydro-3aH-cyclopenta[d][1,3]dioxol-4-yl]methyl acetate To a solution of [(3aR,4R,6R,6aS)-6-(6-chloro-9H-purin-9-yl)-2,2-dimethyltetrahydro-3aH-cyclopenta[d][1,3]dioxol-4-yl]methyl acetate (185 mg, 0.45 mmol) in 2-butanone (8 mL) at 0° C. was added NaI (1.36 g, 9.08 mmol) followed by trifluoroacetic acid (174.8 μL, 2.27 mmol). The reaction was stirred for 3 hours at 0° C., quenched with saturated aq NaHCO$_3$ and extracted with DCM. The organic phase was concentrated and the residue was purified by flash chromatography (0 to 100% EtOAc/DCM) to obtain the title compound (140 mg, 67%).

LCMS: R.t. 1.51 min ES+ 459 (formic acid).

Step b: {(3aR,4R,6R,6aS)-2,2-dimethyl-6-[6-(phenylethynyl)-9H-purin-9-yl]tetrahydro-3aH-cyclopenta[d][1,3]dioxol-4-yl}methanol A solution of [(3aR,4R,6R,6aS)-6-(6-iodo-9H-purin-9-yl)-2,2-dimethyltetrahydro-3aH-cyclopenta[d][1,3]dioxol-4-yl]methyl acetate (140.0 mg, 0.31 mmol), Pd(PPh$_3$)$_2$Cl$_2$ (25 mg, 0.036 mmol), DIPEA (140 μL, 0.80 mmol), CuI (20 mg, 0.1 mmol) and phenylacetylene (170 μL, 1.5 mmol) in DMF (5.0 mL) under an atmosphere of nitrogen was stirred at room temperature for 20 minutes. The reaction was concentrated and the residue taken up in DCM (50 mL). This was washed with saturated aq EDTA.Na$_2$ (2×10 mL) then water (10 mL). The organics were concentrated to provide a black gum. This crude product was dissolved in DCM (5 mL) and 7.0 M of ammonia in methanol (5.0 mL) was added. This was stirred at room temperature for 2 hours. The reaction was concentrated and the residue was purified by flash chromatography (0 to 100% EtOAc/DCM) to provide the title compound (75 mg, 63%).

LCMS: R.t. 1.51 min ES+ 391 (formic acid).

Step c: {(1R,2R,3S,4R)-2,3-dihydroxy-4-[6-(phenylethynyl)-9H-purin-9-yl]cyclopentyl}methyl sulfamate (I-138)

The title compound was prepared following the procedure described in Example 67, steps e-f.

LCMS: R.t. 1.30 min ES+ 430 (formic acid).

$^1$H-NMR (300 MHz, CD$_3$OD): δ 8.87 (s, 1H); 8.64 (s, 1H); 7.78-7.73 (m, 2H); 7.50-7.41 (m, 3H); 4.98 (dd, J=9.3, 17.9 Hz, 1H); 4.61 (dd, J=5.5, 8.8 Hz, 1H); 4.27 (dd, J=2.2, 5.7 Hz, 1H); 4.11 (dd, J=2.9, 5.4 Hz, 1H); 2.57-2.42 (m, 2H); 2.18-2.06 (m, 1H); 1.27-1.24 (m, 1H).

Example 82

N-[((1R,2R,3S,4R)-4-{6-[(1S)-2,3-dihydro-1H-inden-1-ylamino]-9H-purin-9-yl}-2,3-dihydroxycyclopentyl)methyl]sulfamide (I-87)

Step a: tert-Butyl(aminosulfonyl){[(3aR,4R,6R,6aS)-6-(6-chloro-9H-purin-9-yl)-2,2-dimethyltetrahydro-3aH-cyclopenta[d][1,3]dioxol-4-yl]methyl}carbamate To a solution of ((3aR,4R,6R,6aS)-[6-(6-chloro-purin-9-yl)-2,2-dimethyltetrahydro-cyclopenta[1,3]dioxol-4-yl]-methanol (Yang, M.; Wei, Y.; Schneller, S. W. *J. Org. Chem.* 2004, 69, 3993-3996) (250.0 mg, 0.77 mmol), N-Boc-sulfonamide (226.6 mg, 1.16 mmol) and triphenylphosphine (242.3 mg, 0.92 mol) in EtOAc (8 mL) was added diisopropyl azodicarboxylate (227.3 μL, 1.16 mmol) dropwise as a solution in EtOAc (1 mL). The reaction was stirred at r.t. overnight, quenched with water and extracted with EtOAc. The organics were concentrated and the residue purified by flash chromatography (0 to 100% EtOAc/DCM) to obtain the product as an inseparable mixture with triphenylphosphine oxide. The material was carried on as such.

LCMS: R.t. 2.49 min ES+ 503 (formic acid).

Step b: N-[((1R,2R,3S,4R)-4-{6-[(1S)-2,3-dihydro-1H-inden-1-ylamino]-9H-purin-9-yl}-2,3-dihydroxycyclopentyl)methyl]sulfamide (I-87)

To the mixture obtained in step a was added trifluoroacetic acid in DCM (3 M, 50 mL). The resulting solution was stirred for 30 minutes then evaporated. This crude material was combined with (S)-(+)-1-aminoindan (197.6 μL, 1.54 mmol) and Et$_3$N (214.6 μL, 1.54 mmol) and ethanol (5 mL). The mixture was heated to reflux for 4 hours, then cooled and concentrated. The residue was dissolved in TFA/water (9:1, 5 mL), stirred for 10 minutes, and concentrated. The residue was purified by flash chromatography (0 to 10% MeOH/EtOAc) and prep HPLC to obtain the title compound (49 mg, 13% from step a)

LCMS: R.t. 1.26 min ES+ 460 (formic acid).

$^1$H-NMR (300 MHz, d$_6$-DMSO): δ 8.21 (bs, 1H); 8.15 (s, 1H); 7.28-7.05 (m, 4H); 5.74 (bs, 1H); 4.67 (dd, J=9.1, 18.0 Hz, 1H); 4.34 (dd, J=5.5, 8.7 Hz, 1H); 3.83 (dd, J=3.2, 5.2 Hz, 1H); 3.12-2.91 (m, 3H); 2.88-2.75 (m, 1H); 2.32 (td, J=8.8, 12.9 Hz, 1H); 2.18-2.06 (m, 1H); 2.02-1.86 (m, 1H); 1.70 (dd, J=10.4, 20.9 Hz, 1H).

Example 83

((1R,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I-141)

Step a: (1S,2R,4R)-4-{[6-Chloro-5-(2,2-diethoxyethyl)pyrimidin-4-yl]amino}-2-(hydroxymethyl)cyclopentanol A solution of (1S,2R,4R)-4-amino-2-(hydroxymethyl)cyclopentanol (0.485 g, 3.69 mmol) (Ho, J. Z.; Mohareb, R. M.; Anh, J. H.; Sim, T. B.; Rapoport, H. *J. Org. Chem.* 2003, 68, 109-114), 4,6-dichloro-5-(2,2-diethoxyethyl)pyrimidine (0.392 g, 1.48 mmol) (Montgomery, J. A.; Hewson, K. *J. Med. Chem.* 1967, 10, 665-667) and triethylamine (0.30 mL, 2.22 mmol) in butanol (4 mL) was microwave irradiated at 150° C.

for 450 seconds. The solution was concentrated and purified by flash chromatography (100% EtOAc) to give the title compound (0.454 g, 85%).

LCMS: R.t. 1.28 min ES+ 360 (formic acid).

Step b: (1S,2R,4R)-4-(4-Chloro-7H-pyrrolo[2,3-d]pyrimidin-7-yl)-2-(hydroxyethyl)cyclopentanol To a solution of (1S,2R,4R)-4-{[6-chloro-5-(2,2-diethoxyethyl)pyrimidin-4-yl]amino}-2-(hydroxymethyl)cyclopentanol (0.454 g, 1.26 mmol) in dioxane (9 mL) was added 1 N aq HCl (1.8 mL) and the reaction was stirred for 2 days. The reaction was neutralized to pH ~7 with aq NH$_4$OH then concentrated. The desired product was triturated with ethanol to give a white solid (0.339 g, 100%).

LCMS: R.t. 1.16 min ES+ 268 (formic acid).

Step c: ((1R,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I-141)

The title compound was prepared following the procedure described in Example 40, steps a-b and d-g, using (S)-(+)-1-aminoindane in step d.

LCMS: R.t. 1.12 min ES+ 444 (formic acid).
$^1$H-NMR (400 MHz, CD$_3$OD): δ 8.13 (d, J=2.3 Hz, 1H); 7.24-7.06 (m, 5H); 6.58 (t, J=3.6 Hz, 1H); 5.81 (t, J=7.7 Hz, 1H); 5.28 (m, 1H); 4.30-4.16 (m, 2H); 3.72-3.58 (m, 1H); 3.06-2.95 (m, 1H); 2.93-2.81 (m, 1H); 2.64-2.53 (m, 1H); 2.51-2.06 (m, 4H); 2.03-1.91 (m, 1H); 1.83-1.66 (m, 1H).

Example 84

((1R,2S,4R)-4-{6-[(1S)-2,3-dihydro-1H-inden-1-ylamino]-9H-purin-9-yl}-2-hydroxycyclopentyl)methyl sulfamate (I-127)

Step a: (6aR,8R,9S,9aR)-8-(6-chloro-9H-purin-9-yl)-2,2,4,4-tetraisopropylhexahydrocyclopenta[f][1,3,5,2,4]trioxadisilocin-9-ol To a solution of (1R,2S,3R,5R)-3-(6-chloro-purin-9-yl)-5-hydroxymethylcyclopentane-1,2-diol (Shealy, Y. F.; Clayton, J. D. *J. Am. Chem. Soc.* 1969, 91, 3075-308) (0.44 g, 1.55 mmol) and 1,8-diazabicyclo[5.4.0]undec-7-ene (0.461 mL, 3.1 mmol) in AcCN (15 mL) was added 1,3-dichloro-1,1,3,3-tetraisopropyldisiloxane (0.581 mL, 1.8 mmol). The reaction mixture was stirred at room temperature for 14 h then concentrated. The residue was purified by flash chromatography (0 to 50% EtOAc/hexanes) to afford the title compound (0.545 g, 67%)

LCMS: R.t. 2.80 min ES+ 527 (formic acid)

Step b: O-[(6aR,8R,9S,9aR)-8-(6-chloro-9H-purin-9-yl)-2,2,4,4-tetraisopropylhexahydrocyclopenta[f][1,3,5,2,4]trioxadisilocin-9-yl] O-phenyl thiocarbonate To a solution of (6aR,8R,9S,9aR)-8-(6-chloro-9H-purin-9-yl)-2,2,4,4-tetraisopropylhexahydrocyclopenta[f][1,3,5,2,4]trioxadisilocin-9-ol (0.762 g, 1.44 mmol) and N,N-dimethylaminopyridine (0.529 g, 4.34 mmol) in DCM (20 mL) was added phenyl chlorothionocarbonate (0.440 mL, 3.2 mmol) and the solution was stirred for 1 h. The reaction mixture was concentrated and the residue purified by flash chromatography (0 to 50% EtOAc/hexanes) to afford the title compound (0.851 g, 88%).

LCMS: R.t. 3.10 min ES+ 663 (formic acid).

Step c: 6-chloro-9-[(6aR,8R,9aS)-2,2,4,4tetraisopropylhexahydrocyclopenta[f][1,3,5,2,4]-trioxadisilocin-8-yl]-9H-purine To a solution of O-[(6aR,8R,9S,9aR)-8-(6-chloro-9H-purin-9-yl)-2,2,4,4-tetraisopropylhexahydrocyclopenta[f][1,3,5,2,4]trioxadisilocin-9-yl] O-phenyl thiocarbonate (0.851 g, 1.28 mol) in toluene (20 mL) was added tri-n-butyltin hydride (0.680 mL, 2.53 mmol) and 2,2'-azo-bis-isobutyronitrile (0.075 g, 0.46 mmol). This solution was refluxed for 1 h. The reaction mixture was concentrated and purified by flash chromatography (0 to 50% EtOAc/hexanes) to afford the title compound (0.14 g, 74%).

LCMS: R.t. 2.92 min ES+ 512 (formic acid).

Step d: (1S,2R,4R)-4-(6-chloro-9H-purin-9-yl)-2-(hydroxymethyl)cyclopentanol

To a solution of 6-chloro-9-[(6aR,8R,9aS)-2,2,4,4-tetraisopropylhexahydrocyclopenta[f][1,3,5,2,4]trioxadisilocin-8-yl]-9H-purine (0.518 g, 1.0 mmol) in THF/pyridine (5.2 mL, 1:1) was added hydrofluoric acid in pyridine (0.381 mL, 15.2 mmol). The reaction was stirred for 14 h then quenched with saturated aq NaHCO$_3$ and concentrated under reduced pressure. The residue was dissolved in 10% solution of MeOH/DCM, filtered, the organic layer was concentrated and the residue purified by flash chromatography (0 to 10% MeOH/DCM to afford the title compound (0.171 g, 63%).

LCMS: R.t. 0.87 min ES+ 269 (formic acid).

Step e: (1S,2R,4R)-2-({[tert-butyl(dimethyl)silyl]oxy}methyl)-4-(6-chloro-9H-purin-9-yl)-cyclopentanol To a solution of (1S,2R,4R)-4-(6-chloro-9H-purin-9-yl)-2-(hydroxymethyl)cyclopentanol (0.496 g, 0.0018 mol) in DMF (10 mL) was added tert-butyldimethylsilyl chloride (0.348 g, 0.0023 mol), N,N-dimethylaminopyridine (0.023 g, 0.00019 mol) and imidazole (0.276 g, 0.0041 mol). This solution was stirred for 1 h and then the reaction mixture was quenched with water and diluted with ethyl acetate. The organic layer was washed with water, concentrated and purified by flash chromatography (0 to 50% EtOAc/DCM) to afford the title compound (0.462 g, 65%).

LCMS: R.t. 1.99 min ES+ 384 (formic acid).

Step f: (1S,2R,4R)-2-({[tert-butyl(dimethyl)silyl]oxy}methyl)-4-{6-[(1S)-2,3-dihydro-1H-inden-1-ylamino]-9H-purin-9-yl}cyclopentanol A solution of (1S,2R,4R)-2-({[tert-butyl(dimethyl)silyl]oxy}methyl)-4-(6-chloro-9H-purin-9-yl)cyclopentanol (0.091 g, 0.24 mmol), triethylamine (0.1 mL, 0.72 mmol) and (S)-1-aminoindane (0.0662 g, 0.48 mmol) in ethanol (5 mL) was refluxed at 95° C. for 14 h and then concentrated under reduced pressure. The residue was purified by flash chromatography (0 to 60% EtOAc/DCM) to afford the title compound (0.09 g, 80%).

LCMS: R.t. 2.14 min ES+ 480 (formic acid).

Step g: ((1R,2S,4R)-4-{6-[(1S)-2,3-dihydro-1H-inden-1-ylamino]-9H-purin-9-yl}-2-hydroxycyclopentyl)methyl sulfamate (I-127)

The title compound was prepared following the procedure described in Example 40 steps b and e-g.

LCMS: R.t. 1.33 min ES+ 445 (formic acid).

$^1$H-NMR (300 MHz, CD$_3$OD): δ 8.30 (s, 1H), 8.17 (s, 1H), 7.29-7.14 (m, 4H), 5.94-5.82 (m, 1H), 5.24-5.09 (m, 1H), 4.39-4.21 (m, 3H), 3.12-3.02 (m, 1H), 2.98-2.87 (m, 1H), 2.72-2.56 (m, 2H), 2.53-2.35 (m, 2H), 2.31-2.22 (m, 1H), 2.07-1.97 (m, 2H).

Example 85

{(1R,2S,4R)-2-hydroxy-4-[6-(phenylethynyl)-9H-purin-9-yl]cyclopentyl}methyl sulfamate (I-109)

Step a: (1S,2R,4R)-2-({[tert-butyl(dimethyl)silyl]oxy}methyl)-4-[6-(phenylethynyl)-9H-purin-9-yl]cyclopentanol A solution of (1S,2R,4R)-2-({[tert-butyl(dimethyl)silyl]oxy}methyl)-4-(6-chloro-9H-purin-9-yl)cyclopentanol (0.1 g, 0.26 mmol), Pd(PPh$_3$)$_2$Cl$_2$ (0.006 g, 0.0089 mmol), CuI (0.004 g, 0.02 mmol) and triethylamine (0.145 mL, 1.04 mmol) in DMF (5 mL) was heated at 70° C. under argon for 1 h. Phenylacetylene (0.057 mL, 0.52 mmol) was added, the reaction mixture was stirred for 3 h, and the reaction was concentrated. The residue was dissolved in DCM and washed with saturated aq NaHCO$_3$ and saturated aq EDTA.Na$_2$ acid. The organic layer was dried (Na$_2$SO$_4$), concentrated and purified by flash chromatography (0 to 50% EtOAc/DCM) to afford the title compound (0.096 g, 82%).

LCMS: R.t. 2.17 min ES+ 449 (formic acid).

Step b: {(1R,2S,4R)-2-hydroxy-4-[6-(phenylethynyl)-9H-purin-9-yl]cyclopentyl}methyl sulfamate (I-109)

The title compound was prepared following the procedure described in Example 40 steps b and e-g.

LCMS: R.t. 1.35 min ES+ 414 (formic acid).

$^1$H-NMR (400 MHz, CD$_3$OD): δ 8.91 (s, 1H), 8.68 (s, 1H), 7.79 (dd, J=7.6, 1.8 Hz, 2H), 7.55-7.43 (m, 3H), 5.39-5.26 (m, 1H), 4.38-4.25 (m, 2H), 2.72-2.53 (m, 3H), 2.47-2.29 (m, 3H).

Example 86

[(2R,3S,5R)-5-(5-ethyl-7H-pyrrolo[2,3-d]pyrimidine-7-yl)-3-hydroxytetrahydrofuran-2-yl]methylsulfamate (I-133)

Step a: tert-Butyl(chlorosulfonyl)carbamate

Reference: F. Hirayama et al., *Biorg. Med. Chem.*, 2002, 10, 1509-1523.

To a stirred solution of chlorosulfonyl isocyanate (3.20 mL, 36.0 mmol) in benzene (15.0 mL) in a water bath at rt was added tert-butyl alcohol (3.50 mL, 36.2 mmol) dropwise via syringe under an atmosphere of nitrogen. After 2 h, the mixture was diluted with hexanes (30.0 mL) and the resulting white precipitate was filtered and washed with hexanes (3×20 mL). The collected solid was dried in a vacuum desiccator under house vacuum for 10 min to afford the title compound as a white solid (5.08 g, 65%). The product was stored under nitrogen in a freezer.

LCMS: R.t. 0.94 min (ES+) 215 (ammonium acetate).

Step b: 5-iodo-7H-pryrrolo[2,3-d]pyrimidine 7H-pyrrolo[2,3-d]pyrimidine (2.17 g, 18.2 mmol) (P. Reigan et al. *Bioorg. Med. Chem. Lett.* 2004, 14, 5247) and N-iodosuccinimide (4.30 g, 19.1 mmol) were stirred in acetonitrile (30 mL) under an atmosphere of argon for 2 hours. The precipitate was collected to give the title compound as an orange solid (4.33 g, 94%).

LCMS: R.t. 0.80 min ES+ 246 (formic acid)

Step c: 5-[(trimethylsilyl)ethynyl]-7H-pyrrolo[2,3-d]pyrimidine 5-iodo-7H-pryrrolo[2,3-d]pyrimidine (0.111 g, 0.453 mmol), CuI (0.00431 g, 0.0226 mmol), Pd(PPh$_3$)$_2$Cl$_2$ (0.0318 g, 0.0453 mmol), DIPEA (0.158 mL, 0.906 mmol) and (trimethylsilyl)acetylene (0.256 mL, 1.81 mmol) were stirred in DMF (5 mL) under an atmosphere of argon for 3 hours. The mixture was diluted with EtOAc and washed with water (3×) and brine (1×), dried (Na$_2$SO$_4$), filtered and concentrated. The residue was purified by flash chromatography (50 to 100% EtOAc/hexanes) to give the title compound as a brown solid (0.0458 g, 47%).

LCMS: R.t. 1.51 min ES+ 216 (formic acid).

Step d: 5-ethynyl-7H-pyrrolo[2,3-d]pyrimidine

5-[(trimethylsilyl)ethynyl]-7H-pyrrolo[2,3-d]pyrimidine (0.320 g, 1.49 mmol) and potassium carbonate (0.513 g, 3.72 mmol) were stirred in MeOH (6 mL) for 18 hours. The mixture was diluted with EtOAc, washed with saturated ammonium chloride, brine, dried over anhydrous magnesium sulfate, filtered and concentrated to give the title compound as an orange solid (0.185 g, 87%).

LCMS: R.t. 0.70 min (ES+) 144 (formic acid)

Step e: 5-ethyl-7H-pyrrolo[2,3-d]pyrimidine 5-ethynyl-7H-pyrrolo[2,3-d]pyrimidine (0.293 g, 2.05 mmol) and palladium hydroxide [20 weight percent (dry basis)] on carbon [moist] (0.0644 g, 0.0458 mmol) were stirred in ethanol (10 mL) under an atmosphere of hydrogen for 18 hours. The mixture was filtered through a pad of celite and concentrated to give the title compound as an orange solid (0.260 g, 86%).

LCMS: R.t. 0.35 min (ES+) 148 (formic acid).

Step f: (2R,3S,5R)-5-(5-ethyl-7H-pyrrolo[2,3-d]pyrimidin-7-yl)-2-(hydroxymethyl)tetrahydrofuran-3-ol The title compound was prepared following the procedure described in Example 91, steps a-b using 5-ethynyl-7H-pyrrolo[2,3-d]pyrimidine.

LCMS: R.t. 0.62 min (ES+) 264 (formic acid).

Step g: tert-butyl({[(2R,3S,5R)-5-(5-ethyl-7H-pyrrolo[2,3-d]pyrimidin-7-yl)-3 hydroxytetrahydrofuran-2-yl]methoxy}sulfonyl)carbamate To a solution of (2R,3S,5R)-5-(5-ethyl-7H-pyrrolo[2,3-d]pyrimidin-7-yl)-2-(hydroxymethyl)tetrahydrofuran-3-ol (0.0560 g, 0.213 mmol) and 2,6-di-tert-butyl-4-methylpyridine in AcCN (4 mL) at 0° C. was added tert-butyl(chlorosulfonyl)carbamate (0.0573 g, 0.266 mmol), the solution was warmed to room temperature and stirred for 1 hour. The reaction was quenched with 7N ammonia in methanol (2 mL) and concentrated. The residue was purified by flash chromatography (0 to 10% MeOH/DCM) to give the title compound as a white solid (39 mg, 29%).

LCMS: R.t. 1.20 min (ES+) 443 (formic acid standard).

Step h: [(2R,3S,5R)-5-(5-ethyl-7H-pyrrolo[2,3-d] pyrimidine-7-yl)-3-hydroxytetrahydrofuran-2-yl] methylsulfamate (I-133)

A solution of tert-butyl({[(2R,3S,5R)-5-(5-ethyl-7H-pyrrolo[2,3-d]pyrimidin-7-yl)-3-hydroxytetrahydrofuran-2-yl] methoxy}sulfonyl)carbamate (39 mg, 0.617 mmol) in DCM (4 mL) and trifluoroacetic acid (1 mL) was stirred for 30 minutes. The reaction was concentrated to a yellow residue. The residue was purified by flash chromatography (0 to 10% MeOH/DCM) to give the title compound as a white solid (0.0203 g, 93%).

LCMS: R.t. 0.85 min ES+ 343 (formic acid).

$^1$H-NMR (400 MHz, CD$_3$OD): δ 8.94 (s, 1H); 8.75 (s, 1H); 7.63 (s, 1H); 6.81 (dd, J=6.2, 8.0 Hz, 1H); 4.62-4.57 (m, 1H); 4.31 (d, J=3.8 Hz, 2H); 4.19 (dd, J=3.6, 6.5 Hz, 1H); 2.82 (q, J=7.5 Hz, 2H); 2.72-2.61 (m, 1H); 2.42-2.33 (m, 1H); 1.36 (t, J=7.5 Hz, 3H).

Example 87

((2R,3S,4R,5R)-5-{6-[(3,5-Difluorophenyl)ethynyl]-9H-purin-9-yl}-3,4-dihydroxytetrahydrofuran-2-yl) methyl sulfamate (I-146)

The title compound was prepared following the procedure described in Example 67, steps c-f using 1-ethynyl-3,5-difluorobenzene in step c and DCM as the solvent in step e.

LCMS: R.t. 1.42 min ES+ 468 (formic acid).

$^1$H-NMR (300 MHz, d$_6$-DMSO+D$_2$O): δ 8.97 (s, 1H); 8.80 (s, 1H); 7.55-7.35 (m, 3H); 6.08 (d, J=5.1 Hz, 1H); 4.68 (t, J=5.1 Hz, 1H); 4.36-4.15 (m, 4H).

Example 88

((2R,3S,4R,5R)-5-{6-[(2,4-Difluorophenyl)ethynyl]-9H-purin-9-yl}-3,4-dihydroxytetrahydrofuran-2-yl) methyl sulfamate (I-110)

The title compound was prepared following the procedure described in Example 67, steps c-f using 1-ethynyl-2,4-difluorobenzene in step c and DCM as the solvent in step e.

LCMS: R.t. 1.38 min ES+ 468 (formic acid).

$^1$H-NMR (400 MHz, d$_6$-DMSO): δ 8.99 (s, 1H); 8.83 (s, 1H); 7.88 (dd, J=8.5 Hz, J=6.4 Hz, 1H); 7.60 (s, 2H); 7.55 (dt, J=9.6 Hz, J=2.5 Hz, 1H); 7.28 (dt, J=8.5 Hz, J=2.6 Hz, 1H); 6.10 (d, J=5.0 Hz, 1H); 5.70 (bs, 1H); 5.50 (bs, 1H); 4.69 (t, J=5.0 Hz, 1H); 4.35-4.19 (m, 4H).

Example 89

((2R,3S,4R,5R)-5-{6-[(3-Chlorophenyl)ethynyl]-9H-purin-9-yl}-3,4-dihydroxytetrahydrofuran-2-yl)methyl sulfamate (I-134)

The title compound was prepared following the procedure described in Example 67, steps c-f using 1-chloro-3-ethynylbenzene in step c and DCM as the solvent in step e.

LCMS: R.t. 1.01 min ES+ 466 (formic acid)

$^1$H-NMR (400 MHz, d$_6$-DMSO): δ 8.93 (s, 1H); 8.78 (s, 1H); 7.74 (t, J=1.7 Hz, 1H); 7.64 (d, J=7.7 Hz, 1H); 7.58 (dq, J=1.0, 1.1, 8.2 Hz, 1H); 7.54 (s, 2H); 7.50 (t, J=7.9 Hz, 1H); 6.04 (d, J=5.1 Hz, 1H); 5.65 (d, J=5.6 Hz, 1H); 5.44 (d, J=5.2 Hz, 1H); 4.63 (q, J=5.0 Hz, 1H); 4.30-4.13 (m, 4H).

Example 90

((2R,3S,4R,5R)-5-{6-[(3-Bromophenyl)ethynyl]-9H-purin-9-yl}-3,4-dihydroxytetrahydrofuran-2-yl)methyl sulfamate (I-103)

The title compound was prepared following the procedure described in Example 67, steps c-f using 1-bromo-3-ethynylbenzene in step c and DCM as the solvent in step e.

LCMS: R.t. 1.01 min ES+ 512 (formic acid)

$^1$H-NMR (400 MHz, d$_6$-DMSO): δ 8.99 (s, 1H); 8.84 (s, 1H); 7.92 (t, J=1.7 Hz, 1H); 7.77 (d, J=8.1 Hz, 1H); 7.74 (d, J=7.9 Hz, 1H); 7.60 (s, 2H); 7.49 (t, J=7.9 Hz, 1H); 6.10 (d, J=5.1 Hz, 1H); 5.70 (bs, 1H); 5.50 (bs, 1H); 4.69 (bs, 1H); 4.38-4.18 (m, 4H).

Example 91

[(2R,3S,5R)-3-hydroxy-5-(1H-pyrrolo[3,2-c]pyridin-1-yl)tetrahydrofuran-2-yl]-methyl sulfamate (I-142)

Step a: (2R,3S,5R)-2-{[(4-methylbenzoyl)oxy]methyl}-5-(1H-pyrrolo[3,2-c]pyridin-1-yl)tetrahydrofuran-3-yl 4-methylbenzoate To a solution of 5-azaindole (0.152 g, 1.29 mmol) in AcCN (8 mL) was added NaH (60% in oil, 0.034 g, 1.42 mmol). The reaction was stirred for 45 minutes at r.t. then 1-α-chloro-2-deoxy-3,5-bis(p-toluoyl)-α-D-ribofuranosyl chloride (0.500 g, 1.29 mmol) (Zhang, W.; Ramasamy, K. S.; Averett, D. R. *Nucleosides Nucleotides*, 1999, 18, 2357-2365) was added in three portions. The reaction was heated to 50° C. for 1.5 hours. The reaction mixture was filtered through a pad of celite with EtOAc, concentrated and the residue was purified by flash chromatography (20 to 100% EtOAc/hexanes) to yield the product (0.248 g, 41%).

LCMS: R.t. 2.09 min ES+ 471 (formic acid).

Step b: (2R,3S,5R)-2-(hydroxymethyl)-5-(1H-pyrrolo[3,2-c]pyridin-1-yl)tetrahydrofuran-3-ol To a solution of (2R,3S,5R)-2-{[(4-methylbenzoyl)oxy] methyl}-5-(1H-pyrrolo[3,2-c]pyridin-1-yl)tetrahydrofuran-3-yl 4-methylbenzoate (0.764 g, 1.62 mmol) in methanol (30 mL) was added amberlyst A-26 (—OH) resin (7 g) and the suspension was stirred at r.t. overnight. The mixture was filtered with MeOH and concentrated. The residue was purified by flash chromatography (0 to 10% MeOH/DCM) to yield the product (0.762 g, 93%).

LCMS: R.t. 0.28 min ES+ 235 (formic acid).

Step c: (2R,3S,5R)-5-(1H-pyrrolo[3,2-c]pyridin-1-yl)-2-{[(triisopropylsilyl)oxy] methyl}tetrahydrofuran-3-ol To a solution of (2R,3S,5R)-2-(hydroxymethyl)-5-(1H-pyrrolo[3,2-c]pyridin-1-yl)tetrahydrofuran-3-ol (0.348 g, 1.49 mmol) and imidazole (0.228 mg, 3.35 mmol) in DMF (3.0 mL) at 0° C. was added dropwise triisopropylsilyl chloride (0.29 mL, 2.24 mmol). The solution was diluted with water and brine and extracted with EtOAc (4×). The organic layer was concentrated and the residue was purified by flash chromatography (20 to 100% EtOAc/hexanes) to yield the product (0.443 g, 76%).

LCMS: R.t. 1.35 min ES+ 391 (formic acid).

Step d: (2R,3S,5R)-5-(1H-pyrrolo[3,2-c]pyridin-1-yl)-2-{[(triisopropylsilyl)oxy]methyl}tetrahydrofuran-3-yl acetate To a solution of (2R,3S,5R)-5-(1H-pyrrolo[3,2-c]pyridin-1-yl)-2-{[(triisopropylsilyl)oxy]methyl}tetrahydrofuran-3-ol (0.487 g, 1.25 mmol) and a catalytic amount of DMAP in pyridine (1.6 mL) at 0° C. was added acetic anhydride (0.130 mL, 1.38 mmol) dropwise. The reaction was stirred overnight, concentrated, dissolved in EtOAc, washed with 1 M aq HCl (1×), water (1×) and brine (1×). The combined organics were washed with water (2×), dried (Na$_2$SO$_4$), filtered, and concentrated to give the title compound (0.464 g, 95%) which was used without further purification.

LCMS: R.t. 1.49 min ES+ 433 (formic acid).

Step e: [(2R,3S,5R)-3-hydroxy-5-(1H-pyrrolo[3,2-c]pyridin-1-yl)tetrahydrofuran-2-yl]methyl sulfamate (I-142)

The title compound was prepared as described in example 40 steps e-g using (2R,3S,5R)-5-(1H-pyrrolo[3,2-c]pyridin-1-yl)-2-{[(triisopropylsilyl)oxy]methyl}tetrahydrofuran-3-yl acetate.

LCMS: R.t. 0.28 min ES+ 314 (ammonium acetate).

$^1$H-NMR (400 MHz, CD$_3$OD): δ 8.77 (s, 1H); 8.19 (d, J=6.0 Hz, 1H); 7.63 (d, J=3.5 Hz, 1H); 7.61 (d, J=6.0 Hz, 1H); 6.73 (d, J=3.5 Hz, 1H); 6.51 (dd, J=5.9 Hz, 8.1 Hz, 1H); 4.58-4.55 (m, 1H); 4.27 (d, J=3.8 Hz, 2H); 4.19 (dd, J=3.6, 6.6 Hz, 1H); 2.65-2.58 (m, 1H); 2.42-2.37 (m, 1H).

Example 92

[(2R,3S,5R)-3-Hydroxy-5-(4-methoxy-7H-pyrrolo[2,3-d]pyrimidin-7-yl)tetrahydrofuran-2-yl]methyl sulfamate (I-144)

Step a: (2R,3S,5R)-5-(4-chloro-7H-pyrrolo[2,3-d]pyrimidin-7-yl)-2-{[(4-methylbenzoyl)oxy]methyl}tetrahydrofuran-3-yl 4-methylbenzoate The title compound was prepared as described in Example 91 step a using 4-chloropyrrolo[2,3-d]pyrimidine (0.395 g, 2.57 mmol) and purified by flash chromatography (0 to 20% EtOAc/hexanes) (1.07 g, 82%)

LCMS: R.t. 2.41 min ES+ 506 (formic acid).

Step b (2R,3S,5R)-2-(hydroxymethyl)-5-(4-methoxy-7H-pyrrolo[2,3-d]pyrimidin-7-yl)-tetrahydrofuran-3-ol The title compound was prepared as described in Example 91 step b using (2R,3S,5R)-5-(4-chloro-7H-pyrrolo[2,3-d]pyrimidin-7-yl)-2-{[(4-methylbenzoyl)oxy]methyl}tetrahydrofuran-3-yl 4-methylbenzoate (0.400 g, 0.791 mmol) to yield the product as a white solid (0.210 g, 100%).

LCMS: R.t. 1.08 min ES+ 266 (formic acid).

Step c: [(2R,3S,5R)-3-Hydroxy-5-(4-methoxy-7H-pyrrolo[2,3-d]pyrimidin-7-yl)-tetrahydrofuran-2-yl]methyl sulfamate (I-144)

The title compound was prepared as described in Example 91 steps c-e using (2R,3S,5R)-2-(hydroxymethyl)-5-(4-methoxy-7H-pyrrolo[2,3-d]pyrimidin-7-yl)tetrahydrofuran-3-ol.

LCMS: R.t. 1.15 min ES+ 345 (formic acid).

$^1$H-NMR (300 MHz, d$_6$-DMSO): δ 8.44 (s, 1H); 7.58 (bs, 2H); 6.66 (dd, J=6.6 Hz, J=6.7 Hz, 1H); 6.60 (d, J=3.7 Hz, 1H); 5.54 (d, J=4.3 Hz, 1H); 4.45-4.35 (m, 1H); 4.20 (dd, J=4.3 Hz, J=4.1 Hz, 1H); 4.10 (dd, J=5.6 Hz, J=3.5 Hz, 1H); 4.04 (s, 3H); 2.66-2.54 (m, 1H); 2.34-2.23 (m, 2H).

Example 93

((2R,3S,5R)-5-{4-[(1S)-2,3-dihydro-1H-inden-1-ylamino]-7H-pyrrolo[2,3-d]pyrimidin-7-yl}-3-hydroxytetrahydrofuran-2-yl)methyl sulfamate (I-136)

Step a: (2R,3S,5R)-5-{4-[(1S)-2,3-dihydro-1H-inden-1-ylamino]-7H-pyrrolo[2,3-d]pyrimidin-7-yl}-2-{[(4-methylbenzoyl)oxy]methyl}tetrahydrofuran-3-yl 4-methylbenzoate A solution of (2R,3S,5R)-5-(4-chloro-7H-pyrrolo[2,3-d]pyrimidin-7-yl)-2-{[(4-methylbenzoyl)oxy]methyl}tetrahydrofuran-3-yl 4-methylbenzoate (0.355 g, 0.702 mmol) in n-butanol (1 mL), (S)-(+)-1-aminoindan (0.23 mL, 1.77 mmol) and DIPEA (0.4 mL, 2.36 mmol) was microwave irradiated at 190° C. for 1200 seconds. The solution was concentrated and the residue was purified by flash chromatography (0 to 20% EtOAc/hexanes) to yield the product as a pale yellow foam (0.272 g, 64%).

LCMS: R.t. 2.04 min ES+ 603 (formic acid).

Step b: ((2R,3S,5R)-5-{4-[(1S)-2,3-dihydro-1H-inden-1-ylamino]-7H-pyrrolo[2,3-d]pyrimidin-7-yl}-3-hydroxytetrahydrofuran-2-yl)methyl sulfamate (I-136)

The title compound was prepared as described in Example 91 steps b-e using (2R,3S,5R)-5-{4-[(1S)-2,3-dihydro-1H-inden-1-ylamino]-7H-pyrrolo[2,3-d]pyrimidin-7-yl}-2-{[(4-methylbenzoyl)oxy]methyl}tetrahydrofuran-3-yl 4-methylbenzoate.

LCMS: R.t. 1.16 min ES+ 446 (formic acid).

$^1$H-NMR (300 MHz, d$_6$-DMSO): δ 8.20 (s, 1H); 7.85 (d, J=8.73 Hz, 1H); 7.59-7.35 (m, 4H); 6.71 (d, J=3.5 Hz, 1H); 6.60 (dd, J=6.4 Hz, 7.0 Hz, 1H); 5.98-5.85 (m, 1H); 5.51 (d, J=4.2 Hz, 1H); 4.44-4.33 (m, 1H); 4.25-3.98 (m, 3H); 3.09-2.80 (m, 2H); 2.46-2.37 (m, 1H); 2.32-2.17 (m, 1H); 2.06-1.88 (m, 1H).

Example 94

((2R,3S,4R,5R)-5-{6-[(anilinocarbonyl)amino]-9H-purin-9-yl}-3,4-dihydroxytetrahydrofuran-2-yl)methyl sulfamate (I-108)

Step a: ((3aR,4R,6R,6aR)-6-{6-[(anilinocarbonyl)amino]-9H-purin-9-yl}-2,2-dimethyltetrahydrofuro[3,4-d][1,3]dioxol-4-yl)methyl acetate To a solution of [(3aR,4R,6R,6aR)-6-(6-amino-9H-purin-9-yl)-2,2-dimethyltetrahydrofuro[3,4-d][1,3]dioxol-4-yl]

methyl acetate (0.200 g, 0.572 mmol) in AcCN (3 mL) was added phenylisocyanate (0.068 g, 0.572 mmol) dropwise. The white mixture was stirred for two hours at ambient temperature, overnight at 50° C. and then concentrated to give the title compound (0.268 g, 100%).

LCMS: R.t. 1.86 min ES+ 469 (formic acid).

Step b: ((2R,3S,4R,5R)-5-{6-[(anilinocarbonyl) amino]-9H-purin-9-yl}-3,4-dihydroxytetrahydrofuran-2-yl)methyl sulfamate (I-108)

The title compound was prepared following the procedure described in Example 67, steps d-f using ((3aR,4R,6R,6aR)-6-{6-[(anilinocarbonyl)amino]-9H-purin-9-yl}-2,2-dimethyltetrahydrofuro[3,4-d][1,3]dioxol-4-yl)methyl acetate.

LCMS: R.t. 1.34 min ES+ 466 (formic acid).

$^1$H-NMR (400 MHz, d$_6$-DMSO): δ 11.76 (s, 1H); 10.22 (s, 1H); 7.64 (bs, 1H); 7.62 (bs, 2H); 7.36 (dd, J=7.7 Hz, J=8.0 Hz, 2H); 7.09 (t, J=7.4 Hz, 1H); 6.05 (d, J=5.2 Hz, 1H); 4.66 (t, J=5.2 Hz, 1H); 4.36-4.16 (m, 4H).

Example 95

[(2R,3S,5R)-3-hydroxy-5-(7H-pyrrolo[2,3-d]pyrimidin-7-yl)tetrahydrofuran-2-yl]methyl sulfamate (I-118)

Step a: (2R,3S,5R)-5-(4-chloro-7H-pyrrolo[2,3-d]pyrimidin-7-yl)-2-{[(4-methylbenzoyl)oxy]methyl}tetrahydrofuran-3-yl 4-methylbenzoate The title compound was prepared as described for example 91 step a using 4-chloropyrrolo[2,3-d]pyrimidine.

LCMS: R.t. 2.43 min ES+ 506 (formic acid).

Step b: (2R,3S,5R)-2-{[(4-methylbenzoyl)oxy]methyl}-5-(7H-pyrrolo[2,3-d]pyrimidin-7-yl)tetrahydrofuran-3-yl 4-methylbenzoate A suspension of (2R,3S,5R)-5-(4-chloro-7H-pyrrolo[2,3-d]pyrimidin-7-yl)-2-{[(4-methylbenzoyl)oxy]methyl}tetrahydrofuran-3-yl 4-methylbenzoate (480 mg, 0.95 mmol), NaHCO$_3$ (96 mg, 1.14 mmol) and 54 mg wet Pd(OH)$_2$/C (20% Pd dry weight) in ethanol/EtOAc (6 mL, 5:1) was stirred under an atmosphere of hydrogen for 26 hours. The suspension was filtered through celite with methanol/EtOAc, concentrated, and the crude residue (450 mg, >99%) was used without further purification.

LCMS: R.t. 2.20 min ES+ 472 (formic acid).

Step c: [(2R,3S,5R)-3-hydroxy-5-(7H-pyrrolo[2,3-d]pyrimidin-7-yl)tetrahydrofuran-2-yl]-methyl sulfamate (I-118)

The title compound was prepared as described for example 91 steps b-e using (2R,3S,5R)-2-{[(4-methylbenzoyl)oxy]methyl}-5-(7H-pyrrolo[2,3-d]pyrimidin-7-yl)-tetrahydrofuran-3-yl 4-methylbenzoate.

LCMS: R.t. 1.72 min ES+ 315 (formic acid).

$^1$H-NMR (400 MHz, d$_6$-DMSO): δ 9.02 (s, 1H); 8.80 (s, 1H); 7.77 (s, 1H); 7.58 (bs, 2H); 6.81-6.67 (m, 2H); 5.56 (s, 1H); 4.41 (s, 1H); 4.29-4.00 (m, 3H); 2.71-2.57 (m, 1H); 2.39-2.24 (m, 1H).

Example 96

[(2R,3S,5R)-3-hydroxy-5-(6-phenyl-9H-purin-9-yl) tetrahydrofuran-2-yl]-methyl sulfamate (I-93)

Step a: (2R,3S,5R)-5-(6-amino-9I-purin-9-yl)-2-({[tert-butyl(dimethyl)silyl]oxy}methyl)tetrahydrofuran-3-ol To a solution of dry (2R,3S,5R)-5-(6-amino-9H-purin-9-yl)-2-(hydroxymethyl)tetrahydrofuran-3-ol (3.78 g, 15.04 mmol) and imidazole (2.46 g, 36.1 mmol) in DMF (20 mL) was added TBSCl (2.38 g, 15.80 mmol) and the solution was stirred at r.t. for 4 hours. The reaction mixture was diluted with water (100 mL), and extracted with EtOAc (3×100 mL). The combined organics were dried (Na$_2$SO$_4$) and concentrated. The product was isolated as a white solid (4.138 g, 75%) and was used without further purification.

LCMS: R.t. 1.31 min ES+ 366 (formic acid)

Step b: (2R,3S,5R)-5-(6-amino-9H-purin-9-yl)-2-({[tert-butyl(dimethyl)silyl]oxy}methyl)tetrahydrofuran-3-yl acetate To a solution of (2R,3S,5R)-5-(6-amino-9H-purin-9-yl)-2-({[tert-butyl(dimethyl)silyl]oxy}methyl)tetrahydrofuran-3-ol (4.14 g, 11.3 mmol) and catalytic amount of DMAP in pyridine (11.3 mL) at 0° C. was added slowly acetic anhydride (1.12 mL, 11.89 mmol). The solution was stirred while warming to r.t. for 5 hours. The reaction was quenched with 1 N HCl solution (70 mL) and extracted with EtOAc (3×100 mL). The combined organics were washed with saturated aq CuSO$_4$ solution (50 mL) and dried (Na$_2$SO$_4$). A white solid was isolated upon removing the solvent (4.143 g, 90%) and the crude material was used without further purification.

LCMS: R.t. 1.61 min ES+ 409 (formic acid)

Step c: (2R,3S,5R)-5-(6-bromo-9H-purin-9-yl)-2-({[tert-butyl(dimethyl)silyl]oxy}methyl)tetrahydrofuran-3-yl acetate To a solution of (2R,3S,5R)-5-(6-amino-9H-purin-9-yl)-2-({[tert-butyl-(dimethyl)silyl]oxy}methyl)tetrahydrofuran-3-yl acetate (2.00 g, 4.91 mmol) in CH$_2$Br$_2$ (98.2 mL) was added TMSBr (0.717 mL, 5.55 mmol) and t-butylnitrite (3.98 mL, 33.4 mmol). The reaction mixture was stirred at r.t. for 3 hours then slowly poured into 50 mL of a 1:1 mixture of saturated aq NaHCO$_3$:CH$_2$Cl$_2$. The organic layer was washed with water (50 mL), brine (50 mL), dried (Na$_2$SO$_4$) and concentrated. The crude product was purified by flash chromatography (0 to 30% EtOAc/hexanes) to obtain the title compound as a yellow oil (1.26 g, 55%).

LCMS: R.t. 2.16 min ES+ 473 (formic acid).

Step d: (2R,3S,5R)-2-({[tert-butyl(dimethyl)silyl]oxy}methyl)-5-(6-phenyl-9H-purin-9-yl)tetrahydrofuran-3-yl acetate A flame dried flask was charged with Pd(OAc)$_2$ (0.0185 g, 0.0823 mmol), 2-(dicyclohexylphosphino)biphenyl (0.0433 g, 0.123 mmol), phenyl boronic acid (0.151 g, 1.23 mmol), and K$_3$PO$_4$ under an atmosphere of argon. A solution of (2R,3S,5R)-5-(6-bromo-9H-purin-9-yl)-2-({[tert-butyl (dimethyl)silyl]oxy}methyl)tetrahydrofuran-3-yl acetate (0.388 g, 0.823 mmol) in dry dioxane (5.49 mL) was added to the mixture and the solution was stirred at 90° C. overnight.

The reaction mixture was filtered through celite with CH$_2$Cl$_2$, concentrated and purified by flash chromatography (10 to 30% EtOAc/hexanes) to afford the title compound as a clear oil (0.247 g, 64%).

LCMS: R.t. 2.39 min ES+ 469.5 (formic acid)

Step e: [(2R,3S,5R)-3-hydroxy-5-(6-phenyl-9H-purin-9-yl)tetrahydrofuran-2-yl]methyl sulfamate (I-93)

The title compound was prepared as described in Example 40 steps e-g.

LCMS: R.t. 1.31 min ES+ 392 (formic acid)

$^1$H-NMR (400 MHz, d$_6$-DMSO): δ 9.02 (s, 1H); 8.84-8.81 (m, 3H); 7.64-7.56 (m, 5H); 6.58 (t, J=6.8 Hz, 1H); 5.60 (bs, 1H); 4.54 (m, 1H); 4.31-4.27 (m, 1H); 4.22-4.18 (m, 1H); 4.15-4.12 (m, 1H); 2.90 (m, 1H); 2.45 (m, 1H).

Example 97

{(2R,3S,5R)-3-hydroxy-5-[6-(phenylethynyl)-9H-purin-9-yl]tetrahydrofuran-2-yl}methyl sulfamate (I-92)

Step a: (2R,3S,5R)-2-({[tert-butyl(dimethyl)silyl]oxy}methyl)-5-[6-(phenylethynyl)-9H-purin-9-yl]tetrahydrofuran-3-yl acetate To a solution of (2R,3S,5R)-5-(6-bromo-9H-purin-9-yl)-2-({[tert-butyl(dimethyl)silyl]oxy}methyl)tetrahydrofuran-3-yl acetate (1.26 g, 2.67 mmol), CuI (0.102 g, 0.534 mmol), and Pd(PPh$_3$)$_2$Cl$_2$ (0.187 g, 0.267 mmol) in DMF was added DIPEA (0.930 mL, 5.34 mmol) and phenylacetylene (1.17 mL, 10.69 mmol). The mixture was stirred at 75° C. for 1 hour then concentrated. The residue was dissolved in CH$_2$Cl$_2$ (70 mL) and washed with saturated aq EDTA.Na$_2$ (3×50 mL). The combined organics were dried (Na$_2$SO$_4$) and concentrated. The dark crude oil was purified by flash chromatography (40% EtOAc/hexanes) to afford the title compound (1.2 g, 91%).

LCMS: R.t. 2.37 min ES+ 493 (formic acid)

Step b: {(2R,3S,5R)-3-hydroxy-5-[6-(phenylethynyl)-9H-purin-9-yl]tetrahydrofuran-2-yl}-methyl sulfamate (I-92)

The title compound was prepared as described in Example 40 steps e-g.

(LCMS: R.t. 1.28 min ES+ 416 (formic acid)

$^1$H NMR (300 MHz, CD$_3$CN): δ 8.91 (s, 1H); 8.47 (s, 1H); 7.72 (m, 2H); 7.51 (m, 3H); 6.52 (t, J=6.5 Hz, 1H); 5.79 (bs, 2H); 4.63 (m, 1H); 4.39-4.28 (m, 2H); 4.21 (m, 1H); 2.92-2.83 (m, 1H); 2.56-2.47 (m, 1H).

Example 98

[(2R,3S,4R,5R)-3,4-dihydroxy-5-(6-{[2-(trifluoromethyl)phenyl]ethynyl}-9H-purin-9-yl)tetrahydrofuran-2-yl]methyl sulfamate (I-113)

Step a: [(3aR,4R,6R,6aR)-6-(6-iodo-9H-purin-9-yl)-2,2-dimethyltetrahydrofuro[3,4-d][1,3]dioxol-4-yl]methyl sulfamate To a solution of ((3aR,4R,6R,6aR)-6-(6-chloro-9H-purin-9-yl)-2,2-dimethyltetrahydrofuro[3,4-d][1,3]dioxol-4-yl)methyl sulfamate (645 mg, 1.59 mmol) in 2-butanone (30.0 mL) was added NaI (4.77 g, 31.79 mmol). The reaction was cooled to −10° C. and trifluoroacetic acid (612 µL, 7.94 mmol) was added. The reaction was stirred for 4.5 hours, quenched with saturated aq NaHCO$_3$ and extracted with DCM. The crude product was purified by flash chromatography (40% EtOAc/DCM) to isolate the title compound (0.642 g, 81%).

LCMS: R.t. 2.07 min ES+ 498 (formic acid)

Step b: [(3aR,4R,6R,6aR)-2,2-dimethyl-6-(6-{[2-(trifluoromethyl)phenyl]ethynyl}-9H-purin-9-yl)tetrahydrofuro[3,4-d][1,3]dioxol-4-yl]methyl sulfamate To a solution of [(3aR,4R,6R,6aR)-6-(6-iodo-9H-purin-9-yl)-2,2-dimethyltetrahydrofuro[3,4-d][1,3]dioxol-4-yl]methyl sulfamate (0.200 g, 0.402 mmol) in DMF (7 mL) was added DIPEA (0.176 mL, 1.01 mmol), 1-ethynyl-2-trifluoromethyl-benzene (0.224 mL, 1.61 mmol), CuI (0.0191 g, 0.101 mmol), and Pd(PPh$_3$)$_2$Cl$_2$ (0.0282 g, 0.0402 mmol). The mixture was stirred at r.t. for 50 min, diluted with DCM (25 mL) and washed with saturated aq EDTA.Na$_2$ (3×25 mL). The combined organics were washed with brine, dried over Na$_2$SO$_4$, filtered, and concentrated. The crude product was purified by flash chromatography (15 to 50% EtOAc/DCM) to isolate the title compound (0.185 g, 85%).

Step c: [(2R,3S,4R,5R)-3,4-dihydroxy-5-(6-{[2-(trifluoromethyl)phenyl]ethynyl}-9H-purin-9-yl)tetrahydrofuran-2-yl]methyl sulfamate (I-113)

[(3aR,4R,6R,6aR)-2,2-dimethyl-6-(6-{[2-(trifluoromethyl)phenyl]ethynyl}-9H-purin-9-yl)tetrahydrofuro[3,4-d][1,3]dioxol-4-yl]methyl sulfamate (0.185 g, 0.343 mmol) was stirred in 3 mL of 90% TFA/H$_2$O for 4 h at r.t. The solvent was removed and the crude product was purified by flash chromatography (1 to 10% MeOH/CH$_2$Cl$_2$) to isolate the title compound (0.0882 g, 52%).

LCMS: R.t. 1.46 min ES+ 500 (formic acid)

$^1$H-NMR (400 MHz, d$_6$-DMSO): δ 9.00 (s, 1H); 8.84 (s, 1H); 7.83-7.57 (m, 4H); 6.11 (d, J=5.0 Hz, 1H); 5.71 (bs, 1H); 5.50 (bs, 1H); 4.68 (m, 1H); 4.43-4.20 (m, 4H).

Example 99

((2R,3S,4R,5R)-5-{6-[(4-chlorophenyl)ethynyl]-9H-purin-9-yl}-3,4-dihydroxytetrahydrofuran-2-yl)methyl sulfamate (I-91)

The title compound was prepared as described in Example 98 steps a-c using 1-chloro-4-ethynylbenzene in step b.

LCMS: R.t. 1.46 min ES+ 466 (formic acid)

$^1$H-NMR (400 MHz, d$_6$-DMSO): δ 8.98 (s, 1H); 8.83 (s, 1H); 7.76-7.72 (m, 2H); 7.61-7.58 (m, 4H); 6.10 (d, J=5.3 Hz, 1H); 5.71 (d, J=5.8 Hz, 1H); 5.50 (d, J=5.5 Hz, 1H); 4.69 (q, J=5.0, 5.5 Hz, 1H); 4.34-4.20 (m, 4H).

Example 100

((2R,3S,4R,5R)-5-{6-[(2-bromophenyl)ethynyl]-9H-purin-9-yl}-3,4-dihydroxytetrahydrofuran-2-yl)methyl sulfamate (I-140)

The title compound was prepared as described in Example 98, steps a-c, using 1-bromo-2-ethynylbenzene in step b.
LCMS: R.t. 1.41 min ES+ 510 (formic acid)
$^1$H-NMR (400 MHz, CD$_3$OD): δ 8.14 (s, 1H); 7.94 (s, 1H); 7.06 (dd, J=7.5, 1.8 Hz, 1H); 6.94 (dd, J=7.8, 1.3 Hz, 1H); 6.68-6.64 (m, 1H); 6.61-6.57 (m, 1H); 5.42 (d, J=4.8 Hz, 1H); 3.98 (t, J=5.0 Hz, 1H); 3.67-3.62 (m, 2H); 3.59-3.53 (m, 2H).

Example 101

((2R,3S,4R,5R)-3,4-dihydroxy-5-{6-[(4-methoxyphenyl)ethynyl]-9H-purin-9-yl}tetrahydrofuran-2-yl)methyl sulfamate (I-123)

The title compound was prepared as described in Example 98, steps a-c, using 4-ethynylanisole in step b.
LCMS: R.t. 1.34 min ES+ 462 (formic acid)
$^1$H-NMR (400 MHz, d$_6$-DMSO): δ 8.93 (s, 1H); 8.79 (s, 1H); 7.68-7.65 (m, 2H); 7.60 (s, 1H); 7.10-7.06 (m, 2H); 6.10 (d, J=5.0 Hz, 1H); 5.70 (d, J=5.5 Hz, 1H); 5.50 (d, J=5.5 Hz, 1H); 4.71-4.67 (m, 1H); 4.34-4.19 (m, 4H).

Example 102

((2R,3S,4R,5R)-5-{6-[(2-fluorophenyl)ethynyl]-9H-purin-9-yl}-3,4-dihydroxytetrahydrofuran-2-yl)methyl sulfamate (I-152)

The title compound was prepared as described in Example 98, steps a-c, using 1-ethynyl-2-fluorobenzene in step b.
LCMS: R.t. 1.33 min ES+ 450 (formic acid)
$^1$H-NMR (400 MHz, d$_6$-DMSO): δ 8.99 (s, 1H); 8.83 (s, 1H); 7.82-7.77 (m, 1H); 7.66-7.58 (m, 2H); 7.48-7.34 (m, 2H); 6.11 (d, J=5.02 Hz, 1H); 4.71-4.67 (m, 1H); 4.35-4.20 (m, 4H).

Example 103

(2R,3S,4R,5R) Sulfamic acid 5-(6-cyclopropylethynyl-purin-9-yl)-3,4-dihydroxy-tetrahydro-furan-2-ylmethyl ester (I-95)

Step a: (3aR,4R,6R,6aR) Sulfamic acid 6-(6-cyclopropylethynyl-purin-9-yl)-2,2-dimethyltetrahydro-furo[3,4-d][1,3]dioxol-4-ylmethyl ester A solution of (3aR,4R,6R,6aR) sulfamic acid 6-(6-iodo-purin-9-yl)-2,2-dimethyl-tetrahydro-furo[3,4-d][1,3]dioxol-4-ylmethyl ester (172.0 mg, 0.277 mmol), cyclopropyl acetylene (131 μL, 1.11 mmol), CuI (13.2 mg, 0.0692 mmol), Pd(PPh$_3$)$_2$Cl$_2$ (19.4 mg, 0.0277 mmol) and DIPEA (120.5 μL, 0.6918 mmol) in tetrahydrofuran (5.0 mL, degassed with nitrogen) was stirred for 60 minutes at r.t. The reaction was concentrated and taken up in DCM. This was washed with saturated aq EDTA.Na$_2$. The layers were separated, the organic phase was concentrated, and the residue was purified by flash chromatography (0 to 100% EtOAc/DCM) to yield the product (90 mg, 75%).
LCMS: R.t. 2.26 min ES+ 436 (ammonium acetate)

Step b: (2R,3S,4R,5R)Sulfamic acid 5-(6-cyclopropylethynyl-purin-9-yl)-3,4-dihydroxy-tetrahydrofuran-2-ylmethyl ester (I-95)

The title compound was prepared as described in Example 98, steps c.
LCMS: R.t. 1.07 min ES+ 396 (formic acid)
$^1$H-NMR (400 MHz, CD$_3$OD): δ 8.80 (s, 1H), 8.67 (s, 1H), 6.19 (d, J=4.9 Hz, 1H), 4.77 (t, J=5.0 Hz, 1H), 4.48-4.43 (m, 2H), 4.41-4.34 (m, 2H), 1.70 (tt, J=5.2 Hz, 8.0 Hz, 1H), 1.11-1.02 (m, 4H).

Example 104

{(2R,3S,5R)-5-[6-(benzylamino)-9H-purin-9-yl]-3-hydroxytetrahydrofuran-2-yl}methyl sulfamate (I-102)

The title compound was prepared as described in Example 40 steps a-g using benzylamine in step d.
LCMS: R.t. 1.19 min ES+ 421 (formic acid)
$^1$H-NMR (400 MHz, d$_6$-DMSO): δ 8.39 (bs, 1H); 8.31 (s, 1H); 8.21 (s, 1H); 7.53 (bs, 2H); 7.34-7.19 (m, 5H); 6.40 (t, J=6.8 Hz, 1H); 5.54 (bs, 1H); 4.70 (bs, 2H); 4.48 (bs, 1H); 4.25 (m, 1H); 4.14 (m, 1H); 4.07 (m, 1H); 2.82 (m, 1H); 2.34 (m, 1H).

Example 105

{(2R,3S,5R)-5-[4-(benzoylamino)-7H-pyrrolo[2,3-d]pyrimidin-7-yl]-3-hydroxytetrahydrofuran-2-yl}methyl sulfamate (I-128)

Step a: N-{7-[(2R,4S,5R)-4-{[tert-butyl(dimethyl)silyl]oxy}-5-({[tert-butyl(dimethyl)silyl]oxy}methyl)tetrahydrofuran-2-yl]-7H-pyrrolo[2,3-d]pyrimidin-4-yl}benzamide To a solution of N-{7-[(2R,4S,5R)-4-hydroxy-5-(hydroxymethyl)tetrahydrofuran-2-yl]-7H-pyrrolo[2,3-d]pyrimidin-4-yl}benzamide (0.579 g, 1.63 mmol) and imidazole (0.534 g, 7.84 mmol) in DMF (4.1 mL) was added TBSCl (0.675 g, 4.48 mmol) and the mixture was stirred at r.t. overnight. Additional TBSCl (0.300 g, 1.99 mmol) was added and the solution stirred for 3 h. The reaction mixture was diluted with H$_2$O (30 mL) and extracted with EtOAc (3×30 mL). The combined organics were washed with brine (60 mL), dried (Na$_2$SO$_4$), filtered, and concentrated. The crude material was purified by flash chromatography (0 to 30% EtOAc/DCM) to afford the title compound (0.839 g, 88%).
LCMS: R.t. 3.36 min ES+ 583 (formic acid)

Step b: N-{7-[(2R,4S,5R)-4-{[tert-butyl(dimethyl)silyl]oxy}-5-(hydroxymethyl)tetrahydrofuran-2-yl]-7H-pyrrolo[2,3-d]pyrimidin-4-yl}benzamide To a solution of N-{7-[(2R,4S,5R)-4-{[tert-butyl(dimethyl)silyl]oxy}-5-({[tert-butyl(dimethyl)silyl]oxy}methyl)tetrahydrofuran-2-yl]-7H-pyrrolo[2,3-d]pyrimidin-4-yl}benzamide (1.06 g, 1.82 mmol) in 18 mL THF/pyridine (1:1) was added approximately 20 drops of hydrofluoridic acid in pyridine. The mixture was stirred at r.t. for 30 h. The reaction was quenched by slowly adding to saturated aq NaHCO$_3$ (100 mL) and the solution was extracted with EtOAc (3×50 mL). The combined organics were washed with saturated aq Cu(SO$_4$)$_2$ (50 mL) and saturated aq EDTA.Na$_2$.

The combined organics were dried (Na$_2$SO$_4$), filtered, and concentrated. The residue was purified by flash chromatography (15 to 50% EtOAc/hexanes) to isolate the title compound as a white foam (0.264 g, 31%).

LCMS: R.t. 2.09 min ES+ 469 (formic acid).

Step c: ((2R,3S,5R)-5-[4-(benzoylamino)-7H-pyrrolo[2,3-d]pyrimidin-7-yl]-3-{[tert-butyl(dimethyl)silyl]oxy}tetrahydrofuran-2-yl)methyl sulfamate Using essentially the same procedure as example 43 step f, N-{7-[(2R,4S,5R)-4-{[tert-butyl(dimethyl)silyl]oxy}-5-(hydroxymethyl)tetrahydrofuran-2-yl]-7H-pyrrolo[2,3-d]pyrimidin-4-yl}benzamide (0.524 g, 1.12 mmol) was reacted with chlorosulfonamide and the product was purified by flash chromatography (20 to 50% EtOAc/hexanes) to afford the title compound as a white foam (0.292 g, 48%).

LCMS: R.t. 2.02 min ES+ 548 (formic acid)

Step d: {(2R,3S,5R)-5-[4-(benzoylamino)-7H-pyrrolo[2,3-d]pyrimidin-7-yl]-3-hydroxytetrahydrofuran-2-yl}methyl sulfamate (I-128)

To a solution of ((2R,3S,5R)-5-[4-(benzoylamino)-7H-pyrrolo[2,3-d]pyrimidin-7-yl]-3-{[tert-butyl(dimethyl)silyl]oxy}tetrahydrofuran-2-yl)methyl sulfamate (0.292 g, 0.533 mmol) in 5.4 mL pyridine/THF (1:1) was added approximately 5 drops of hydrofluoridic acid in pyridine. The solution was stirred at r.t. overnight, quenched by slowly adding saturated aq NaHCO$_3$ (20 mL) and extracted with DCM (2×25 mL) and EtOAc (25 mL). The organics were combined, dried (Na$_2$SO$_4$), filtered, and concentrated. The crude material was purified by flash chromatography (1 to 10% MeOH/DCM) to afford the final compound (0.177 g, 77%).

LCMS: R.t. 1.28 min ES+ 434 (formic acid).

$^1$H-NMR (400 MHz, CD$_3$CN) δ 9.23 (bs, 1H); 8.55 (s, 1H); 8.02 (d, J=7.5 Hz, 2H); 7.66-7.53 (m, 3H); 7.47 (d, J=3.8 Hz, 1H); 6.91 (d, J=3.5 Hz, 1H); 6.77 (t, J=6.8 Hz, 1H); 5.77 (bs, 2H); 4.57-4.53 (m, 1H); 4.33-4.24 (m, 2H); 4.16-4.13 (m, 1H); 3.62 (d, J=4.3 Hz, 1H); 2.68-2.61 (m, 1H); 2.43-2.37 (m, 1H).

Example 106

((2R,3S,4R,5R)-5-{6-[(4-bromobenzoyl)amino]-9H-purin-9-yl}-3,4-dihydroxytetrahydrofuran-2-yl)methyl sulfamate (I-112)

Step a: 4-bromo-N-{9-[(3aR,4R,6R,6aR)-6-(hydroxymethyl)-2,2-dimethyltetrahydrofuro[3,4-d][1,3]dioxol-4-yl]-9H-purin-6-yl}benzamide

[(3aR,4R,6R,6aR)-6-(6-amino-9H-purin-9-yl)-2,2-dimethyltetrahydrofuro[3,4-d][1,3]dioxol-4-yl]methanol (0.400 g, 1.30 mmol) was dried by co-evaporation with pyridine, then suspended in dry pyridine (6.5 mL). TMSCl (0.330 mL, 2.60 mmol) was added and the mixture was stirred for 15 min. 4-Bromobenzoylchloride (0.342 g, 1.56 mmol) was added to the mixture and stirred for 2 h. The solution was cooled to 0° C. and 1 mL of H$_2$O was added. After 5 min a 29% NH$_3$ aq solution (0.847 mL) was added and the reaction mixture was stirred for 30 min while warming to r.t. The mixture was then concentrated and the residue was diluted with H$_2$O (40 mL). The product was extracted with EtOAc (60 mL) and concentrated. The crude material was purified by flash chromatography (65 to 100% EtOAc/hexanes) to afford the title compound (0.305 g, 49%).

LCMS: R.t. 1.46 min ES+ 492 (formic acid)

Step b: (3aR,4R,6R,6aR)-6-{6-[(4-bromobenzoyl)amino]-9H-purin-9-yl}-2,2-dimethyltetrahydrofuro[3,4-d][1,3]dioxol-4-yl)methyl sulfamate Using essentially the same procedure as example 39, step c, 4-bromo-N-{9-[(3aR,4R,6R,6aR)-6-(hydroxymethyl)-2,2-dimethyltetrahydrofuro[3,4-d][1,3]dioxol-4-yl]-9H-purin-6-yl}benzamide (0.305 g, 0.622 mmol) was reacted with chlorosulfonamide, and the product was purified by flash chromatography (50 to 100% EtOAc/hexanes) to afford the title compound (0.243 g, 69%).

LCMS: R.t. 1.57 min ES+ 571 (formic acid).

Step c: 2R,3S,4R,5R)-5-{6-[(4-bromobenzoyl)amino]-9H-purin-9-yl}-3,4-dihydroxytetrahydrofuran-2-yl)methyl sulfamate (I-112)

((3aR,4R,6R,6aR)-6-{6-[(4-bromobenzoyl)amino]-9H-purin-9-yl}-2,2-dimethyltetrahydrofuro[3,4-d][1,3]dioxol-4-yl)methyl sulfamate (0.243 g, 0.427 mmol) was stirred in 3 mL of 90% TFA in H$_2$O for 4 h. The solution was concentrated and MeOH was added to the residue. The title compound precipitated out of the solution as a white solid (0.0794 g, 35%)

LCMS: R.t. 1.27 min ES+ 531 (formic acid).

$^1$H-NMR (400 MHz, d$_6$-DMSO): δ 11.36 (s, 1H); 8.77 (s, 1H); 8.64 (s, 1H); 7.98 (d, J=8.53 Hz, 2H); 7.77 (d, J=8.53 Hz, 2H); 7.62 (s, 2H); 6.08 (d, J=5.77 Hz, 1H); 5.74 (bs, 1H); 5.53 (bs, 1H); 4.72-4.67 (m, 1H); 4.34-4.17 (m, 4H).

Example 107

((2R,3S,4R,5R)-5-{6-[(4-chlorobenzoyl)amino]-9H-purin-9-yl}-3,4-dihydroxytetrahydrofuran-2-yl)methyl sulfamate (I-119)

The title compound was prepared as described in Example 106 steps a-c using 4-chlorobenzoylchloride in step a.

LCMS: R.t. 1.23 min ES+ 485 (formic acid).

$^1$H-NMR (400 MHz, d$_6$-DMSO): δ 11.35 (s, 1H); 8.77 (s, 1H); 8.64 (s, 1H); 8.08-8.04 (m, 2H); 7.65-7.61 (m, 4H); 6.09 (d, J=5.3 Hz, 1H); 5.73 (d, J=5.3 Hz, 1H); 5.52 (d, J=5.8 Hz, 1H); 4.72-4.67 (m, 1H); 4.34-4.17 (m, 4H).

Example 108

((2R,3S,4R,5R)-3,4-dihydroxy-{6-[(2-methoxybenzoyl)amino]-9H-purin-9-yl}tetrahydrofuran-2-yl)methyl sulfamate (I-150)

The title compound was prepared as described in Example 106 steps a-c using 2-methoxybenzoylchloride in step a.

LCMS: R.t. 1.17 min ES+ 481 (formic acid).

$^1$H-NMR (400 MHz, d$_6$-DMSO): δ 11.14 (s, 1H); 8.72 (s, 1H); 8.67 (s, 1H); 7.95 (dd, J=7.5, 1.5 Hz, 1H); 7.66-7.60 (m, 3H); 7.29 (d, J=8.3 Hz, 1H); 7.16 (t, J=7.0 Hz, 1H); 6.08 (d, J=5.3 Hz, 1H); 4.69 (t, J=5.3 Hz, 1H); 4.34-4.18 (m, 4H); 4.04 (s, 3H).

Example 109

[(2R,3R,4S,5R)-5-(6-chloro-9H-purin-9-yl)-3-hydroxy-4-methoxytetrahydrofuran-2-yl]methyl sulfamate (I-99)

Step a: (6aR,8R,9S,9aS)-8-(6-chloro-9H-purin-9-yl)-2,2,4,4-tetraisopropyltetrahydro-6H-furo[3,2-f][1,3,5,2,4]trioxadisilocin-9-ol (6aR,8R,9S,9aR)-8-(6-chloro-9H-purin-9-yl)-2,2,4,4-tetraisopropyltetrahydro-6H-furo[3,2-f][1,3,5,2,4]trioxadisilocin-9-yl acetate (3.51 g, 6.14 mmol) (Kittaka, A.; Yamada, N.; Tanaka, H.; Nakamura, K. T.; Miyasaka, T. *Nucleosides Nucleotides,* 1996, 15, 1447-1457) was stirred in 7N $NH_3$ in MeOH (2.33 mL) for 2.5 h. The mixture was then concentrated and the residue was purified by flash chromatography (20 to 50% EtOAc/hexanes) to give title compound as a light yellow foam (3.06 g, 92%).

LCMS: R.t. 2.72 min ES+ 529 (formic acid)

Step b: 6-chloro-9-[(6aR,8R,9S,9aR)-2,2,4,4-tetraisopropyl-9-methoxytetrahydro-6H-furo[3,2-f][1,3,5,2,4]trioxadisilocin-8-yl]-9H-purine To a suspension of (6aR,8R,9S,9aS)-8-(6-chloro-9H-purin-9-yl)-2,2,4,4-tetraisopropyltetrahydro-6H-furo[3,2-f][1,3,5,2,4]trioxadisilocin-9-ol (3.06 g, 5.79 mmol) and $Cs_2CO_3$ (18.86 g, 57.9 mmol) in DMF (58 mL) at 0° C. was added methyl iodide (3.60 mL, 57.9 mmol) dropwise and reaction was stirred for 3 h while warming to r.t. The solution was diluted with $CH_2Cl_2$ (150 mL) and washed with saturated aq $NH_4Cl$. The aq layer was extracted with $CH_2Cl_2$ (2×100 mL) and the combined organics were dried ($Na_2SO_4$), filtered, and concentrated. The crude material was purified by flash chromatography (5 to 30% EtOAc/hexanes) to afford the title compound (1.51 g, 48%).

LCMS: R.t. 3.14 min ES+ 543 (formic acid)

Step c: (2R,3R,4S,5R)-5-(6-chloro-9H-purin-9-yl)-2-(hydroxymethyl)-4-methoxytetrahydrofuran-3-ol To a solution of 6-chloro-9-[(6aR,8R,9S,9aR)-2,2,4,4-tetraisopropyl-9-methoxytetrahydro-6H-furo[3,2-f][1,3,5,2,4]trioxadisilocin-8-yl]-9H-purine (1.31 g, 2.41 mmol) in THF/pyridine (12 mL, 1:1) was added approximately 20 drops of hydrofluoric acid in pyridine. This solution was stirred at r.t. overnight. The reaction was diluted with EtOAc (10 mL) and quenched with saturated aq $NaHCO_3$. The aq layer was extracted with EtOAc (3×40 mL) and the combined organics were dried ($Na_2SO_4$), filtered, and concentrated. The crude material was purified by flash chromatography (0 to 10% MeOH/DCM) to afford the title compound (0.690 g, 74%).

LCMS: R.t. 0.94 min ES+ 301 (formic acid)

Step d: [(2R,3R,4S,5R)-5-(6-chloro-9H-purin-9-yl)-3-hydroxy-4-methoxytetrahydrofuran-2-yl]methyl sulfamate (I-99)

The title compound was prepared as described in Example 40 steps a-b and example 40 steps e-g.

LCMS: R.t. 1.08 min ES+ 380 (formic acid).

$^1$H-NMR (400 MHz, $CD_3OD$): δ 8.76 (s, 1H); 8.63 (s, 1H); 6.69 (d, J=5.3 Hz, 1H); 4.49 (t, J=4.8 Hz, 1H); 4.45-4.37 (m, 2H); 4.23-4.18 (m, 1H); 4.13-4.10 (m, 1H); 3.26 (s, 3H).

Example 110

[(2R,3S,5R)-5-(4-chloro-1H-pyrrolo[3,2-c]pyridin-1-yl)-3-hydroxytetrahydrofuran-2-yl]methyl sulfamate (I-106)

Step a: (2R,3S,5R)-5-(4-chloro-1H-pyrrolo[3,2-c]pyridin-1-yl)-2-(hydroxymethyl)tetrahydrofuran-3-ol The title compound was prepared as described in Example 91 steps a-b using 4-chloro-1H-pyrrolo[3,2-c]pyridine (Bilodeau, M. T.; Manley, P. J.; Hartman, G. D. Tyrosine Kinase Inhibitors. International Patent WO03009852 A1, Feb. 6, 2003) in step a.

LCMS: R.t. 1.03 min ES+ 269 (formic acid)

Step b: [(2R,3S,5R)-5-(4-chloro-1H-pyrrolo[3,2-c]pyridin-1-yl)-3-hydroxytetrahydrofuran-2-yl]methyl sulfamate (I-106)

The title compound was prepared as described in Example 40 steps a-b and example 40 steps e-g starting with (2R,3S,5R)-5-(4-chloro-1H-pyrrolo[3,2-c]pyridin-1-yl)-2-(hydroxymethyl)tetrahydrofuran-3-ol.

LCMS: R.t. 1.09 min ES+ 346 (formic acid).

$^1$H-NMR (400 MHz, $CD_3OD$): δ 8.01 (d, J=6.0 Hz, 1H); 7.69 (d, J=3.8 Hz, 1H); 7.61 (dd, J=6.0, 0.8 Hz, 1H); 6.72 (d, J=3.5 Hz, 1H); 6.51-6.46 (m, 1H); 4.60-4.55 (m, 1H); 4.30-4.27 (m, 2H); 4.23-4.19 (m, 1H); 2.64-2.56 (m, 1H); 2.45-2.39 (m, 1H).

Example 111

{(2-R,3S,5R)-5-[4-(benzylamino)-1H-pyrrolo[3,2-c]pyridin-1-yl]-3-hydroxytetrahydrofuran-2-yl}methyl sulfamate (I-143)

Step a: 1-[(2R,4S,5R)-4-[tert-butyl(dimethyl)silyl]oxy-5-({[tert-butyl(dimethyl)silyl]oxy}methyl)tetrahydrofuran-2-yl]-4-chloro-1H-pyrrolo[3,2-c]pyridine A solution of (2R,3S,5R)-5-(4-chloro-1H-pyrrolo[3,2-c]pyridin-1-yl)-2-(hydroxymethyl)tetrahydrofuran-3-ol (1.41 g, 0.945 mmol), imidazole (0.433 g, 6.36 mmol), and TBSCl (0.533 g, 3.54 mmol) was stirred in DMF (13.2 mL) at r.t. for 4.5 h. The solution was diluted with water (40 mL) and extracted with EtOAc (3×50 mL). The combined organics were washed with brine, dried ($Na_2SO_4$), filtered, and concentrated. The crude material was purified by flash chromatography (0 to 25% EtOAc/hexanes) to afford the title compound (0.686 g, 98%).

LCMS: R.t. 3.30 min ES+ 497 (formic acid).

Step b: ((2R,3S,5R)-5-[4-(benzylamino)-1H-pyrrolo[3,2-c]pyridin-1-yl]-3-{[tert-butyl(dimethyl)silyl]oxy}tetrahydrofuran-2-yl)methanol A flame dried Schlenk flask was charged with 1-[(2R,4S,5R)-4-{[tert-butyl(dimethyl)silyl]oxy}-5-({[tert-butyl(dimethyl)silyl]oxy}methyl)tetrahydrofuran-2-yl]-4-chloro-1H-pyrrolo[3,2-c]pyridine (0.343 g, 0.690 mmol), 1,4 dioxane (1.40 mL), benzylamine (0.226 mL, 2.07 mmol), tris(dibenzylideneacetone)dipalladium(0) (0.0126 g, 0.0138 mmol), 2-(dicyclohexylphosphino)biphenyl (0.00686 g, 0.0196 mmol), and sodium tert-butoxide (0.186 g, 1.93 mmol). The tube purged with $N_2$ (3×), sealed and the mixture was heated at 95° C. overnight. The reaction mixture was cooled to r.t., diluted with CH$_2$Cl$_2$ (20 mL) and washed with water (20 mL). The aq layer was extracted with CH$_2$Cl$_2$ (3×20 mL) and the combined organics were dried (Na$_2$SO$_4$), filtered, and concentrated. The crude oil was purified by flash chromatography (10 to 40% EtOAc/hexanes) to give the title compound as a light yellow foam (0.313 g, 28%).

LCMS: R.t. 1.42 min ES+ 454 (formic acid).

Step c: ((2R,3S,5R)-5-[4-(benzylamino)-1H-pyrrolo[3,2-c]pyridin-1-yl]-3-{[tert-butyl(dimethyl)silyl]oxy}tetrahydrofuran-2-yl)methyl sulfamate Using essentially the same procedure as example 43, step f, ((2R,3S,5R)-5-[4-(benzylamino)-1H-pyrrolo[3,2-c]pyridin-1-yl]-3-{[tert-butyl(dimethyl)silyl]oxy}tetrahydrofuran-2-yl)methanol (0.0876 g, 0.193 mmol) was reacted with chlorosulfonamide, and the product was purified by flash chromatography (60 to 100% EtOAc/CH$_2$Cl$_2$) to afford the title compound (0.0300 g, 29%).

LCMS: R.t. 1.42 min ES+ 533 (formic acid).

Step d: {(2R,3S,5R)-5-[4-(benzylamino)-1H-pyrrolo[3,2-c]pyridin-1-yl]-3-hydroxytetrahydrofuran-2-yl}methyl sulfamate (I-143)

To a solution of ((2R,3S,5R)-5-[4-(benzylamino)-1H-pyrrolo[3,2-c]pyridin-1-yl]-3-{[tert-butyl(dimethyl)silyl]oxy}tetrahydrofuran-2-yl)methyl sulfamate (0.0300 g, 0.0563 mmol) in THF/pyridine (1 mL, 1:1) was added hydrofluoric acid in pyridine (3 drops) and stirred overnight. The reaction was diluted with EtOAc (5 mL) and quenched with saturated aq NaHCO$_3$ (10 mL). The aq layer was extracted with EtOAc (3×10 mL) and the combined organics were dried (Na$_2$SO$_4$), filtered, and concentrated. The crude material was purified by preparative plate chromatography (10% MeOH/EtOAc) to give the final compound (0.00590 g, 25%).

LCMS: R.t. 1.03 min ES+ 419 (formic acid).
$^1$H-NMR (400 MHz, CD$_3$OD): δ 7.60 (d, J=6.3 Hz, 1H); 7.40-7.19 (m, 6H); 6.90 (dd, J=6.5, 0.8 Hz, 1H); 6.77 (d, J=3.3 Hz, 1H); 6.42-6.36 (m, 1H); 4.72 (s, 2H); 4.57-4.52 (m, 1H); 4.29-4.25 (m, 2H); 4.20-4.16 (m, 1H); 2.62-2.54 (m, 1H); 2.41-2.34 (m, 1H).

Example 112

{(2R,3R,4S,5R)-4-fluoro-3-hydroxy-5-[6-(2-phenylethyl)-9H-purin-9-yl]-tetrahydrofuran-2-yl}methyl rel-sulfamate (I-147)

Step a: (2R,3R,4S,5R)-4-fluoro-5-[6-(2-phenylethyl)-9H-purin-9-yl]-2-[(trityloxy)methyl]tetrahydrofuran-3-yl benzoate (2R,3R,4S,5R)-5-(6-Chloro-9H-purin-9-yl)-4-fluoro-2-[(trityloxy)methyl]tetrahydrofuran-3-yl benzoate (0.330 g, 0.520 mmol), tris(dibenzylideneacetone)dipalladium(0) (0.012 g, 0.013 mmol) and triphenylphosphine (0.027 g, 0.104 mmol) were added to a flame-dried flask under argon. Tetrahydrofuran (2.5 mL) was added followed by the dropwise addition of phenethylzinc bromide (2.08 mL, 1.04 mmol). The mixture was heated at 50° C. for two hours. The reaction was added to saturated aq NH$_4$Cl, extracted with DCM (3×), dried (Na$_2$SO$_4$), filtered, and concentrated. The residue was purified by flash chromatography (0 to 35% EtOAc/hexanes) to give the product (0.193 g, 51%).

LCMS: R.t. 2.53 min ES+ 705 (formic acid)

Step b: {(2R,3R,4S,5R)-4-fluoro-3-hydroxy-5-[6-(2-phenylethyl)-9H-purin-9-yl]tetrahydrofuran-2-yl}methyl rel-sulfamate (I-147)

The title compound was prepared as described in Example 68 steps e-g using (2R,3R,4S,5R)-4-fluoro-5-[6-(2-phenylethyl)-9H-purin-9-yl]-2-[(trityloxy)methyl]tetrahydrofuran-3-yl benzoate.

LCMS: R.t. 1.38 min ES+ 438 (formic acid).
$^1$H-NMR (300 MHz, CD$_3$OD): δ 8.82 (s, 1H); 8.52 (d, J=2.2 Hz, 1H); 7.24-7.07 (m, 5H); 6.65 (dd, J=13.5 Hz, 3.8 Hz, 1H); 5.17 (ddd, J=51.8, 3.7, 2.8 Hz, 1H); 4.58 (ddd, J=15.9, 3.1, 2.8 Hz, 1H); 4.39 (d, J=5.0 Hz, 2H); 4.25 (q, J=4.6 Hz, 1H); 3.44 (dd, J=7.3, 5.9 Hz, 2H); 3.15 (dd, J=7.3, 6.1 Hz, 2H).

Example 113

N-({(2R,3S,4R,5R)-3,4-dihydroxy-5-[6-(phenylethynyl)-9H-purin-9-yl]-tetrahydrofuran-2-yl}methyl) sulfamide (I-115)

Step a: N-{[(3a-R,4R,6R,6aR)-6-(6-iodo-9H-purin-9-yl)-2,2-dimethyltetrahydrofuro[3,4-d][1,3]dioxol-4-yl]methyl}sulfamide To a solution of N-({(3aR,4R,6R,6aR)-2,2-dimethyl-6-[6-chloro-9H-purin-9-yl]tetrahydrofuro[3,4-d][1,3]dioxol-4-yl]methyl)sulfamide (0.3 g, 0.74 mmol) in 2-butanone (15 mL) was added NaI (2.22 g, 0.14 mol) and trifluoroacetic acid (570 μL, 0.074 mol). The reaction mixture was stirred at −10° C. for 3.5 h quenched with saturated aq NaHCO$_3$ (20 mL), extracted with DCM (3×25 mL) and the organic layers dried (Na$_2$SO$_4$) and concentrated. The residue was purified via flash chromatography (0 to 60% EtOAc/DCM) to give the title compound (0.14 g, 61%).

LCMS: R.t. 1.26 min ES+ 497 (formic acid)

Step b: N-({(3aR,4R,6R,6aR)-2,2-dimethyl-6-[6-(phenylethynyl)-9H-purin-9-yl]tetrahydrofuro[3,4-d][1,3]dioxol-4-yl}methyl)sulfamide To a solution of N-{[(3aR,4R,6R,6aR)-6-(6-iodo-9H-purin-9-yl)-2,2-dimethyltetrahydrofuro[3,4-d][1,3]dioxol-4-yl]methyl}sulfamide (0.14 g, 0.28 mmol) in DMF was added phenylacetylene (0.115 g, 1.13 mmol), CuI (10.6 mg, 0.056 mmol), DIPEA (98 μL, 0.56 mmol) and Pd(PPh$_3$)$_2$Cl$_2$ (10 mg, 0.028 mmol) The solution was stirred for 1 h at r.t. and concentrated. The residue was taken up in DCM, washed with saturated aq EDTA.Na$_2$ (3×20 mL), dried (Na$_2$SO$_4$) concentrated and purified by flash chromatography (20 to 60% EtOAc/DCM) to give the title compound (0.08 g, 60%).

LCMS: R.t. 1.60 min ES+ 471 (formic acid).

Step c: N-({(2R,3S,4R,5R)-3,4-dihydroxy-5-[6-(phenylethynyl)-9H-purin-9-yl]tetrahydrofuran-2-yl}methyl)sulfamide (I-115)

The title compound was prepared following the procedure described in Example 1, step d.

LCMS: R.t. 1.36 min ES+ 431 (formic acid)
$^1$H-NMR (300 MHz, d$_6$-DMSO): δ 8.94 (s, 1H); 8.89 (s, 1H) 7.72 (dd, J=9.4 Hz, 2H); 7.53 (m, 3H); 6.99-6.97 (m, 1H);

6.61 (s, 2H); 6.01 (d, J=6.5 Hz, 1H); 5.55 (d, J=6.0 Hz, 1H); 5.33 (d, J=4.2 Hz, 1H); 4.18 (m, 1H); 4.12 (m, 1H).

Example 114

{(2R,3S,4R,5R)-5-[6-({12-[(acetylamino)methyl] benzyl}amino)-9H-purin-9-yl]-3,4-dihydroxytetrahydrofuran-2-yl}methyl sulfamate (I-148)

Step a: N-[2-(aminomethyl)benzyl]acetamide

To a solution of tert-butyl[2-(aminomethyl)benzyl]carbamate (0.2 g, 0.93 mmol) and triethylamine (260 µL, 1.9 mmol) in DCM (10 mL) was added AC$_2$O (0.285 g, 0.00279 mol) dropwise and the reaction stirred for 2 h at r.t. The reaction was concentrated, the residue dissolved in EtOAc (20 mL) then washed with saturated aq NaHCO$_3$ (2×10 mL). The organic layer was dried (Na$_2$SO$_4$) and concentrated to give the crude product (0.25 g, 90%). To a solution of this in DCM (5 mL) was added 2 mL of 4M HCl/dioxane and the solution was stirred for 1 h. The reaction was concentrated to give the title compound (0.16 g, 95%) which was used without further purification.

LCMS: R.t. 1.08 min ES+ 179 (formic acid).

Step b: {(2R,3S,4R,5R)-5-[6-({2-[(acetylamino) methyl]benzyl}amino)-9H-purin-9-yl]-3,4-dihydroxytetrahydrofuran-2-yl}methyl sulfamate (I-148)

The title compound was prepared following the procedure described in Example 1, steps b-d, using N-[2-(aminomethyl) benzyl]acetamide in step b.

LCMS: R.t. 1.08 min ES+ 508 (formic acid).

$^1$H-NMR (300 MHz, d$_6$-DMSO): δ 8.08 (s, 1H); 8.04 (t, J=5.5 Hz, 1H); 7.97 (s, 1H); 7.32 (s, 1H); 6.97 (m, 4H); 5.70 (d, J=5.3 Hz, 1H); 4.43 (m, 2H); 4.14 (d, J=5.7 Hz, 2H); 3.97 (m, 5H); 1.64 (s, 3H).

Example 115

((2R,3S,4R,5R)-5-{6-[(1S)-2,3-dihydro-1H-inden-1-yl(methyl)amino]-9H-purin-9-yl}-3,4-dihydroxytetrahydrofuran-2-yl)methyl sulfamate (I-130)

Step a: (1S)-N-methylindan-1-amine

To a solution of (S)-(+)-1-aminoindan (176 mg, 1.29 mmol) in THF (10.0 mL) was added Et$_3$N (0.200 mL, 1.43 mmol) followed by di-tert-butyldicarbonate (286 mg, 1.31 mmol). The mixture was stirred under an atmosphere of nitrogen for 3 days, concentrated, diluted with DCM (100 mL), and washed with 0.1 N aq hydrochloric acid (50.0 mL) and aq NaCl. The organic layer was dried (MgSO$_4$), filtered and concentrated. The tan solid was taken up in tetrahydrofuran (10.0 mL) and to this was added with a 1.00 M solution of lithium aluminum hydride (1.0 M in THF, 5.80 mL). The mixture was heated at reflux for 6 hours, quenched with water (0.300 mL), 15% aq NaOH solution (0.300 mL) and water (0.900 mL). This was stirred for 10 minutes, filtered through celite, diluted with EtOAc (100 mL), dried (MgSO$_4$), filtered and concentrated. The residue was purified via flash chromatography (0 to 100% EtOAc/hexanes to 10% MeOH/DCM) to afford the title compound as a black solid (146 mg, 77%).

LCMS: R.t. 0.83 min ES+ 148 (ammonium acetate).

Step b: [(3aR,4R,6R,6aR)-6-(6-chloro-9H-purin-9-yl)-2,2-dimethyltetrahydrofuro[3,4-d][1,3]dioxol-4-yl]methyl tritylsulfamate To a solution of [(3aR,4R,6R,6aR)-6-(6-chloro-9H-purin-9-yl)-2,2-dimethyltetrahydrofuro[3,4-d][1,3]dioxol-4-yl] methyl sulfamate (13.4 g, 33.1 mmol) in DCM (330 mL) at r.t. was added DIPEA (11.5 mL, 66.2 mmol) followed by Ph$_3$CCl (9.23 g, 33.1 mmol). The reaction was stirred at r.t. for 4 hours. The mixture was diluted with DCM, the layers were separated, and the organic layer was washed with 1N HCl followed by brine. The combined organic phases were dried (Na$_2$SO$_4$) and concentrated to yield the title compound as a white solid (17.6 g, 82%).

LCMS: R.t. 2.07 min ES+ 648, ES-646 (formic acid).

Step c: ((3aR,4R,6R,6aR)-6-{6[(1S)-2,3-dihydro-1H-inden-1-yl(methyl)amino]-9H-purin-9-yl}-2,2-dimethyltetrahydrofuro[3,4-d][1,3]dioxol-4-yl) methanol A suspension of (1S)-N-methylindan-1-amine (67.8 mg, 0.461 mmol), [(3aR,4R,6R,6aR)-6-(6-chloro-9H-purin-9-yl)-2,2-dimethyltetrahydrofuro[3,4-d][1,3]dioxol-4-yl]methyl tritylsulfamate (200 mg, 0.309 mmol) and DIPEA (0.160 mL, 0.919 mmol) in ethanol (3.0 mL) was heated at 150° C. for 600 s using microwave irradiation. The residue was purified via flash chromatography (0 to 100% EtOAc/DCM) to afford the title compound as a brown oil (74.3 mg, 55%).

LCMS: R.t. 1.93 min ES+ 438 (ammonium acetate).

Step d: ((2R,3S,4R,5R)-5-{6-[(1S)-2,3-dihydro-1H-inden-1-yl(methyl)amino]-9H-purin-9-yl}-3,4-dihydroxytetrahydrofuran-2-yl)methyl sulfamate (I-130)

The title compound was prepared following the procedure described in Example 39 step c, using AcCN as the solvent and purification by HPLC.

LCMS: R.t. 1.46 min, ES+ 477 (ammonium acetate).

$^1$H-NMR (400 MHz, d$_6$-DMSO): δ 8.34 (s, 1H); 8.32 (s, 1H); 7.61 (s, 2H); 7.33 (d, J=7.3 Hz, 1H); 7.26 (dd, J=7.2, 7.2 Hz, 1H); 7.19 (dd, J=7.3, 7.3 Hz, 1H); 7.10 (d, J=7.4 Hz, 1H); 6.01 (d, J=5.1 Hz, 1H); 5.75-5.61 (m, 1H); 5.54-5.42 (m, 1H); 4.67-4.56 (m, 1H); 4.35-4.12 (m, 4H); 3.13-2.99 (m, 1H); 2.98-2.79 (m, 2H); 2.46-2.36 (m, 1H); 2.19-2.03 (m, 1H).

Example 116

[(2R,3S,4R,5R)-3,4-dihydroxy-5-(6-isobutyl-9H-purin-9-yl)tetrahydrofuran-2-yl]methyl sulfamate (I-98)

Step a: [(3aR,4R,6R,6aR)-6-(6-isobutyl-9H-purin-9-yl)-2,2-dimethyltetrahydrofuro[3,4-d]-[1,3]dioxol-4-yl]methyl acetate To a solution of [(3aR,4R,6R,6aR)-6-(6-chloro-9H-purin-9-yl)-2,2-dimethyltetrahydrofuro[3,4-d][1,3]dioxol-4-yl] methyl acetate (320.0 mg, 0.87 mmol) and Pd(PPh$_3$)$_4$ (56 mg, 0.048 mmol) in THF (7 mL, 0.09 mol, degassed with nitrogen) was added a solution of 0.5 M isobutylzinc bromide in THF (2.60 mL) dropwise over 15 min. The reaction was heated at 60° C. under an atmosphere of nitrogen for 1 hour, cooled and quenched with saturated aq NH₄Cl. This mixture was extracted with EtOAc, the combined organics were washed with saturated aq EDTA.Na₂, water, concentrated and then purified by flash chromatography (0 to 100% EtOAc/DCM) to yield the product (304 mg, 85%)
LCMS: R.t. 1.60 min ES+ 391 (formic acid).

Step b: [(2R,3S,4R,5R)-3,4-dihydroxy-5-(6-isobutyl-9H-purin-9-yl)tetrahydrofuran-2-yl]methyl sulfamate (I-98)

The title compound was prepared as described in Example 67 steps d-f and purified by HPLC.
LCMS: R.t. 1.08 min ES+ 388 (formic acid).
1H-NMR (300 MHz) δ 8.81 (s, 1H); 8.60 (s, 1H); 6.17 (d, J=5.1 Hz, 1H); 4.74 (t, J=5.1 Hz, 1H); 4.45-4.28 (m, 4H); 3.01 (d, J=7.3 Hz, 2H); 2.37-2.23 (m, 1H); 0.94 (d, J=6.7 Hz, 6H).

Example 117

((2R,3S,4R,5R)-3,4-dihydroxy-5-6-[(E)-2-phenylvinyl]-9H-purin-9-yltetrahydrofuran-2-yl)methyl sulfamate (I-69)

Step a: ((3aR,4R,6R,6aR)-2,2-dimethyl-6-(6-(E)-styryl-9H-purin-9-yl)-tetrahydrofuro[3,4-d][1,3]dioxol-4-yl)methyl acetate Under an atmosphere of nitrogen, a solution of (3aR,4R,6R,6aR)acetic acid 2,2-dimethyl-6-(6-vinyl-purin-9-yl)-tetrahydro-furo[3,4-d][1,3]dioxol-4-ylmethyl ester (340.0 mg, 0.94 mmol), Pd(OAc)₂ (21.2 mg, 0.094 mmol), DIPEA (493.0 μL, 2.83 mmol), and iodobenzene (132 μL, 1.18 mmol) in DMF (4.0 mL, degassed with nitrogen) was stirred at 60° C. overnight. The reaction was cooled and concentrated and the residue was purified by flash chromatography (0 to 100% EtOAc/hexanes) to yield the product (304 mg, 74%).
LCMS: R.t. 1.94 min ES+ 437 (formic acid).

Step b: ((2R,3S,4R,5R)-3,4-dihydroxy-5-6-[(E)-2-phenylvinyl]-9H-purin-9-yltetrahydrofuran-2-yl) methyl sulfamate (I-69)

The title compound was prepared as described in Example 67 steps d-f.
LCMS: R.t. 2.10 min ES+ 434 (formic acid).
¹H-NMR (400 MHz, d₆-DMSO): δ 8.90 (s, 1H); 8.76 (s, 1H); 8.40 (d, J=16.2 Hz, 1H); 7.79 (d, J=7.2 Hz, 2H); 7.66 (d, J=16.2 Hz, 1H); 7.60 (bs, 2H); 7.49-7.39 (m, 3H); 6.10 (d, J=5.2 Hz, 1H); 5.86-5.22 (bs, 2H); 4.70 (t, J=5.1 Hz, 1H); 4.35-4.18 (m, 4H).

Example 118

2-((2R,3S,4R,5R)-5-6-[(3,3-dimethyl-2,3-dihydro-1H-inden-1-yl)amino]-9H-purin-9-yl-3,4-dihydroxytetrahydrofuran-2-yl)ethanesulfonamide (I-100)

The title compound was prepared following the procedure described in Example 49 steps h-i, using 3,3-dimethylindan-1-amine in step h.
LCMS: R.t. 1.42 min ES+ 489 (ammonium acetate).
¹H-NMR (300 MHz, CD₃OD): δ 8.31 (s, 1H); 8.16 (s, 1H); 7.22 (m, 4H); 5.94 (bs, 2H); 4.78 (t, J=5.4 Hz, 1H); 4.27 (t, J=5.3 Hz, 1H); 4.12 (dd, J=6.1, 12.1 Hz, 1H); 3.23 (dd, J=7.1, 15.2 Hz, 2H); 2.52 (dd, J=7.4, 12.5 Hz, 1H); 2.29 (dd, J=7.3, 15.2 Hz, 2H); 1.91 (dd, J=8.5, 12.5 Hz, 1H); 1.42 (s, 3); 1.27 (s, 3H).

Example 119

((2R,3S,4R,5R)-5-(4-((S)-2,3-dihydro-1H-inden-1-ylamino)-1H-imidazo[4,5-d]pyridazin-1-yl)-3,4-dihydroxy-tetrahydrofuran-2-yl)methylsulfamate (I-139)

Step a: (3aR,4R,6R,6aR) [6-(4-Chloro-imidazo[4,5-d]pyridazin-1-yl)-2,2-dimethyltetrahydro-furo[3,4-d][1,3]dioxol-4-yl]-methanol A suspension of (2R,3R,4S,5R)-2-(4-chloro-1H-imidazo[4,5-d]pyridazin-1-yl)-5-(hydroxymethyl)tetrahydrofuran-3,4-diol (299.0 mg, 1.04 mmol) (Bussolari, J. C.; Ramesh, K.; Stoeckler, J. D.; Chen, S-F.; Panzica, R. P. *J. Med. Chem.* 1993, 36, 4113-4120), 2,2-dimethoxypropane (640 μL, 5.2 mmol) and p-toluenesulfonic acid monohydrate (199 mg, 1.05 mmol) in acetone (16 mL) was stirred overnight at room temperature. To this was added saturated aq NaHCO₃ (20 mL) and the mixture was concentrated. The aqueous residue was extracted with CHCl₃ (4×50 mL) and the combined organics were dried (Na₂SO₄), filtered and concentrated to yield the product (340 mg, 100%).
LCMS: R.t. 1.08 min ES+ 327, 329 (formic acid).

Step b: ((3aR,4R,6R,6aR)-6-(4-((S)-2,3-dihydro-1H-inden-1-ylamino)-1H-imidazo[4,5-d]pyridazin-1-yl)-2,2-dimethyl-tetrahydrofuro[3,4-d][1,3]dioxol-4-yl) methanol A solution of (3aR,4R,6R,6aR)[6-(4-Chloro-imidazo[4,5-d]pyridazin-1-yl)-2,2-dimethyl-tetrahydro-furo[3,4-d][1,3]dioxol-4-yl]-methanol 1 (80.0 mg, 0.245 mmol), (S)-(+)-1-aminoindan (54.9 μL, 0.428 mmol) and DIPEA (74.6 μL, 0.428 mmol) in butanol (2.2 mL) was heated at 200° C. for 20 minutes using microwave irradiation. The reaction was concentrated and the residue purified by flash chromatography (0 to 20% EtOH/DCM) to yield the product (40 mg, 39%).
LCMS: R.t. 2.22 min ES+ 424 (formic acid).

Step c: ((2R,3S,4R,5R)-5-(4-((S)-2,3-dihydro-1H-inden-1-ylamino)-1H-imidazo[4,5-d]pyridazin-1-yl)-3,4-dihydroxy-tetrahydrofuran-2-yl)methylsulfamate (I-139)

The title compound was prepared as described in Example 67 steps e-f, and purified by preparative HPLC.
LCMS: R.t. 1.19 min ES+ 463 (formic acid).
¹H-NMR (300 MHz, CD₃OD): c 9.07 (s, 1H); 8.48 (s, 1H); 7.36 (d, J=7.4 Hz, 1H); 7.29 (d, J=7.4 Hz, 1H); 7.24 (t, J=7.3 Hz, 1H); 7.18 (t, J=7.1 Hz, 1H); 6.04 (d, J=6.3 Hz, 1H); 5.93 (t, J=7.2 Hz, 1H); 4.44-4.38 (m, 4H); 4.33 (dd, J=2.6, 5.3 Hz, 1H); 3.10 (ddd, J=4.0, 8.6, 15.7 Hz, 1H); 2.96 (td, J=8.1, 16.0 Hz, 1H); 2.78-2.70 (m, 1H); 2.05 (ddd, J=8.3, 12.7, 15.8 Hz, 1H).

Example 120

[(2R,3S,4R,5R)-5-(6-ethyl-9H-purin-9-yl)-3,4-dihydroxytetrahydrofuran-2-yl]-methyl sulfamate (I-132)

Step a: [(3aR,4R,6R,6aR)-2,2-dimethyl-6-(6-vinyl-9H-purin-9-yl)tetrahydrofuro[3,4-d][1,3]dioxol-4-yl] methyl tritylsulfamate A solution of [(3aR,4R,6R,6aR)-6-(6-chloro-9H-purin-9-yl)-2,2-dimethyltetrahydrofuro[3,4-d][1,3]dioxol-4-yl]methyl tritylsulfamate (1.00 g, 1.54 mmol), (2-ethenyl)tri-n-butyltin (900.0 µL, 3.08 mmol), and Pd(PPh$_3$)$_2$Cl$_2$ (55.0 mg, 0.0784 mmol) in 1,2-dichloroethane (30.0 mL, degassed with N$_2$) was heated to reflux under an atmosphere of nitrogen for 4.5 hours. The reaction was concentrated and the residue was purified by flash chromatography (0 to 100% EtOAc/hexanes) to yield the product (550 mg, 56%).

LCMS: R.t. 2.06 min ES+ 640 (ammonium acetate).

Step b: [(3aR,4R,6R,6aR)-6-(6-ethyl-9H-purin-9-yl)-2,2-dimethyltetrahydrofuro[3,4-d][1,3]dioxol-4-yl] methyl tritylsulfamate A suspension of [(3aR,4R,6R,6aR)-2,2-dimethyl-6-(6-vinyl-9H-purin-9-yl)tetrahydrofuro[3,4-d][1,3]dioxol-4-yl] methyl tritylsulfamate (150.0 mg, 0.23 mmol) and Pd/C (10% Pd by weight, 10 mg) in MeOH (3.0 mL, degassed with N$_2$) was stirred under an atmosphere of hydrogen for 90 minutes. The suspension was filtered through celite with methanol and the filtrate was concentrated to yield the crude product (149 mg, 99%).

LCMS: R.t. 1.92 min ES+ 642 (ammonium acetate).

Step c: [(2R,3S,4R,5R)-5-(6-ethyl-9H-purin-9-yl)-3,4-dihydroxytetrahydrofuran-2-yl]-methyl sulfamate (I-132)

A solution of [(3aR,4R,6R,6aR)-6-(6-ethyl-9H-purin-9-yl)-2,2-dimethyltetrahydrofuro[3,4-d][1,3]dioxol-4-yl]methyl tritylsulfamate (149.0 mg, 0.23 mmol) in TFA/water (5.0 mL, 9:1) was stirred for 30 minutes, concentrated to dryness, dissolved in methanol and concentrated again. The residue was purified by prep HPLC to yield the title compound (70 mg, 84%).

LCMS: R.t. 0.83 min ES+ 360 (ammonium acetate).

$^1$H-NMR (400 MHz, CD$_3$OD): δ 8.81 (s, 1H); 8.62 (s, 1H); 6.18 (d, J=5.0 Hz, 1H); 4.76 (t, J=5.1 Hz, 1H); 4.47-4.41 (m, 2H); 4.39-4.32(m, 2H); 3.17 (q, J=7.6 Hz, 2H); 1.38 (t, J=7.6 Hz, 3H).

Example 121

N-[((2R,3S,4R,5R)-5-{6-[(4-fluorobenzyl)amino]-9H-purin-9-yl}-3,4-dihydroxytetrahydrofuran-2-yl)methyl]sulfamide (I-126)

A solution of N-{[(3aR,4R,6R,6aR)-6-(6-chloro-9H-purin-9-yl)-2,2-dimethyltetrahydrofuro[3,4-d][1,3]dioxol-4-yl]methyl}sulfamide (25.0 mg, 0.0618 mmol), 4-fluorobenzylamine (14.1 µL, 0.124 mmol), and DIPEA (10.8 µL, 0.0618 mmol) in EtOH (0.4 mL) was heated at 100° C. for 10 minutes using microwave irradiation. Upon cooling, the mixture was concentrated and the residue dissolved in TFA/water (1 mL, 9:1). The solution was stirred for 10 minutes, concentrated, taken up in MeOH, then concentrated. The residue was purified by reverse phase HPLC to yield 6.5 mg (23%) of final compound.

LCMS: Rt. 1.28 min ES+ 454 (formic acid).

$^1$H-NMR (300 MHz, CD$_3$OD): δ 8.32 (s, 1H); 8.16 (s, 1H); 7.43-7.36 (m, 2H); 7.07-6.99 (m, 2H); 5.87 (d, J=7.0 Hz, 1H); 4.89 (dd, J=5.5, 7.0 Hz, 1H); 4.81-4.75(m, 2H); 4.36-4.28 (m, 2H); 3.40-3.35 (m, 2H).

Example 122

((2R,3S,4R,5R)-3,4-dihydroxy-5-(6-methyl-9H-purin-9-yl)-tetrahydrofuran-2-yl)methyl sulfamate (I-104)

Step a: [(3aR,4R,6R,6aR)-6-(6-chloro-9H-purin-9-yl)-2,2-dimethyltetrahydrofuro[3,4-d][1,3]dioxol-4-yl]methyl tritylsulfamate To a solution of ((3aR,4R,6R,6aR)-(6-(6-chloro-9H-purin-9-yl)-2,2-dimethyltetrahydrofuro[3,4-d][1,3]dioxol-4-yl) methyl tritylsulfamate (0.150 g, 0.231 mmol) in THF (2.0 mL) was added Pd(PPh$_3$)$_4$ (0.015 g) followed by a solution of MeZnCl in THF (2M, 0.17 mL, 0.347 mmol) over 15 min. The reaction was heated at 60° C. for 1 h under atmosphere of argon. The reaction was cooled to r.t., quenched with saturated NH$_4$Cl and extracted with EtOAc. The combined organics were washed with saturated aq EDTA.Na$_2$, water, dried (Na$_2$SO$_4$) and concentrated to give the product (0.28 g) which was used without further purification.

LCMS: R.t=2.00 min, ES+ 628 (ammonium acetate).

Step b: ((2R,3S,4R,5R)-3,4-dihydroxy-5-(6-methyl-9H-purin-9-yl)-tetrahydrofuran-2-yl)methyl sulfamate (I-104)

The title compound was prepared as described in Example 67 step f, and purified by preparative HPLC.

LCMS: R.t=0.79 min, ES+ 346 (formic acid).

$^1$H-NMR (400 MHz, d$_6$-DMSO): δ 8.80 (s, 1H); 8.67 (s, 1H); 7.60 (bs, 2H); 6.06 (d, J=5.2 Hz, 1H); 5.70-5.65 (m, 1H); 5.53-5.47 (m, 1H); 4.70-4.66 (m, 1H); 4.32-4.17 (m, 2H); 2.73 (s, 3H).

Example 123

{(2R,3S,4R,5R)-5-[6-(1,3-dihydro-2H-isoindol-2-ylmethyl)-9H-purin-9-yl]-3,4-dihydroxytetrahydrofuran-2-yl}methyl sulfamate (I-122)

Step a: ((3aR,4R,6R,6aR)-6-{6-[(1,3-dioxo-1,3-dihydro-2H-isoindol-2-yl)methyl]-9H-purin-9-yl}-2,2-dimethyltetrahydrofuro[3,4-d][1,3]dioxol-4-yl)methyl tritylsulfamate To a suspension of Zn (1.17 g, 17.9 mmol) in DMF (5.0 mL), was added Me$_3$SiCl (30.0 µL, 0.237 mmol) and 1,2 dibromoethane (20.0 µL, 0.232 mmol). The mixture was stirred at r.t. for 15 min then cooled to 0° C. To this was added N-bromomethylphthalimide (4.30 g, 17.9 mmol) in DMF (20.0 mL) dropwise, the greenish mixture was stirred at r.t. overnight then transferred into a solution of Pd(PPh$_3$)$_4$ (0.047 g, 0.040 mmol) and [(3aR,4R,6R,6aR)-6-(6-chloro-9H-purine-9-yl)-2,2-dimethyltetrahydrofuro[3,4-d][1,3]dioxol-4-yl]methyltritylsulfamate (0.5 g, 0.818 mmol) in DMF (8.0 mL) under argon. The mixture was stirred at r.t. for 2 days. The reaction was concentrated and the residue was dissolved in DCM, extracted with saturated aq EDTA.Na$_2$, dried (MgSO$_4$), filtered and concentrated. The crude product was purified by flash chromatography (20 to 75% EtOAc/hexanes) to afford the title compound (0.243 g, 39%).

LCMS: R.t. 2.13 min ES+ 773 (formic acid)

Step b: {(3aR,4R,6R,6aR)-6-[6-(aminomethyl)-9H-purin-9-yl]-2,2-dimethyltetrahydrofuro[3,4-d][1,3]dioxol-4-yl}methyl tritylsulfamate A solution of [(3aR,4R,6R,6aR)-6-{6[(1,3]dioxol 1,3-dihdro-2H-isoindol-2yl)methyl]-9H-purine-9-yl)-2,2-dimethyltetrahyrofuro[3,4-d][1,3]dioxol-4-yl]-methyltritylsulfamate (0.286 g, 0.370 mmol) and hydrazine hydrate (0.20 mL, 3.70 mmol) in EtOH (7.0 mL) was heated at reflux for 45 min. The mixture was cooled to r.t., filtered and concentrated to give the title compound (0.219 g, 92%) which was used without further purification LCMS: R.t. 1.41 min ES+ 643 (ammonium acetate).

Step c: {(3aR,4R,6R,6aR)-6-[6-(1,3-dihydro-2H-isoindol-2-ylmethyl)-9H-purin-9-yl]-2,2-dimethyltetrahydrofuro[3,4-d][1,3]dioxol-4-yl}methyl tritylsulfamate A solution of [(3aR,4R,6R,6aR)-6-[6-(aminomethyl)-9H-purine-9-yl)-2,2-dimethyltetrahyrofuro[3,4-d][1,3]dioxol-4-yl]methyltritylsulfamate (0.156 g, 0.243 mmol), o-xylene dibromide (0.065 g, 0.243 mmol), n-Bu$_4$NI (0.03 g, 0.08 mmol), and Na$_2$CO$_3$ (0.052 g, (0.485 mmol) in THF (5.00 mL) was heated at reflux for 3 h. Water (5 mL) was added and the reaction mixture was extracted with ethyl acetate, dried over MgSO$_4$, and concentrated. The crude product was purified by flash chromatography (0 to 10% MeOH/DCM) to afford the title compound (0.10 g, 76%).

LCMS: R.t. 1.61 min ES+ 745 (ammonium acetate).

Step d: {(2R,3S,4R,5R)-5-[6-(1,3-dihydro-2H-isoindol-2-ylmethyl)-9H-purin-9-yl]-3,4-dihydroxytetrahydrofuran-2-yl}methyl sulfamate (I-122)

The title compound was prepared as described in Example 67, step f, and purified by preparative HPLC.

LCMS: R.t. 0.92 min ES+ 463 (formic acid)

$^1$H-NMR (300 MHz, CD$_3$OD): δ 8.90 (s, 1H); 8.70 (s, 1H); 7.29-7.25 (m, 4H); 6.22 (d, J=4.9 Hz, 1H); 4.84-4.71 (m, 3H); 4.48-4.34 (m, 8H).

Example 124

((2R,3S,4R,5S)-5-(6-((2,3-dihydro-1H-inden-2-yl)methyl)-9H-purin-9-yl)-3,4-dihdrofuran-2-yl)methyl sulfamate (I-111)

Step a: ((3aR,4R,6S,6aR)-6-(6-((2,3-dihdro-1H-inden-2-yl)methyl)-9H-purin-9yl)-2-2-dimethyl-tetrahydrofuro[3,4-d][1,3]dioxol-4-yl)methyl tritylsulfamate To a suspension of Zn (0.184 g, 2.82 mmol) in THF (0.8 mL) under argon was added Me$_3$SiCl (4.4 μL, 0.035 mmol) and 1,2-dibromoethane (3.0 μL, 0.035 mmol). The mixture was stirred at r.t. for 15 min and then cooled to 0° C. 2-(Iodomethyl)-2,3-dihydro-1H-indene (0.364 g, 1.40 mmol) (Taniguchi, K.; Kuroda, S.; Tsubaki, K.; Shimizu, Y.; Takasugi, H. Preparation of piperidino derivatives which promote growth hormone release. WO9851687) in 3.2 mL THF was added dropwise. The greenish solution was stirred at 40° C. overnight. The resulting mixture was transferred into a solution of Pd(PPh$_3$)$_4$ (0.04 g, 0.035 mmol) and [(3aR,4R,6R,6aR)-6-(6-chloro-9H-purine-9-yl)-2,2-dimethyltetrahyrofuro[3,4-d][1,3]dioxol-4-yl]methyltritylsulfamate (0.456 g, 0.704 mmol) in THF (3.2 mL) under argon and stirred at 40° C. for 5 h then concentrated. The residue was dissolved in DCM, extracted with saturated aq EDTA.Na$_2$, dried (MgSO$_4$), filtered and concentrated. The crude product was purified by flash chromatography (0 to 5% MeOH/DCM) to afford the title compound (0.098 g, 17%).

LCMS: R.t. 2.77 min ES+ 744 (ammonium acetate).

Step b: ((2R,3S,4R,5S)-5-(6-((2,3-dihydro-1H-inden-2-yl)methyl)-9H-purin-9-yl)-3,4-dihdrofuran-2-yl)methyl sulfamate (I-111)

The title compound was prepared as described in Example 67, step f, and purified by preparative HPLC.

LCMS: R.t. 2.19 min; ES+ 446 (formic acid).

$^1$H-NMR (300 MHz, CD$_3$OD): δ 8.51 (s, 1H); 8.47 (s, 1H); 7.22-7.19 (m, 2H); 7.12-7.09 (m, 2H); 6.15 (d, J=4.9 Hz, 1H); 4.74-4.71 (m, 1H); 4.64.59 (m, 2H); 4.45-4.32 (m, 2H); 3.40-2.85 (m, 7H).

Example 125

[(2R,3S,4R,5R)-5-(6-cyclopropyl-9H-purin-9-yl)-3,4-dihydroxytetrahydrofuran-2-yl]methyl sulfamate (I-114)

Step a: [(3aR,4R,6R,6aR)-2,2-dimethyl-6-(6-vinyl-9H-purin-9-yl)tetrahydrofuro[3,4d][1,3]dioxol-4-yl]methyl acetate To a solution of [(3aR,4R,6R,6aR)-6-(6-chloro-9H-purin-9-yl)-2,2-dimethyltetrahydrofuro[3,4-d][1,3]dioxol-4-yl]methyl acetate (1.24 g, 3.36 mmol) in dichloroethane (20 mL) were added tributyl(vinyl)stannane (1.50 mL, 5.10 mmol) and Pd(PPh$_3$)$_2$Cl$_2$ (118 mg, 0.16 mmol). The rxn mixture was heated at reflux until the starting material was consumed, concentrated, and the residue was purified by flash chromatography (0 to 50% EtOAc/hexanes) to obtain the title compound as a viscous oil (1.03 g, 85%).

LCMS: R.t. 1.38 min ES+ 361 (formic acid).

Step b: [(3aR,4R,6R,6aR)-6-(6-cyclopropyl-9H-purin-9-yl)-2,2-dimethyltetrahydrofuro[3,4-d][1,3]dioxol-4-yl]methanol A suspension of trimethylsulfoxonium iodide (150 mg, 0.68 mmol and NaH (60% in mineral oil, 18 mg, 0.75 mmol) in DMSO (2.00 mL) was stirred for 30 minutes at r.t. [(3aR, 4R,6R,6aR)-2,2-dimethyl-6-(6-vinyl-9H-purin-9-yl)tetrahydrofuro[3,4-d][1,3]dioxol-4-yl]methyl acetate (50 mg, 0.0.13 mmol) in DMSO (3 mL) was added slowly and the reaction was stirred at r.t. for 90 minutes. The reaction mixture was treated with saturated aq NH$_4$Cl and extracted with DCM. The combined organics were washed with brine, dried (MgSO$_4$), filtered and concentrated. The residue was purified by flash chromatography (0 to 50% EtOAc/hexanes) to yield the title compound (15 mg, 33%).

LCMS: R.t. 1.20 min ES+ 333 (formic acid).

Step c: [(2R,3S,4R,5R)-5-(6-cyclopropyl-9H-purin-9-yl)-3,4-dihydroxytetrahydrofuran-2-yl]methyl sulfamate (I-114)

The title compound was prepared following the procedure described in Example 1, steps c-d.

LCMS: R.t. 1.29 min ES+ 372 (formic acid).

$^1$H-NMR (400 MHz, CD$_3$OD): δ 8.68 (s, 1H), 8.57 (s, 1H), 6.16 (d, J=5.0 Hz, 1H), 4.73 (t, J=5.0 Hz, 2H), 4.44-4.41 (m, 2H), 4.33-4.32 (m, 1H), 2.76-2.69 (m, 1H), 1.39-1.35 (m, 2H), 1.27-1.23 (m, 2H).

Example 126

(2R,3S,4R,5R)-3,4-dihydroxy-5-[6-(2-methoxyethyl)-9H-purin-9-yl]tetrahydrofuran-2-yl)methyl sulfamate (I-137)

Step a: 9-[(3aR,4R,6R,6a-R)-6-({[tert-butyl(dimethyl)silyl]oxy}methyl)-2,2-dimethyltetrahydrofuro[3,4-d][1,3]dioxol-4-yl]-6-chloro-9H-purine To a solution of [(3aR,4R,6R,6aR)-6-(6-chloro-9H-purin-9-yl)-2,2-dimethyltetrahydrofuro[3,4-d][1,3]dioxol-4-yl]methanol (2.00 g, 6.12 mmol) and imidazole (0.83 g, 12.24 mmol) in DMF (40 mL) at 0° C. was added TBSCl in DMF (10 mL) dropwise. The solution was stirred for 30 minutes at 0° C. and r.t. for 2 h. The reaction was concentrated and the residue was diluted with DCM and washed with water. The organic layer was dried (Na$_2$SO$_4$), filtered and concentrated. The residue was purified by flash chromatography (0 to 30% EtOAc/hexanes) to yield the title compound (1.82 g, 68%).

Step b: 9-[(3aR,4R,6R,6aR)-6-({[tert-butyl(dimethyl)silyl]oxy}methyl)-2,2-dimethyltetrahydrofuro[3,4-d][1,3]dioxol-4-yl]-6-vinyl-9H-purine To a solution of 9-[(3aR,4R,6R,6aR)-6-({[tert-butyl(dimethyl)silyl]oxy}methyl)-2,2-dimethyltetrahydrofuro[3,4-d][1,3]dioxol-4-yl]-6-chloro-9H-purine (330 mg, 0.74 mmol) and tributyl(vinyl)stannane (0.26 mL, 0.88 mmol) in 1,2 dichloroethane (10 mL) was added Pd(Ph$_3$P)$_2$Cl$_2$ (26 mg, 0.03 mmol) and the rxn mixture was heated at reflux overnight. The solvent was removed and the residue purified by flash chromatography (0 to 20% EtOAc/hexanes) to yield 215 mg (67%) of the title compound.
LCMS: R.t. 2.31 min ES+ 434 (formic acid).

Step c: 9-[(3aR,4R,6R,6aR)-6-({[tert-butyl(dimethyl)silyl]oxy}methyl)-2,2-dimethyltetrahydrofuro[3,4-d][1,3]dioxol-4-yl]-6-(2-methoxyethyl)-9H-purine To a stirred solution of 9-[(3aR,4R,6R,6aR)-6-({[tert-butyl(dimethyl)silyl]oxy}-methyl)-2,2-dimethyltetrahydrofuro[3,4-d][1,3]dioxol-4-yl]-6-vinyl-9H-purine (100 mg, 0.23 mmol) in DCM (5.0 mL) was added NaOMe (0.5M in MeOH, 4.6 mL, 2.2 mmol) at 0° C. The reaction was stirred for 2 h at 0° C. and r.t. overnight. The mixture was diluted with DCM and washed with saturated aq NH$_4$Cl. The organic layer was dried (Na$_2$SO$_4$), filtered and concentrated. The residue was purified by flash chromatography (0 to 10% MeOH/DCM) to yield 70 mg (66%) of the title compound.
LCMS: R.t. 2.11 min ES+ 466 (formic acid).

Step d: {(3aR,4R,6R,6aR)-6-[6-(2-methoxyethyl)-9H-purin-9-yl]-2,2-dimethyltetrahydrofuro[3,4-d][1,3]dioxol-4-yl}methanol To a solution of 9-[(3aR,4R,6R,6aR)-6-({[tert-butyl(dimethyl)silyl]oxy}methyl)-2,2-dimethyltetrahydrofuro[3,4-d][1,3]dioxol-4-yl]-6-(2-methoxyethyl)-9H-purine (70 mg, 0.15 mmol) in THF/pyridine (1.5 mL, 1:1) was added hydrofluoric acid in pyridine (15 drops). The reaction was stirred overnight, quenched with saturated aq NaHCO$_3$, extracted with EtOAc, dried (Na$_2$SO$_4$), filtered and concentrated. The residue was purified by flash chromatography (0 to 50% DCM/EtOAc to furnish 37 mg (70%) of the title compound.
LCMS: R.t. 1.12 min ES+ 351 (formic acid).

Step e: 2R,3S,4R,5R)-3,4-dihydroxy-5-[6-(2-methoxyethyl)-9H-purin-9-yl]tetrahydrofuran-2-yl}methyl sulfamate (I-137)

The title compound was prepared following the procedure described in Example 1, steps c-d.
LCMS: R.t. 1.11 min ES+ 390 (formic acid).
$^1$H-NMR (400 MHz, d$_6$-DMSO): δ 8.84 (s, 1H); 8.67 (s, 1H); 6.05 (d, J=5.5 Hz, 1H); 4.68 (t, J=5.3 Hz, 2H); 4.31-4.17 (m, 4H); 3.88 (t, J=6.5 Hz, 2H); 3.33 (t, J=6.5 Hz, 2H); 3.15 (s, 3H).

Example 127

(2R,3S,4R,5R)-3,4-dihydroxy-5-(6-{[(pyridin-3-ylcarbonyl)amino]methyl}-9H-purin-9-yl)tetrahydrofuran-2-yl]methyl sulfamate (I-105)

Step a: [(3aR,4R,6R,6aR)-2,2-dimethyl-6-(6-{[(pyridin-3-ylcarbonyl)amino]methyl}-9H-purin-9-yl)tetrahydrofuro[3,4-d][1,3]dioxol-4-yl]methyltritylsulfamate To a solution of {(3aR,4R,6R,6aR)-6-[6-(aminomethyl)-9H-purin-9-yl]-2,2-dimethyltetrahydrofuro[3,4-d][1,3]dioxol-4-yl}methyl tritylsulfamate (145 mg, 0.22) and DIPEA (0.08 mL, 0.48 mmol) at 0° C. in DCM (5.0 mL) was added nicotinoyl chloride (64 mg, 0.36 mmol). After one hour, the reaction was quenched with saturated aq NH$_4$Cl and extracted with DCM. The combined organics were dried (Na$_2$SO$_4$), filtered and concentrated. The residue was purified by flash chromatography (0 to 10% MeOH/DCM to furnish the title compound (65 mg, 40%).
LCMS: R.t. 86 min ES+ 748 (formic acid).

Step b: (2R,3S,4R,5R)-3,4-dihydroxy-5-(6-{[(pyridin-3-ylcarbonyl)amino]methyl}-9H-purin-9-yl)tetrahydrofuran-2-yl]methyl sulfamate (I-105)

The title compound was prepared following the procedure described in Example 1 step d.
LCMS: R.t. 1.05 min ES+ 466 (formic acid).
$^1$H-NMR (300 MHz, CD$_3$OD): δ 9.08-9.07 (m, 1H); 8.87 (s, 1H); 8.7-8.66 (m, 1H); 8.63 (s, 1H); 8.35-8.31 (m, 1H); 7.58-7.53 (m, 1H); 6.21 (d, J=4.9 Hz, 1H); 5.11 (s, 2H); 4.75 (t, J=5.0 Hz, 1H); 4.45-4.32 (m, 4H).

Example 128

(2R,3S,4R,5R)-3,4-dihydroxy-5-(6-{[(2-methoxybenzoyl)amino]methyl}-9H-purin-9-yl)tetrahydrofuran-2-yl]methyl sulfamate (I-116)

Step a: [(3aR,4R,6R,6aR)-6-(6-{[(2-methoxybenzoyl)amino]methyl}-9H-purin-9-yl)-2,2-dimethyltetrahydrofuro[3,4-d][1,3]dioxol-4-yl]methyl tritylsulfamate The title compound was prepared following the procedure described in Example 127, step a using {(3aR,4R,6R,6aR)-6-[6-(aminomethyl)-9H-purin-9-yl]-2,2-dimethyltetrahydrofuro[3,4-d][1,3]dioxol-4-yl}methyl tritylsulfamate and 2-methoxybenzoyl chloride.
LCMS: R.t. 2.14 min ES+ 777 (formic acid).

Step b: (2R,3S,4R,5R)-3,4-dihydroxy-5-(6-{[(2-methoxybenzoyl)amino]methyl}-9H-purin-9-yl) tetrahydrofuran-2-yl]methyl sulfamate (I-116)

The title compound was prepared following the procedure described in Example 1 step d.
LCMS: R.t. 1.16 min ES+ 495 (formic acid).
$^1$H-NMR (300 MHz, d$_6$-DMSO): δ 8.92 (s, 1H); 8.75 (s, 1H); 7.93-7.9 (m, 1H); 7.54-7.48 (m, 2H); 7.14 (d, 1H); 7.06 (t, J=7.2 Hz, 1H); 6.10 (d, J=5.2 Hz, 1H); 5.74-5.52 (m, 2H); 5.03-5.02 (m, 2H); 4.71-4.67 (m, 1H); 4.28-4.20 (m, 4H); 3.99 (s, 3H).

Example 129

(2R,3S,4R,5R)-5-(6-{[(3,5-difluorobenzoyl)amino] methyl}-9H-purin-9-yl)-3,4-dihydroxytetrahydrofuran-2-yl]methyl sulfamate (I-125)

Step a: [(3aR,4R,6R,6aR)-6-(4[(3aR,4R,6R,6aR)-6-(6-{[(3,5-difluorobenzoyl)amino]methyl}a.9H-purin-9-yl)-2,2-dimethyltetrahydrofuro[3,4-d][1,3]dioxol-4-yl]methyl tritylsulfamate The title compound was prepared following the procedure described in Example 127, step a using {(3aR,4R,6R,6aR)-6-[6-(aminomethyl)-9H-purin-9-yl]-2,2-dimethyltetrahydrofuro[3,4-d][1,3]dioxol-4-yl}methyl tritylsulfamate and 3,5-difluorobenzoyl chloride.
LCMS: R.t. 2.14 min ES+ 783 (formic acid).

Step b: (2R,3S,4R,5R)-5-(6-{[(3,5-difluorobenzoyl) amino]methyl}-9H-purin-9-yl)-3,4-dihydroxytetrahydrofuran-2-yl]methyl sulfamate (I-125)

The title compound was prepared following the procedure described in Example 1 step d.
LCMS: R.t. 1.23 min ES+ 501 (formic acid).
$^1$H-NMR (300 MHz, CD$_3$OD): δ 8.88 (s, 1H); 8.65 (s, 1H); 7.54-7.51 (m, 2H); 7.21-7.14 (m, 1H); 6.21 (d, J=4.9 Hz, 1H); 5.08 (s, 2); 4.75 (t, J=5.0 Hz, 1H); 4.45-4.32 (m, 4H).

Example 130

((2R,3S,4R,5R)-5-{6-[(benzoylamino)methyl]-9H-purin-9-yl}-3,4-dihydroxytetrahydrofuran-2-yl)methyl sulfamate (I-129)

The title compound was prepared as described in Example 127 steps a-b, using benzoyl chloride in step a and purified by preparative HPLC.
LCMS: R.t=0.97 min, ES+ 465 (formic acid).
$^1$H-NMR (400 MHz, d$_6$-DMSO): δ 9.18 (t, J=6.1 Hz, 1H); 8.88 (s, 1H); 8.73 (s, 1H); 7.92 (d, J=7.5 Hz, 2H); 7.61-7.46 (m, 5H); 6.09 (d, J=5.5 Hz, 1H); 5.73 (d, J=5.8 Hz, 1H); 5.53 (d, J=3.3 Hz, 1H); 4.93 (d, J=5.5 Hz, 2H); 4.70 (q, J=5.2 Hz, 1H), 4.32-4.17 (m, 4H).

Example 131

((2R,3S,4R,5R)-5-{6-[(1,3-dioxo-1,3-dihydro-2H-isoindol-2-yl)methyl]-9H-purin-9-yl}-3,4-dihydroxytetrahydrofuran-2-yl)methyl sulfamate (I-120)

The title compound was prepared as described in Example 67, step f, using [(3aR,4R,6R,6aR)-6-{6[(1,3]dioxol 1,3-dihdro-2H-isoindol-2yl)-methyl]-9H-purine-9-yl)-2,2-dimethyltetrahyrofuro[3,4-d][1,3]dioxol-4-yl]methyltritylsulfamate and purified by preparative HPLC.
LCMS: R.t=1.21 min, ES+ 491 (formic acid).
$^1$H-NMR (400 MHz, d$_6$-DMSO): δ 8.84 (s, 1H); 8.69 (s, 1H); 7.97-7.89 (m, 4H); 7.58 (bs, 2H); 6.06 (d, J=5.3 Hz, 1H); 5.72 (d, J=5.5H, 1 Hz); 5.51 (d, J=5.3 Hz, 1H); 5.28 (s, 2H); 4.67 (q, J=5.5, 10.5 Hz, 1H); 4.30-4.16 (m, 4H).

Example 132

{(2R,3S,5R)-3-Hydroxy-5-[5-iodo-4-(2-phenylethyl)-7H-pyrrolo[2,3-d]pyrimidin-7-yl]tetrahydrofuran-2-yl}methyl sulfamate (I-117)

Step a:
5-Iodo-4-phenethyl-7H-pyrrolo[2,3-d]pyrimidine

To a solution of 4-phenethyl-7H-pyrrolo[2,3-d]pyrimidine (3.15 g, 14.1 mmol) in AcCN was added N-iodosuccinimide and the mixture was stirred at r.t. for 12 hr. The precipitate was collected and recrystallized from MeOH to give the title compound (4.06 g, 83%).
LCMS: R.t. 1.59 min ES+ 350 (ammonium acetate).

Step b: {(2R,3S,5R)-3-Hydroxy-5-[5-iodo-4-(2-phenylethyl)-7H-pyrrolo[2,3-d]pyrimidin-7-yl]tetrahydrofuran-2-yl}methyl sulfamate (I-117)

The title compound was prepared following the procedure described in Example 91, steps a-e, using TBSCl instead of TIPSCl in step c, and using 5-iodo-4-phenethyl-7H-pyrrolo-[2,3-d]pyrimidine in step a.
LCMS: R.t. 7.15 min (15 min run) ES+ 545 (ammonium acetate).
$^1$H-NMR (400 MHz, CD$_3$OD): δ 8.70 (s, 1H); 7.88 (s, 1H); 7.30-7.35 (m, 2H); 7.23-7.28 (m, 2H); 7.15-7.19 (m, 1H); 6.78 (dd, J=6.3, 8.0 Hz, 1H); 4.60-4.56 (m, 1H); 4.31-4.29 (m, 2H); 4.20-4.17 (m, 1H); 3.61-3.57 (m, 2H); 3.10-3.02 (m, 2H); 2.66-2.60 (m, 1H); 2.43-2.37 (m, 1H).

Example 133

{(2R,3S,5R)-5-[5-Ethynyl-4-(2-phenylethyl)-7H-pyrrolo[2,3-d]pyrimidin-7-yl]-3-hydroxytetrahydrofuran-2-yl}methyl sulfamate (I-135)

Step a: (2R,3S,5R)-2-({[tert-Butyl(dimethyl)silyl] oxy}methyl)-5-{4-(2-phenylethyl)-5-[(trimethylsilyl) ethynyl]-7H-pyrrolo[2,3-d]pyrimidin-7-yl}tetrahydrofuran-3-yl acetate To a suspension of (2R,3S,5R)-2-((tert-butyldimethylsilyloxy)methyl)-5-(5-iodo-4-phenethyl-7H-pyrrolo[2,3-d]pyrimidin-7-yl)-tetrahydrofuran-3-yl acetate 9 obtained from example 132, step d) (0.36 g, 0.578 mmol), CuI (0.022 g, 0.0116 mmol), Pd(PPh$_3$)$_2$Cl$_2$ (0.040 g, 0.0570 mmol) and DIPEA (0.20 mL, 1.15 mmol) in DMF was added ethynyltrimethylsilane (0.230 g, 2.34 mmol). The mixture was stirred at r.t. for 12 h. The reaction mixture was diluted with EtOAc. The organic layer was washed with H$_2$O, dried (MgSO$_4$), filtered, and concentrated. The residue was purified by flash chromatography (0 to 25% EtOAc/hexanes) to give the title compound (0.305 g, 58%).
LCMS: R.t. 2.96 min ES+ 592 (ammonium acetate).

Step b: (2R,3S,5R)-2-{[(Aminosulfonyl)oxy]methyl}-5-{4-(2-phenylethyl)-5-[(trimethylsilyl)ethynyl]-7H-pyrrolo[2,3-d]pyrimidin-7-yl}tetrahydrofuran-3-yl acetate The title compound was prepared following the procedure described in Example 40, steps e-f.
LCMS: R.t. 2.12 min ES+ 557 (ammonium acetate).

Step c: {(2R,3S,5R)-5-[5-Ethynyl-4-(2-phenylethyl)-7H-pyrrolo[2,3-d]pyrimidin-7-yl]-3-hydroxytetrahydrofuran-2-yl}methyl sulfamate (I-135)

To a solution of (2R,3S,5R)-2-{[(aminosulfonyl)oxy]methyl}-5-{4-(2-phenylethyl)-5-[(trimethylsilyl)ethynyl]-7H-pyrrolo[2,3-d]pyrimidin-7-yl}tetrahydrofuran-3-yl acetate (0.254 g, 0.457 mmol) in MeOH (5 mL) at r.t. was added $K_2CO_3$ (0.168 g, 1.22 mmol) and the mixture was stirred for 2 h. The reaction mixture was diluted with $CH_2Cl_2$, washed with saturated aq $NaHCO_3$ dried over $MgSO_4$, filtered, and concentrated. The residue was purified by flash chromatography (0 to 10% MeOH/DCM) to give the title compound (0.126 g, 62%).
LCMS: R.t. 1.51 min ES+ 433 (ammonium acetate).
$^1$H-NMR (400 MHz, $CD_3OD$): δ 8.71 (s, 1H); 7.95 (s, 1H); 7.34-7.22 (m, 4H); 7.20-7.13 (m, 1H); 6.77 (dd, J=8.0, 6.3 Hz, 1H); 4.61-4.56 (m, 1H); 4.33-4.29 (m, 2H); 4.21-4.17 (m, 1H); 3.77 (s, 1H); 3.59-3.54 (m, 2H); 3.10-3.06 (m, 2H); 2.67-2.60 (m, 1H); 2.45-2.44 (m, 1H).

Example 134

{(2R,3S,5R)-5-[5-Ethyl-4-(2-phenylethyl)-7H-pyrrolo[2,3-d]pyrimidin-7-yl]-3-hydroxytetrahydrofuran-2-yl}methyl sulfamate (I-124)

A suspension of {(2R,3S,5R)-5-[5-ethynyl-4-(2-phenylethyl)-7H-pyrrolo[2,3-d]pyrimidin-7-yl]-3-hydroxytetrahydrofuran-2-yl}methyl sulfamate (0.0824 g, 0.190 mmol) and Pd/C (10% wt, ~50% $H_2O$, 0.01 g) in EtOH (10 mL) was stirred under an atmosphere of $H_2$ (1 atm) for 5 h at r.t. The reaction mixture was filtered through celite and the filtrate was concentrated. The residue was purified by flash chromatography (0 to 10% MeOH/DCM) to give the title compound (0.010 g, 11%).
LCMS: R.t. 7.70 min (15 min run) ES+ 447 (ammonium acetate).
$^1$H-NMR (400 MHz, $CD_3OD$): δ 8.65 (s, 1H); 7.43 (s, 1H); 7.26-7.12 (m, 5H); 6.81 (dd, J=8.3, 6.3 Hz, 1H); 4.58-4.56 (m, 1H); 4.30-4.29 (m, 2H); 4.19-4.16 (m, 1H); 3.37-3.33 (m, 2H); 3.10-3.05 (m, 2H); 2.85-2.78 (m, 2H); 2.65-2.59 (m, 1H); 2.38-2.32 (m, 1H); 1.31 (t, J=7.5 Hz, 3H).

Example 135

{(2R,3S,5R)-5-[5-[3-(Diethylamino)prop-1-yn-1-yl]-4-(2-phenylethyl)-7H-pyrrolo[2,3-d]pyrimidin-7-yl]-3-hydroxytetrahydrofuran-2-yl}methyl sulfamate (I-131)

Step a: (2R,3S,5R)-2-{[(Aminosulfonyl)oxy]methyl}-5-[5-[3-(diethylamino)prop-1-yn-1-yl]-4-(2-phenylethyl)-7H-pyrrolo[2,3-d]pyrimidin-7-yl]tetrahydrofuran-3-yl acetate The title compound was prepared following the procedure described in Example 133, step a using N,N-diethylprop-2-yn-1-amine.
LCMS: R.t. 1.56 min ES+ 570 (ammonium acetate)

Step b: {(2R,3S,5R)-5-[5-[3-(Diethylamino)prop-1-yn-1-yl]-4-(2-phenylethyl)-7H-pyrrolo[2,3-d]pyrimidin-7-yl]-3-hydroxytetrahydrofuran-2-yl}methyl sulfamate (I-131)

The title compound was prepared following the procedure described in Example 40, step g and purified by HPLC.
LCMS: R.t. 1.60 min ES+ 528 (ammonium acetate).
$^1$H-NMR (400 MHz, $CD_3OD$): 8.74 (s, 1H); 8.02 (s, 1H); 7.31-7.22 (m, 4H); 7.20-7.15 (m, 1H); 6.79 (dd, J=7.8, 6.3 Hz, 1H); 4.59-4.56 (m, 1H); 4.32-4.30 (m, 2H); 4.22-4.20 (m, 1H); 3.93 (s, 2H); 3.62-3.55 (m, 2H); 3.16-3.10 (m, 2H); 2.94-2.82 (m, 4H); 2.63-2.57 (m, 1H); 2.47-2.39 (m, 1H); and 1.14 (t, J=7.0 Hz, 6H).

Example 136

((2R,3S,4R,5R)-5-{4-[(1S)-2,3-dihydro-1H-inden-1-ylamino]-1H-imidazo[4,5-c]pyridin-1-yl}-3,4-dihydroxytetrahydrofuran-2-yl)methyl sulfamate (I-149)

Step a: 4-amino-2-chloro-3-nitropyridine

To a solution of 4-amino-2-chloropyridine (10.0 g, 77.8 mmol) in concentrated $H_2SO_4$ (60 mL) at 0° C. was added 90% nitric acid (30 mL) dropwise. The solution was stirred at 0-5° C. for 30 min then poured onto ice (carefully). The pH was brought to ~3 with concentrated aq ammonium hydroxide (~150 mL) to obtain a white precipitate which was isolated and dried by filtration. The white solid was dissolved in sulfuric acid (100 mL), heated at 80° C. for 5 h, stirred at r.t. overnight, then poured on crushed ice. At 0° C. the pH was adjusted to ~3 with concentrated aq ammonium hydroxide (~250 mL) to obtain a yellow precipitate which was isolated by filtration. The solid was dried under vacuum overnight to obtain ~13 g of a mixture of 3- and 5-nitro isomers. A sample (4.0 g) was purified by flash chromatography (0 to 20% DCM/EtOAc) to obtain 1.77 g of the product as a fluffy yellow solid.
LCMS: R.t=1.15 min, ES+ 174 (formic acid).

Step b: N(2)-[(1S)-2,3-dihydro-1H-inden-1-yl]-3-nitropyridine-2,4-diamine 4-amino-2-chloro-3-nitropyridine (1.67 g, 9.6 mmol), (S)-(+)-1-aminoindan (1.85 mL, 14.4 mmol) and triethylamine (2.68 mL, 19.2 mmol) were refluxed in EtOH (20 mL) for 14 h. The reaction was concentrated and the residue was purified by flash chromatography (0 to 25% DCM/EtOAc) to obtain the product (2.59 g, 72%) as a yellow solid.
LCMS: R.t=1.16 min, ES+ 271 (formic acid).

Step c: N(2)-[(1S)-2,3-dihydro-1H-inden-1-yl]pyridine-2,3,4-triamine

To a suspension of N(2)-[(1S)-2,3-dihydro-1H-inden-1-yl]-3-nitropyridine-2,4-diamine (1.042 g, 3.9 mmol) and iron (1.29 g, 23.1 mmol) in i-PrOH/water (40 mL, 3:1) was added concentrated hydrochloric acid (400 μL). The reaction was heated at 60° C. for 2 h and filtered through a pad of celite. The filtrate was concentrated to dryness to obtain the product as a grey solid (1.0 g, quantitative) which was used without further purification.
LCMS: R.t=0.90 min, ES+ 241 (formic acid).

Step d: N-[(1S)-2,3-dihydro-1H-inden-1-yl]-1H-imidazo[4,5-c]pyridin-4-amine

To a suspension of N(2)-[(1S)-2,3-dihydro-1H-inden-1-yl]pyridine-2,3,4-triamine (1.0 g, 4.2 mmol) in ethyl orthoformate (20 mL) was added conc. hydrochloric acid (1.0 mL). The reaction was stirred for 14 h, the solution was concentrated and the residue was purified by flash chromatography (1 to 10% MeOH/DCM) to obtain the product as a brown solid (947 mg, 91%).
LCMS: R.t=0.89 min, ES+ 251 (formic acid).

Step e: (2R,3R,4R,5R)-2-[(benzoyloxy)methyl]-5-{4-[(1S)-2,3-dihydro-1H-inden-1-ylamino]-1H-imidazo[4,5-c]pyridin-1-yl}tetrahydrofuran-3,4-diyl dibenzoate To a solution of N-[(1S)-2,3-dihydro-1H-inden-1-yl]-1H-imidazo[4,5-c]pyridin-4-amine (160 mg, 0.64 mmol) in AcCN (5 mL) was added N,O-bis(trimethylsilyl)acetamide (474 µL, 1.92 mmol) dropwise to obtain a clear solution which was refluxed for 10 min. The solution was allowed to cool to r.t and 1-O-acetyl-2,3,5-tri-O-benzoyl-β-D-ribofuranose (322 mg, 0.64 mmol) was added as a solution in AcCN (3 mL). Trimethylsilyl trifluoromethanesulfonate (115 µL, 0.64 mmol) was added dropwise and the reaction was heated at reflux for 3 h. The reaction was quenched with MeOH, concentrated, and the residue was purified by flash chromatography (0 to 25% DCM/EtOAc) to obtain the product as a white solid (266 mg, 60%).
LCMS: R.t=1.63 min, ES+ 695 (formic acid).

Step f: ((3aR,4R,6R,6aR)-6-{4-[(1S)-2,3-dihydro-1H-inden-1-ylamino]-1H-imidazo[4,5-c]pyridin-1-yl}-2,2-dimethyltetrahydrofuro[3,4-d][1,3]dioxol-4-yl)methanol A solution of (2R,3R,4R,5R)-2-[(benzoyloxy)methyl]-5-{4-[(1S)-2,3-dihydro-1H-inden-1-ylamino]-1H-imidazo[4,5-c]pyridin-1-yl}tetrahydrofuran-3,4-diyl dibenzoate (250 mg, 0.36 mmol) in 7 M ammonia in methanol (15 mL) was stirred for 16 h. The reaction was concentrated and the residue dissolved in acetone (5 mL). To this was added p-toluenesulfonic acid monohydrate (70 mg, 0.4 mmol) and 2,2-dimethoxypropane (500 µL, 4 mmol) and the reaction was stirred for 16 h. To this was added 0.5M aq NaHCO$_3$ (20 mL) and the volume was reduced in vacuo. The aq residue was extracted with CHCl$_3$ (3×), the combined organics were dried (Na$_2$SO$_4$), filtered, and concentrated. The residue was purified by flash chromatography (25 to 100% DCM/EtOAc) to obtain the product as a white powder (94 mg, 62%).
LCMS: R.t=1.05 min, ES+ 423 (formic acid).

Step g: ((2R,3S,4R,5R)-5-{4-[(1S)-2,3-dihydro-1H-inden-1-ylamino]-1H-imidazo[4,5-c]pyridin-1-yl}-3,4-dihydroxytetrahydrofuran-2-yl)methyl sulfamate (I-149)

The title compound was prepared following the procedure described in Example 67, steps e-f and purified by HPLC.
LCMS: R.t=0.91 min, ES+ 462 (formic acid).
$^1$H-NMR (300 MHz, d$_6$-DMSO): δ 8.25 (s, 1H); 8.16 (s, 1H); 7.80 (d, J=5.8 Hz, 1H); 7.66 (s, 2H); 7.26-7.08 (m, 4H); 6.92 (d, J=5.8 Hz, 1H); 6.76 (d, J=8.6 Hz, 1H); 5.90 (dd, J=16.2, 8.3 Hz, 1H); 5.83 (d, J=6.2 Hz); 4.37 (dd, 1H, J=5.9, 5.9 Hz); 4.29-4.10 (m, 4H); 2.99 (m, 1H); 2.83 (m, 1H); 2.47 (m, 1H); 2.07 (m, 1H).

Example 137

{(2R,3S,5R)-3-methoxy-5-[6-(2-phenylethyl)-9H-purin-9-yl]tetrahydrofuran-2-yl}methyl sulfamate (I-151)

Step a: 4-(2-phenylethyl)-7H-pyrrolo[2,3-d]pyrimidine

Phenethyl magnesium bromide (0.5 M solution in THF, 12 mL, 6.15 mmol) was added dropwise to a stirred solution of 4-chloro-7H-pyrrolo[2,3-d]pyrimidine (0.210 g, 1.37 mmol) and Fe(acac)$_3$ (0.1 g 0.273 mmol) in THF (5.0 mL) under Ar. The resulting reaction mixture was stirred at r.t. for 8 h. The mixture was poured onto a mixture of ice (10 mL) and NH$_4$Cl (0.5 g) and the product was extracted with CHCl$_3$. The combined organics were dried (Na$_2$SO$_4$), filtered and concentrated. The crude product was purified by flash chromatography (0 to 10% MeOH/DCM) to afford the title compound (0.166 g, 54%).
LCMS: R.t. 1.50 min ES+ 224 (ammonium acetate).

Step b: (2R,3S,5R)-2-({[tert-butyl(dimethyl)silyl]oxy}methyl)-5-[6-(2-phenylethyl)-9H-purin-9-yl]tetrahydrofuran-3-ol The title compound was prepared following the procedure described in Example 91 steps a-c using 4-(2-phenylethyl)-7H-pyrrolo[2,3-d]pyrimidine in step a and TBSCl instead of TIPSCl in step c.
LCMS: R.t. 2.06 min ES+ 455 (formic acid).

Step c: 9-[(2R,4S,5R)-5-({[tert-butyl(dimethyl)silyl]oxy}methyl)-4-methoxytetrahydrofuran-2-yl]-6-(2-phenylethyl)-9H-purine To a solution of (2R,3S,5R)-2-({[tert-butyl(dimethyl)silyl]oxy}methyl)-5-[6-(2-phenylethyl)-9H-purin-9-yl]tetrahydrofuran-3-ol (98 mg, 0.22 mmol) in THF (1.5 mL) at 0° C. was added NaH (60% in oil, 13 mg, 0.33 mmol) and the suspension stirred for 10 minutes. MeI (26 µL, 0.26 mmol) was added dropwise and the reaction was warmed to room temperature. After one hour the reaction was quenched with saturated aq NH$_4$Cl, partitioned between brine and EtOAc, separated, and the aq layer was extracted with EtOAc (5×). The combined organics were washed with brine, dried (Na$_2$SO$_4$), filtered, and concentrated. The residue was purified by flash chromatography (20 to 50% EtOAc/hexanes) to give the title compound (67 mg, 65%).
LCMS: R.t. 2.39 min ES+ 469 (formic acid).

Step d: {(2R,3S,5R)-3-methoxy-5-[6-(2-phenylethyl)-9H-purin-9-yl]tetrahydrofuran-2-yl]-methyl sulfamate (I-151)

The title compound was prepared following the procedure described in Example 40 steps e-f.
LCMS: R.t. 1.28 min ES+ 434 (formic acid).
$^1$H-NMR (400 MHz, CDCl$_3$) δ 8.86 (s, 1H); 8.27 (s, 1H); 7.25-7.16 (m, 5H); 6.44 (dd, J=6.2, 7.8 Hz, 1H); 5.82 (s, 2H); 4.40 (m, 3H); 4.21 (m, 1H); 3.43 (dd, J=7.8, 10.5 Hz, 2H); 3.38 (s, 3H); 3.17 (dd, J=5.8, 8.5 Hz, 2H); 2.82 (ddd, J=6.0, 7.9, 13.7 Hz, 1H); 2.57 (ddd, J=2.8, 6.2, 9.0 Hz, 1H).

Example 138

Enzyme Preparation

All protein accession numbers provided herein refer to the Entrez Protein database maintained by the National Center for Biotechnology Information (NCBI), Bethesda, Md.

Generation of E1 Enzymes

Following manufacturer instructions, baculoviruses were generated with the Bac-to-Bac Expression System (Invitrogen) for the following proteins: untagged NAEα (APPBP1; NP_003896.1), N-terminally His-tagged NAEβ (UBE1C; NP_003959.3), untagged SAEα (SAE1; NP_005491.1), N-terminally His-tagged SAEβ (UBA2; NP_005490.1), N-terminally His-tagged murine UAE (UBE1X; NP_033483). NAEα/His-NAEβ and SAEα/His-SAEβ complexes were generated by co-infection of Sf9 cells, which were harvested after 48 hours. His-mUAE was generated by single infection of Sf9 cells and harvested after 72 hours. Expressed proteins were purified by affinity chromatography (Ni-NTA agarose, Qiagen) using standard buffers.

Generation of E2 Enzymes

Ubc12 (UBE2M; NP_003960.1), Ubc9 (UBE2I; NP_003336.1), Ubc2 (UBE2A; NP_003327.2) were subcloned into pGEX (Pharmacia) and expressed as N-terminally GST tagged fusion proteins in *E. coli*. Expressed proteins were purified by conventional affinity chromatography using standard buffers.

Generation of Ubl Proteins

Nedd8 (NP_006147), Sumo-1 (NP_003343) and Ubiquitin (with optimized codons) were subcloned into pFLAG-2 (Sigma) and expressed as N-terminally Flag tagged fusion proteins in *E. coli*. Expressed proteins were purified by conventional chromatography using standard buffers.

Example 139

E1 Enzyme Assays

Nedd8-Activating Enzyme (NAE) HTRF Assay.

The NAE enzymatic reaction totaled 50 µL and contained 50 mM HEPES (pH 7.5), 0.05% BSA, 5 mM $MgCl_2$, 20 µM ATP, 250 µM GSH, 0.01 µM Ubc12-GST, 0.075 µM Nedd8-Flag and 0.28 nM recombinant human NAE enzyme. The enzymatic reaction mixture, with and without compound inhibitor, was incubated at 24° C. for 90 minutes in a 384-well plate before termination with 25 µL of Stop/Detection buffer (0.1M HEPES pH 7.5, 0.05% Tween20, 20 mM EDTA, 410 mM KF, 0.53 nM Europium-Cryptate labeled monoclonal anti-FLAG M2 antibody (CisBio International) and 8.125 µg/mL PHYCOLINK goat anti-GST allophycocyanin (XL-APC) antibody (Prozyme)). After incubation for 3 hours at 24° C., quantification of the FRET was performed on the Analyst™ HT 96.384 (Molecular Devices).

Compounds I-1, I-2, I-3, I-4, I-5, I-6, I-7, I-8, I-9, I-10, I-11, I-12, I-13, I-14, I-15, I-16, I-17, I-18, I-19, I-21, I-22, I-23, I-24, I-25, I-26, I-27, I-28, I-29, I-30, I-31, I-32, I-33, I-34, I-35, I-36, I-37, I-38, I-39, I-41, I-42, I-43, I-44, I-45, I-46, I-47, I-48, I-50, I-51, I-53, I-54, I-55, I-56, I-57, I-58, I-59, I-60, I-61, I-62, I-63, I-64, I-65, I-66, I-67, I-68, I-69, I-71, I-79, I-87, I-88, I-90, I-91, I-92, I-94, I-95, I-96, I-97, I-98, I-100, I-101, I-102, I-103, I-104, I-105, I-107, I-108, I-109, I-110, I-111, I-112, I-113, I-114, I-115, I-116, I-118, I-119, I-120, I-121, I-122, I-123, I-124, I-125, I-126, I-127, I-128, I-129, I-130, I-132, I-134, I-135, I-136, I-137, I-138, I-139, I-140, I-141, I-143, I-144, I-145, I-146, I-147, I-148, I-149, I-150, and I-152 exhibited $IC_{50}$ values less than or equal to 1 µM in this assay.

Compounds I-1, I-2, I-3, I-4, I-5, I-6, I-7, I-8, I-9, I-10, I-11, I-12, I-13, I-14, I-15, I-16, I-17, I-18, I-19, I-21, I-22, I-23, I-24, I-25, I-26, I-27, I-28, I-29, I-30, I-31, I-32, I-33, I-37, I-39, I-42, I-43, I-45, I-46, I-47, I-48, I-50, I-51, I-53, I-54, I-55, I-56, I-57, I-58, I-59, I-60, I-61, I-62, I-63, I-64, I-65, I-66, I-67, I-68, I-69, I-71, I-79, I-87, I-88, I-90, I-91, I-92, I-94, I-95, I-96, I-100, I-101, I-102, I-103, I-104, I-105, I-107, I-108, I-109, I-110, I-111, I-112, I-113, I-114, I-115, I-116, I-118, I-119, I-120, I-121, I-122, I-123, I-125, I-126, I-127, I-128, I-129, I-130, I-132, I-134, I-136, I-137, I-138, I-139, I-140, I-141, I-145, I-146, I-147, I-148, I-149, I-150, and I-152 exhibited $IC_{50}$ values less than or equal to 100 nM in this assay.

Sumo-Activating Enzyme (SAE) HTRF Assay.

The SAE enzymatic reaction was conducted as outlined above for NAE except that Ubc12-GST and Nedd8-Flag were replaced by 0.01 µM Ubc9-GST and 0.125 µM Sumo-Flag respectively and the concentration of ATP was 0.5 µM. Recombinant human SAE (0.11 nM) was the source of enzyme.

Ubiquitin-Activating Enzyme (UAE) HTRF Assay.

The UAE enzymatic reaction was conducted as outlined above for NAE except that Ubc12-GST and Nedd8-Flag were replaced by 0.005 µM Ubc2-GST and 0.125 µM Ubiquitin-Flag respectively and the concentration of ATP was 0.1 µM. Recombinant mouse UAE (0.3 nM) was the source of enzyme.

Example 140

Cellular Assays

Anti-Proliferation Assay (WST)

Calu-6 (2400/well) or other tumor cells in 80 µL of appropriate cell culture medium (MEM for Calu6, Invitrogen) supplemented with 10% fetal bovine serum (Invitrogen) was seeded in wells of a 96-well cell culture plate and incubated for 24 hours in a tissue culture incubator. Compound inhibitors were added in 20 µL culture media to the wells and the plates was incubated for 72 hours at 37° C. 10% final concentration of WST-1 reagent (Roche) was added to each well and incubated for 3.5 hours (for Calu6) at 37° C. The optical density for each well was read at 450 nm using a spectrophotometer (Molecular Devices). Percent inhibition was calculated using the values from a DMSO control set to 100% viability.

Anti-Proliferation Assay (ATPLite)

Calu-6 (1500 cells/well) or other tumor cells were seeded in 72 µL of appropriate cell culture medium (MEM for Calu6, Invitrogen) supplemented with 10% fetal bovine serum (Invitrogen) in wells of a 384-well Poly-D-Lysine coated cell culture plate. Compound inhibitors were added in 8 µL 10% DMSO/PBS to the wells and the plates were incubated for 72 hours at 37° C. Cell culture medium was aspirated, leaving 25 µL in each well. 25 µL of ATPlite Istep™ reagent (Perkin Elmer) was added to each well. The luminescence for each well was read using the LeadSeeker Microplate Reader (Molecular Devices). Percent inhibition was calculated using the values from a DMSO control set to 100% viability.

Example 141

In vivo Assays

In vivo Tumor Efficacy Model

Calu6 (5×10⁶ cells), HCT116 (2×10⁶ cells) or other tumor cells in 100 μL phosphate buffered saline were aseptically injected into the subcutaneous space in the right dorsal flank of female Ncr nude mice (age 5-8 weeks, Charles River) using a 26-gauge needle. Beginning on day 7 after inoculation, tumors were measured twice weekly using a vernier caliper. Tumor volumes were calculated using standard procedures (0.5×(length×width²)). When the tumors reached a volume of approximately 200 mm³ mice were randomized into groups and injected intravenously in the tail vein with compound inhibitor (100 μL) at various doses and schedules. Alternatively, compound inhibitor may be delivered to mice by intraperitoneal or subcutaneous injection or oral administration. All control groups received vehicle alone. Tumor size and body weight was measured twice a week and the study terminated when the control tumors reached approximately 2000 mm³.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

While a number of embodiments of this invention have been described, it is apparent that the provided basic examples may be altered to convey other embodiments, which utilize the compounds and methods of this invention. It will thus be appreciated that the scope of this invention has been represented herein by way of example and is not intended to be limited by the specific embodiments, rather is defined by the appended claims.

What is claimed is:

1. A compound of formula (I-A):

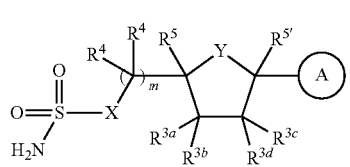

(I-A)

or a pharmaceutically acceptable salt thereof, wherein:

Ring A is:

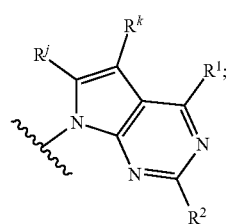

A-ii wherein one ring nitrogen atom in Ring A optionally is oxidized;

X is —$CH_2$—, —CHF—, —$CF_2$—, —NH—, or —O—;

Y is —O—, —S—, or —C($R^m$)($R^n$)—;

$R^j$ is hydrogen;

$R^k$ is hydrogen, halo, or an optionally substituted $C_{1-4}$ aliphatic group;

$R^m$ and $R^n$ are each hydrogen;

$R^1$ is hydrogen, chloro, bromo, fluoro, iodo, —$NR^7R^8$, —$R^9$, —SH, —$SCH_3$, —S—$R^{10}$, —OH, —$OCH_3$, or —O—$R^{11}$;

$R^2$ is hydrogen, chloro, bromo, fluoro, iodo, —N($R^6$)$_2$, —CN, —O—($C_{1-4}$ aliphatic), —OH, —$SR^6$, or an optionally substituted $C_{1-4}$ aliphatic group;

$R^{3a}$ is hydrogen, fluoro, —CN, —$N_3$, hydroxy, —$OR^{21}$, —$NH_2$, —NH($R^{21}$), —N(H)$CO_2R^{21}$, —N(H)C(O)$R^{21}$, —CON(H)$R^{21}$, —C(O)$R^5$, —OC(O)N(H)$R^{21}$, —OC(O)$R^{21}$, —OC(O)O$R^{21}$, —$C_{1-4}$ fluoroaliphatic, or a —$C_{1-4}$ aliphatic optionally substituted with one or two substituents independently selected from the group consisting of —$OR^{5x}$, —N($R^{4x}$)($R^{4y}$), —$CO_2R^{5x}$, and —C(O)N($R^{4x}$)($R^{4y}$);

$R^{3b}$ is selected from the group consisting of hydrogen, fluoro, $C_{1-4}$ aliphatic, and $C_{1-4}$ fluoroaliphatic;

$R^{3c}$ is hydrogen, fluoro, —CN, —$N_3$, hydroxy, —$OR^{21}$, —$NH_2$, —NH($R^{21}$), —N(H)$CO_2R^{21}$, —N(H)C(O)$R^{21}$, —CON(H)$R^{21}$, —OC(O)N(H)$R^{21}$, —OC(O)$R^{21}$, —OC(O)O$R^{21}$, —$C_{1-4}$ fluoroaliphatic, or a —$C_{1-4}$ aliphatic optionally substituted with one or two substituents independently selected from the group consisting of —$OR^{5x}$, —N($R^{4x}$)($R^{4y}$), —$CO_2R^{5x}$, and —C(O)N($R^{4x}$)($R^{4y}$);

$R^{3d}$ is selected from the group consisting of hydrogen, fluoro, $C_{1-4}$ aliphatic, and $C_{1-4}$ fluoroaliphatic;

each $R^4$ is independently hydrogen, fluoro, $C_{1-4}$ aliphatic, or $C_{1-4}$ fluoroaliphatic; or two $R^4$, taken together with the carbon atom to which they are attached, form a 3- to 6-membered carbocyclic ring; or one $R^4$, taken together with $R^5$ and the intervening carbon atoms, forms a 3- to 6-membered ring; or two $R^4$ together form =O;

$R^5$ is hydrogen, or $C_{1-4}$ aliphatic; or $R^5$, taken together with one $R^4$ and the intervening carbon atoms, forms a 3- to 6-membered ring;

$R^{5'}$ is hydrogen, or $C_{1-4}$ aliphatic;

each $R^6$ is independently hydrogen or $C_{1-4}$ aliphatic;

$R^7$ is an optionally substituted aryl, heteroaryl, or heterocyclyl group;

$R^8$ is hydrogen or $C_{1-4}$ aliphatic;

$R^9$ is —V—Z—$R^{12a}$, —V—Z—$R^{12b}$, —$R^{12c}$, or an optionally substituted aliphatic, aryl, heterocyclyl, or heteroaryl group, wherein the heteroaryl group is attached at a carbon atom;

$R^{10}$ is an unsubstituted $C_{2-10}$ aliphatic, a substituted $C_{1-10}$ aliphatic, or an optionally substituted aryl, heteroaryl, or heterocyclyl;

$R^{11}$ is an unsubstituted $C_{2-10}$ aliphatic, a substituted $C_{1-10}$ aliphatic, or an optionally substituted aryl, heteroaryl, or heterocyclyl;

$R^{4x}$ is hydrogen, $C_{1-4}$ alkyl, $C_{1-4}$ fluoroalkyl, or $C_{6-10}$ ar($C_{1-4}$)alkyl, the aryl portion of which is optionally substituted;

$R^{4y}$ is hydrogen, $C_{1-4}$ alkyl, $C_{1-4}$ fluoroalkyl, $C_{6-10}$ ar ($C_{1-4}$)alkyl, the aryl portion of which is optionally substituted, or an optionally substituted 5- or 6-membered aryl, heteroaryl, or heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, or an optionally substituted $C_{6-10}$ aryl or $C_{6-10}$ ar($C_{1-4}$)alkyl;

V is —S(O)$_2$—, —S(O)—, —C(O)O—, —C(O)—, —C(NR$^{13}$)=N—, —C(=N(R$^{13}$))—N(R$^{13}$)—, —C(OR$^{11}$)=N—, —CON(R$^{13}$)—, —N(R$^{13}$)C (O)—, —N(R$^{13}$)C(O)N(R$^{13}$)—, —N(R$^{13}$)S(O)$_2$—, —N(R$^{13}$)SO$_2$—N(R$^{13}$)—, —N(R$^{13}$)CO$_2$—, —SO$_2$N(R$^{13}$)—, —OC(O)—, —OC(O)O—, —OC(O)N(R$^{13}$)—, or —N(R$^{13}$)—N(R$^{13}$)—;

Z is an optionally substituted $C_{1-6}$ alkylene chain, wherein the alkylene chain is optionally interrupted by —C(R$^{13}$)=C(R$^{13}$)—, —C≡C—, —O—, —S—, —N(R$^{13}$)—, —N(R$^{13}$)CO—, —N(R$^{13}$)CO$_2$—, —C(O)N(R$^{13}$)—, —C(O)—, —C(O)—C(O)—, —CO$_2$—, —OC(O)—, —OC(O)O—, —N(R$^{13}$)C(O)N(R$^{13}$)—, —N(R$^{13}$)N(R$^{13}$)—, —OC(O)N (R$^{13}$)—, —S(O)—, —S(O)$_2$—, —N(R$^{13}$)S(O)$_2$—, or —S(O)$_2$N(R$^{13}$)—;

$R^{12a}$ is an optionally substituted aryl, heteroaryl, heterocyclyl, or cycloaliphatic group;

$R^{12b}$ is halo, —NO$_2$, —CN, —OR$^{14}$, —SR$^{15}$, —N(R$^{16}$)$_2$, —N(R$^{16}$)C(O)R$^{15}$, —N(R$^{16}$)C(O)N (R$^{16}$)$_2$, —N(R$^{16}$)CO$_2$R$^{14}$, —O—CO$_2$—R$^{14}$, —OC(O)N(R$^{16}$)$_2$, —OC(O)R$^{14}$, —N(R$^{16}$)—N(R$^{16}$)$_2$, —N(R$^{16}$)—OR$^{15}$, —N(R$^{16}$)S(O)$_2$R$^{15}$, —N(R$^{16}$)SO$_2$—N(R$^{16}$)$_2$, —C(R$^{14}$)=C(R$^{14}$)$_2$, —C≡C—R$^{14}$, —S(O)R$^{15}$, —SO$_2$R$^{15}$, —SO$_2$—N(R$^{16}$)$_2$, —C(R$^{14}$)=N—OR$^{14}$, —CO$_2$R$^{14}$, —C(O)—C(O)R$^{14}$, —C(O)R$^{14}$, —C(O)N(R$^{16}$)$_2$, —C(=NR$^{16}$)—N(R$^{16}$)$_2$, or —C(=NR$^{16}$)—OR$^{14}$;

$R^{12c}$ is —NO$_2$, —CN, —S(O)R$^{15}$, —SO$_2$R$^{15}$, —SO$_2$—N(R$^{16}$)$_2$, —C(R$^{14}$)=N—OR$^{14}$, —N(R$^{16}$)C(O)R$^{15}$, —N(R$^{16}$)C(O)N(R$^{16}$)$_2$, —O—CO$_2$—R$^{14}$—, —OC(O)N(R$^{16}$)$_2$, —OC(O)R$^{14}$, —CO$_2$ R$^{14}$, —C(O)—C(O)R$^{14}$, —C(O)R$^{14}$, —C(O)N(R$^{16}$)$_2$, —C(=NR$^{16}$)—N(R$^{16}$)$_2$, —C(=NR$^{16}$)—OR$^{14}$, —N(R$^{16}$)—N(R$^{16}$)$_2$, —N(R$^{16}$)—OR$^{15}$, —N(R$^{16}$)S(O)$_2$R$^{15}$, or —N(R$^{16}$)SO$_2$—N(R$^{16}$)$_2$;

each $R^{13}$ is independently hydrogen, or an optionally substituted aliphatic, aryl, heteroaryl, or heterocyclyl group;

each $R^{14}$ independently is hydrogen, or an optionally substituted aliphatic, aryl, heteroaryl, or heterocyclyl group;

each $R^{15}$ independently is an optionally substituted aliphatic, or aryl group;

each $R^{16}$ independently is an optionally substituted aliphatic, aryl, heteroaryl, or heterocyclyl group; or two $R^{16}$ on the same nitrogen atom, taken together with the nitrogen atom, form an optionally substituted five to eight membered heterocylyl ring having, in addition to the nitrogen atom, zero to two additional ring heteroatoms selected from the group consisting of N, O, and S;

each $R^{21}$ independently is an optionally substituted $C_{1-10}$ aliphatic, aryl, heteroaryl, or heterocyclyl group;

wherein:

in each recitation of optionally substituted aryl, the aryl group, when substituted, contains on an unsaturated carbon atom one or more substituents independently selected from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$;

in each recitation of optionally substituted heteroaryl, the heteroaryl group, when substituted, contains one or more substituents independently selected, if on an unsaturated carbon atom, from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, and, if on a substitutable nitrogen atom, from —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

in each recitation of optionally substituted aliphatic, the aliphatic group, when substituted, contains on a saturated carbon atom one or more substituents independently selected from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R$^o$, =N—NHSO$_2$R$^o$, and =N—R*; and in each recitation of optionally substituted heterocyclyl, the heterocyclyl group, when substituted, contains one or more substituents independently selected, if on an unsaturated carbon atom, from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R$^o$, =N—NHSO$_2$R$^o$, and =N—R*, and, if on a substitutable nitrogen atom, from —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

wherein:

each occurrence of R$^o$ is independently an aliphatic or aryl group;

each occurrence of R$^+$ is independently hydrogen or an aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms selected from N, O, and S; and each occurrence of R* is independently hydrogen or an aliphatic, aryl, heteroaryl, or heterocyclyl group; and m is 1, 2, or 3.

2. The compound of claim 1, or a pharmaceutically acceptable salt thereof, characterized by one or more of the following features:

(a) X is —O—;
(b) Y is —O— or —CH$_2$—;
(c) R$^{3a}$ is —OH;
(d) R$^{3b}$ and R$^{3d}$ are each independently hydrogen or C$_{1-4}$ aliphatic;
(e) R$^{3c}$ is hydrogen, fluoro, OH, or —OCH$_3$;
(f) R$^5$ and R$^{5'}$ are each hydrogen;
(g) each R$^4$ is hydrogen;
(h) each R$^2$ is hydrogen;
(i) R$^j$ is hydrogen; and
(j) R$^k$ is hydrogen, halo, or C$_{1-4}$ aliphatic.

3. A compound of formula (I):

(I)

or a pharmaceutically acceptable salt thereof, wherein:

X is —CH$_2$—, —NH—, or —O—;

Y is —O—, or —CH$_2$—;

Q is CH;

R$^1$ is chloro, bromo, fluoro, iodo, —NR$^7$R$^8$, —R$^9$, —S—R$^{10}$, or —O—R$^{11}$;

R$^2$ is hydrogen, chloro, bromo, fluoro, iodo, —N(R$^6$)$_2$, —CN, —O—(C$_{1-4}$ aliphatic), —OH, —SR$^6$, or an optionally substituted C$_{1-4}$ aliphatic group;

R$^{3a}$ is selected from the group consisting of hydrogen, hydroxy, —NH$_2$, —C$_{1-4}$ aliphatic, fluoro, —CN, —C$_{1-4}$ fluoroaliphatic, —OR$^{21}$, —NH(R$^{21}$), —N(H)CO$_2$R$^{21}$, —N(H)C(O)R$^{21}$, —CON(H)R$^{21}$, —OC(O)N(H)R$^{21}$, —OC(O)R$^{21}$, and —OC(O)OR$^{21}$;

R$^{3b}$ is selected from the group consisting of hydrogen, fluoro, C$_{1-4}$ aliphatic, and C$_{1-4}$ fluoroaliphatic;

R$^{3c}$ is selected from the group consisting of hydrogen, hydroxy, —NH$_2$, —C$_{1-4}$ aliphatic, fluoro, —CN, —C$_{1-4}$ fluoroaliphatic, —OR$^{21}$, —NH(R$^{21}$), —N(H)CO$_2$R$^{21}$, —N(H)C(O)R$^{21}$, —CON(H)R$^{21}$, —OC(O)N(H)R$^{21}$, —OC(O)R$^{21}$, and —OC(O)OR$^{21}$;

R$^{3d}$ is selected from the group consisting of hydrogen, fluoro, C$_{1-4}$ aliphatic, and C$_{1-4}$ fluoroaliphatic;

each R$^4$ is independently hydrogen or C$_{1-4}$ aliphatic; or two R$^4$, taken together with the carbon atom to which they are attached, form a 3- to 6-membered carbocyclic ring; or one R$^4$, taken together with R$^5$ and the intervening carbon atoms, forms a 3- to 6-membered spirocyclic ring;

R$^5$ is hydrogen, or C$_{1-4}$ aliphatic; or R$^5$, taken together with one R$^4$ and the intervening carbon atoms, forms a 3- to 6-membered spirocyclic ring;

each R$^6$ is independently hydrogen or C$_{1-4}$ aliphatic;

R$^7$ is an optionally substituted aryl, heteroaryl, or heterocyclyl group;

R$^8$ is hydrogen or C$_{1-4}$ aliphatic;

R$^9$ is —V—Z—R$^{12a}$, —V—Z—R$^{12b}$, —R$^{12c}$, or an optionally substituted aliphatic, aryl, heterocyclyl, or heteroaryl group, wherein the heteroaryl group is attached at a carbon atom;

R$^{10}$ is an optionally substituted C$_{2-10}$ aliphatic, aryl, heteroaryl, or heterocyclyl;

R$^{11}$ is an optionally substituted C$_{2-10}$ aliphatic, aryl, heteroaryl, or heterocyclyl;

V is —S(O)$_2$—, —S(O)—, —C(O)O—, —C(O)—, —C(NR$^{13}$)=N—, —C(=N(R$^{13}$))—N(R$^{13}$)—, —C(OR$^{11}$)=N—, —CON(R$^{13}$)—, —N(R$^{13}$)C(O)—, —N(R$^{13}$)C(O)N(R$^{13}$)—, —N(R$^{13}$)S(O)$_2$—, —N(R$^{13}$)SO$_2$—N(R$^{13}$)—, —N(R$^{13}$)CO$_2$—, —SO$_2$N(R$^{13}$)—, —OC(O)—, —OC(O)O—, —OC(O)N(R$^{13}$)—, —N(R$^{13}$)—N(R$^{13}$)—;

Z is an optionally substituted C$_{1-6}$ alkylene chain, wherein the alkylene chain is optionally interrupted by —C(R$^{13}$)=C(R$^{13}$)—, —C≡C—, —O—, —S—, —N(R$^{13}$)—, —N(R$^{13}$)CO—, —N(R$^{13}$)CO$_2$—, —C(O)N(R$^{13}$)—, —C(O)—, —C(O)—C(O)—, —CO$_2$—, —OC(O)—, —OC(O)O—, —N(R$^{13}$)C(O)N(R$^{13}$)—, —N(R$^{13}$)N(R$^{13}$)—, —OC(O)N(R$^{13}$)—, —S(O)—, —S(O)$_2$—, —N(R$^{13}$)S(O)$_2$—, or —S(O)$_2$N(R$^{13}$)—;

R$^{12a}$ is an optionally substituted aryl, heteroaryl, heterocyclyl, or cycloaliphatic group;

R$^{12b}$ is halo, —NO$_2$, —CN, —OR$^{14}$, —SR$^{15}$, —N(R$^{16}$)$_2$, —N(R$^{16}$)C(O)R$^{15}$, —N(R$^{16}$)C(O)N(R$^{16}$)$_2$, —N(R$^{16}$)CO$_2$R$^{14}$, —O—CO$_2$—R$^{14}$, —OC(O)N(R$^{16}$)$_2$, —OC(O)R$^{14}$, —N(R$^{16}$)—N(R$^{16}$)$_2$, —N(R$^{16}$)S(O)$_2$R$^{15}$, —N(R$^{16}$)SO$_2$—N(R$^{16}$)$_2$—C(R$^{14}$)=C(R$^{14}$)$_2$, —C≡C—R$^{14}$, —S(O)R$^{15}$, —SO$_2$R$^{15}$, —SO$_2$—N(R$^{16}$)$_2$, —C(R$^{14}$)=N—OR$^{14}$, —CO$_2$R$^{14}$, —C(O)—C(O)R$^{14}$, —C(O)R$^{14}$, —C(O)N(R$^{16}$)$_2$, —C(=NR$^{16}$)—N(R$^{16}$)$_2$, or —C(=NR$^{16}$)—OR$^{14}$;

R$^{12c}$ is —NO$_2$, —CN, —S(O)R$^{15}$, —SO$_2$R$^{15}$, —SO$_2$—N(R$^{16}$)$_2$, —C(R$^{14}$)=N—OR$^{14}$, —N(R$^{16}$)C(O)R$^{15}$, —N(R$^{16}$)C(O)N(R$^{16}$)$_2$, —O—CO$_2$—R$^{14}$—, —OC(O)N(R$^{16}$)$_2$, —OC(O)R$^{14}$, —CO$_2$R$^{14}$, —C(O)—C(O)R$^{14}$, —C(O)R$^{14}$, —C(O)N(R$^{16}$)$_2$, —C(=NR$^{16}$)—N(R$^{16}$)$_2$, —C(=NR$^{16}$)—OR$^{14}$, —N(R$^{16}$)—N(R$^{16}$)$_2$, —N(R$^{16}$)S(O)$_2$R$^{15}$, or —N(R$^{16}$)SO$_2$—N(R$^{16}$)$_2$;

each R$^{13}$ is independently hydrogen, or an optionally substituted aliphatic, aryl, heteroaryl, or heterocyclyl group;

each R$^{14}$ independently is hydrogen, or an optionally substituted aliphatic, aryl, heteroaryl, or heterocyclyl group;

each R$^{15}$ independently is an optionally substituted aliphatic, or aryl group;

each $R^{16}$ independently is an optionally substituted aliphatic, aryl, heteroaryl, or heterocyclyl group; or two $R^{16}$ on the same nitrogen atom, taken together with the nitrogen atom, form an optionally substituted five to eight membered heterocylyl ring having, in addition to the nitrogen atom, zero to two additional ring heteroatoms selected from the group consisting of N, O, and S; and each $R^{21}$ independently is an optionally substituted $C_{1-10}$ aliphatic, aryl, heteroaryl, or heterocyclyl group; wherein:

in each recitation of optionally substituted aryl, the aryl group, when substituted, contains on an unsaturated carbon atom one or more substituents independently selected from halo, —$NO_2$, —CN, —R*, —C(R*)=C(R*)$_2$, —C≡C—R*, —OR*, —SR$^o$, —S(O)R$^o$, —$SO_2R^o$, —$SO_2N(R^+)_2$, —$N(R^+)_2$, —$NR^+C(O)R^*$, —$NR^+C(O)N(R^+)_2$, —$NR^+CO_2R^o$, —O—$CO_2R^*$, —$OC(O)N(R^+)_2$, —O—C(O)R*, —$CO_2R^*$, —C(O)—C(O)R*, —C(O)R*, —$C(O)N(R^+)_2$, —C(=$NR^+$)—$N(R^+)_2$, —C(=$NR^+$)—OR*, —$N(R^+)$—$N(R^+)_2$, —$N(R^+)C(=NR^+)$—$N(R^+)_2$, —$NR^+SO_2R^o$, —$NR^+SO_2N(R^+)_2$, —$P(O)(R^*)_2$, —$P(O)(OR^*)_2$, —O—P(O)—OR*, and —$P(O)(NR^+)$—$N(R^+)_2$;

in each recitation of optionally substituted heteroaryl, the heteroaryl group, when substituted, contains one or more substituents independently selected, if on an unsaturated carbon atom, from halo, —$NO_2$, —CN, —R*, —C(R*)=C(R*)$_2$, —C≡C—R*, —OR*, —SR$^o$, —S(O)R$^o$, —$SO_2R^o$, —$SO_2N(R^+)_2$, —$N(R^+)_2$, —$NR^+C(O)R^*$, —$NR^+C(O)N(R^+)_2$, —$NR^+CO_2R^o$, —O—$CO_2R^*$, —$OC(O)N(R^+)_2$, —O—C(O)R*, —$CO_2R^*$, —C(O)—C(O)R*, —C(O)R*, —$C(O)N(R^+)_2$, —C(=$NR^+$)—$N(R^+)_2$, —C(=$NR^+$)—OR*, —$N(R^+)$—$N(R^+)_2$, —$N(R^+)C(=NR^+)$—$N(R^+)_2$, —$NR^+SO_2R^o$, —$NR^+SO_2N(R^+)_2$, —$P(O)(R^*)_2$, —$P(O)(OR^*)_2$, —O—P(O)—OR*, and —$P(O)(NR^+)$—$N(R^+)_2$, and, if on a substitutable nitrogen atom, from —R*, —$N(R^*)_2$, —C(O)R*, —$CO_2R^*$, —C(O)—C(O)R*, —$C(O)CH_2C(O)R^*$, —$SO_2R^*$, —$SO_2N(R^*)_2$, —C(=S)$N(R^*)_2$, —C(=NH)—$N(R^*)_2$, and —$NR^*SO_2R^*$;

in each recitation of optionally substituted aliphatic, the aliphatic group, when substituted, contains on a saturated carbon atom one or more substituents independently selected from halo, —$NO_2$, —CN, —R*, —C(R*)=C(R*)$_2$, —C≡C—R*, —OR*, —SR$^o$, —S(O)R$^o$, —$SO_2R^o$, —$SO_2N(R^+)_2$, —$N(R^+)_2$, —$NR^+C(O)R^*$, —$NR^+C(O)N(R^+)_2$, —$NR^+CO_2R^o$, —O—$CO_2R^*$, —$OC(O)N(R^+)_2$, —O—C(O)R*, —$CO_2R^*$, —C(O)—C(O)R*, —C(O)R*, —$C(O)N(R^+)_2$, —C(=$NR^+$)—$N(R^+)_2$, —C(=$NR^+$)—OR*, —$N(R^+)$—$N(R^+)_2$, —$N(R^+)C(=NR^+)$—$N(R^+)_2$, —$NR^+SO_2R^o$, —$NR^+SO_2N(R^+)_2$, —$P(O)(R^*)_2$, —$P(O)(OR^*)_2$, —O—P(O)—OR*, —$P(O)(NR^+)$—$N(R^+)_2$, =O, =S, =C(R*)$_2$, =N—$N(R^+)_2$, =N—OR*, =N—NHC(O)R*, =N—$NHCO_2R^o$, =N—$NHSO_2R^o$, and =N—R*; and in each recitation of optionally substituted heterocyclyl, the heterocyclyl group, when substituted, contains one or more substituents independently selected, if on an unsaturated carbon atom, from halo, —$NO_2$, —CN, —R*, —C(R*)=C(R*)$_2$, —C≡C—R*, —OR*, —SR$^o$, —S(O)R$^o$, —$SO_2R^o$, —$SO_2N(R^+)_2$, —$N(R^+)_2$, —$NR^+C(O)R^*$, —$NR^+C(O)N(R^+)_2$, —$NR^+CO_2R^o$, —O—$CO_2R^*$, —$OC(O)N(R^+)_2$, —O—C(O)R*, —$CO_2R^*$, —C(O)—C(O)R*, —C(O)R*, —$C(O)N(R^+)_2$, —C(=$NR^+$)—$N(R^+)_2$, —C(=$NR^+$)—OR*, —$N(R^+)$—$N(R^+)_2$, —$N(R^+)C(=NR^+)$—$N(R^+)_2$, —$NR^+SO_2R^o$, —$NR^+SO_2N(R^+)_2$, —$P(O)(R^*)_2$, —$P(O)(OR^*)_2$, —O—P(O)—OR*, —$P(O)(NR^+)$—$N(R^+)_2$, =O, =S, =C(R*)$_2$, =N—$N(R^+)_2$, =N—OR*, =N—NHC(O)R*, =N—$NHCO_2R^o$, =N—$NHSO_2R^o$, and =N—R*, and, if on a substitutable nitrogen atom, from —R*, —$N(R^*)_2$, —C(O)R*, —$CO_2R^*$, —C(O)—C(O)R*, —C(O)R*, —$C(O)CH_2C(O)R^*$, —$SO_2R^*$, —$SO_2N(R^*)_2$, —C(=S)$N(R^*)_2$, —C(=NH)—$N(R^*)_2$, and —$NR^*SO_2R^*$;

wherein:

each occurrence of R$^o$ is independently an aliphatic or aryl group;

each occurrence of R$^+$ is independently hydrogen or an aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms selected from N, O, and S; and each occurrence of R* is independently hydrogen or an aliphatic, aryl, heteroaryl, or heterocyclyl group.

4. The compound of claim 3, or a pharmaceutically acceptable salt thereof, characterized by one or more of the features (a) through (f):

(a) $R^{3a}$ is selected from the group consisting of hydrogen, hydroxy, methoxy, $C_{1-4}$ aliphatic, $C_{1-4}$ fluoroaliphatic, and fluoro;

(b) $R^{3b}$ is hydrogen;

(c) $R^{3c}$ is hydrogen or hydroxy;

(d) $R^{3d}$ is hydrogen;

(e) each $R^4$ is hydrogen; and (f) $R^5$ is hydrogen.

5. The compound of claim 4, having the formula (II-A) or (II-B):

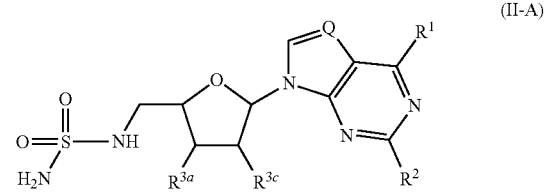

(II-A)

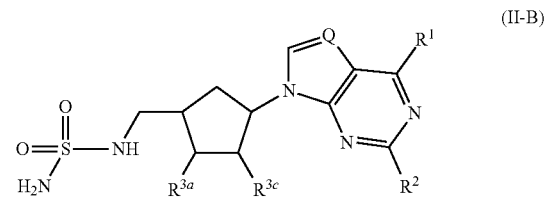

(II-B)

or a pharmaceutically acceptable salt thereof.

6. The compound of claim 4, having the formula (III-A) or (III-B):

(III-A)

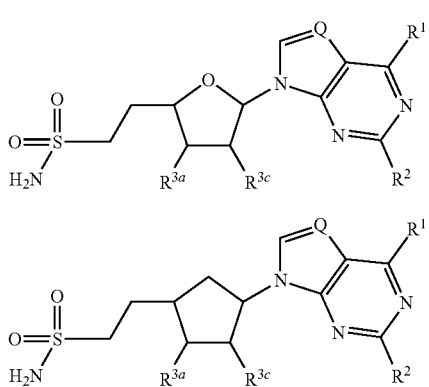

(III-B)

or a pharmaceutically acceptable salt thereof.

7. The compound of claim 4, or a pharmaceutically acceptable salt thereof, having the formula (IV-A) or (IV-B):

(IV-A)

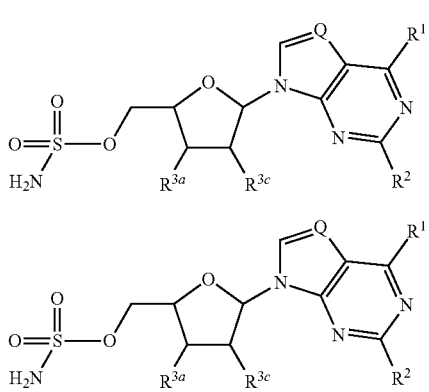

(IV-B)

or a pharmaceutically acceptable salt thereof.

8. A compound of formula (V):

(V)

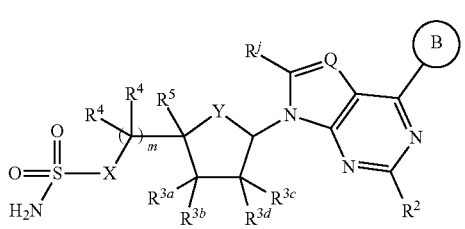

or a pharmaceutically acceptable salt thereof,
wherein:
Q is CH;
$R^j$ is hydrogen;
X is —$CH_2$—, —CHF—, —$CF_2$—, —NH—, or —O—;
Y is —O—, —S—, or —C($R^m$)($R^n$)—;
$R^m$ and $R^n$ are each hydrogen;
$R^2$ is hydrogen, chloro, bromo, fluoro, iodo, —N($R^6$)$_2$, —CN, —O—($C_{1-4}$ aliphatic), —OH, —$SR^6$, or an optionally substituted $C_{1-4}$ aliphatic group;

$R^{3a}$ is hydrogen, fluoro, —CN, —$N_3$, hydroxy, —$OR^{21}$, —$NH_2$, —NH($R^{21}$), —N(H)$CO_2R^{21}$, —N(H)C(O)$R^{21}$, —CON(H)$R^{21}$, —C(O)$R^5$, —OC(O)N(H)$R^{21}$, —OC(O)$R^{21}$, —OC(O)O$R^{21}$, —$C_{1-4}$ fluoroaliphatic, or a —$C_{1-4}$ aliphatic optionally substituted with one or two substituents independently selected from the group consisting of —$OR^{5x}$, —N($R^{4x}$)($R^{4y}$), —$CO_2R^{5x}$, and —C(O)N($R^{4x}$)($R^{4y}$);

$R^{3b}$ is selected from the group consisting of hydrogen, fluoro, $C_{1-4}$ aliphatic, and $C_{1-4}$ fluoroaliphatic;

$R^{3c}$ is hydrogen, fluoro, —CN, —$N_3$, hydroxy, —$OR^{21}$, —$NH_2$, —NH($R^{21}$), —N(H)$CO_2R^{21}$, —N(H)C(O)$R^{21}$, —CON(H)$R^{21}$, —OC(O)N(H)$R^{21}$, —OC(O)$R^{21}$, —OC(O)O$R^{21}$, —$C_{1-4}$ fluoroaliphatic, or a —$C_{1-4}$ aliphatic optionally substituted with one or two substituents independently selected from the group consisting of —$OR^{5x}$, —N($R^{4x}$)($R^{4y}$), —$CO_2R^{5x}$, and —C(O)N($R^{4x}$)($R^{4y}$);

$R^{3d}$ is selected from the group consisting of hydrogen, fluoro, $C_{1-4}$ aliphatic, and $C_{1-4}$ fluoroaliphatic;

each $R^4$ is independently hydrogen, fluoro, $C_{1-4}$ aliphatic, or $C_{1-4}$ fluoroaliphatic; or two $R^4$, taken together with the carbon atom to which they are attached, form a 3- to 6-membered carbocyclic ring; or one $R^4$, taken together with $R^5$ and the intervening carbon atoms, forms a 3- to 6-membered ring; or two $R^4$ together form =O;

$R^5$ is hydrogen, or $C_{1-4}$ aliphatic; or $R^5$, taken together with one $R^4$ and the intervening carbon atoms, forms a 3- to 6-membered ring;

each $R^6$ is independently hydrogen or $C_{1-4}$ aliphatic;

$R^{4x}$ is hydrogen, $C_{1-4}$ alkyl, $C_{1-4}$ fluoroalkyl, or $C_{6-10}$ ar($C_{1-4}$)alkyl, the aryl portion of which is optionally substituted;

$R^{4y}$ is hydrogen, $C_{1-4}$ alkyl, $C_{1-4}$ fluoroalkyl, $C_{6-10}$ ar($C_{1-4}$)alkyl, the aryl portion of which is optionally substituted, or an optionally substituted 5- or 6-membered aryl, heteroaryl, or heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, or an optionally substituted $C_{6-10}$ aryl or $C_{6-10}$ ar($C_{1-4}$)alkyl;

each $R^{21}$ independently is an optionally substituted $C_{1-10}$ aliphatic, aryl, heteroaryl, or heterocyclyl group;

m is 1, 2, or 3;

Ring B is an optionally substituted 5- or 6-membered aryl or heteroaryl ring having zero to three ring nitrogen atoms and optionally one additional ring heteroatom selected from oxygen and sulfur;

substitutable ring carbon atoms in Ring B are substituted with 0-2 substituents independently selected from the group consisting of $C_{1-6}$ aliphatic, $C_{1-6}$ fluoroaliphatic, halo, —$R^{a17}$, —$R^{b17}$, —$Z^{17}$—$R^{a17}$, and —$Z^{17}$—$R^{b17}$, or two adjacent substituents, taken together with the intervening ring atoms, form an optionally substituted fused 5- or 6-membered aromatic or non-aromatic ring having 0-3 ring heteroatoms selected from the group consisting of O, N, and S;

$Z^{17}$ is an optionally substituted $C_{1-6}$ alkylene chain, wherein the alkylene chain optionally is interrupted by —C($R^{14}$)=C($R^{14}$)—, —C≡C—, —O—, —S—, —S(O)—, —S(O)$_2$—, —$SO_2$N($R^{15}$)—, —N($R^{15}$)—, —N($R^{15}$)C(O)—, —$NR^{15}$C(O)N($R^{15}$)—, —N($R^{15}$)$CO_2$—, —N($R^{15}$)$SO_2$—, —C(O)N($R^{15}$)—, —C(O)—, —CO$_2$—, —OC(O)—, —OC(O)O—, or —OC(O)N(R$^{15}$)—, and wherein Z$^{17}$ or a portion thereof optionally forms part of a 3-7 membered ring;

each R$^{a17}$ independently is an optionally substituted aryl, heteroaryl, heterocyclyl, or cycloaliphatic ring;

each R$^{b17}$ independently is —NO$_2$, —CN, —C(R$^{14}$)=C(R$^{14}$)$_2$, —C≡C—R$^{14}$, —OR$^{14}$, —SR$^{15}$, —S(O)R$^{15}$, —SO$_2$R$^{15}$, —SO$_2$N(R$^{16}$)$_2$, —N(R$^{16}$)$_2$, —NR$^{16}$C(O)R$^{14}$, —NR$^{16}$C(O)N(R$^{16}$)$_2$, —NR$^{16}$CO$_2$R$^{14}$, —O—CO$_2$R$^{14}$, —OC(O)N(R$^{16}$)$_2$, —O—C(O)R$^{14}$, —CO$_2$R$^{14}$, —C(O)R$^{14}$, —C(O)N(R$^{16}$)$_2$, —C(O)N(R$^{16}$)C(=NR$^{16}$)—N(R$^{16}$)$_2$, —C(=NR$^{16}$)—N(R$^{16}$)$_2$, —C(=NR$^{16}$)—OR$^{14}$, —C(R$^{14}$)=N—OR$^{14}$, —N(R$^{16}$)C(=NR$^{16}$)—N(R$^{16}$)$_2$, —N(R$^{16}$)SO$_2$R$^{15}$, or —N(R$^{16}$)SO$_2$N(R$^{16}$)$_2$;

each R$^{14}$ independently is hydrogen, or an optionally substituted aliphatic, aryl, heteroaryl, or heterocyclyl group;

each R$^{15}$ independently is an optionally substituted aliphatic, or aryl group; and each R$^{16}$ independently is an optionally substituted aliphatic, aryl, heteroaryl, or heterocyclyl group; or two R$^{16}$ on the same nitrogen atom, taken together with the nitrogen atom, form an optionally substituted five to eight membered heterocyclyl ring having, in addition to the nitrogen atom, zero to two additional ring heteroatoms selected from the group consisting of N, O, and S;

wherein:

in each recitation of optionally substituted aryl, the aryl group, when substituted, contains on an unsaturated carbon atom one or more substituents independently selected from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$;

in each recitation of optionally substituted heteroaryl, the heteroaryl group, when substituted, contains one or more substituents independently selected, if on an unsaturated carbon atom, from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, and, if on a substitutable nitrogen atom, from —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

in each recitation of optionally substituted aliphatic, the aliphatic group, when substituted, contains on a saturated carbon atom one or more substituents independently selected from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R$^o$, =N—NHSO$_2$R$^o$, and =N—R*; and in each recitation of optionally substituted heterocyclyl, the heterocyclyl group, when substituted, contains one or more substituents independently selected, if on an unsaturated carbon atom, from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R$^o$, =N—NHSO$_2$R$^o$, and =N—R*, and, if on a substitutable nitrogen atom, from —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

wherein:

each occurrence of R$^o$ is independently an aliphatic or aryl group;

each occurrence of R$^+$ is independently hydrogen or an aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms selected from N, O, and S; and each occurrence of R* is independently hydrogen or an aliphatic, aryl, heteroaryl, or heterocyclyl group.

9. A compound of formula (I-A):

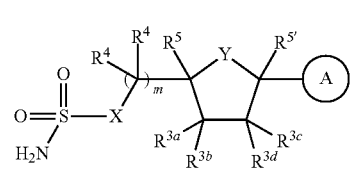

(I-A)

or a pharmaceutically acceptable salt thereof, wherein:

Ring A is:

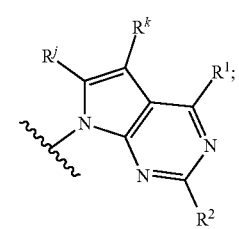

A-ii wherein one ring nitrogen atom in Ring A optionally is oxidized;

X is —$CH_2$—, —CHF—, —$CF_2$—, —NH—, or —O—;

Y is —O—, —S—, or —C($R^m$)($R^n$)—;

$R^j$ is hydrogen;

$R^k$ is hydrogen, halo, or an optionally substituted $C_{1-4}$ aliphatic group;

$R^m$ and $R^n$ are each hydrogen;

$R^1$ is $C_{1-10}$ aliphatic, —Z—$R^{12a}$, —Z—$R^{12b}$, —L—Z—$R^{12a}$, —L—Z—$R^{12b}$, —L—$R^{12a}$ or —L—$R^{12d}$;

L is —C($R^{13}$)=C($R^{13}$)— or —C≡C—;

$R^2$ is hydrogen, chloro, bromo, fluoro, iodo, —N($R^6$)$_2$, —CN, —O—($C_{1-4}$ aliphatic), —OH, —$SR^6$, or an optionally substituted $C_{1-4}$ aliphatic group;

$R^{3a}$ is hydrogen, fluoro, —CN, —$N_3$, hydroxy, —$OR^{21}$, —$NH_2$, —NH($R^{21}$), —N(H)$CO_2R^{21}$, —N(H)C(O)$R^{21}$, —CON(H)$R^{21}$, —C(O)$R^5$, —OC(O)N(H)$R^{21}$, —OC(O)$R^{21}$, —OC(O)$OR^{21}$, —$C_{1-4}$ fluoroaliphatic, or a —$C_{1-4}$ aliphatic optionally substituted with one or two substituents independently selected from the group consisting of —$OR^{5x}$, —N($R^{4x}$)($R^{4y}$), —$CO_2R^{5x}$, and —C(O)N($R^{4x}$)($R^{4y}$);

$R^{3b}$ is selected from the group consisting of hydrogen, fluoro, $C_{1-4}$ aliphatic, and $C_{1-4}$ fluoroaliphatic;

$R^{3c}$ is hydrogen, fluoro, —CN, —$N_3$, hydroxy, —$OR^{21}$, —$NH_2$, —NH($R^{21}$), N(H)$CO_2R^{21}$, —N(H)C(O)$R^{21}$, —CON(H)$R^{21}$, —OC(O)N(H)$R^{21}$, —OC(O)$R^{21}$, —OC(O)$OR^{21}$, —$C_{1-4}$ fluoroaliphatic, or a —$C_{1-4}$ aliphatic optionally substituted with one or two substituents independently selected from the group consisting of —$OR^{5x}$, —N($R^{4x}$)($R^{4y}$), —$CO_2R^{5x}$, and —C(O)N($R^{4x}$)($R^{4y}$);

$R^{3d}$ is selected from the group consisting of hydrogen, fluoro, $C_{1-4}$ aliphatic, and $C_{1-4}$ fluoroaliphatic;

each $R^4$ is independently hydrogen, fluoro, $C_{1-4}$ aliphatic, or $C_{1-4}$ fluoroaliphatic; or two $R^4$, taken together with the carbon atom to which they are attached, form a 3- to 6-membered carbocyclic ring; or one $R^4$, taken together with $R^5$ and the intervening carbon atoms, forms a 3- to 6-membered ring; or two $R^4$ together form =O;

$R^5$ is hydrogen, or $C_{1-4}$ aliphatic; or $R^5$, taken together with one $R^4$ and the intervening carbon atoms, forms a 3- to 6-membered ring;

$R^{5'}$ is hydrogen, or $C_{1-4}$ aliphatic;

each $R^6$ is independently hydrogen or $C_{1-4}$ aliphatic;

$R^{4x}$ is hydrogen, $C_{1-4}$ alkyl, $C_{1-4}$ fluoroalkyl, or $C_{6-10}$ ar($C_{1-4}$)alkyl, the aryl portion of which is optionally substituted;

$R^{4y}$ is hydrogen, $C_{1-4}$ alkyl, $C_{1-4}$ fluoroalkyl, $C_{6-10}$ ar($C_{1-4}$) alkyl, the aryl portion of which is optionally substituted, or an optionally substituted 5- or 6-membered aryl, heteroaryl, or heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, or an optionally substituted $C_{6-10}$ aryl or $C_{6-10}$ ar($C_{1-4}$)alkyl;

Z is an optionally substituted $C_{1-6}$ alkylene chain, wherein the alkylene chain is optionally interrupted by —C($R^{13}$)=C($R^{13}$)—, —C≡C—, —O—, —S—, —N($R^{13}$)—, —N($R^{13}$)CO—, —N($R^{13}$)$CO_2$—, —C(O)N($R^{13}$)—, —C(O)—, —C(O)—C(O)—, —$CO_2$—, —OC(O)—, —OC(O)O—, —N($R^{13}$)C(O)N($R^{13}$)—, —N($R^{13}$)N($R^{13}$)—, —OC(O)N($R^{13}$)—, —S(O)—, —S(O)$_2$—, —N($R^{13}$)S(O)$_2$—, or —S(O)$_2$N($R^{13}$)—;

$R^{12a}$ is an optionally substituted aryl, heteroaryl, heterocyclyl, or cycloaliphatic group;

$R^{12b}$ is halo, —$NO_2$, —CN, —$OR^{14}$, —$SR^{15}$, —N($R^{16}$)$_2$, —N($R^{16}$)C(O)$R^{15}$, —N($R^{16}$)C(O)N($R^{16}$)$_2$, —N($R^{16}$)$CO_2R^{14}$, —O—$CO_2$—$R^{14}$, —OC(O)N($R^{16}$)$_2$, —OC(O)$R^{14}$, —N($R^{16}$)—N($R^{16}$)$_2$, —N($R^{16}$)—$OR^{15}$, —N($R^{16}$)S(O)$_2R^{15}$, —N($R^{16}$)$SO_2$—N($R^{16}$)$_2$, —C($R^{14}$)=C($R^{14}$)$_2$, —C≡C—$R^{14}$, —S(O)$R^{15}$, —$SO_2R^{15}$, —$SO_2$—N($R^{16}$)$_2$, —C($R^{14}$)=N—$OR^{14}$, —$CO_2R^{14}$, —C(O)—C(O)$R^{14}$, —C(O)$R^{14}$, —C(O)N($R^{16}$)$_2$, —C(=$NR^{16}$)—N($R^{16}$)$_2$, or —C(=$NR^{16}$)—$OR^{14}$;

$R^{12d}$ is —$NO_2$, —CN, —S(O)$R^{15}$, —$SO_2R^{15}$, —$SO_2$—N($R^{16}$)$_2$, —$CO_2R^{14}$, —C(O)$R^{14}$, or —C(O)N($R^{16}$)$_2$;

each $R^{13}$ is independently hydrogen, or an optionally substituted aliphatic, aryl, heteroaryl, or heterocyclyl group;

each $R^{14}$ independently is hydrogen, or an optionally substituted aliphatic, aryl, heteroaryl, or heterocyclyl group;

each $R^{15}$ independently is an optionally substituted aliphatic, or aryl group;

each $R^{16}$ independently is an optionally substituted aliphatic, aryl, heteroaryl, or heterocyclyl group; or two $R^{16}$ on the same nitrogen atom, taken together with the nitrogen atom, form an optionally substituted five to eight membered heterocyclyl ring having, in addition to the nitrogen atom, zero to two additional ring heteroatoms selected from the group consisting of N, O, and S;

each $R^{21}$ independently is an optionally substituted $C_{1-10}$ aliphatic, aryl, heteroaryl, or heterocyclyl group;

wherein:

in each recitation of optionally substituted aryl, the aryl group, when substituted, contains on an unsaturated carbon atom one or more substituents independently selected from halo, —$NO_2$, —CN, —R*, —C(R*)=C(R*)$_2$, —C≡C—R*, —OR*, —SR°, —S(O)R°, —$SO_2R°$, —$SO_2N(R^+)_2$, —N($R^+$)$_2$, —$NR^+C(O)R*$, —$NR^+C(O)N(R^+)_2$, —$NR^+CO_2R°$, —O—$CO_2R*$, —OC(O)N($R^+$)$_2$, —O—C(O)R*, —$CO_2R*$, —C(O)—C(O)R*, —C(O)R*, —C(O)N($R^+$)$_2$, —C(=$NR^+$)—N($R^+$)$_2$, —C(=$NR^+$)—OR*, —N($R^+$)—N($R^+$)$_2$, —N($R^+$)C(=$NR^+$)—N($R^+$)$_2$, —$NR^+SO_2R°$, —$NR^+SO_2N(R^+)_2$, —P(O)(R*)$_2$, —P(O)(OR*)$_2$, —O—P(O)—OR*, and —P(O)(NR$^+$)—N($R^+$)$_2$;

in each recitation of optionally substituted heteroaryl, the heteroaryl group, when substituted, contains one or more substituents independently selected, if on an unsaturated carbon atom, from halo, —$NO_2$, —CN, —R*, —C(R*)=C(R*)$_2$, —C≡C—R*, —OR*, —SR°, —S(O)R°, —$SO_2R°$, —$SO_2N(R^+)_2$, —N($R^+$)$_2$, —$NR^+C(O)R*$, —$NR^+C(O)N(R^+)_2$, —$NR^+CO_2R°$, —O—$CO_2R*$, —OC(O)N($R^+$)$_2$, —O—C(O)R*, —$CO_2R*$, —C(O)—C(O)R*, —C(O)R*, —C(O)N($R^+$)$_2$, —C(=$NR^+$)—N($R^+$)$_2$, —C(=$NR^+$)—OR*, —N($R^+$)—N($R^+$)$_2$, —N($R^+$)C(=$NR^+$)—N($R^+$)$_2$, —$NR^+SO_2R°$, —$NR^+SO_2N(R^+)_2$, —P(O)(R*)$_2$, —P(O)(OR*)$_2$, —O—P(O)—OR*, and —P(O)(NR$^+$)—N($R^+$)$_2$, and, if on a substitutable nitrogen atom, from —R*, —N(R*)$_2$, —C(O)

R*, —CO₂R*, —C(O)—C(O)R*, —C(O)CH₂C(O)R*, —SO₂R*, —SO₂N(R*)₂, —C(=S)N(R*)₂, —C(=NH)—N(R*)₂, and —NR*SO₂R*;

in each recitation of optionally substituted aliphatic, the aliphatic group, when substituted, contains on a saturated carbon atom one or more substituents independently selected from halo, —NO₂, —CN, —R*, —C(R*)=C(R*)₂, —C≡C—R*, —OR*, —SR°, —S(O)R°, —SO₂R°, —SO₂N(R⁺)₂, —N(R⁺)₂, —NR⁺C(O)R*, —NR⁺C(O)N(R⁺)₂, —NR⁺CO₂R°, —O—CO₂R*, —OC(O)N(R⁺)₂, —O—C(O)R*, —CO₂R*, —C(O)—C(O)R*, —C(O)R*, —C(O)N(R⁺)₂, —C(=NR⁺)—N(R⁺)₂, —C(=NR⁺)—OR*, —N(R⁺)—N(R⁺)₂, —N(R⁺)C(=NR⁺)—N(R⁺)₂, —NR⁺SO₂R°, —NR⁺SO₂N(R⁺)₂, —P(O)(R*)₂, —P(O)(OR*)₂, —O—P(O)—OR*, —P(O)(NR⁺)—N(R⁺)₂, =O, =S, =C(R*)₂, =N—N(R⁺)₂, =N—OR*, =N—NHC(O)R*, =N—NHCO₂R°, =N—NHSO₂R°, and =N—R*; and in each recitation of optionally substituted heterocyclyl, the heterocyclyl group, when substituted, contains one or more substituents independently selected, if on an unsaturated carbon atom, from halo, —NO₂, —CN, —R*, —C(R*)=C(R*)₂, —C≡C—R*, —OR*, —SR°, —S(O)R°, —SO₂R°, —SO₂N(R⁺)₂, —N(R⁺)₂, —NR⁺C(O)R*, —NR⁺C(O)N(R⁺)₂, —NR⁺CO₂R°, —O—CO₂R*, —OC(O)N(R⁺)₂, —O—C(O)R*, —CO₂R*, —C(O)—C(O)R*, —C(O)R*, —C(O)N(R⁺)₂, —C(=NR⁺)—N(R⁺)₂, —C(=NR⁺)—OR*, —N(R⁺)—N(R⁺)₂, —N(R⁺)C(=NR⁺)—N(R⁺)₂, —NR⁺SO₂R°, —NR⁺SO₂N(R⁺)₂, —P(O)(R*)₂, —P(O)(OR*)₂, —O—P(O)—OR*, —P(O)(NR⁺)—N(R⁺)₂, =O, =S, =C(R*)₂, =N—N(R⁺)₂, =N—OR*, =N—NHC(O)R, =N—NHCO₂R°, =N—NHSO₂R°, and =N—R*, and, if on a substitutable nitrogen atom, from —R*, —N(R*)₂, —C(O)R*, —CO₂R*, —C(O)—C(O)R*, —C(O)CH₂C(O)R*, —SO₂R*, —SO₂N(R*)₂, —C(=S)N(R*)₂, —C(=NH)—N(R*)₂, and —NR*SO₂R*;

wherein:
each occurrence of R° is independently an aliphatic or aryl group;
each occurrence of R⁺ is independently hydrogen or an aliphatic, aryl, heteroaryl, or heterocyclyl group, or two R⁺ on the same nitrogen atom, taken together with the nitrogen atom, form a five to eight membered aromatic or non-aromatic ring having, in addition to the nitrogen atom, zero to two ring heteroatoms selected from N, O, and S; and
each occurrence of R* is independently hydrogen or an aliphatic, aryl, heteroaryl, or heterocyclyl group; and
m is 1, 2, or 3.

10. A compound of formula (I-A):

(I-A)

or a pharmaceutically acceptable salt thereof, wherein:
Ring A is:

A-ii wherein one ring nitrogen atom in Ring A optionally is oxidized;
X is —CH₂—, —CHF—, —CF₂—, —NH—, or —O—;
Y is —O—, —S—, or —C(Rᵐ)(Rⁿ)—;
Rʲ is hydrogen;
Rᵏ is hydrogen, halo, or an optionally substituted C₁₋₄ aliphatic group;
Rᵐ and Rⁿ are each hydrogen;
R¹ is —V—R¹²ᵃ, —V—Z—R¹²ᵃ, V—Z—R¹²ᵇ, or —Z—V—R¹²ᵃ;
R² is hydrogen, chloro, bromo, fluoro, iodo, —N(R⁶)₂, —CN, —O—(C₁₋₄ aliphatic), —OH, —SR⁶, or an optionally substituted C₁₋₄ aliphatic group;
R³ᵃ is hydrogen, fluoro, —CN, —N₃, hydroxy, —OR²¹, —NH₂, —NH(R²¹), —N(H)CO₂R²¹, —N(H)C(O)R²¹, —CON(H)R²¹, —C(O)R⁵, —OC(O)N(H)R²¹, —OC(O)R²¹, —OC(O)OR²¹, —C₁₋₄ fluoroaliphatic, or a —C₁₋₄ aliphatic optionally substituted with one or two substituents independently selected from the group consisting of —OR⁵ˣ, —N(R⁴ˣ)(R⁴ʸ), —CO₂R⁵ˣ, and —C(O)N(R⁴ˣ)(R⁴ʸ);
R³ᵇ is selected from the group consisting of hydrogen, fluoro, C₁₋₄ aliphatic, and C₁₋₄ fluoroaliphatic;
R³ᶜ is hydrogen, fluoro, —CN, —N₃, hydroxy, —OR²¹, —NH₂, —NH(R²¹), —N(H)CO₂R²¹, —N(H)C(O)R²¹, —CON(H)R²¹, —OC(O)N(H)R²¹, —OC(O)R²¹, —OC(O)OR²¹, —C₁₋₄ fluoroaliphatic, or a —C₁₋₄ aliphatic optionally substituted with one or two substituents independently selected from the group consisting of —OR⁵ˣ, —N(R⁴ˣ)(R⁴ʸ), —CO₂R⁵ˣ, and —C(O)N(R⁴ˣ)(R⁴ʸ);
R³ᵈ is selected from the group consisting of hydrogen, fluoro, C₁₋₄ aliphatic, and C₁₋₄ fluoroaliphatic;
each R⁴ is independently hydrogen, fluoro, C₁₋₄ aliphatic, or C₁₋₄ fluoroaliphatic; or two R⁴, taken together with the carbon atom to which they are attached, form a 3- to 6-membered carbocyclic ring; or one R⁴, taken together with R⁵ and the intervening carbon atoms, forms a 3- to 6-membered ring; or two R⁴ together form =O;
R⁵ is hydrogen, or C₁₄ aliphatic; or R⁵, taken together with one R⁴ and the intervening carbon atoms, forms a 3- to 6-membered ring;
R⁵ is hydrogen, or C₁₄ aliphatic;
each R⁶ is independently hydrogen or C₁₋₄ aliphatic;
R⁴ˣ is hydrogen, C₁₋₄ alkyl, C₁₋₄ fluoroalkyl, or C₆₋₁₀ ar(C₁₋₄)alkyl, the aryl portion of which is optionally substituted;
R⁴ʸ is hydrogen, C₁₋₄ alkyl, C₁₋₄ fluoroalkyl, C₆₋₁₀ ar(C₁₋₄)alkyl, the aryl portion of which is optionally substituted, or an optionally substituted 5- or 6-membered aryl, heteroaryl, or heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, or an optionally substituted $C_{6-10}$ aryl or $C_{6-10}$ ar($C_{1-4}$)alkyl;

V is —S(O)$_2$—, —S(O)—, —C(O)O—, —C(O)—, —C(NR$^{13}$)=N—, —C(=N(R$^{13}$))—N(R$^{13}$)—, —C(OR$^{11}$)=N—, —CON(R$^{13}$)—, —N(R$^{13}$)C(O)—, —N(R$^{13}$)C(O)N(R$^{13}$)—, —N(R$^{13}$)S(O)$_2$—, —N(R$^{13}$)SO$_2$—N(R$^{13}$)—, —N(R$^{13}$)CO$_2$—, —SO$_2$N(R$^{13}$)—, —OC(O)—, —OC(O)O—, —OC(O)N(R$^{13}$)—, or —N(R$^{13}$)—N(R$^{13}$)—;

Z is an optionally substituted $C_{1-6}$ alkylene chain, wherein the alkylene chain is optionally interrupted by —C(R$^{13}$)=C(R$^{13}$)—, —C≡C—, —O—, —S—, —N(R$^{13}$)—, —N(R$^{13}$)CO—, —N(R$^{13}$)CO$_2$—, —C(O)N(R$^{13}$)—, —C(O)—, —C(O)—C(O)—, —CO$_2$—, —OC(O)—, —OC(O)O—, —N(R$^{13}$)C(O)N(R$^{13}$)—, —N(R$^{13}$)N(R$^{13}$)—, —OC(O)N(R$^{13}$)—, —S(O)—, —S(O)$_2$—, —N(R$^{13}$)S(O)$_2$—, or —S(O)$_2$N(R$^{13}$)—;

$R^{12a}$ is an optionally substituted aryl, heteroaryl, heterocyclyl, or cycloaliphatic group;

$R^{12b}$ is halo, —NO$_2$, —CN, —OR$^{14}$, —SR$^{15}$, —N(R$^{16}$)$_2$, —N(R$^{16}$)C(O)R$^{15}$, —N(R$^{16}$)C(O)N(R$^{16}$)$_2$, —N(R$^{16}$)CO$_2$R$^{14}$, —O—CO$_2$—R$^{14}$, —OC(O)N(R$^{16}$)$_2$, —OC(O)R$^{14}$, —N(R$^{16}$)—N(R$^{16}$)$_2$, —N(R$^{16}$)—OR$^{15}$, —N(R$^{16}$)S(O)$_2$R$^{15}$, —N(R$^{16}$)SO$_2$—N(R$^{16}$)$_2$, —C(R$^{14}$)=C(R$^{14}$)$_2$, —≡C—R$^{14}$, —S(O)R$^{15}$, —SO$_2$R$^{15}$, —SO$_2$N(R$^{16}$)$_2$, —C(R$_{14}$)=N—OR$^{14}$, —CO$_2$R$^{14}$, —C(O)—C(O)R$^{14}$, —C(O)R$^{14}$, —C(O)N(R$^{16}$)$_2$, —C(=NR$^{16}$)—N(R$^{16}$)$_2$, or —C(=NR$^{16}$)—OR$^{14}$;

each $R^{13}$ is independently hydrogen, or an optionally substituted aliphatic, aryl, heteroaryl, or heterocyclyl group;

each $R^{14}$ independently is hydrogen, or an optionally substituted aliphatic, aryl, heteroaryl, or heterocyclyl group;

each $R^{15}$ independently is an optionally substituted aliphatic, or aryl group;

each $R^{16}$ independently is an optionally substituted aliphatic, aryl, heteroaryl, or heterocyclyl group; or two $R^{16}$ on the same nitrogen atom, taken together with the nitrogen atom, form an optionally substituted five to eight membered heterocyclyl ring having, in addition to the nitrogen atom, zero to two additional ring heteroatoms selected from the group consisting of N, O, and S;

each $R^{21}$ independently is an optionally substituted $C_{1-10}$ aliphatic, aryl, heteroaryl, or heterocyclyl group;

wherein:

in each recitation of optionally substituted aryl, the aryl group, when substituted, contains on an unsaturated carbon atom one or more substituents independently selected from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$;

in each recitation of optionally substituted heteroaryl, the heteroaryl group, when substituted, contains one or more substituents independently selected, if on an unsaturated carbon atom, from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, and, if on a substitutable nitrogen atom, from —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

in each recitation of optionally substituted aliphatic, the aliphatic group, when substituted, contains on a saturated carbon atom one or more substituents independently selected from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R$^o$, =N—NHSO$_2$R$^o$, and =N—R*; and in each recitation of optionally substituted heterocyclyl, the heterocyclyl group, when substituted, contains one or more substituents independently selected, if on an unsaturated carbon atom, from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R$^o$, =N—NHSO$_2$R$^o$, and =N—R*, and, if on a substitutable nitrogen atom, from —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

wherein:

each occurrence of R$^o$ is independently an aliphatic or aryl group;

each occurrence of R$^+$ is independently hydrogen or an aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms selected from N, O, and S; and each occurrence of R* is independently hydrogen or an aliphatic, aryl, heteroaryl, or heterocyclyl group; and m is 1, 2, or 3.

11. A compound of formula (VII):

(VII)

or a pharmaceutically acceptable salt thereof,
wherein:
Q is CH;
X is —CH$_2$—, —CHF—, —CF$_2$—, —NH—, or —O—;
Y is —O—, —S—, or —C(R$^m$)(R$^n$)—;
R$^j$ is hydrogen;
R$^m$ and R$^n$ are each hydrogen;
R$^2$ is hydrogen, chloro, bromo, fluoro, iodo, —N(R$^6$)$_2$, —CN, —O—(C$_{1-4}$ aliphatic), —OH, —SR$^6$, or an optionally substituted C$_{1-4}$ aliphatic group;
R$^{3a}$ is —OH;
R$^{3b}$ is selected from the group consisting of hydrogen, fluoro, C$_{1-4}$ aliphatic, and C$_{1-4}$ fluoroaliphatic;
R$^{3c}$ is hydrogen, fluoro, —CN, —N$_3$, hydroxy, —OR$^{21}$, —NH$_2$, —NH(R$^{21}$), —N(H)CO$_2$R$^{21}$, —N(H)C(O)R$^{21}$, —CON(H)R$^{21}$, —OC(O)N(H)R$^{21}$, —OC(O)R$^{21}$, —OC(O)OR$^{21}$, —C$_{1-4}$ fluoroaliphatic, or a —C$_{1-4}$ aliphatic optionally substituted with one or two substituents independently selected from the group consisting of —OR$^{5x}$, —N(R$^{4x}$)(R$^{4y}$), —CO$_2$R$^{5x}$, and —C(O)N(R$^{4x}$)(R$^{4y}$);
R$^{3d}$ is selected from the group consisting of hydrogen, fluoro, C$_{1-4}$ aliphatic, and C$_{1-4}$ fluoroaliphatic;
each R$^4$ is independently hydrogen, fluoro, C$_{1-4}$ aliphatic, or C$_{1-4}$ fluoroaliphatic; or two R$^4$, taken together with the carbon atom to which they are attached, form a 3-to 6-membered carbocyclic ring; or one R$^4$, taken together with R$^5$ and the intervening carbon atoms, forms a 3-to 6-membered ring; or two R$^4$ together form =O;
R$^5$ is hydrogen, or C$_{1-4}$ aliphatic; or R$^5$, taken together with one R$^4$ and the intervening carbon atoms, forms a 3-to 6-membered ring;
each R$^6$ is independently hydrogen or C$_{1-4}$ aliphatic;
R$^8$ is hydrogen or C$_{1-4}$ aliphatic;
R$^{4x}$ is hydrogen, C$_{1-4}$ alkyl, C$_{1-4}$ fluoroalkyl, or C$_{6-10}$ ar(C$_{1-4}$)alkyl, the aryl portion of which is optionally substituted;
R$^{4y}$ is hydrogen, C$_{1-4}$ alkyl, C$_{1-4}$ fluoroalkyl, C$_{6-10}$ ar(C$_{1-4}$)alkyl, the aryl portion of which is optionally substituted, or an optionally substituted 5-or 6-membered aryl, heteroaryl, or heterocyclyl ring; or
R$^{4x}$ and R$^{4y}$, taken together with the nitrogen atom to which they are attached, form an optionally substituted 4-to 8-membered heterocyclyl ring having, in addition to the nitrogen atom, 0-2 ring heteroatoms independently selected from N, O, and S;
each R$^{5x}$ independently is hydrogen, C$_{1-4}$ alkyl, C$_{1-4}$ fluoroalkyl, or an optionally substituted C$_{6-10}$ aryl or C$_{6-10}$ ar(C$_{1-4}$)alkyl;
each R$^{21}$ independently is an optionally substituted C$_{1-10}$ aliphatic, aryl, heteroaryl, or heterocyclyl group;
Ring D is an optionally substituted mono-or bicyclic aryl, heteroaryl, heterocyclyl, or cycloaliphatic ring;
wherein:
in each recitation of optionally substituted awl, the aryl group, when substituted, contains on an unsaturated carbon atom one or more substituents independently selected from halo, —NO$_2$, —CN, —R*, —C(R*)=C(R*)$_2$, —C≡C—R*; —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$;
in each recitation of optionally substituted heteroaryl, the heteroaryl group, when substituted, contains one or more substituents independently selected, if on an unsaturated carbon atom, from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, and, if on a substitutable nitrogen atom, from —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;
in each recitation of optionally substituted aliphatic, the aliphatic group, when substituted, contains on a saturated carbon atom one or more substituents independently selected from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, —P(O)(NR$^+$)—N(R$^+$)$_2$, =O, =S, =C(R*)$_2$, =N—N(R*)$_2$, =N—OR*, =N—NHC(O)R*, =N—NHCO$_2$R$^o$, =N—NHSO$_2$R$^o$, and =N—R*; and
in each recitation of optionally substituted heterocyclyl, the heterocyclyl group, when substituted, contains one or more substituents independently selected, if on an unsaturated carbon atom, from halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO₂R*, —C(O)—C(O)R*,
—C(O)R*, —C(O)N(R⁺)₂, —C(=NR⁺)—N(R⁺)₂,
—C(=NR⁺)—OR*, —N(R⁺)—N(R⁺)₂, —N(R⁺)C
(=NR⁺)—N(R⁺)₂, —NR⁺SO₂R°, —NR⁺SO₂N
(R⁺)₂, —P(O)(R*)₂, —P(O)(OR*)₂, —O—P(O)—
OR*, —P(O)(NR⁺)—N(R⁺)₂, =O, =S, =C(R*)₂,
=N—N(R⁺)₂, =N—OR*, =N—NHC(O)R*,
=N—NHCO₂R°, =N—NHSO₂R°, and =N—R*,
and, if on a substitutable nitrogen atom, from —R*,
—N(R*)₂, —C(O)R*, —CO₂R*, —C(O)—C(O)R*,
—C(O)CH₂C(O)R*, —SO₂R*, —SO₂N(R*)₂,
—C(=S)N(R*)₂, —C(=NH)—N(R*)₂, and
—NR*SO₂R*;

wherein:
each occurrence of R° is independently an aliphatic or aryl group;
each occurrence of R⁺ is independently hydrogen or an aliphatic, aryl, heteroaryl, or heterocyclyl group, or two R⁺ on the same nitrogen atom, taken together with the nitrogen atom, form a five to eight membered aromatic or non-aromatic ring having, in addition to the nitrogen atom, zero to two ring heteroatoms selected from N, O, and S; and
each occurrence of R* is independently hydrogen or an aliphatic, aryl, heteroaryl, or heterocyclyl group; and m is 1, 2, or 3.

12. The compound of claim 11, or a pharmaceutically acceptable salt thereof, wherein:
each substitutable saturated ring carbon atom in Ring D is unsubstituted or substituted with =O, =S, =C(R*)₂, =N—N(R⁺)₂, =N—OR*, =N—NHC(O)R*, =N—NHCO₂R°, =N—NHSO₂R°, =N—R*, or —R^d, provided that no occurrence of R⁺ is hydrogen, and further provided that when two R⁺ on the same nitrogen atom form a ring, the ring is a heterocyclyl ring;
each substitutable unsaturated carbon atom in Ring D is unsubstituted or substituted with —R^d;
each R^d independently is selected from the group consisting of C₁₋₆ aliphatic, halo, —R^{a7}, and —R^{b7};
each R^{a7} independently is an aryl, heteroaryl, heterocyclyl, or cycloaliphatic ring; and
each R^{b7} independently is —NO₂, —CN, —C(R*)=C(R*)₂, —C≡C—R*, —OR*, —SR°, —S(O)R°, —SO₂R°, —SO₂N(R⁺)₂, —N(R⁺)₂, —NR⁺C(O)R*, —NR⁺C(O)N(R⁺)₂, —NR⁺CO₂R°, —O—CO₂R*, —OC(O)N(R⁺)₂, —O—C(O)R*, —CO₂R*, —C(O)R*, —C(O)N(R⁺)₂, —C(=NR⁺)—N(R⁺)₂, —C(=NR⁺)—OR*, —N(R⁺)C(=NR⁺)—N(R⁺)₂, —N(R⁺)SO₂R°, or —N(R⁺)SO₂N(R⁺)₂, provided that no occurrence of R⁺ is hydrogen, and further provided that when two R⁺ on the same nitrogen atom form a ring, the ring is a heterocyclyl ring.

13. The compound of claim 12, or a pharmaceutically acceptable salt thereof, wherein Ring D is an optionally substituted phenyl, naphthyl, or indanyl ring.

14. A compound of formula (I-A):

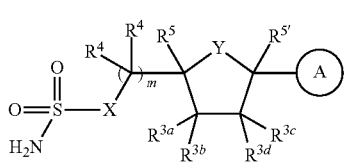

(I-A)

or a pharmaceutically acceptable salt thereof, wherein:
Ring A is:

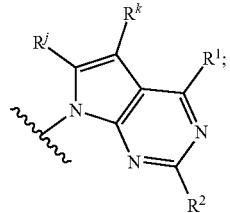

A-ii wherein one ring nitrogen atom in Ring A optionally is oxidized;
X is —CH₂—, —CHF—, —CF₂—, —NH—, or —O—;
Y is —O—, —S—, or —C(R^m)(R^n)—;
R^j is hydrogen;
R^k is hydrogen, halo, or an optionally substituted C₁₋₄ aliphatic group;
R^m and R^n are each hydrogen;
R¹ is —O—R¹¹, —S—R¹⁰, or —NR⁷R⁸;
R² is hydrogen, chloro, bromo, fluoro, iodo, —N(R⁶)₂, —CN, —O—(C₁₋₄ aliphatic), —OH, —SR⁶, or an optionally substituted C₁₋₄ aliphatic group;
R^{3a} is hydrogen, fluoro, —CN, —N₃, hydroxy, —OR²¹, —NH₂, —NH(R²¹), —N(H)CO₂R²¹, —N(H)C(O)R²¹, —CON(H)R²¹, —C(O)R⁵, —OC(O)N(H)R²¹, —OC(O)R²¹, —OC(O)OR²¹, —C₁₋₄ fluoroaliphatic, or a —C₁₋₄ aliphatic optionally substituted with one or two substituents independently selected from the group consisting of —OR^{5x}, —N(R^{4x})(R^{4y}), —CO₂R^{5x}, and —C(O)N(R^{4x})(R^{4y});
R^{3b} is selected from the group consisting of hydrogen, fluoro, C₁₋₄ aliphatic, and C₁₋₄ fluoroaliphatic;
R^{3c} is hydrogen, fluoro, —CN, —N₃, hydroxy, —OR²¹, —NH₂, —NH(R²¹), —N(H)CO₂R²¹, —N(H)C(O)R²¹, —CON(H)R²¹, —OC(O)N(H)R²¹, —OC(O)R²¹, —OC(O)OR²¹, —C₁₋₄ fluoroaliphatic, or a —C₁₋₄ aliphatic optionally substituted with one or two substituents independently selected from the group consisting of —OR^{5x}, —N(R^{4x})(R^{4y}), —CO₂R^{5x}, and —C(O)N(R^{4x})(R^{4y});
R^{3d} is selected from the group consisting of hydrogen, fluoro, C₁₋₄ aliphatic, and C₁₋₄ fluoroaliphatic;
each R⁴ is independently hydrogen, fluoro, C₁₋₄ aliphatic, or C₁₋₄ fluoroaliphatic; or two R⁴, taken together with the carbon atom to which they are attached, form a 3- to 6-membered carbocyclic ring; or one R⁴, taken together with R⁵ and the intervening carbon atoms, forms a 3- to 6-membered ring; or two R⁴ together form =O;
R⁵ is hydrogen, or C₁₋₄ aliphatic; or R⁵, taken together with one R⁴ and the intervening carbon atoms, forms a 3- to 6-membered ring;
R⁵' is hydrogen, or C₁₋₄ aliphatic;
each R⁶ is independently hydrogen or C₁₋₄ aliphatic;
R^{4x} is hydrogen, C₁₋₄ alkyl, C₁₋₄ fluoroalkyl, or C₆₋₁₀ ar(C₁₋₄)alkyl, the aryl portion of which is optionally substituted;
R^{4y} is hydrogen, C₁₋₄ alkyl, C₁₋₄ fluoroalkyl, C₆₋₁₀ ar(C₁₋₄)alkyl, the aryl portion of which is optionally substituted, or an optionally substituted 5- or 6-membered aryl, heteroaryl, or heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, or an optionally substituted $C_{6-10}$ aryl or $C_{6-10}$ ar($C_{1-4}$)alkyl;

each $R^{21}$ independently is an optionally substituted $C_{1-10}$ aliphatic, aryl, heteroaryl, or heterocyclyl group;

$R^7$, $R^{10}$, and $R^{11}$ are each independently —$Z^a R^{18}$, —$Z^a R^{19}$, or —$Z^b R^{20}$;

$Z^a$ is an optionally substituted $C_{1-6}$ alkylene chain, wherein the alkylene chain is optionally interrupted by —C(R*)=C(R*)—, —C≡C—, —O—, —S—, —N(R*)—, —N(R*)CO—, —N(R*)CO$_2$—, —C(O)N(R*)—, —C(O)—, —C(O)—C(O)—, —CO$_2$—, —OC(O)—, —OC(O)O—, —N(R*)C(O)N(R*)—, —N(R*)N(R*)—, —OC(O)N(R*)—, —S(O)—, —S(O)$_2$—, —N(R*)S(O)$_2$, or —S(O)$_2$N(R*)—;

$Z^b$ is an optionally substituted $C_{2-6}$ alkylene chain, wherein the alkylene chain is optionally interrupted by —C(R*)=C(R*)—, —C≡C—, —O—, —S—, —N(R*)—, —N(R*)CO—, —N(R*)CO$_2$—, —C(O)N(R*)—, —C(O)—, —C(O)—C(O)—, —CO$_2$, —OC(O)13, —OC(O)O—, —N(R*)C(O)N(R*)—, —N(R*)N(R*)—, —OC(O)N(R*)—, —S(O)—, —S(O)$_2$—, —N(R*)S(O)$_2$, or —S(O)$_2$N(R*)—;

$R^{18}$ is an optionally substituted aryl, heteroaryl, heterocyclyl, or cycloaliphatic group;

$R^{19}$ is —C(R*)=C(R*)$_2$, —C≡C—R*, —S(O)R°, —SO$_2$R°, —SO$_2$—N(R$^+$)$_2$, —C(R*)=N—OR*, —CO$_2$R*, —C(O)—C(O)R*, —C(O)R*, —C(O)N(R$^+$)$_2$, —C(=NR$^+$)—N(R$^+$)$_2$, or —C(=NR$^+$)—OR*, provided that no occurrence of R$^+$ is hydrogen, and further provided that when two R$^+$ on the same nitrogen atom form a ring, the ring is a heterocyclyl ring;

$R^{20}$ is halo, —NO$_2$, —CN, —OR*, —SR°, —N(R$^+$)$_2$, —N(R$^+$)C(O)R°, —N(R$^+$)C(O)N(R$^+$)$_2$, —N(R$^+$)C(O)$_2$R*, —O—CO$_2$—R*, —OC(O)N(R$^+$)$_2$, —OC(O)R*, —N(R$^+$)—N(R$^+$)$_2$, —N(R$^+$)S(O)$_2$R°, or —N(R$^+$)SO$_2$—N(R$^+$)$_2$, provided that no occurrence of R$^+$ is hydrogen, and further provided that when two R$^+$ on the same nitrogen atom form a ring, the ring is a heterocyclyl ring;

$R^8$ is hydrogen;

wherein:

in each recitation of optionally substituted aryl, the aryl group, when substituted, contains on an unsaturated carbon atom one or more substituents independently selected from halo, —NO$_2$, —CN, —R*, —C(R*)=C(R*)$_2$, —C≡C—R*, —OR*, —SR°, —S(O)R°, —SO$_2$R°, —SO$_2$N(R$^+$)$_2$, —N(R$^+$)$_2$, —NR$^+$C(O)R*, —NR$^+$C(O)N(R$^+$)$_2$, —NR$^+$CO$_2$R°, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R°, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$;

in each recitation of optionally substituted heteroaryl, the heteroaryl group, when substituted, contains one or more substituents independently selected, if on an unsaturated carbon atom, from halo, —NO$_2$, —CN, —R*, —C(R*)=C(R*)$_2$, —C≡C—R*, —OR*, —SR°, —S(O)R°, —SO$_2$R°, —SO$_2$N(R$^+$)$_2$, —N(R$^+$)$_2$, —NR$^+$C(O)R*, —NR$^+$C(O)N(R$^+$)$_2$, —NR$^+$CO$_2$R°, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R°, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, and, if on a substitutable nitrogen atom, from —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

in each recitation of optionally substituted aliphatic, the aliphatic group, when substituted, contains on a saturated carbon atom one or more substituents independently selected from halo, —NO$_2$, —CN, —R*, —C(R*)=C(R*)$_2$, —C≡C—R*, —OR*, —SR°, —S(O)R°, —SO$_2$R°, —SO$_2$N(R$^+$)$_2$, —N(R$^+$)$_2$, —NR$^+$C(O)R*, —NR$^+$C(O)N(R$^+$)$_2$, —NR$^+$CO$_2$R°, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R°, —NR$^+$SO$_2$N(R$^+$)$_2$, —P(O)(R*)$_2$, —P(O)(OR*)$_2$, —O—P(O)—OR*, —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R°, =N—NHSO$_2$R°, and =N—R*; and in each recitation of optionally substituted heterocyclyl, the heterocyclyl group, when substituted, contains one or more substituents independently selected, if on an unsaturated carbon atom, from halo, —NO$_2$, —CN, —R*, —C(R*)=C(R*)$_2$, —C≡C—R*, —OR*, —SR°, —S(O)R°, —SO$_2$R°, —SO$_2$N(R$^+$)$_2$, —N(R$^+$)$_2$, —NR$^+$C(O)R*, —NR$^+$C(O)N(R$^+$)$_2$, —NR$^+$CO$_2$R°, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R°, —NR$^+$SO$_2$N(R$^+$)$_2$, —P(O)(R*)$_2$, —P(O)(OR*)$_2$, —O—P(O)—OR*, aid —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R°, =N—NHSO$_2$R°, and =N—R*, and, if on a substitutable nitrogen atom, from —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

wherein:

each occurrence of R° is independently an aliphatic or aryl group;

each occurrence of R$^+$ is independently hydrogen or an aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms selected from N, O, and S; and each occurrence of R* is independently hydrogen or an aliphatic, aryl, heteroaryl, or heterocyclyl group; and m is 1, 2, or 3.

15. The compound of claim 14, or a pharmaceutically acceptable salt thereof, wherein:

$Z^a$ is a $C_{1-4}$ alkylene chain optionally substituted with one or two groups selected from the group consisting of —F, —OH, $C_{1-3}$ aliphatic and aryl; and $Z^b$ is a $C_{2-4}$ alkylene chain optionally substituted with one or two groups selected from the group consisting of —F, —OH, $C_{1-3}$ aliphatic and aryl.

16. The compound of claim 15, characterized by formula (VIII):

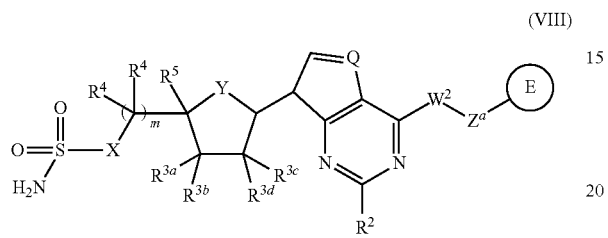

(VIII)

or a pharmaceutically acceptable salt thereof;
wherein:

Q is CH;

$W^2$ is —O—, —S—, or —N($R^8$)—;

Ring E is a mono- or bicyclic aryl, heteroaryl, heterocyclyl, or cycloaliphatic group;

each substitutable ring nitrogen atom in Ring E is unsubstituted or is substituted with —C(O)R*, —CO$_2$R*, —SO$_2$R*, —SO$_2$N(R*)$_2$, or an optionally substituted aliphatic, provided that no occurrence of R⁺ is hydrogen, and further provided that when two R⁺ on the same nitrogen atom form a ring, the ring is a heterocyclyl ring;

substitutable ring carbon atoms in Ring E are substituted with 0-4 substituents independently selected from the group consisting of $C_{1-6}$ aliphatic, halo, —$R^{a18}$, and —$R^{b18}$;

each $R^{a18}$ independently is an aryl, heteroaryl, heterocyclyl, or cycloaliphatic ring; and each $R^{b18}$ independently is —NO$_2$, —CN, —C(R*)=C(R*)$_2$, —C≡C—R*, —OR*, —SR°, —S(O)R°, —SO$_2$R°, —SO$_2$N(R⁺)$_2$, —N(R⁺)$_2$, —NR⁺C(O)R*, —NR⁺C(O)N(R⁺)$_2$, —NR⁺CO$_2$R°, —O—CO$_2$R*, —OC(O)N(R⁺)$_2$, —O—C(O)R*, —CO$_2$R*, —C(O)R*, —C(O)N(R⁺)$_2$, —C(=NR⁺)—N(R⁺)$_2$, —C(=NR⁺)—OR*, —N(R⁺)C(=NR⁺)—N(R⁺)$_2$, —N(R⁺)SO$_2$R°, or —N(R⁺)SO$_2$N(R⁺)$_2$, provided that no occurrence of R⁺ is hydrogen, and further provided that when two R⁺ on the same nitrogen atom form a ring, the ring is a heterocyclyl ring.

17. The compound of claim 16, or a pharmaceutically acceptable salt thereof, wherein Ring E is a an optionally substituted $C_{3-6}$ cycloaliphatic, phenyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, or tetrahydropyrimidinyl ring.

18. The compound of claim 16, or a pharmaceutically acceptable salt thereof, wherein Ring E is an optionally substituted phenyl, naphthyl, indanyl, furanyl, thienyl, pyrrolyl, pyrrolidinyl, isoxazolyl, pyrazolyl, piperidinyl, piperazinyl, pyrazinyl, morpholinyl, benzothiophenyl, or benzodioxolyl ring.

19. A pharmaceutical composition, comprising a compound of claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO.         : 7,951,810 B2
APPLICATION NO.    : 11/346469
DATED              : May 31, 2011
INVENTOR(S)        : Stephen Critchley et al.

It is certified that error appears in the above-identified patent and that said Letters Patent is hereby corrected as shown below:

In the specification

Column 21, lines 40 to 50, formula (VII) should appear as follows:

(VII)

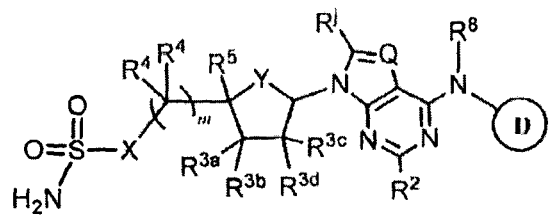

Column 24, lines 41 to 52, formula (VIII) should appear as follows:

(VIII)

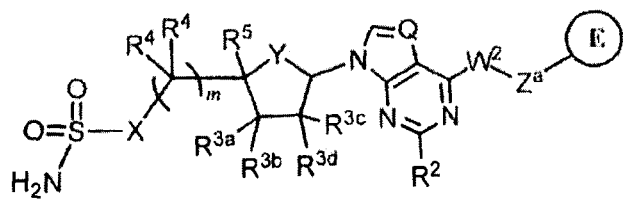

Signed and Sealed this
Seventeenth Day of May, 2016

Michelle K. Lee
*Director of the United States Patent and Trademark Office*

CERTIFICATE OF CORRECTION (continued)
U.S. Pat. No. 7,951,810 B2

In the claims

Claim 11, column 201, lines 10 to 20, formula (VII) should appear as follows:

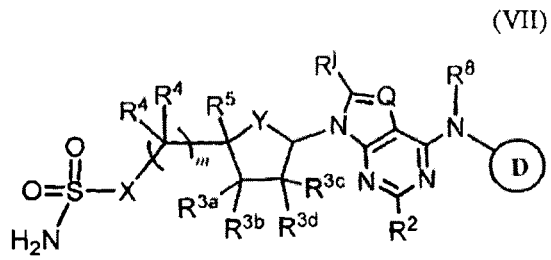

(VII)

Claim 16, column 207, lines 11 to 23, formula (VIII) should appear as follows:

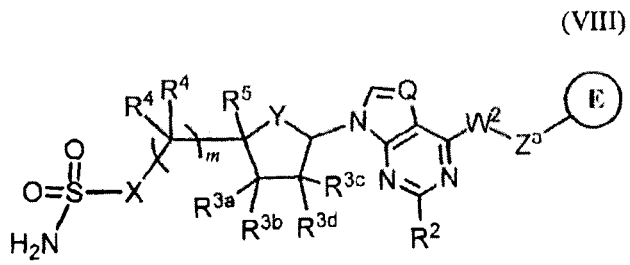

(VIII)